US011116953B2

(12) United States Patent
Kobayashi et al.

(10) Patent No.: US 11,116,953 B2
(45) Date of Patent: Sep. 14, 2021

(54) MICRONEEDLE APPLICATOR AND MICRONEEDLE PATCH APPLICATION DEVICE

(71) Applicant: MEDRX CO., LTD., Higashikagawa (JP)

(72) Inventors: Katsunori Kobayashi, Tokushima (JP); Hidetoshi Hamamoto, Tokushima (JP)

(73) Assignee: MEDRX CO., LTD., Higashikagawa (JP)

( * ) Notice: Subject to any disclaimer, the term of this patent is extended or adjusted under 35 U.S.C. 154(b) by 312 days.

(21) Appl. No.: 14/911,909

(22) PCT Filed: Dec. 21, 2015

(86) PCT No.: PCT/JP2015/085707
§ 371 (c)(1),
(2) Date: Feb. 12, 2016

(87) PCT Pub. No.: WO2016/129184
PCT Pub. Date: Aug. 18, 2016

(65) Prior Publication Data
US 2016/0354589 A1 Dec. 8, 2016

(30) Foreign Application Priority Data

Feb. 13, 2015 (JP) .............................. JP2015-026887
Feb. 13, 2015 (JP) .............................. JP2015-026889
(Continued)

(51) Int. Cl.
*A61M 37/00* (2006.01)
(52) U.S. Cl.
CPC . *A61M 37/0015* (2013.01); *A61M 2037/0023* (2013.01); *A61M 2037/0046* (2013.01);
(Continued)

(58) Field of Classification Search
CPC . A61B 17/205; A61B 17/20; A61B 5/150984; A61B 5/150977;
(Continued)

(56) References Cited

U.S. PATENT DOCUMENTS 6,537,242 B1 * 3/2003 Palmer .............. A61M 37/0015
600/309
6,743,211 B1 6/2004 Prausnitz et al.
(Continued)

FOREIGN PATENT DOCUMENTS

JP 2005-527249 A 9/2005
JP 2006-149818 A 6/2006
(Continued)

OTHER PUBLICATIONS

Office Action (Notification of Reasons for Refusal) dated Nov. 7, 2017, by the Japanese Patent Office in corresponding Japanese Patent Application No. 2016-508885, and an English Translation of the Office Action. (14 pages).
(Continued)

*Primary Examiner* — Brandy S Lee
*Assistant Examiner* — Hong-Van N Trinh
(74) *Attorney, Agent, or Firm* — Buchanan Ingersoll & Rooney PC

(57) ABSTRACT

A device for inserting needles of a microneedle patch into a skin includes a housing. The housing includes a support portion for supporting a microneedle patch, a pressure-receiving portion to which the user applies a force to press the microneedle patch against the skin, and a plurality of leg portions each having at its one end a connecting portion connected to the pressure-receiving portion and having at its other end a tip portion coming into contact with the skin. The housing is designed to deform when a force is applied to the
(Continued)

pressure-receiving portion, to cause a tension in a portion of the skin facing the support portion.

9 Claims, 101 Drawing Sheets

(30) Foreign Application Priority Data

Feb. 13, 2015 (JP) .............................. JP2015-026892
Dec. 3, 2015 (JP) .............................. JP2015-236682

(52) U.S. Cl.
CPC ............... *A61M 2037/0053* (2013.01); *A61M 2205/332* (2013.01); *A61M 2205/581* (2013.01); *A61M 2205/582* (2013.01); *A61M 2205/583* (2013.01)

(58) Field of Classification Search
CPC .......... A61B 5/150022; A61B 5/15117; A61B 5/15115; A61B 5/14514; A61B 5/6846; A61B 5/6847; A61B 5/685; A61M 37/0015; A61M 2037/0023; A61M 2037/0046; A61M 2037/0061; A61M 2205/581; A61M 2205/582; A61M 37/00; A61M 2037/0007; A61M 2037/2037; A61M 2037/0053; A61M 2037/003; A61M 5/14248; A61M 5/425; A61M 5/322; A61M 2005/1585; A61M 2037/0038; A61M 5/42; A61M 5/46; A61K 9/0019; A61K 9/0021; A61K 9/00
See application file for complete search history.

(56) References Cited

U.S. PATENT DOCUMENTS

| | | |
|---|---|---|
| 2002/0032415 A1 | 3/2002 | Trautman et al. |
| 2008/0183144 A1 | 7/2008 | Trautman et al. |
| 2008/0195035 A1* | 8/2008 | Frederickson .... A61M 37/0015 604/22 |
| 2008/0208146 A1 | 8/2008 | Brandwein et al. |
| 2009/0157041 A1 | 6/2009 | Pettis et al. |
| 2009/0198189 A1 | 8/2009 | Simons et al. |
| 2010/0256568 A1 | 10/2010 | Frederickson et al. |
| 2011/0276027 A1 | 11/2011 | Trautman et al. |
| 2012/0184916 A1 | 7/2012 | Kobayashi et al. |
| 2013/0006187 A1 | 1/2013 | Kobayashi et al. |
| 2013/0006219 A1 | 1/2013 | Cantor et al. |
| 2013/0023749 A1* | 1/2013 | Afanasewicz ....... A61B 5/6885 600/386 |
| 2016/0121092 A1 | 5/2016 | Kato |

FOREIGN PATENT DOCUMENTS

| | | |
|---|---|---|
| JP | 2008-520369 A | 6/2008 |
| JP | 2008-535587 A | 9/2008 |
| JP | 2008-543528 A | 12/2008 |
| JP | 2010-516337 A | 5/2010 |
| JP | 2013-027492 A | 2/2013 |
| JP | 2014-042788 A | 3/2014 |
| WO | WO 2006/055795 A1 | 5/2006 |
| WO | WO 2006/108185 A1 | 10/2006 |
| WO | WO 2007/002522 A1 | 1/2007 |
| WO | WO 2008/091602 A2 | 7/2008 |
| WO | WO 2009/107806 A2 | 9/2009 |
| WO | 2011/016230 A1 | 2/2011 |
| WO | WO 2011/089907 A1 | 7/2011 |
| WO | 2015005143 | 1/2015 |

OTHER PUBLICATIONS

Notification of Transmittal of the International Search Report and the Written Opinion of the International Searching Authority (Forms PCT/ISA/220 and PCT/ISA/210) dated Apr. 5, 2016, by the Japanese Patent Office in corresponding International Application No. PCT/JP2015/085707. (6 pages).

International Preliminary Report on Patentability and Written Opinion of the International Searching Authority (Forms PCT/IB/338, PCT/IB/373 and PCT/ISA/237) dated Aug. 24, 2017, by the International Bureau of WIPO, in corresponding International Application No. PCT/JP2015/085707. (7 pages).

International Search Report (Form PCT/ISA/210) dated Apr. 4, 2017, by the Japanese Patent Office in International Application No. PCT/JP2016/087965 and an English translation of the Search Report. (6 pages).

Extended European Search Report issued in corresponding European Patent Application No. 16878704.2, dated Jun. 4, 2019 (7 pages).

The extended European Search Report dated Oct. 14, 2020, by the European Patent Office in corresponding European Application No. 20180240.2. (8 pages).

* cited by examiner

Fig.6
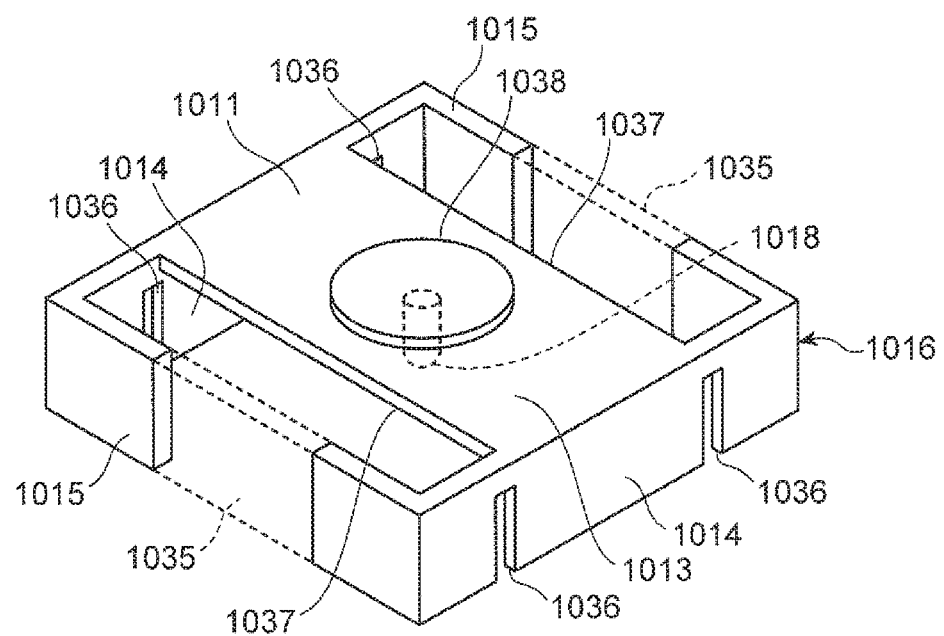
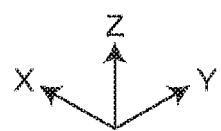

Fig.7
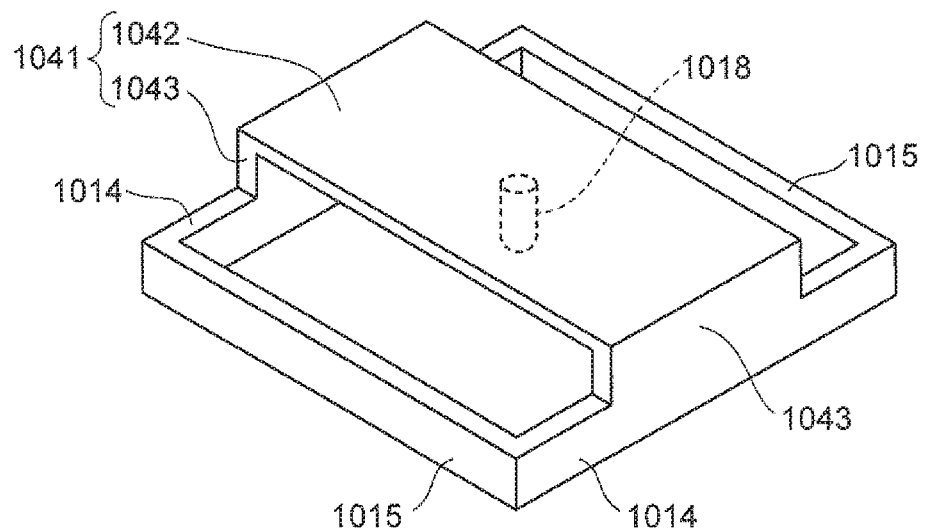
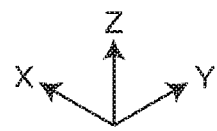

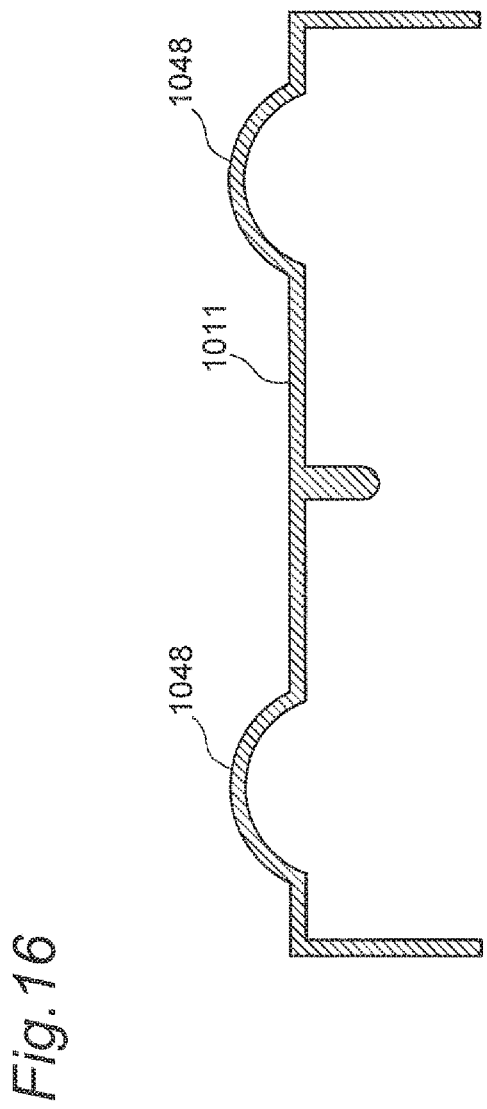

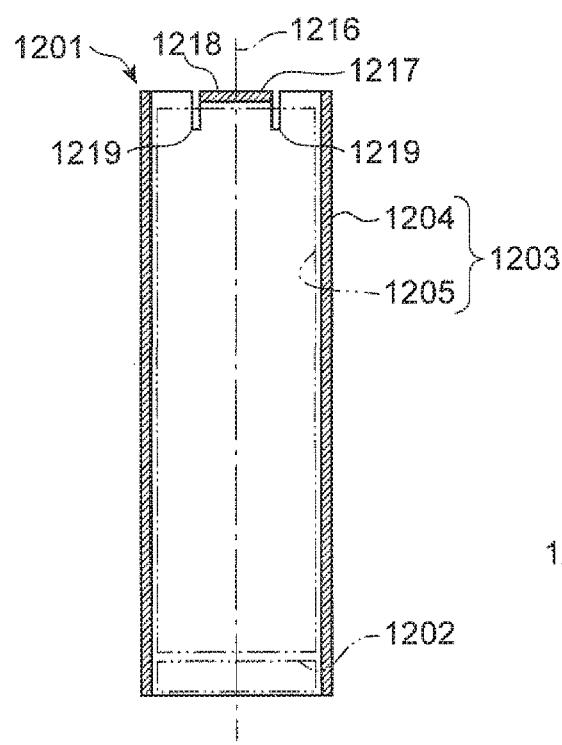
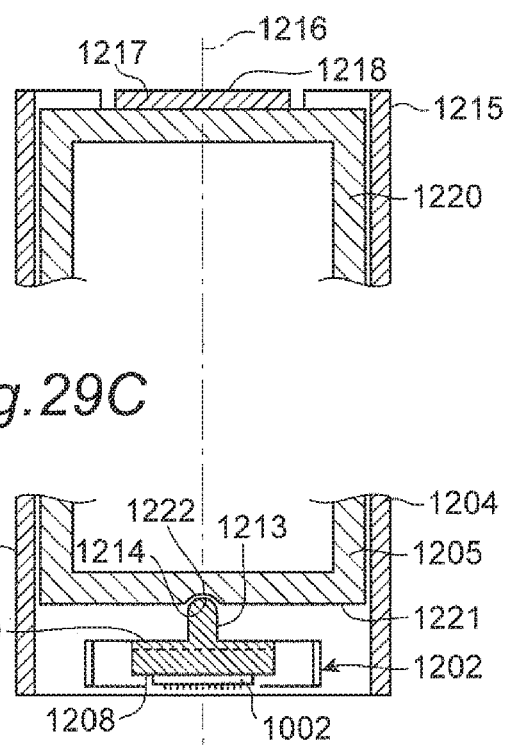
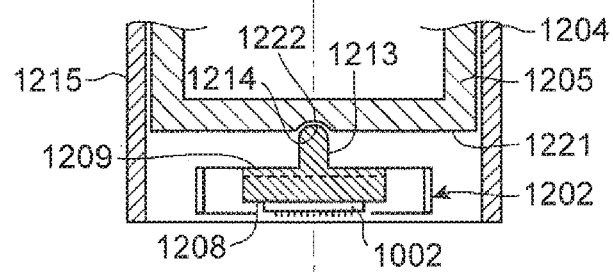
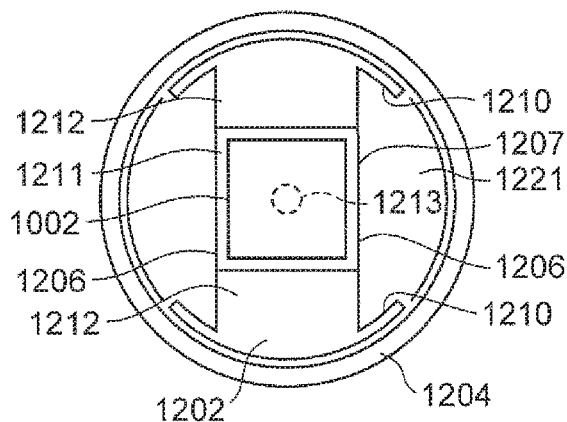

Fig. 116
| HOUSING MODIFICATION | I | J | K |
|---|---|---|---|
| APPEARANCE | 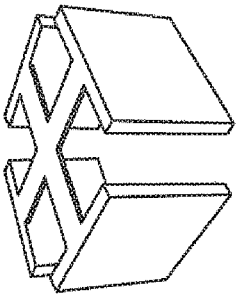 | 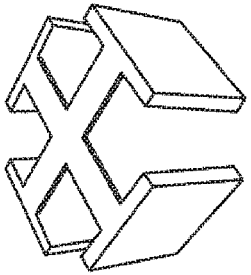 | 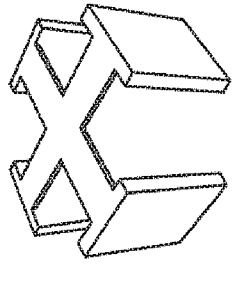 |
| ADJACENT LEG DISTANCE (mm) | 5 | 7 | 10 |
| OPPOSED LEG DISTANCE (mm) (PRE-DEFORMATION) | 30 | 30 | 30 |
| OPPOSED LEG DISTANCE (mm) (POST-DEFORMATION) | 32 | 34 | 35 |
| SKIN EXPANSION (mm) | 2 | 4 | 5 |
| SKIN EXPANSION RATE (%) | 6.7 | 13.3 | 16.7 |
| PRESSURE-RECEIVING PORTION WIDTH (mm) | 5 | 5 | 5 |

Fig. 118
| HOUSING MODIFICATION | L | M | N |
|---|---|---|---|
| APPEARANCE | 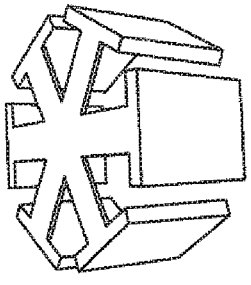 | 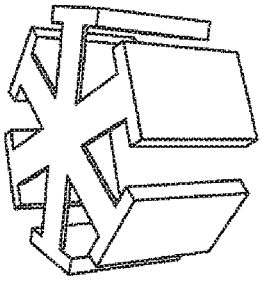 | 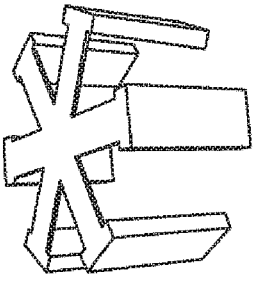 |
| ADJACENT LEG DISTANCE (mm) | 2 | 4.5 | 7 |
| OPPOSED LEG DISTANCE (mm) (PRE-DEFORMATION) | 30 | 30 | 30 |
| OPPOSED LEG DISTANCE (mm) (POST-DEFORMATION) | 32 | 34 | 35 |
| SKIN EXPANSION (mm) | 2 | 4 | 5 |
| SKIN EXPANSION RATE (%) | 6.7 | 13.3 | 16.7 |
| PRESSURE-RECEIVING PORTION WIDTH (mm) | 5 | 5 | 5 |

MICRONEEDLE APPLICATOR AND MICRONEEDLE PATCH APPLICATION DEVICE

TECHNICAL FIELD

The present invention relates to a device for inserting microneedles into a human or animal skin. The present invention relates also to a device for applying a microneedle patch on the human or animal skin.

BACKGROUND ART

Recent attention has been given to a drug administration system using a drug-coated microneedle patch, among transdermally absorbed drug administration systems (see Patents Documents 1 to 7). The microneedle patch has thin protuberances or needles of several hundred microns in length formed densely on its base material. The needles carrying thereon or therein a target drug (molecules such as vaccine, protein, and peptide) are inserted in a skin to directly deliver the drug to a dermis or an epidermis of patient. The drug administration system has various advantages. For example, the patient receives substantially little harmful effect on his or her liver unlike oral administration. Also, substantially no pain is induced at the insertion of the needles unlike injections. Further, side effects due to temporal and excessive administration of drug are reduced.

Because the needles of the microneedle patch are extremely thin and even the roots have about several tens of microns in root diameter, they may be damaged or broken by resistance applied thereto at the insertion into the skin. For example, a part of metal needle made of titanium, for example, remains in the patient's skin for a long time, which may result in harmful effect on the patient. The biodegradable resin needles are more likely to be damaged or broken than the metal needles. In particular, the tilted needles result in a less ability of insertion thereof into the skin or tend to be damaged by a bending force acting thereon.

In order to attain an efficient transdermal drug administration using the microneedle patch, preferably all the needles are uniformly inserted in the skin. To this end, an applicator may be provided to support a microneedle patch on a flat surface of the applicator and then force the microneedle patch onto the skin. This technique may result in that, due to the existence of adhesive provided for retaining the microneedle patch on the applicator, the microneedle which has been applied on the skin may be removed from the skin when raising the applicator away from the skin after application of the microneedle patch.

Further, in order to attain an efficient transdermal drug administration using the microneedle patch, preferably all the needles are inserted a predetermined depth in the skin. To this end, the needles are needed to be pressed against the skin with a predetermined force. However, the needles are invisibly supported on a bottom surface of the microneedle patch so that the operator is unable to see if the needles are inserted a predetermined depth.

PRIOR ART DOCUMENTS

Patent Documents

Patent Document 1: JP-A-2006-149818
Patent Document 2: JP-T-2008-520369
Patent Document 3: JP-T-2008-543528
Patent Document 4: JP-T-2008-535587
Patent Document 5: JP-T-2010-516337
Patent Document 6: JP-Re-2009-107806
Patent Document 7: JP-Re-2011-089907

SUMMARY OF THE INVENTION

Problem to be Solved by the Invention

It is therefore an object of the present invention to provide a device for inserting microneedles or microneedle array, which prevents the microneedles from being bent, damaged, or broken at the insertion of the needles.

Another object of the present invention is to provide a device capable of separating an applicator from the skin while keeping the needles inserted in the skin.

A further object of the present invention is the provision of a device allowing the amount of insertion of the microneedles or microneedle array to be checked.

A still further object of the present invention is to provide a device capable of securely inserting the needles of the microneedle patch into the skin.

For at least any one of these objects, in the process of developing a device capable of securely inserting needles of the microneedle patch (which are likely to be damaged than the metal needles) into the skin without being damaged, the inventors found that a force needed to insert the needles into the tensioned skin (i.e., a portion of skin stretched in all directions) is smaller than that into the loosed skin. One of the conceivable reasons is that the loosed skin moves back with the advancement of the needles, but the tensioned skin does not move back and therefore allows the needles to readily insert thereinto.

Thus, an embodiment of the invention is a device applying a microneedle patch onto a skin, which comprises
 a housing supporting a microneedle patch,
 the housing including:
 a support portion supporting the microneedle patch in a state where needles on the microneedle patch are directed toward a skin;
 a pressure-receiving portion to which the user applies a force to press the microneedle patch against the skin in a ready condition where the housing is placed on the skin; and
 a plurality of leg portions each having at its one end a connecting portion connected to the pressure-receiving portion and having at its other end a tip portion coming into contact with the skin in the ready condition, the leg portions keeping the patch support portion apart from the skin in the ready condition,
 the housing being designed to deform when the force is applied to the pressure-receiving portion so that at least one of the plurality of leg portions moves away from the support portion while being in contact with skin, to impart a tension to a portion of the skin opposing the support portion.

The device applying a microneedle patch onto a skin of another embodiment of the present invention includes:
 a pressure-receiving portion receiving a force applied along the direction of a central axis extending substantially vertically with respect to the skin in a applying condition where the microneedle patch is applied on the skin; and
 a plurality of leg portions connected to the pressure-receiving portion, wherein
 the plurality of leg portions extend radially from the central axis and are arranged at regular intervals along a circle around the central axis, wherein the plurality of leg portions each have an extremity portion pressed against the skin, and wherein d, θ, and L satisfy the following equation:

$$L \geq (2d/3)\sin\theta$$

where

"d" is a distance from the central axis to the extremity portion;

"2θ" is a center angle between adjacent leg portions; and

"L" is a distance between adjacent leg extremity portions.

The device applying a microneedle patch onto a skin of another modification of the present invention includes:

a pressure-receiving portion for receiving a force applied along the direction of a central axis extending substantially vertically with respect to the skin in a applying condition where the microneedle patch is applied on the skin; and a plurality of leg portions connected to the pressure-receiving portion, wherein the plurality of leg portions extend radially from the central axis and are arranged at regular intervals along a circle around the central axis, the plurality of leg portions each having an extremity portion pressed against the skin, the device including:

a first deformable portion formed between the pressure-receiving portion and the leg portion.

The leg portion has a second deformable portion, and the first deformable portion and the second deformable portion are configured so that, when a force is applied to the pressure-receiving portion, an amount of deformation of the first deformable portion is larger than that of the second deformable portion.

The device applying a microneedle patch onto a skin of another embodiment of the present invention includes:

a pressure-receiving portion for receiving a force applied along the direction of a central axis extending substantially vertically with respect to the skin in a applying condition where the microneedle patch is applied on the skin;

a pair of first leg portions connected to the pressure-receiving portion and arranged symmetrically with respect to the central axis and facing a first direction orthogonal to the central axis; and a pair of second leg portions arranged symmetrically with respect to the central axis and facing a second direction orthogonal to the central axis and to the first direction, wherein with respect to the direction parallel to the central axis, extremity portions of the pair of first leg portions are further apart from the pressure-receiving portion than extremity portions of the pair of second leg portions.

A first deformable portion is formed between the pressure-receiving portion and the leg portion.

The first leg portion has a second deformable portion, and the first deformable portion and the second deformable portion are configured so that when a force is applied to the pressure-receiving portion, the amount of deformation of the first deformable portion is larger than the amount of deformation of the second deformable portion.

In one embodiment of the present invention, the device applying a microneedle patch onto a skin includes:

a plate portion having a top surface, a bottom surface, and a pair of opposed edges; and a pair of leg portions extending downward from the pair of opposed edges of the plate portion, wherein the plate portion has partially or entirely a curvilinear portion that is curved upward or downward into a convex shape.

In this embodiment, the plate portion supports a microneedle patch on its bottom surface, directly or indirectly through another member. The top surface functions as a pressure-receiving portion against which the user abuts the finger to apply a force in use. Preferably, the plate portion and the leg portions are integrally formed with a resilient material. Preferably, each of the pair of leg portions has partially or entirely a curvilinear portion that curves outward or inward into a convex shape. The curvilinear portion of the leg portion acts as a deformable portion.

Thus, according to this embodiment, when a force is applied to the pressure-receiving portion, the leg portions (resilient material) deform to increase the interval between the pair of leg portions. Until the expansion of the skin reaches its limit, the microneedles come closer to the skin due to the deformation of the leg portions. Then, when the expansion of the skin reaches its limit, tops of the leg portions slide on the skin while increasing the interval between the pair of leg portions. This allows the microneedles to insert into the skin while imparting a predetermined tension to the skin.

By combining the deformable portions having different resiliencies, when the interval between the pair of leg portions increases until the expansion of the skin reaches its limit, a movement of spreading the skin is stopped without sliding of the tips of the leg portions on the skin, bringing about a movement of advancing the microneedles into the skin. This allows the microneedles to insert into the skin while imparting a predetermined tension to the skin.

According to the embodiment of the device of the present invention so constructed, when pressing the pressure-receiving portion by a finger with the device placed on the skin, a portion in contact with the skin of at least one leg portion pulls the skin toward the outside from the device center, thereby imparting a tension to a portion of the skin which the microneedle patch oppose. For this reason, the needles on the microneedle patch insert easily into the portion of the skin to which the tension is imparted. Accordingly, without any damage or breakage of the needles, substantially all the needles insert securely into the skin so that the drug carried on the needles can certainly be administered.

The present invention relates also to a device for inserting an array of microneedles into a skin, the device acting as a protection housing for accommodating the microneedle patch and a device for inserting microneedles into the skin, the device receiving the microneedle patch on the bottom portion of the concave housing and having a seal as a lid, the concave housing including a flat plate portion forming the bottom portion and deformable portions surrounding the flat plate portion.

The microneedle patch is carried on the flat plate portion and the pressure-receiving portion is provided on the reverse side thereof.

The material of the concave housing is not limited, but one preferred resin is selected from a group consisting of resins such as polypropylene, polyethylene, nylon, ABS resin, PET, acrylic resin, polystyrene, vinylidene chloride, polypropylene, polycarbonate, fluorine (Teflon), vinyl chloride, vinylidene chloride, polyamide, rubber, and silicone, and foam resins such as foamed styrene, foamed urethane, and foamed melamine.

The flat plate portion is an deformable member, which has a plurality of edges.

In order that the flat plate portion deforms uniformly, ridge lines and the flat plate portion have the deformable portions in the form of folds, the thinned portions, etc.

The central portion of the flat plate portion is made of a rigid resin.

A spacer may be provided to protect the microneedles.

The present invention relates also to a device for inserting a microneedle patch into a skin, the device including:

a first surface supporting a microneedle array;

a second surface spaced apart from and opposing the first surface;

an elastic member urging the first surface and the second surface toward directions away from each other; and an indicator for indicating that a predetermined insert ion force is applied to microneedles when the second surface moves a predetermined distance toward the first surface against an urging force of the elastic member.

Another embodiment of the present invention is a device wherein the microneedle array forms a microneedle patch in conjunction with a sheet substrate supporting the microneedle array through a pressure-sensitive adhesive, and the pressure-sensitive adhesive and the microneedle patch are pressed against a skin so that a pressure-sensitive adhesive force of a layer of the pressure-sensitive adhesive with the skin enables the microneedle array to be retained on the skin in a state where needles of the microneedle array insert into the skin, the device including:

a first surface supporting a microneedle array;

a second surface spaced apart from and opposing the first surface;

an elastic member urging the first surface and the second surface toward directions away from each other; and an indicator for indicating that a predetermined insertion force is applied to microneedles when the second surface moves a predetermined distance toward the first surface against an urging force of the elastic member.

In another embodiment of the present invention, the indicator provides a visual, auditory, or tactile change when the second surface moves a predetermined distance toward the first surface against an urging force of the elastic member.

According to the device of the present invention, application of a pressing force to the second surface allows the second surface to come closer to the first surface against the biasing force of the elastic member. The characteristics of the elastic member are determined so that, when the second surface moves a predetermined distance toward the first surface, a visual, auditory, or tactile change is provided to the exterior. Thus, by recognizing the visual, auditory, or tactile change, it can be recognized that a predetermined force is applied to the second surface, i.e., that a predetermined magnitude of force is applied to the needles.

The present invention relates also to a device applying a microneedle patch onto a skin, the device including:

a first element including integrally a central plate portion having a first flat bottom portion formed between a pair of parallel edges; and a pair of inclined plate portions having a pair of second flat bottom portions extending diagonally upward from the pair of edges of the central plate portion so as to go apart from each other, the first element being configured so that, when a downward force is applied to extremities of the pair of inclined plate portions, the pair of inclined plate portions deform downward with respect to the central plate portion, the first bottom portion and the second bottom portion supporting the microneedle patch, and a second element provided on the first element and including a contact portion in contact with each of the extremities of the pair of inclined plate portions, wherein the downward force is applied to the extremities of the pair of inclined plate portions by way of the contact portions of the second element.

In another embodiment of the present invention, the first element has weakened or deformable portions formed continuously or intermittently along the pair of edges.

In another embodiment of the present invention, the contact portions of the second element have a pair of contact regions with which the pair of inclined plate ends are in contact, and the pair of contact regions have a pair of inclined surfaces extending diagonally upward so as to go apart from each other.

Another embodiment of the present invention includes a third element provided on the second element, the third element receiving the force and transmitting the force to the first element by way of the second element.

Another embodiment of the present invention includes a microneedle patch supported on the first element, the microneedle patch including:

a sheet substrate having a top surface and a bottom surface, the sheet substrate having a pressure-sensitive adhesive layer on the bottom surface, the top surface being located on the first bottom surface portion and the pair of second bottom surface portions;

an adhesive material provided on the pair of second bottom surface portions, the adhesive material adhering opposite substrate portions located on the pair of second bottom surface portions to the pair of second bottom surface portions; and a microneedle array retained on a central substrate portion of the sheet substrate located under the first bottom surface portion.

In the attachment device according to the present invention, in use, a pressing force is applied to the second element in the state where the attachment device retaining the microneedle patch on the bottom surface of the first element is placed on a skin of a human being or an animal. The pressing force applied to the second element is transmitted to the microneedle patch retained on the bottom surface of the first plate portion by way of the contact portion of the second element and extremities of the pair of inclined plate portions in contact therewith. As a result, the microneedle patch supported on the bottom surface of the central plate portion and of the inclined plate portions is pressed against the skin. At this time, not only the central plate portion but also the inclined plate portions are pressed against the skin. Since the pair of inclined plate portions deform so that their extremities go apart from each other, the inclined plate portions are also pressed against the skin with a suitable force. Hence, not only the microneedle patch supported on the central plate portion is pressed against the skin with a suitable force, but also both-end pressure-sensitive adhesive portions of the microneedle patch supported on the inclined plate portions are pressed against the skin with a suitable force, for pressure-sensitive adhesion. Afterward, when the pressing force is removed, the inclined plate portions restore to the pre-deformation states based on their resiliencies, but at this time, the patch both-end portions adhered to the skin are separated from the inclined plate portions, together with the skin portion to which the patch is adhered. In conjunction with the restoration to the pre-deformation state of the inclined plate portions apart from the skin, the microneedle patch transfers more easily to the skin. Accordingly, when separating the attachment device from the skin, the microneedle patch is prevented from peeling off from the skin while adhering to the attachment device, so that the needles once stuck into the skin remain left in the skin.

The present invention relates also to a device for inserting microneedles into a skin, including:

(a) a first element having a first surface supporting microneedles and a second surface located opposite to the first surface; and (b) a second element having a first surface opposing the second surface of the first element and a second surface located opposite to the second element, wherein (c) one of the second surface of the first element and the first surface of the second element is provided at a position corresponding to a center of the first element and has a protrusion protruding toward the other of the second surface of the first element and the first surface of the second element, (d) the other of the second surface of the first element and the first surface of the second element has a contact portion against which a tip of the protrusion abuts, and (e) a pressing force applied to the second surface of the second element is transmitted to the first element by way of the protrusion and the contact portion.

In another embodiment of the present invention, the second element includes a central plate portion having a pair of straight edges extending in parallel, and a pair of side plate portions extending in opposite directions so as to go apart from the straight edges.

In another embodiment of the present invention, the pair of straight edges have respective weakened portions extending along the straight edges.

In another embodiment of the present invention, the weakened portion has a cut.

In another embodiment of the present invention, the cut is formed in the first surface of the first element.

In another embodiment of the present invention, the cut is formed in the second surface of the first element.

In another embodiment of the present invention, the weakened portion has a groove or a slit.

In another embodiment of the present invention, the microneedles are carried on an adhesive material to form a microneedle patch.

In another embodiment of the present invention, the device is a device applying a microneedle patch onto a skin.

In another embodiment of the present invention, the first element has a predetermined outer peripheral shape; the second element has a frame with a predetermined inner peripheral shape; and the inner peripheral shape is configured to at least partially surround the outer peripheral shape of the first element, whereby the first element moves along a first vertical direction vertical to the first surface of the first element while being guided along the inner peripheral shape of the second element.

In another embodiment of the present invention, the frame has a plurality of notches extending along the first direction, whereby a portion of the frame between the adjacent notches is tilted inward by the pressing force.

Another embodiment of the present invention includes an urging member urging the first and the second elements so as to go apart from each other against the pressing force.

In another embodiment of the present invention, an extremity portion of the protrusion is rounded.

In another embodiment of the present invention, an extremity portion of the protrusion is tapered.

In another embodiment of the present invention, the contact portion is recessed so as to receive the protrusion.

In another embodiment of the present invention, the protrusion is in the shape of a rod.

In another embodiment of the present invention, the protrusion is in the shape of a wall extending along a direction orthogonal to the first direction.

In another embodiment of the present invention, the first element has a first sub-element and a second sub-element, the first sub-element having a first surface of the first element, the second sub-element having a second surface of the first element, the first sub-element and the second sub-element being configured so that the pressing force from the second element is transmitted through the second sub-element to the first sub-element.

In another embodiment of the present invention, the first sub-element includes a central plate portion having a pair of side edges extending in parallel to each other toward a first horizontal direction, and a pair of inclined plate portions extending toward a second horizontal direction orthogonal to the first horizontal direction so as to go apart from the pair of side edges, the pair of inclined plate portions being tilted toward the second sub-element;

the first sub-element is made of a resilient material; and when subjected to the pressing force, the pair of inclined plate portions deform toward the second horizontal direction so as to go apart from each other.

In another embodiment of the present invention, the second sub-element extends along the second horizontal direction, the device including a guide portion that when subjected to the pressing force, guides extremities of the second side plate portions in such a manner that the second side plate portions deform along the second horizontal direction and go apart from each other.

In another embodiment of the present invention, the guide portion of the second sub-element has a pair of contact portions for receiving the extremity portions of the side plate portions, the contact portions being tilted so as to go apart from each other from the first sub-element toward the extremities.

In another embodiment of the present invention, the first surface of the first element supports a microneedle patch.

According to the device of the present invention, the pressing force applied to the second element is transmitted through the protrusion to the center of the first element. Hence, even if the point of action of the pressing force is off-centered in the device, the pressing force acts on the center of the first element. Accordingly, the needles penetrate vertically into the skin. This prevents the needles from being bent, damaged, or broken during the insertion of the needles.

BRIEF DESCRIPTION OF DRAWINGS

FIG. 6 is an exploded perspective view showing a modification 1-1 of the first embodiment.

FIG. 7 is an exploded perspective view showing a modification 1-2 of the first embodiment.

FIG. 16 is an exploded perspective view showing a modification 1-11 of the first embodiment.

FIGS. 29A-29D are views showing an applicator according to a fifth embodiment.

FIG. 116 is a view showing a housing modification used in experiments.

FIG. 118 is a view showing a housing modification used in experiments.

FIG. 119 is a perspective view of a device of a stabilizer-free modification, viewed from diagonally above.

FIG. 120 is a perspective view showing a housing of another modification.

FIG. 121 is a front view showing a housing of another modification.

FIG. 122 is a front view showing a housing of another modification.

FIG. 123 is a perspective view showing a housing of another modification.

FIG. 124 is an exploded perspective view of a device according to a nineteenth embodiment.

FIG. 125 is a perspective view of the device according to the nineteenth embodiment.

FIG. 126 is a front view of the device according to the nineteenth embodiment.

FIG. 127 is a perspective view showing a modification of the device according to the nineteenth embodiment.

FIG. 128 is a perspective view showing a modification of the device according to the nineteenth embodiment.

FIG. 129 is a perspective view showing a modification of the device according to the nineteenth embodiment.

FIG. 130 is a perspective view showing a modification of the device according to the nineteenth embodiment.

PREFERRED EMBODIMENTS OF THE INVENTION

Figure 1:
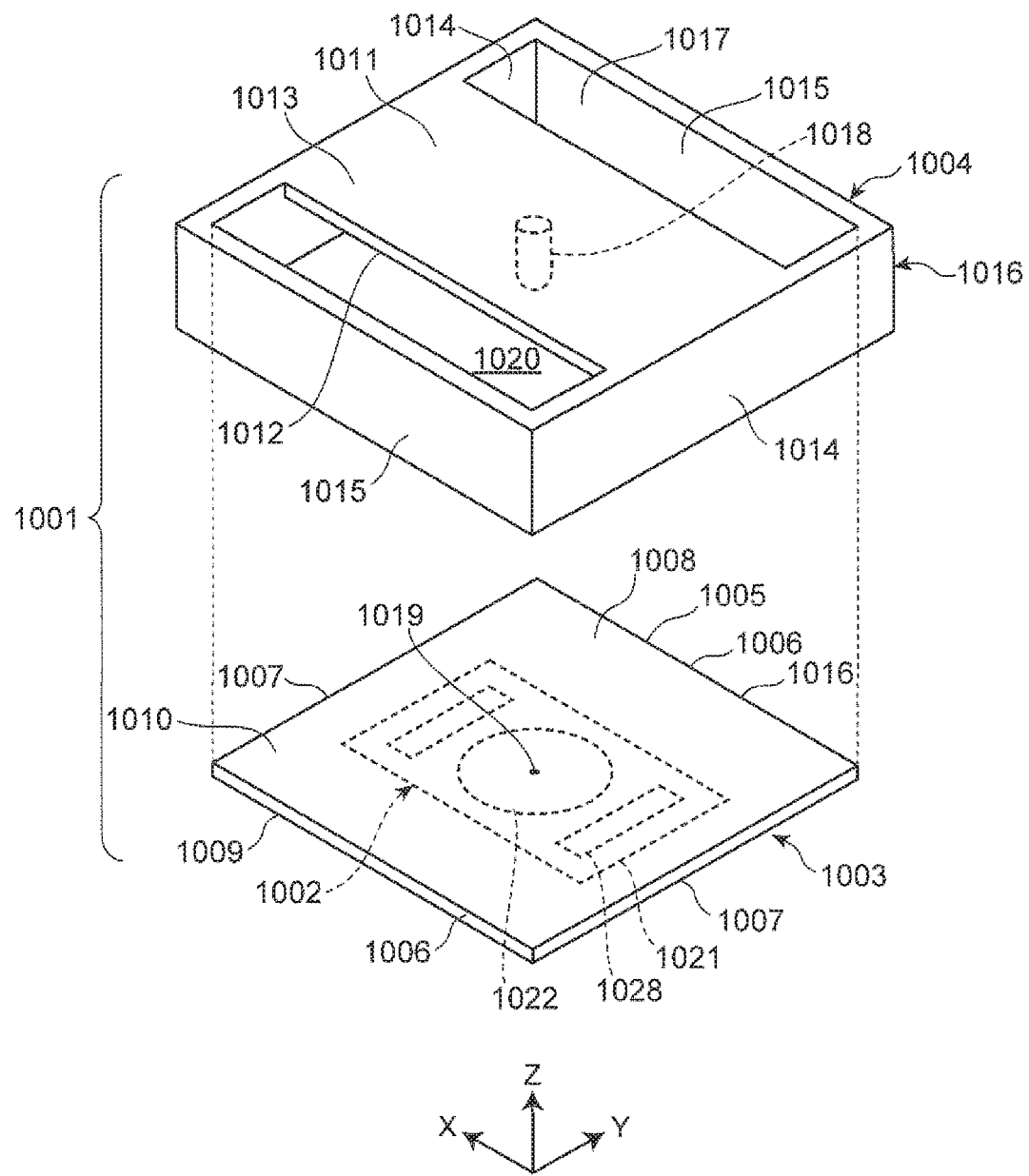
FIG. 1 is an exploded perspective view showing a first embodiment of an applicator according to the present invention.

Embodiments of a microneedle applicator and a microneedle patch application device according to the present invention will now be described with reference to the accompanying drawings. Although in the following description in reference to the drawings, terms indicative of the directions such as "top", "bottom", "right", "left", "horizontal", and "vertical" are used to facilitate the understanding of the present invention, those terms are used only for the purpose of describing the shapes and the structures of parts depicted in the drawings. Accordingly, the technical scope of the present invention is not to be construed as being limited by those terms but should be defined based on the description of the claims.

First Embodiment

FIG. 1 shows a first embodiment of a microneedle patch applicator (hereinafter, referred to as "applicator") according to the present invention. In the drawings, the applicator of the first embodiment, which is generally designated at reference numeral 1001, includes a first element 1003 for supporting a microneedle patch (hereinafter, referred to as "patch") 1002 which will be described later and a second element 1004 for pressing the patch 1002 supported by the first element 1003 against a human or animal skin. The first element 1003 and the second element are made of a resin or a metal.

In the first embodiment, the first element 1003 is in the form of a plate 1008 having a rectangular outer peripheral shape 1005 defined by edges 1006 and 1007 horizontally extending in two orthogonal directions (X-direction and Y-direction), and has a bottom surface 1009 which will be opposed to a human or animal skin in use and a top surface 1010 opposite the bottom surface 1009. In the first embodiment, the bottom surface 1009 and the top surface 1010 of the plate 1008 form a first surface and a second surface, respectively, of the first element.

In the first embodiment, the second element 1004 has a plate-like bridge 1011 extending in the X-direction, which is a major portion of the second element 1004. As shown, the bridge 1011 has a bottom surface 1012 and a top surface 1013. In the first embodiment, the bottom surface 1012 and the top surface 1013 of the bridge 1011 form a first surface and a second surface, respectively, of the second element.

Either end of the bridge 1011 is connected to upper ends of a pair of walls 1014 extending in parallel in the Y-direction. Either end of the walls 1014 in the Y-direction is connected to a pair of walls 1015 extending in parallel in the X-direction so that a rectangular frame 1016 is formed by the walls 1014 and 1015 in the Y-direction and X-direction.

An inner peripheral shape 1017 of the frame 1016 formed by inner surfaces of the walls 1014 and 1015 is larger than the outer peripheral shape 1005 of the first element 1003. This means that the inner dimensions of the frame 1016 in the X and Y directions are larger than outer dimensions of the first element 1003 in the X and Y directions. This allows that the first element 1003 can be received within the frame 1016 so that the first element 1003 moves within the frame 1016.

The bridge 1011 has a projection 1018 formed integrally with the bottom surface 1012 thereof. The projection 1018 is positioned so that it opposes a contact portion 1019 positioned at a center or substantially at a center on the top surface 1010 when the first element 1003 is received in the second element frame 1016. In the first embodiment, the projection 1018 is in the form of an elongated rod shape extending along the vertical direction. The length of the projection 1018 is preferably determined so that the bottom surface 1009 of the first element 1003 or the bottom surface of the patch 1002 supported by the bottom surface 1009 positions at or above the lower end of the frame 1016, i.e., within an inner space 1020 of the frame 1016 when the first element 1003 is received within the frame 1016 so that the extremity of the projection 1018 abuts against the contact portion 1019 of the first element 1003.

The rectangular first element 1003 of the first embodiment has lengths of about 2 cm to about 5 cm, for example, in the X- and Y-directions. Preferably, the inner dimensions of the frame 1016 of the second element 1004 are about 1 mm to about 3 mm greater than the corresponding portions of the first element 1003.

Although the thickness of the plate 1008 of the first element 3 varies according to the materials of the plate, it is preferably determined so that, when the first element 1003 is placed on a human or animal skin and then a force is applied to the central contact portion 1019, the plate 1008 does not bend excessively and a substantially entire portion of the patch 1002 is evenly forced onto the skin at substantially the same pressure. The material (in particular, modulus of elasticity) and the dimensions (in particular, length in Z-direction) of the second element 1004 (in particular, the bridge 1011) is determined so that, when a force 1032 is applied on the top surface 1003 by a finger, the bridge 1011 bends toward the first element 1003 and thereby the patch 1002 supported by the bottom surface 109 of the first element 1003 is forced onto the skin at a desired pressure through the central projection 1018 and the contact portion 1019. The material (in particular, the modulus of elasticity) and the dimensions (in particular, the thickness) of the second element frame 1016 (in particular, the walls 1014 extending in the Y-direction and supporting the bridge 1011) are determined so that, when a force is applied on the bridge 1011 from above, the lower ends of the walls 1014 move outwardly relative to the upper ends thereof to tilt the walls 1014 are tilted with the deformation of the bridge 1011.

Figure 2:
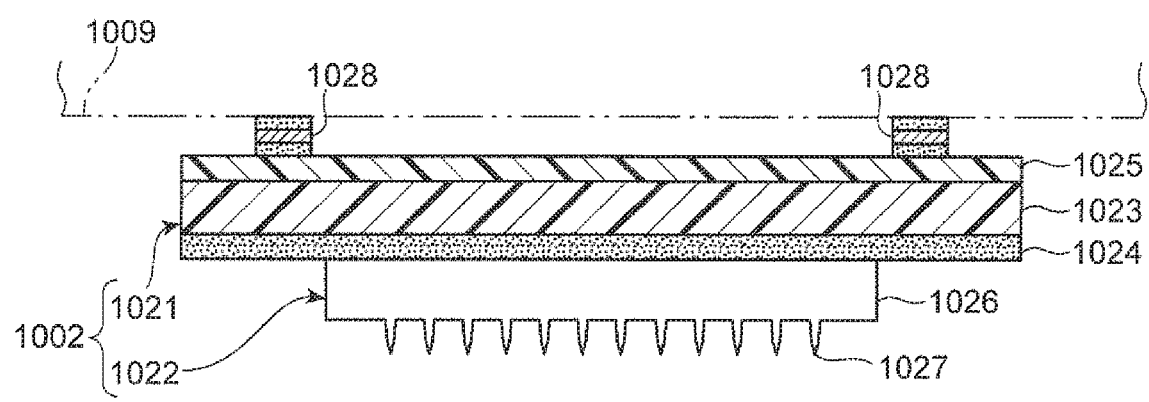
FIG. 2 is a sectional view showing the structure of a microneedle patch for use with the applicator according to the first embodiment.
Figure 3:
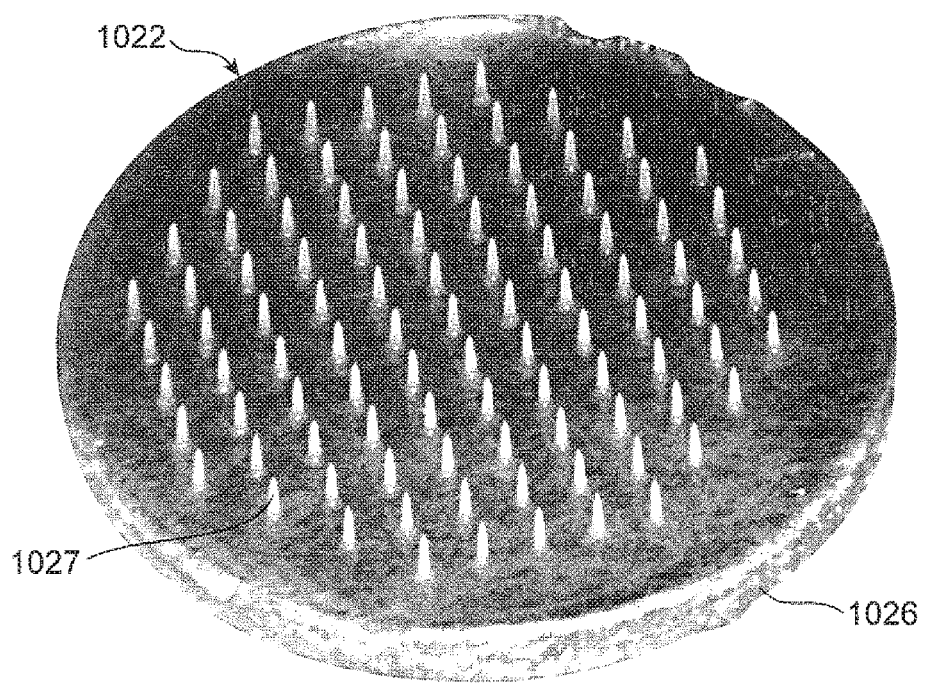
FIG. 3 is a photograph of an actual microneedle array taken diagonally from below.

For the applicator 1001 so constructed, the patch 1002 is applied to the bottom surface 1009 of the first element 1003. As shown in FIG. 2, the patch 1002 has a sheet substrate 1021 and a microneedle array 1022 supported thereon. The sheet substrate 1021 has a substrate film 1023, a pressure-sensitive adhesive layer 1024 provided on the bottom surface of the substrate film 1023 for supporting the microneedle array 1022, and a releasing layer 1025 provided on a top surface of the substrate film 1023 opposing the applicator 1. As shown in FIG. 3, the microneedle array 1022 has a circular or rectangular base 1026 and a plurality of elongated needles 1027 having a height of about 300 micrometers to about 1,000 micrometers, arrayed at predetermined intervals of about 300 micrometers to about 1,000 micrometers in a lattice or honeycomb pattern on a bottom surface of the base 1026. The microneedle array 1022 is formed, for example, by filling a biodegradable synthetic polymer material such as hyaluronic acid, collagen, polylactic acid, or polyglycolic acid, into a correspondingly shaped mold. Although not shown, distal end portions of the needles 1027 are coated with a target drug such as vaccine, protein, or peptide. Alternatively, or additionally, the target drug may be contained in the needles 1027 by adding the target drug in the material of the needles in the process of manufacturing of the microneedle array 1022.

The sheet substrate 1021 and the microneedle array 1022 are combined so that the base 1026 of the microneedle array 1022 is applied on the pressure-sensitive adhesive layer 1024 of the sheet substrate 1021. As shown, the sheet substrate 1021 is larger than the microneedle array 1022 so that a sufficient area of the pressure-sensitive adhesive layer 1024 extends out of the microneedle array 1022 when the microneedle array 1022 is applied on the sheet substrate 1021.

The sheet substrate 1021 of the patch 1002 for constructed is applied to the bottom surface 1009 of the first element 1003 by use of a double-sided adhesive tape 1029 having pressure-sensitive adhesive layers provided on both sides of a sheet substrate. The double-sided adhesive tape 1028 serves to retain the patch 1002 on the first element 1003 before the patch 1002 is applied to the skin. Various conditions such as dimension, shape, position, and pressure-sensitive adhesive force of the double-sided adhesive tape 1028 are preferably determined so that the patch 1002 can be retained on the first element 1003 and so that the patch 1002 applied to the skin by the pressure-sensitive adhesive layer 1024 is not removed from the skin by an adhesive force between the skin double-sided adhesive tape 1028 and the first element 1003 when the applicator 1001 is removed from the patch 1002 after application to the skin. Considering the conditions, the double-sided adhesive tape 1028 in the first embodiment is sized as small as possible and is applied to a position which is a predetermined distance away from either end of the sheet substrate 1021.

Figure 4:
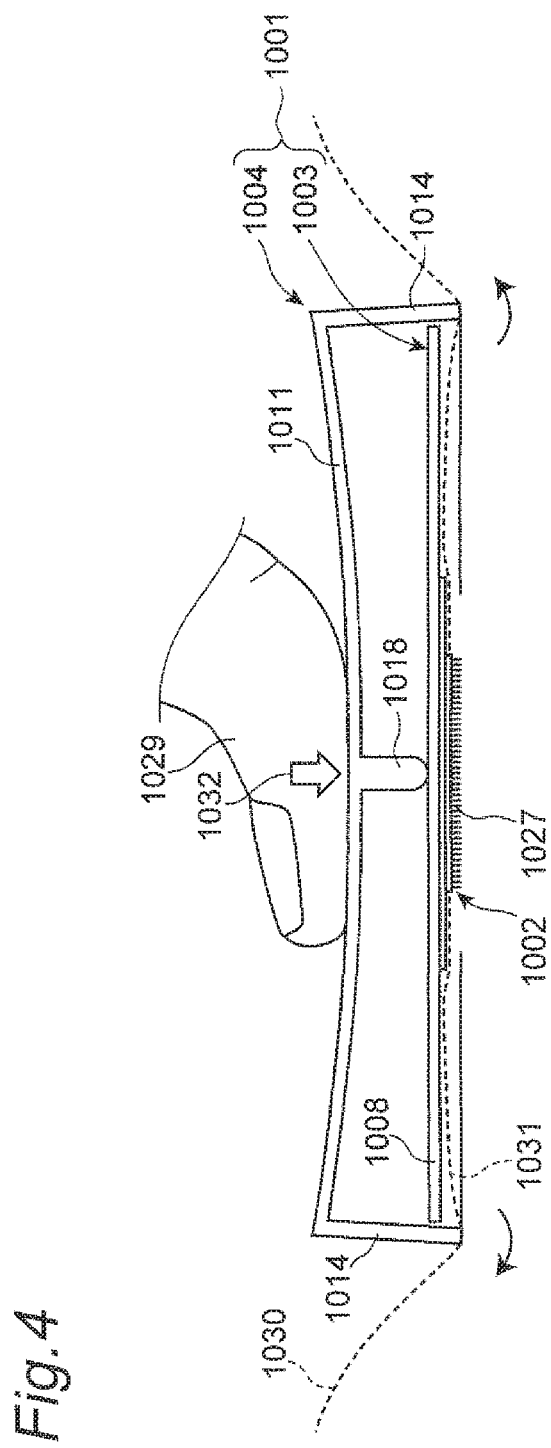
FIG. 4 is a sectional view showing the usage state of the applicator according to the first embodiment.
Figure 5A:
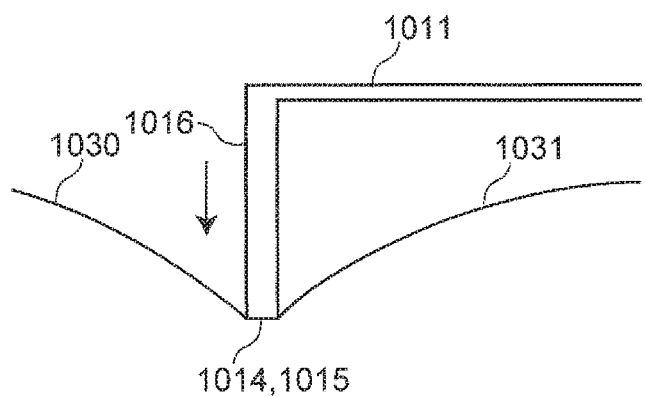
FIGS. 5A and 5B are views showing a wall deformation at the time of patch application.

Using the applicator 1001 so constructed, the patch 1002 is applied to the human or animal skin. In this operation, the bridge 1011 is pressed at its center by a finger 1029 placed thereon as shown in FIG. 4. This allows the lower ends of the walls 1014 and 1015 of the frame 1011 to be pressed toward a skin 1030, as shown in FIG. 5A. As a result, a portion of the skin 1031 surrounded by the walls 1014 and 1015 is raised in an inner space 1020 of the frame 1016. At the same time, the raised portion of the skin 1031 is tensioned in all directions toward the surrounding walls 1014 and 1015. Also, as shown in FIG. 4, the bridge 1011 bends toward the skin 1031 so that the needles 1027 of the patch 1002 are pressed through the center projection 1018 against the skin 1031. As described above, the skin 1031 is tensioned in all directions, the needles 1027 insert into the skin 1031 smoothly. Even though the pressing force 1032 is applied not exactly at the center of the bridge 1011, the pressing force 1032 applied to the bridge 1011 acts on the center of the first element 1003 by way of the projection 1018, which ensures that the needles 1027 insert vertically into the skin 1031. The vertical insertion of the needles 1027 into the skin 1031 prevents the needles from being bent, damaged, or broken during the insertion.

The above described applicator 1 of the first embodiment may be modified in various ways.

Modification 1-1

Figure 5B:
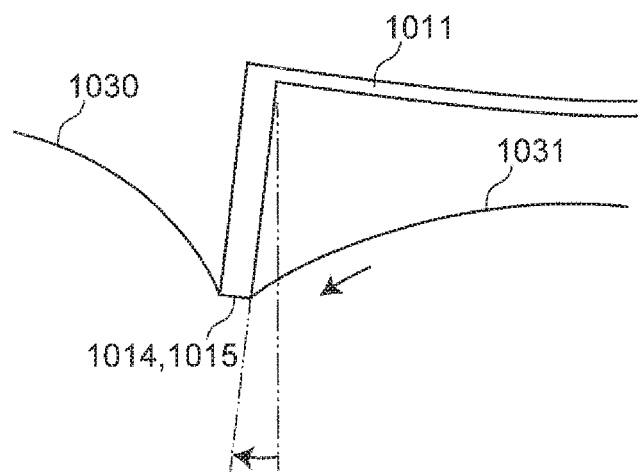

As shown in FIG. 6, disconnected portions 1035 may be formed by removing central portions of the walls 1015, constituting a part of the frame 1016 of the second embodiment and extending in the X-direction in parallel with the bridge 1011. In this modification, an application of the pressing force 1032 to the bridge 1011 deforms the lower ends of the walls 1014 in Y-direction connected to the bridge 1011 outwardly away from each other (see FIG. 5B). As a result, a portion of the skin 1031 positioned between the walls 1014 is tensioned outward by the outward displacement of the lower ends of the walls relative to the portion of the skin 1031. This improves the insertion of the needles into the skin. As described above, according to the invention the needles are inserted in the skin with a smaller pressing force and a smaller pressing movement. Contrarily, the conventional device by which the skin is not positively tensioned needs a substantial force for inserting the needles into the skin.

As shown in FIG. 6, notches 1036 made of slots or slits are formed on the walls 1014 extending in the Y-direction in regions outside lines running along the opposite longitudinal edges of the bridge 1011 so that they extend upwardly from the bottom edges of the walls 1014. According to this modification, a portion of each wall 1014 between the notches 1036 deforms outwardly according to the deformation of the bridge 1011 to tension a part of the skin 1031 between the notches, which ensures a smooth insertion of the needles into the portion of the skin. Also, the needles are inserted in the skin with a smaller pressing force and a smaller pressing movement.

As shown in FIG. 6, a central portion of the top surface 103 of the bridge 101 may be formed with a finger rest 1038 at which the finger is rested with the pressing force. This modification ensures the bridge 1011 to be pressed at its center, which results in a further improved insertion of the needles. Although in the modification 1 illustrated the finger rest 1038 is a circular raised platform, it may be a raised portion or a recessed portion with different planar shape such as polygon (including rectangular), oval, or star, or may be a spherically raised or recessed portion. Alternatively, the finger rest may be indicated by a marking or pattern.

Modification 1-2

As shown in FIG. 7, a bridge 1041 of a second element 4 may be made of a rectangular plate portion 1042 and leg portions 1043 connecting between the opposite ends of the plate portion 1042 and the walls 1014 together. This modification enables the bridge 1041 to obtain a required deformation with a smaller pressing force.

Modification 1-3

Figure 8:
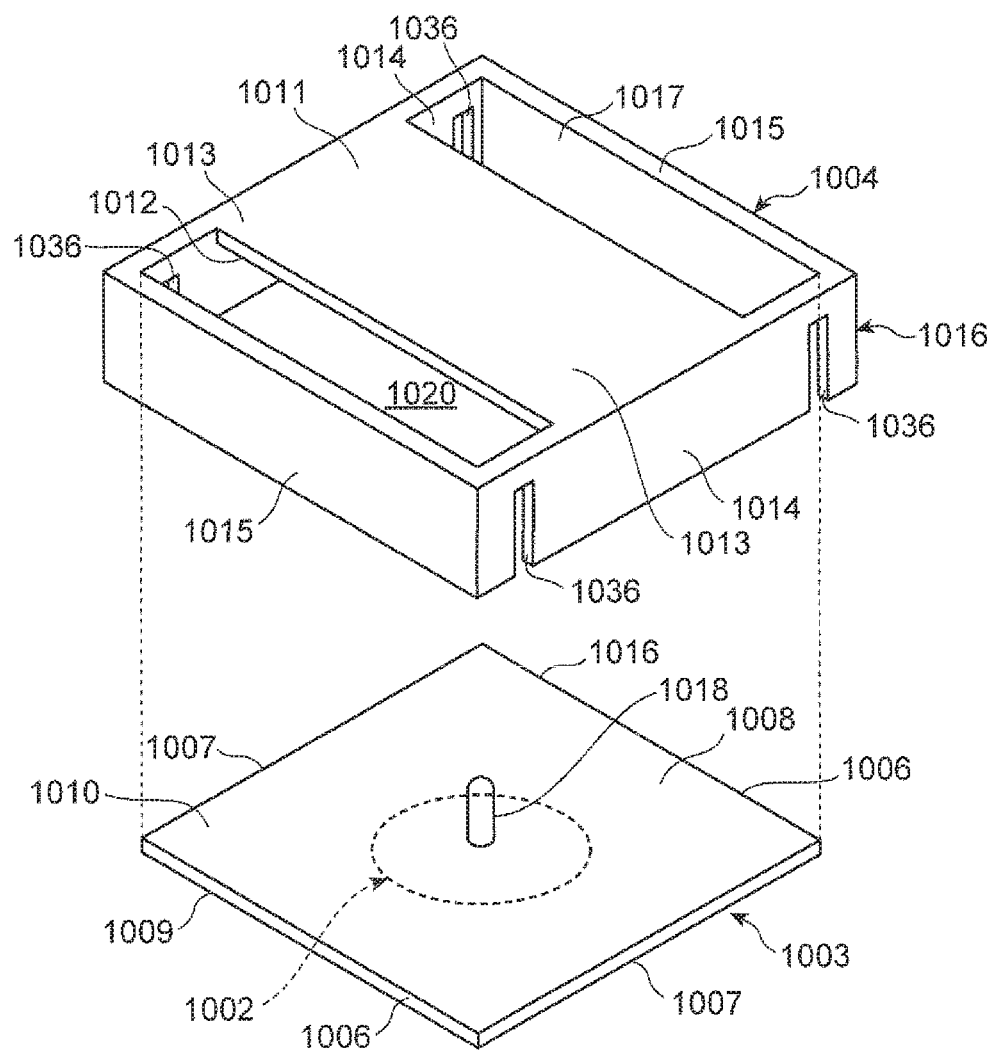
FIG. 8 is an exploded perspective view showing a modification 1-3 of the first embodiment.

As shown in FIG. 8, a projection 1018 may be provided at the center of the first element 1003. This modification also results in the same advantages as those of the first embodiment and its modification 1-2.

Modification 1-4

Figure 9:
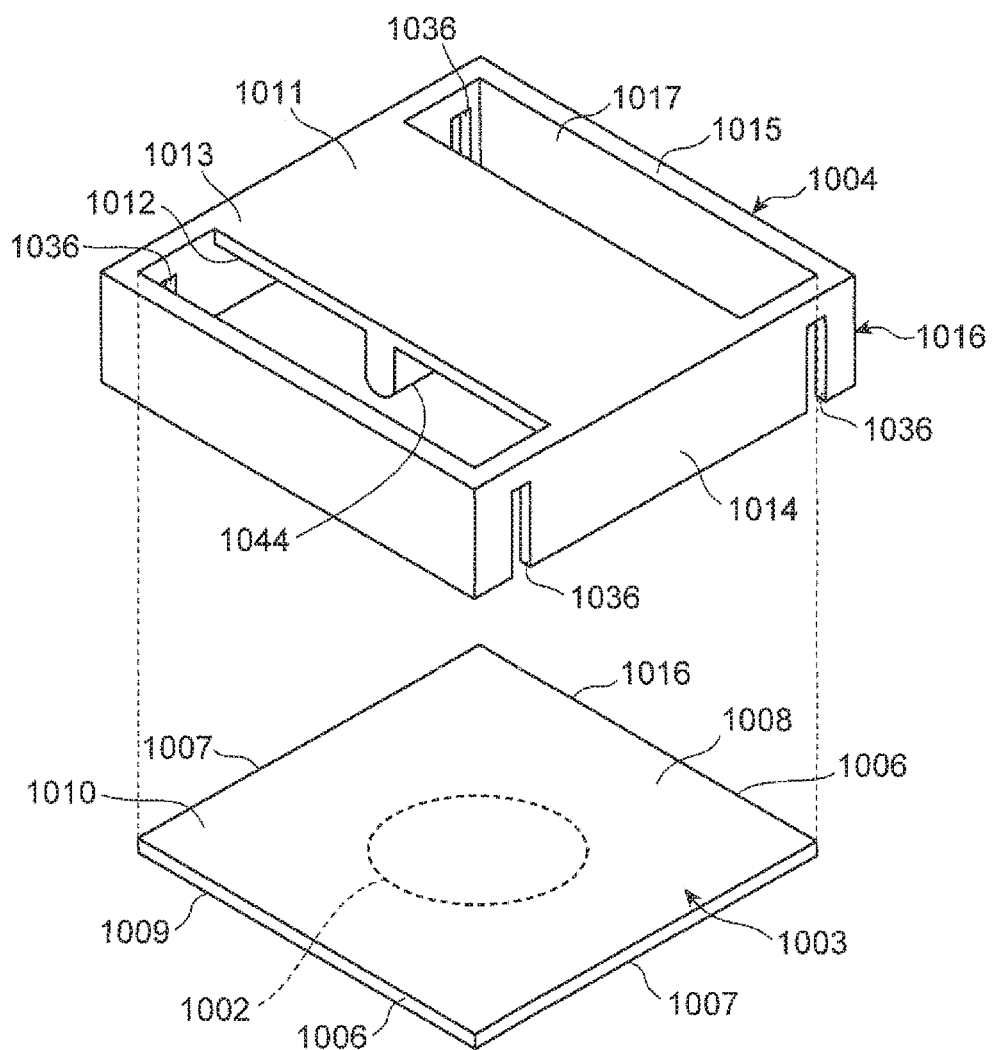
FIG. 9 is an exploded perspective view showing a modification 1-4 of the first embodiment.

As shown in FIG. 9, the projection may be a wall-shaped projection 1044 extending straightly in parallel with the Y-direction walls 1014 supporting the bridge 1011. Preferably, the wall-shaped projection 1044 may be located to run across the central portion of the first element 1003. According to this modification, the pressing force 1032 applied to the bridge 1011 acts at the center of the first element 1003 by way of the projection 1044, allowing the needles 1027 to insert vertically into the skin 1031.

Modification 1-5

Figure 10:
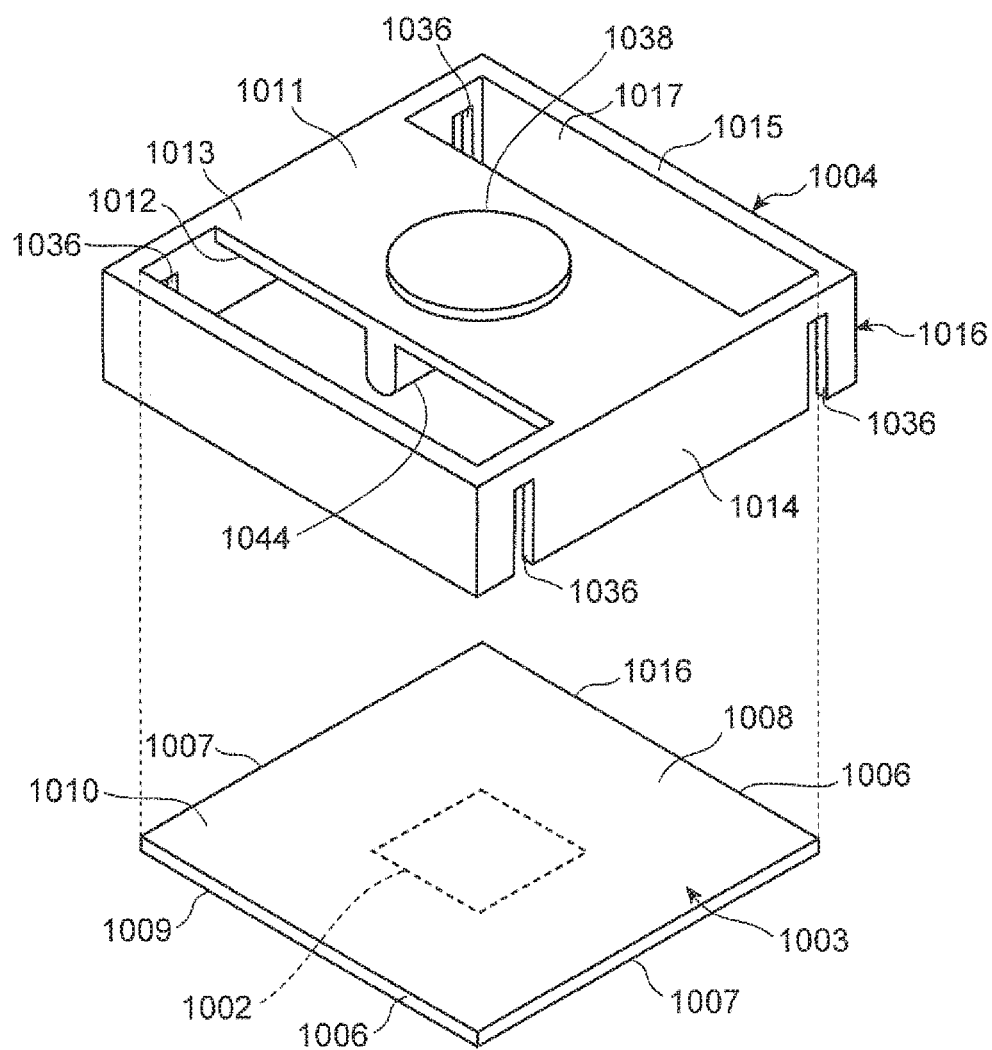
FIG. 10 is an exploded perspective view showing a modification 1-5 of the first embodiment.

As shown in FIG. 10, a finger rest 1038 may be provided at the center of the top surface 1013 of the bridge 1011. The finger rest 1038 may have any shape. This modification ensures the central portion of the bridge 1011 to be pressed, which in turn ensures a vertical insertion of the needles. The finger rest 1038 may be a raised portion or a recessed portion of different shape such as polygon (such as rectangular), oval, or star, or may be a spherically raised or recessed portion. Alternatively, the finger rest may be indicated by a marking or pattern.

Modification 1-6

Figure 11:
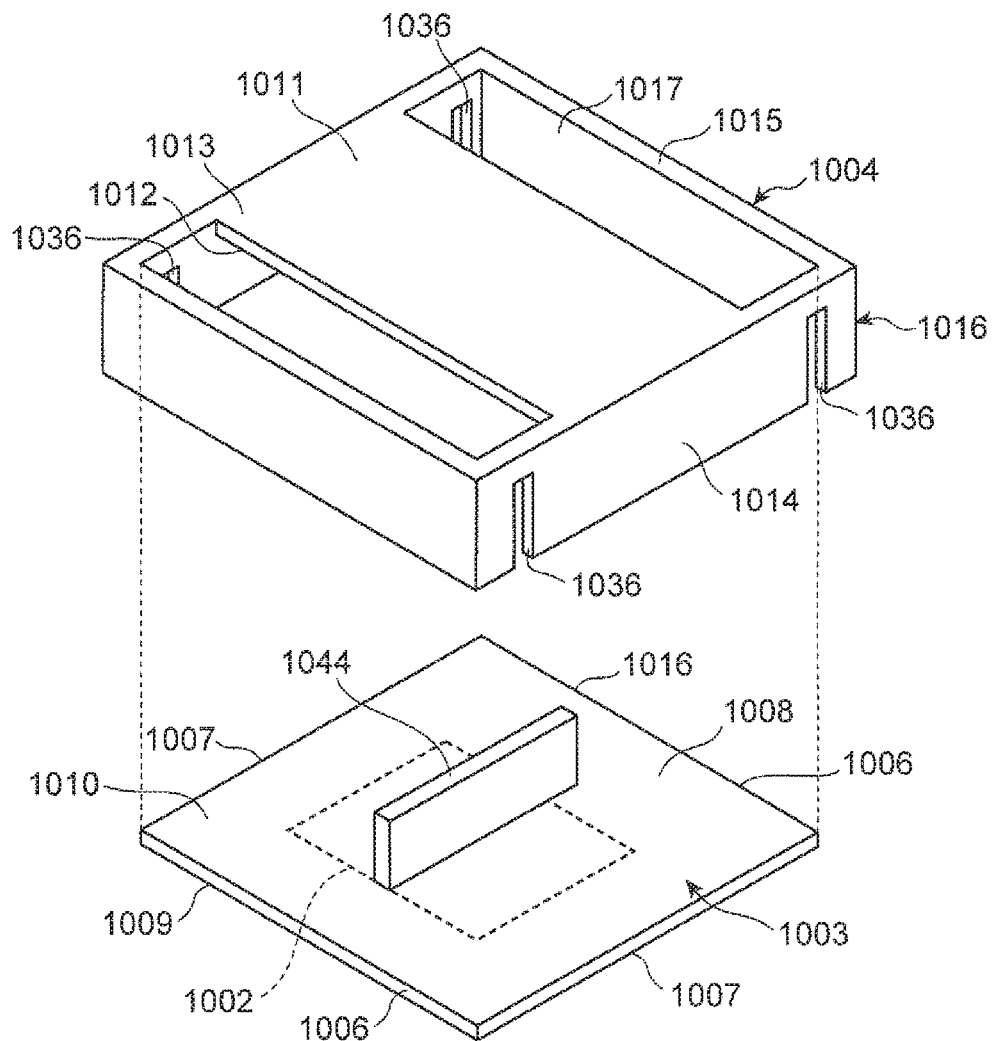
FIG. 11 is an exploded perspective view showing a modification 1-6 of the first embodiment.

As shown in FIG. 11, the straight wall-shaped projection 1044 may be provided at the center of the plate 1008 of the first element 1003. This modification results in the same advantages as those of the first embodiment and its modifications 1-1 to 1-5 described above.

Modification 1-7

Figure 12:
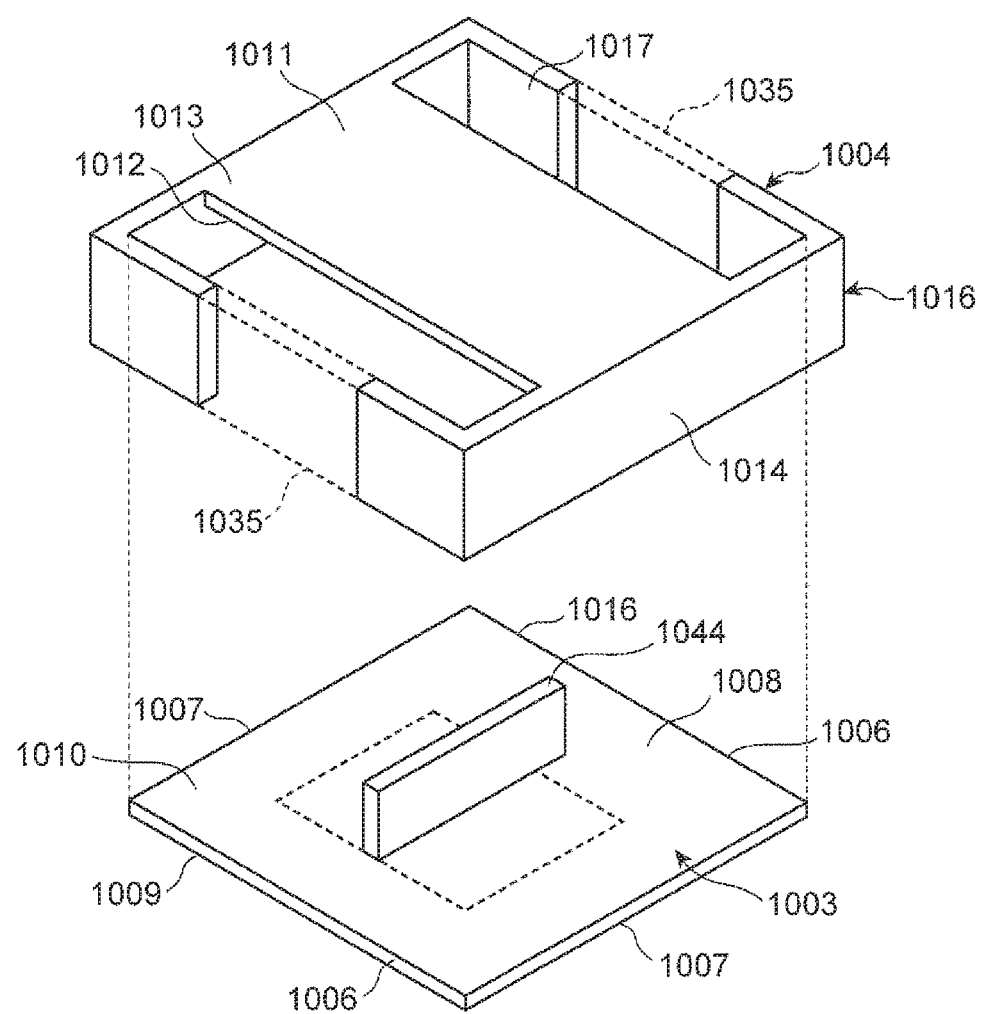
FIG. 12 is an exploded perspective view showing a modification 1-7 of the first embodiment.

As shown in FIG. 12, disconnected portions 1035 may be formed in the modification 1-5 by cutting the central portions of the walls 1015 extending in the X-direction in parallel with the bridge 1011. According to this modification, the portion of the skin positioned between the walls 1014 and 1015 is tensioned, which improves the vertical insertion of the needles. As described in connection with the modification 1-1, the needles are inserted in the skin with a smaller pressing force and a smaller pressing movement.

Modification 1-8

Figure 13:
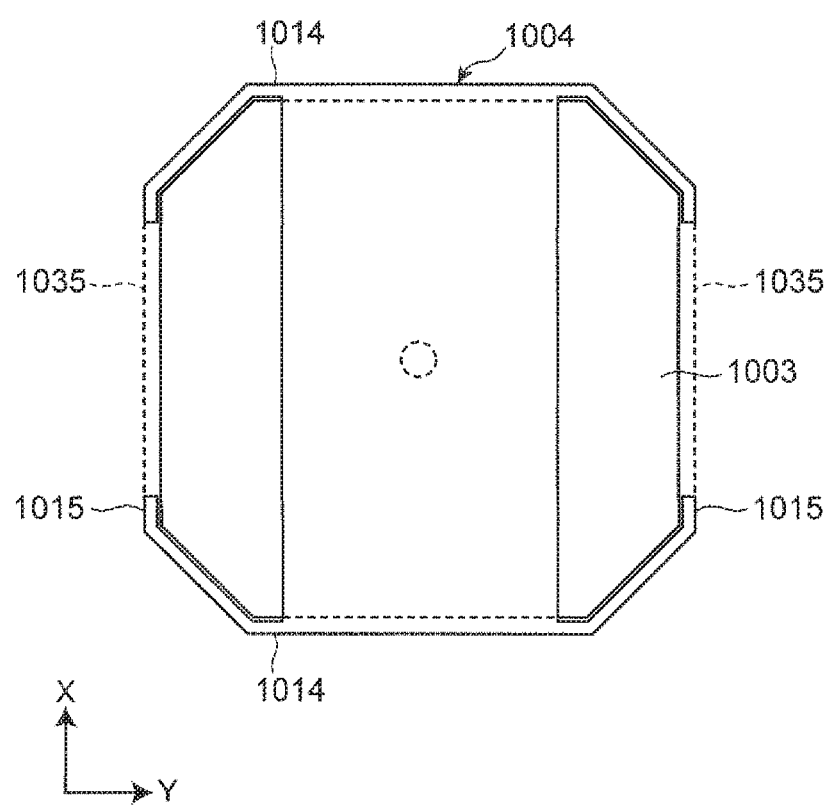
FIG. 13 is an exploded perspective view showing a modification 1-8 of the first embodiment.

As shown in FIG. 13, the plate of the first element 1003 may have an octagon shape. This shape may be obtained by cutting corners of the quadrangle. Also, the frame 1016 of the second element frame 1016 may also have an octagon shape. In this modification, central portions of the X-direction walls 1015 extending in parallel with the bridge 1011 may be removed to form the disconnected portions 1035. According to this modification, the portion of the skin positioned between the walls 1014 is tensioned, which ensures a further improved vertical insertion of the needles into the skin. As described in connection with the modification 1-1, the needles are inserted into the skin with a smaller pressing force and a smaller pressing movement.

Modification 1-9

Figure 14:
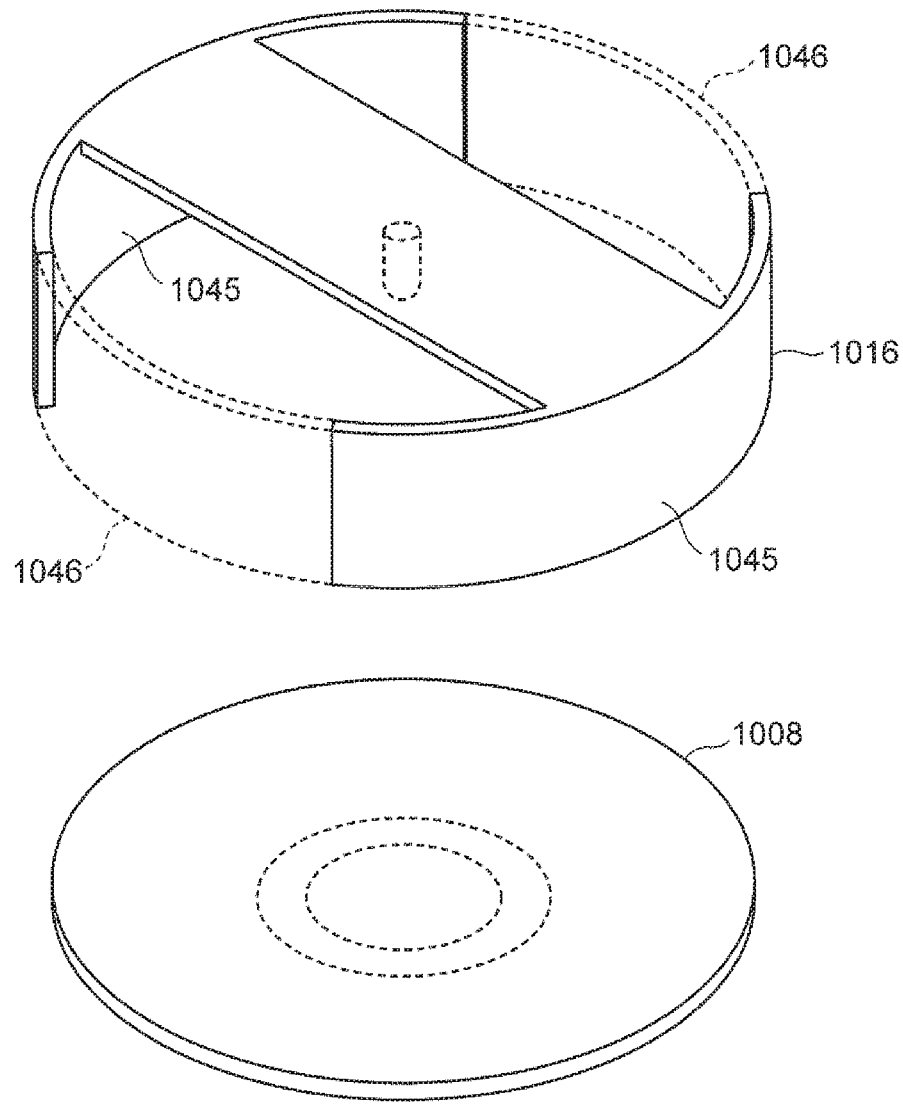
FIG. 14 is an exploded perspective view showing a modification 1-9 of the first embodiment.

As shown in FIG. 14, the plate 1008 of the first element 1003 may be circular. In conformity to the shape of the first element 3, preferably the second element frame 1016 may also have a circular or arc shape. As shown, wall portions 1046, rather than wall portions 1045, supporting the opposite ends of the bridge 1011 may be removed. According to this modification, the portion of the skin positioned between the walls portions 1045 is tensioned, which results in a further improved vertical insertion of the needles into the skin. As described in connection with the modification 1-1, the needles are inserted into the skin with a smaller pressing force and a smaller pressing movement.

Modification 1-10

Figure 15A:
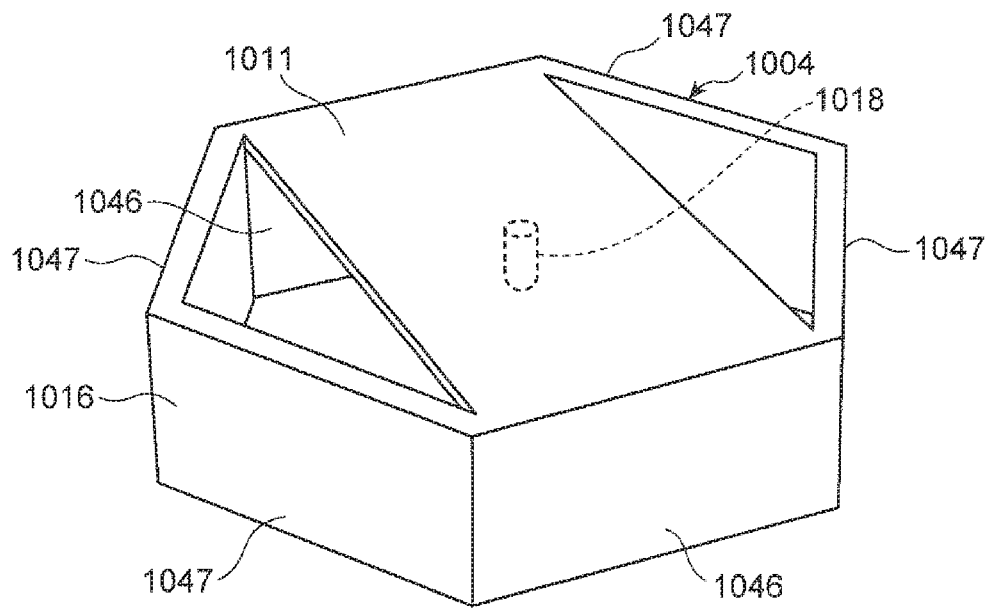
FIGS. 15A and 15B are exploded perspective views showing a modification 1-10 of the first embodiment.
Figure 15B:
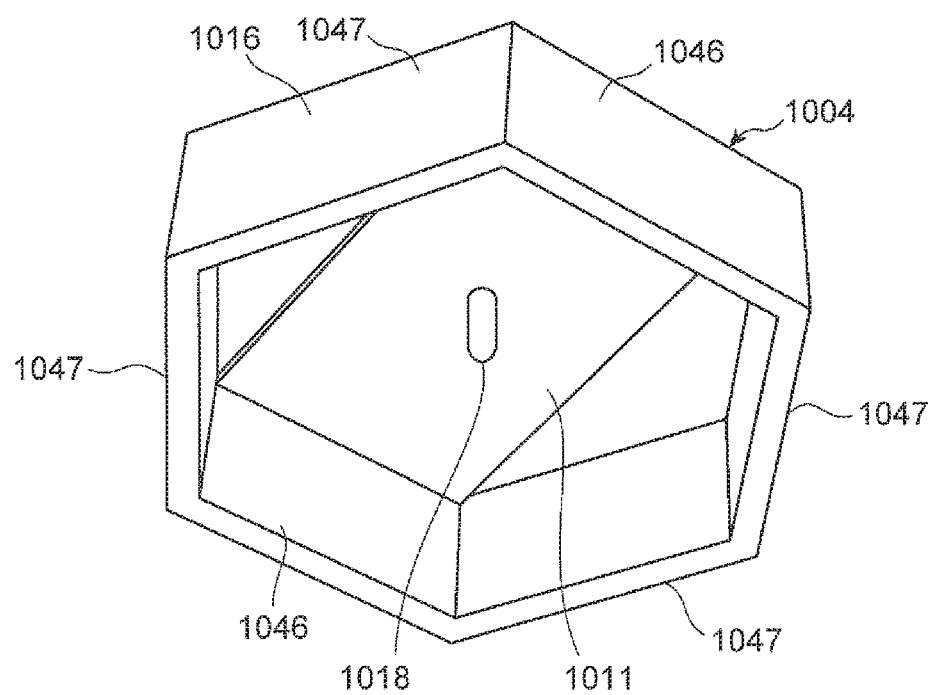

As shown in FIG. 15, the frame 1016 of the second element 1004 may have a hexagonal shape. In this modification, preferably the opposing walls 1047 are connected by the bridge 1011. According to this modification, the deformation or bending of the bridge 1011 causes the walls 1047, other than the walls 1046 connected by the bridge 1011, deform inwardly toward the bridge 1011, which allows an increased deformations of the bridge 1011 and the walls 1046.

Modification 1-11

As shown in FIG. 16, the bridge 1011 of the second element 1004 may have a curved portion. In this modification, a required deformation is provided for the bridge 11 by a smaller pressing force.

Modification 1-12

Figure 17:
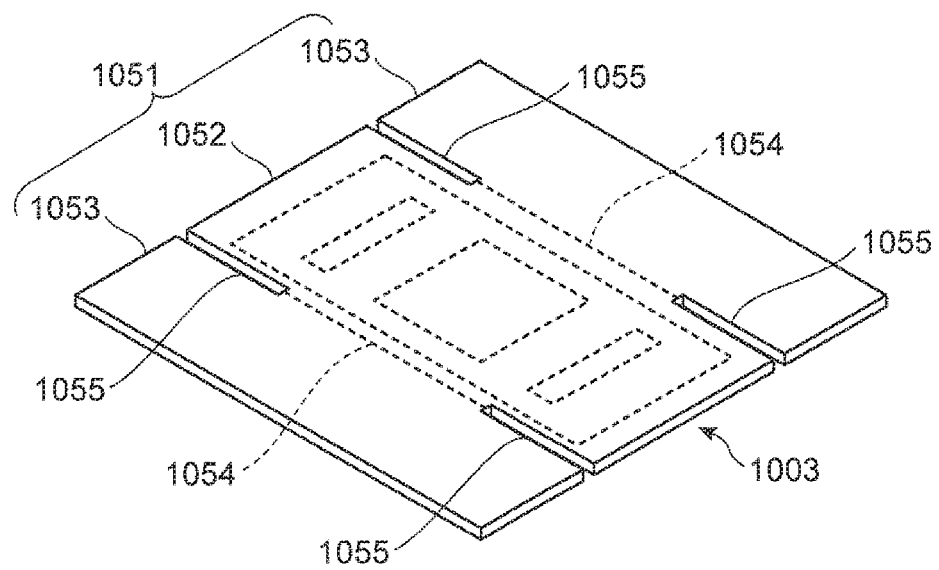
FIG. 17 is an exploded perspective view showing a modification 1-12 of the first embodiment.

FIG. 17 shows another modification. In this Modification, the first element 1003 is in the form of a rectangular plate 1051. The plate is partitioned into a rectangular central region 1052 and rectangular side regions 1053 connected to a pair of opposing straight edges (boundaries) 1054 of the central region 1052. The straight boundaries 1054 include weakened portions formed therealong. In the modification, the weakened portions are formed by X-direction slots or slits 1055. The slits 1055 may be formed only on either end portions of the boundaries 1054 as shown. The slots or slits may be intermittently formed at predetermined intervals over the full length. The patch 1002 is supported on the bottom surface of the central region 1052.

According to this modification so constructed, when a pressing force is applied to the bridge 1011 and then, by way of the projection, to the center of the patch 1002, the side regions 1053 bend relative to the central region 1052 along the boundaries 1054. As a result, the area of the side regions 1053 in contact with the skin decreases and, as a result, the pressing force is concentrated at the central region 1052, which facilitates the insertion of the needles 1027 into the skin.

When the first element 3 of this modification is combined with the wall-shaped projection shown in FIGS. 9, 10, 11, and 12, the wall-shaped projection may be oriented in either X or Y direction.

Modification 1-13

Figure 18:
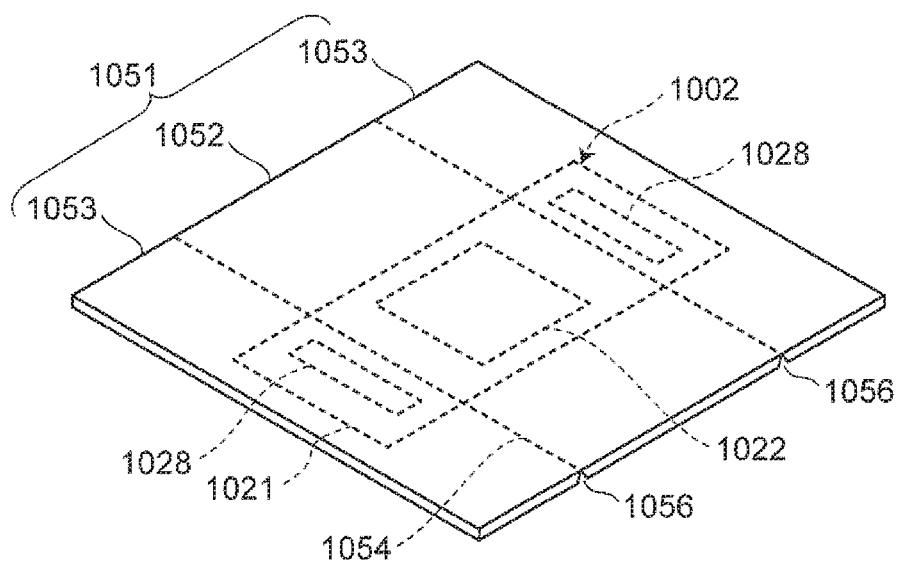
FIG. 18 is an exploded perspective view showing a modification 1-13 of the first embodiment.

FIG. 18 shows another modification. In this modification, the weakened portions have U- or V-shaped grooves 1056 or cuts which extends continuously or intermittently in the bottom surface of the first element 1003 along the boundaries 1054. The grooves 1056 may be formed in the top surface of the first element 1003 along the boundaries 1054. In this modification, the patch 1003 is supported on the central region 1052 and the two side regions 1053 so that the microneedle array 1022 is positioned on the bottom surface of the central region 1052 and the double-sided adhesive tapes 1028 are positioned on the bottom surfaces of the side regions 1053.

Figure 19A:
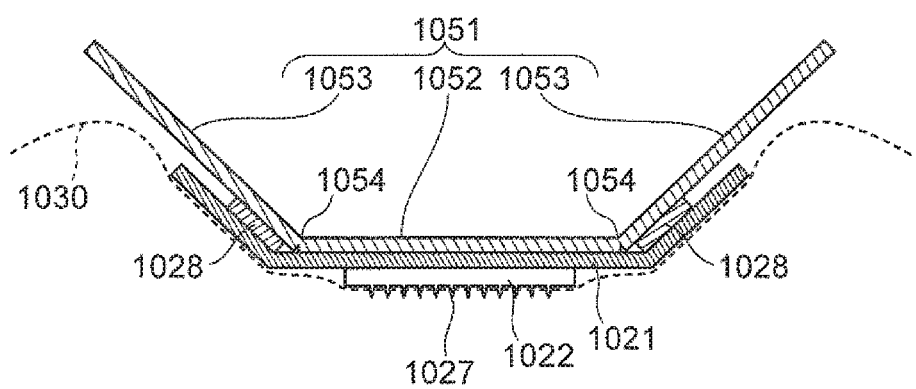
FIGS. 19A and 19B are views showing the state where the microneedle patch is applied on a skin.
Figure 19B:
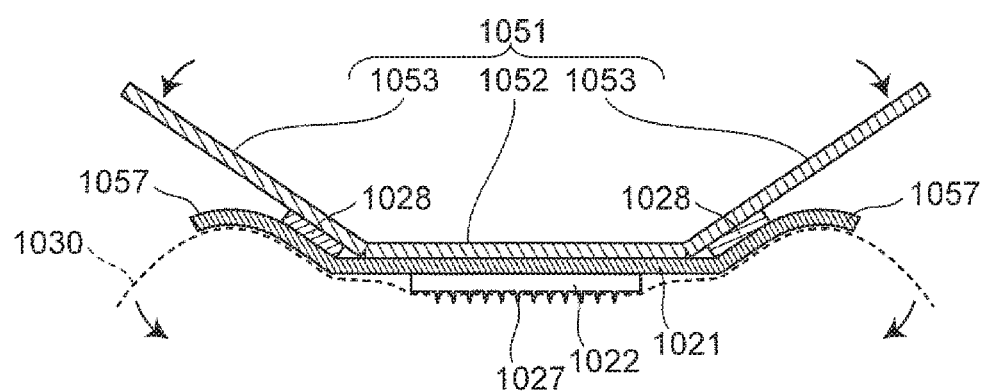

According to this modification so constructed, when a pressing force acts, from the bridge 1011 through the projection, on the center of the patch 1002, the side regions 1053 bend relative to the central region 1052 along the boundaries 1054 as shown in FIGS. 19A and 19B. The pressure-sensitive adhesive layer of the sheet substrate 1021 is then pressed against the skin. The needles 1027 of the microneedle array 1022 positioned in the central region 1052 insert into a skin in contact with the central region 1052. Subsequently, when the pressing force is removed, end portions 1057 of the sheet substrate 1021 adhering to the skin 1031 are separated from the associated side regions 1053. During the separation, a peeling or separation force concentrates at incremental peeling edges of the double-sided adhesive tapes 1028. Additionally, the side regions 1053 separating from the skin 1030 returns to their original state. This ensures that the sheet substrate 1021 is easily detached from the double-sided adhesive tapes 1028 as the sheet substrate 1021 adheres to the skin 1031. Thus, according to this modification, the patch 1002 applied to the skin is separated from the applicator and the patch 1002 is securely retained on the skin.

Figure 20A:
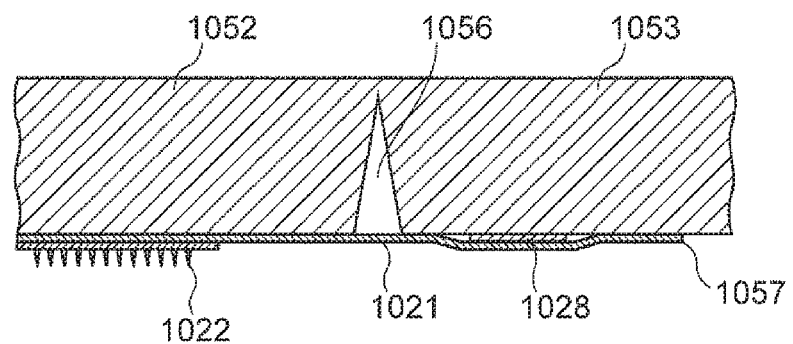
FIGS. 20A and 20B are views showing the state of deformation of a first element.
Figure 20B:
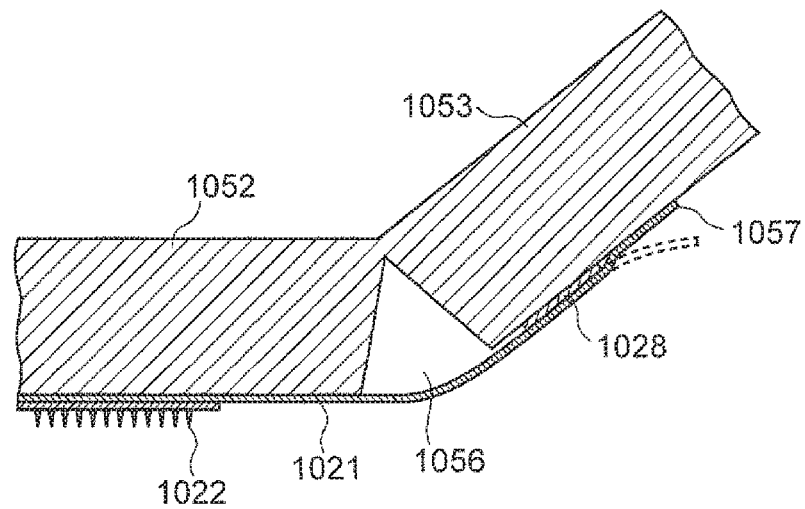

Although as described above, the grooves 1056 may be provided in either the bottom surface or the top surface of the first element 1003, more preferably they are provided in the bottom surface. The reason is that, as shown in FIGS. 20A and 20B, when the side regions 1053 bend relative to the central region 1052, the openings of the grooves 1056 in the bottom surface expand in the transverse directions thereof, causing shear stress between the side regions 1053 and the double-sided adhesive tape 1028 applied thereon to break the adhesive bonding thereof, which allows that the sheet substrate portions are easily separated from the double-sided adhesive tape 1028 on the side regions 1053 and thereby the patch 1002 are securely transfer onto the skin.

Second Embodiment

Figure 21:
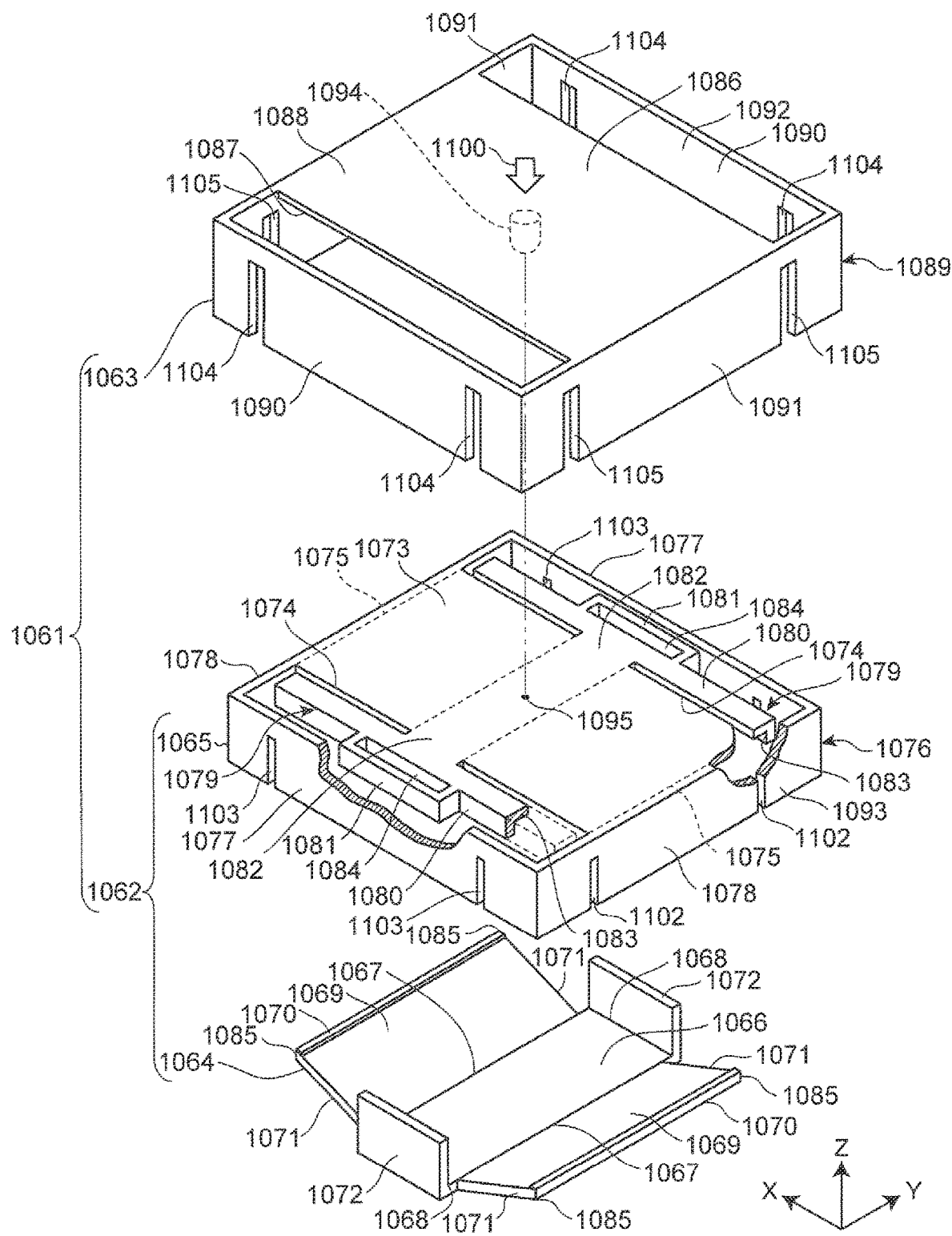
FIG. 21 is an exploded perspective view showing a second embodiment of an applicator according to the present invention.

FIG. 21 shows a second embodiment of the applicator according to the present invention. In the drawing, the applicator of the second embodiment, which is generally designated at reference numeral 1061, includes a first element 1062 and a second element 1063, and the first element 1062 includes a first sub-element 1064 and a second sub-element 1065.

The first sub-element 1064 has a central plate portion 1066 and an inclined plate portion 1069 connected integrally with opposite sides of the central plate portion 1066. The central plate portion 1066 is a rectangular plate portion outlined by edges 1067 and 1068 extending in the Y-direction and X-direction, respectively. The inclined plate portion 1069 is a rectangular plate portion outlined by a pair of edges 1071 and a pair of edges 1070. The edges 1071 extend outward and diagonally upward in parallel from portions adjacent the opposite ends of the Y-direction edges 1067. The edges 1070 connects the edges 107 and extend in parallel with the edges 1067 of the central plate portion 1066. Rectangular vertical plate portions 1072 extend upward from the X-direction edges 1068 of the central plate portion 1072 and are formed integrally with the edges 1068. Bottom surfaces of the central plate portion 1066 and the inclined side portions 1069 form a first surface of the first element.

Preferably, the first sub-element 1064 so constructed has a certain elasticity so that, forcing the extremity edges 1070 of the inclined plate portions 1069 downward decreases the angle of inclination of the inclined plate portions 1069 relative to the central plate portion 1066.

The second sub-element 1065 has a bridge 1073. The bridge 1073 is a rectangular plate portion outlined by a pair of edges 1074 extending in X-direction and a pair of edges 1075 extending in Y-direction. The top surface of the bridge 1073 forms a second surface of the first element. The second sub-element 1065 also includes a rectangular frame 1076 connecting a pair of walls 1077 extending in X-direction and a pair of walls 1078 extending in Y-direction. The Y-direction edges 1075 of the bridge 1073 are integrally connected to the Y-direction walls 1078 of the frame 1076. The second sub-element 1065 further includes guide portions 1079 between the X-direction edges 1074 of the bridge 1073 and the X-direction walls 1077 of the frame 1076 opposing the edges 1074. Each of the guide portions 1079 includes an inverted-L-shaped horizontal guide 1080 extending in X-direction and a vertical guide 1081. The central portion of the horizontal guide 1080 and the central portion of the bridge 1073 corresponding thereto are connected by a connecting portion 1082.

A distance between the inverted-L-shaped guide surface 1083 of the horizontal guide 108C on one hand and the inverted-L-shaped guide surface 1083 of the horizontal guide 1080 on the other is substantially equal to the distance between end corners 1085 of the inclined plate portion 1069. The inner shape of a through-hole 1084 of the vertical guide 1081 is substantially the same as the cross section of the vertical plate portion 1072 of the first sub-element 1064. Accordingly, the first sub-element 1064 and the second sub-element 1065 are combined together, with the vertical plate portion 1072 of the first sub-element 1064 inserted in the through-hole 1084 of the second sub-element 1065, and also with the end corners 1085 of the inclined plate portions 1069 of the first sub-element 1064 abutted against the inverted-L-shaped guide surfaces 1083 of the second sub-element 1065. In this combined state, the first sub-element 1064 is retained under the second sub-element 1065 by a frictional force between the vertical plate portion 1072 and the through-hole 1084.

The second element 1063 has substantially the same structure as the second element of the first embodiment. Specifically, the second element 1063 has a plate-like bridge 1086 extending in X-direction, or a major portion of the second element. As shown, the bridge 1086 has a bottom surface 1087 and a top surface 1088. The bottom surface 1087 and the top surface 1088 are a first surface and a second surface, respectively, of the second element. Either end of the bridge 1086 is connected to a frame 1089. The frame 1089 is configured to couple together a pair of walls 1090 extending in X-direction and a pair of walls 1091 extending in Y-direction, with ends of the bridge 1086 integrally connected to central upper ends of the Y-direction walls 1091.

An inner peripheral shape 1092 of the frame 1089 formed by inner surfaces of the walls 1090 and 1091 is slightly larger than an outer peripheral shape 1093 of the frame 1076 of the first element 1062. Specifically, X-direction and Y-direction inner dimensions of the frame 1089 of the second element 1063 are slightly larger than X-direction and Y-direction outer dimensions of the frame 1076 of the first element 1063 so that the frame 1076 of the first element 1062 is received inside the frame 1089 of the second element 1063 and also the first element 1062 received inside the frame 1089 of the second element 1063 moves relative to the second element 1063.

The bridge 1086 has a projection 1094 formed integrally on the bottom surface 1087 thereof. The projection 1094 is positioned so as to oppose a contact portion 1095 positioned at a center on the top surface of the bridge 1073 of the first element 1062 when the first element 1062 is received in the frame 1089 of the second element 1063. In the second embodiment, the projection 1094 is in the shape of a vertically extending elongated rod. The projection 1094 may be provided at the center indicated at 1095 of the bridge 1073 of the first element 1062, rather than on the bridge 1086 of the second element 1063.

The first element 1062 (first sub-element 1064 and second sub-element 1065) and second element 1063 so constructed are made of elastic resin or metal. Specifically, both the first and second elements 1062 and 1063 is made of resin or metal, or one of the first and second elements 1062 and 1063 is made of a resin and the other may be mace of a metal. Likewise, the first and second sub-elements 1064 and 1065 is made of a resin or a metal, or one of first and second sub-elements 1064 is made of resin and the other is made of metal.

The sizes of the first and second elements 1062 and 1063 may be varied depending on the size of the patch. For example, in the second embodiment the X-direction and Y-direction lengths of the second sub-element 1065 are about 2 cm to about 5 cm. Preferably, the inner dimension of the frame 1089 of the second element 1063 is about 1 mm to 3 mm longer than a portion corresponding thereto of the second sub-element 1065.

In operation of the applicator 1061 of the second embodiment, the first element 1062, or the combination of the first sub-element 1064 and the second sub-element 1065, is received inside the second element 1063.

Figure 22A:
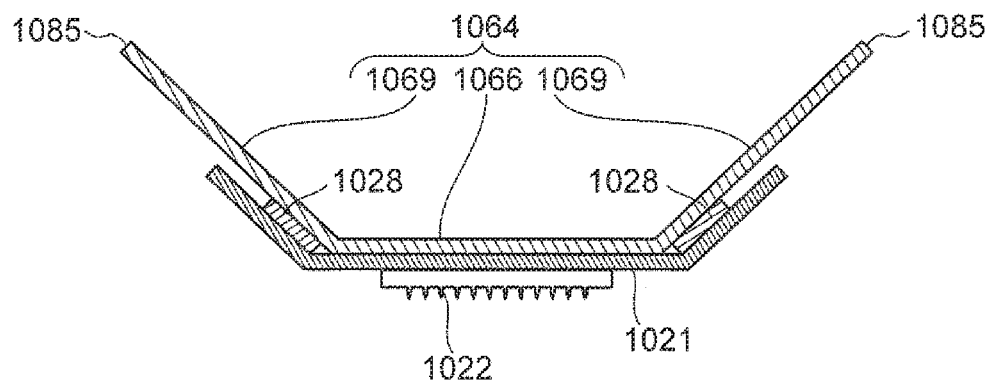
FIGS. 22A-22C are views showing a deformation of the first element and a state where the microneedle patch is applied to the skin.

As shown in FIG. 22A, the patch 1002 is arranged so that the microneedle array 1022 positions on the central plate portion 1066 and the double-sided adhesive tapes 1028 position on the opposite inclined plate portions 1069.

Figure 22B:
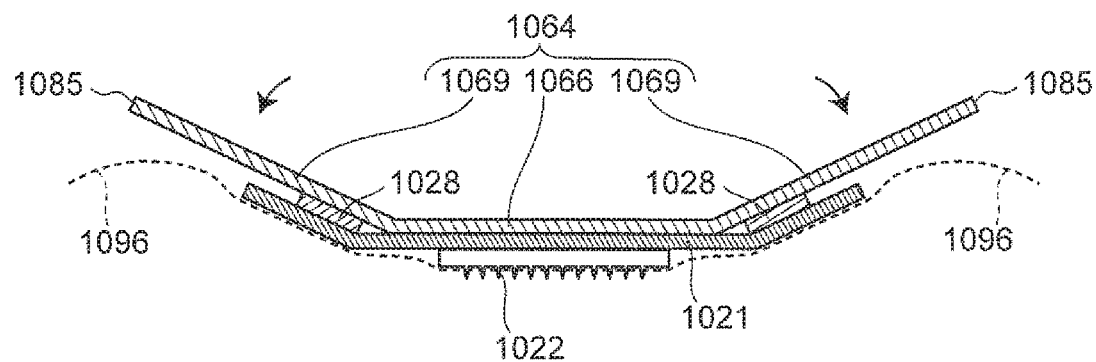

To attach the assembled patch 1002 onto human or animal skin, a pressing force 1100 is applied to a central portion on the bridge 1086 of the second element 1063. The pressing force 1100 is transmitted through the center projection 1094 to the center contact portion 1095. The pressing force 1100 is further transmitted from the horizontal guides 1080 of the first element 1062 to the inclined plate portions 1069 of the first element 1062. As a result, as shown in FIGS. 22A and 22B, the patch 2 supported on the bottom surface of the first element 1062 is pressed onto the skin 1096. In this process, the end corners 1085 of the inclined plate portions 1069 move in opposite directions as being guided by the inverted-L-shaped guide surfaces 1083 of the horizontal guides 1080 and, as a result, the inclined plate portions 1069 expand outward, while the vertical plate portions 1072 of the first element 1062 are guided along the vertical guides 1081. This results in that, as shown in FIG. 22B, the pressure-sensitive adhesive layer of the sheet substrate 1021 supported on the inclined plate portions is pressed by a suitable force and thereby adhered onto the skin 1096.

Figure 22C:
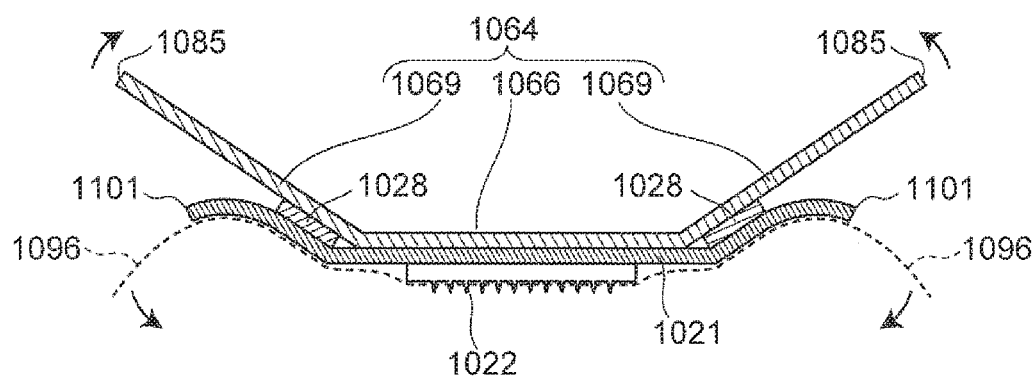

Once the pressing force 1100 is removed, the inclined plate portions 1069 of the first element 1062 begin to return to their original states. This results in that, as shown in FIG. 22C, ends 1101 of the sheet substrate 1021 adhering to the skin 1096 begin to separate from the inclined plate portions 1069 together with the portion of the skin to which the ends 1101 adhere. At this moment, as the side regions 1053 leave from the associated portions of the skin 1030, a force of separation concentrates on the outermost edges of the double-sided adhesive tapes 1028, which ensures that the sheet substrate 1021 easily peels off from the double-sided adhesive tapes 1028 while remaining adhered to the skin 1096. Therefore, the patch 1002 adhered to the skin is reliably separated from the applicator 1061 as it is securely retained on the skin.

The pressing force 1100 applied to the bridge 1086 of the second element 1063 is transmitted through the projection 1094 to the center contact portion 1095 of the first element 1062. Accordingly, even if the pressing force 1100 is not applied at the center of the bridge 1086, it is transmitted to the center of the first element 1062. This allows the needles 1027 to insert vertically into the skin 1096. Also, the needles 1027 are prevented from being bent, damaged, or broken at the insertion into the skin.

The above described applicator of the second embodiment may be modified in various ways.

Modification 2-1

Preferably, as shown in FIG. 21, the walls 1078 supported the bridge 1073 in the first element 1062 has slits 1102 which extend from the lower ends of the walls 1078 toward the upper ends thereof. In this modification, the bridge 1073 is bent downward by the pressing force 1100 transmitted from the projection 1094, easily allowing the outward expansion of the portions of the walls between the slits 1102, which ensures that the portion of the skin in contact with the lower ends of the portions of the walls is tensioned in a suitable manner. This in turn improves the vertical insertion of the needles into the skin.

As shown in the drawing, slits 1103 may be formed in the walls 1077 forming the frame 1076 of the first element 1062. In this modification, the skin surrounded by the frame 1076 is tensioned in four directions, which improves the vertical insertion of the needles into the skin.

Similar slits 1104 and 1105 may be formed in the four walls 1090 and 1091 of the frame 1089 in the second element 1063. The slits may extend in the opposite direction from the upper ends toward the lower ends.

Modification 2-2

Figure 23:
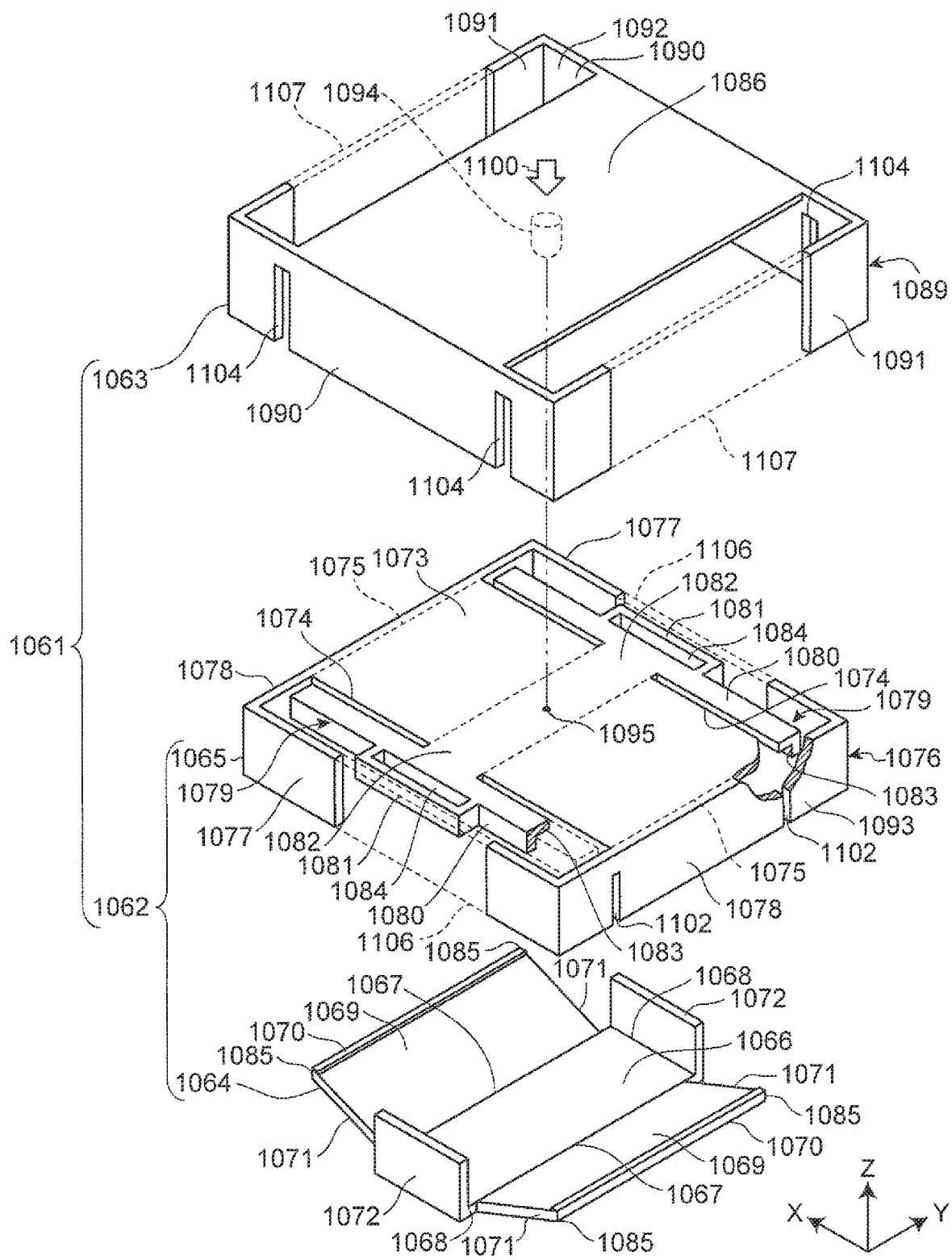
FIG. 23 is an exploded perspective view showing a modification 2-2 of the second embodiment.

Although the bridge 1073 of the first element 1062 and the bridge 1086 of the second element 1063 are oriented in the same direction (X-direction) in previous embodiment, the bridge 1073 of the first element 1062 may be oriented in X-direction and the bridge 1086 of the second element 1063 may be oriented in Y-direction, for example, as shown in FIG. 23. Also, for example, the frame 1076 of the first element 1062 and the frame 1089 of the second element 1063 may have a square shape, and the bridge 1086 of the second element 1063 may be oriented in a direction parallel or orthogonal to the bridge 1073 of the first element 1062.

Modification 2-3

As shown in FIG. 23, the frames 1076 and 1089 of the first and second elements 1062 and 1063 may be formed with disconnected portions 1106 and 1107 by removing central portions of the walls 1077 and 1091 opposing the side edges of the bridges 1073 and 1086. According to this modification, the bridges 1073 and 1086 deform easily. In particular, the walls 1078 supporting the opposite ends of the bridge 1073 in the first element 1062 deform outward easily to cause an appropriate tension in the skin, which improves the vertical insertion of the needles into the skin.

Modification 2-4

Although not shown, the frames 1076 and 1089 of the first and second elements 1062 and 1063 may be of a shape other than the quadrangle, such as circle, hexagon, or octagon.

Modification 2-5

Figure 24A:
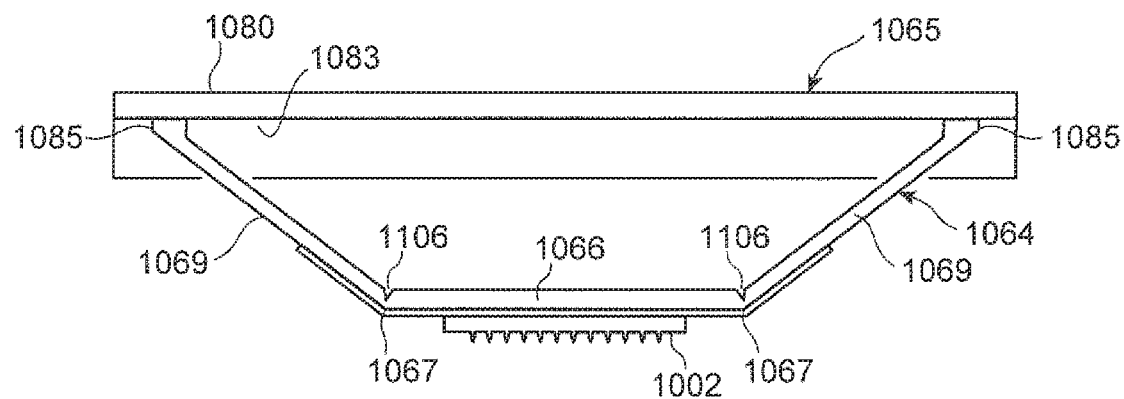
FIGS. 24A and 24B are sectional views showing a modification 2-5 of the second embodiment.
Figure 24B:
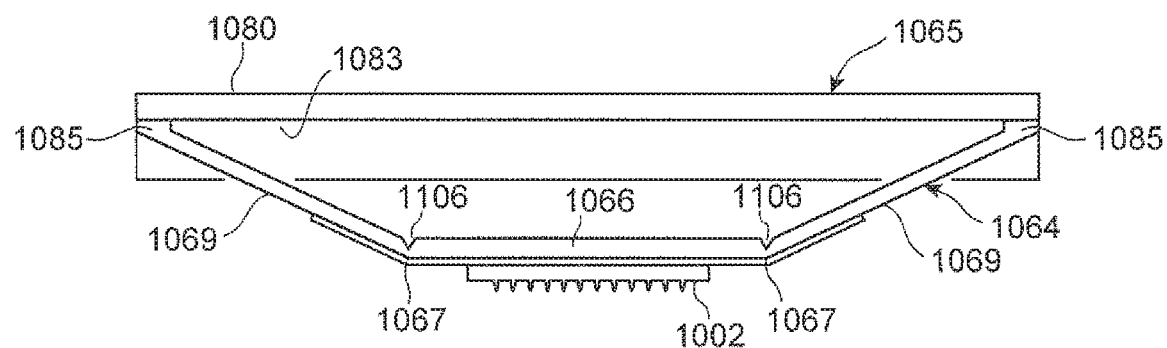

As shown in FIGS. 24A and 24B, the thickness of the central plate portion 1066 of the first sub-element 1064 may be larger than that of the inclined plate portions 1069. In this modification, the needles are pressed at substantially the same force against the skin and, therefore, they are evenly inserted into the skin.

As shown in FIGS. 24A and 24B, continuously or intermittently extending grooves 1106 or cuts may be formed in the top surface and/or the bottom surface of the first sub-element 1064 at the boundaries which correspond to the edges 1067 and between the central plate portion 1066 and the inclined plate portions 1069. In this modification, similar to the modification described with reference to FIGS. 19A and 19B, the sheet substrate can easily be separated, from its outermost end, from the first element 1062.

Third Embodiment

Figure 25:
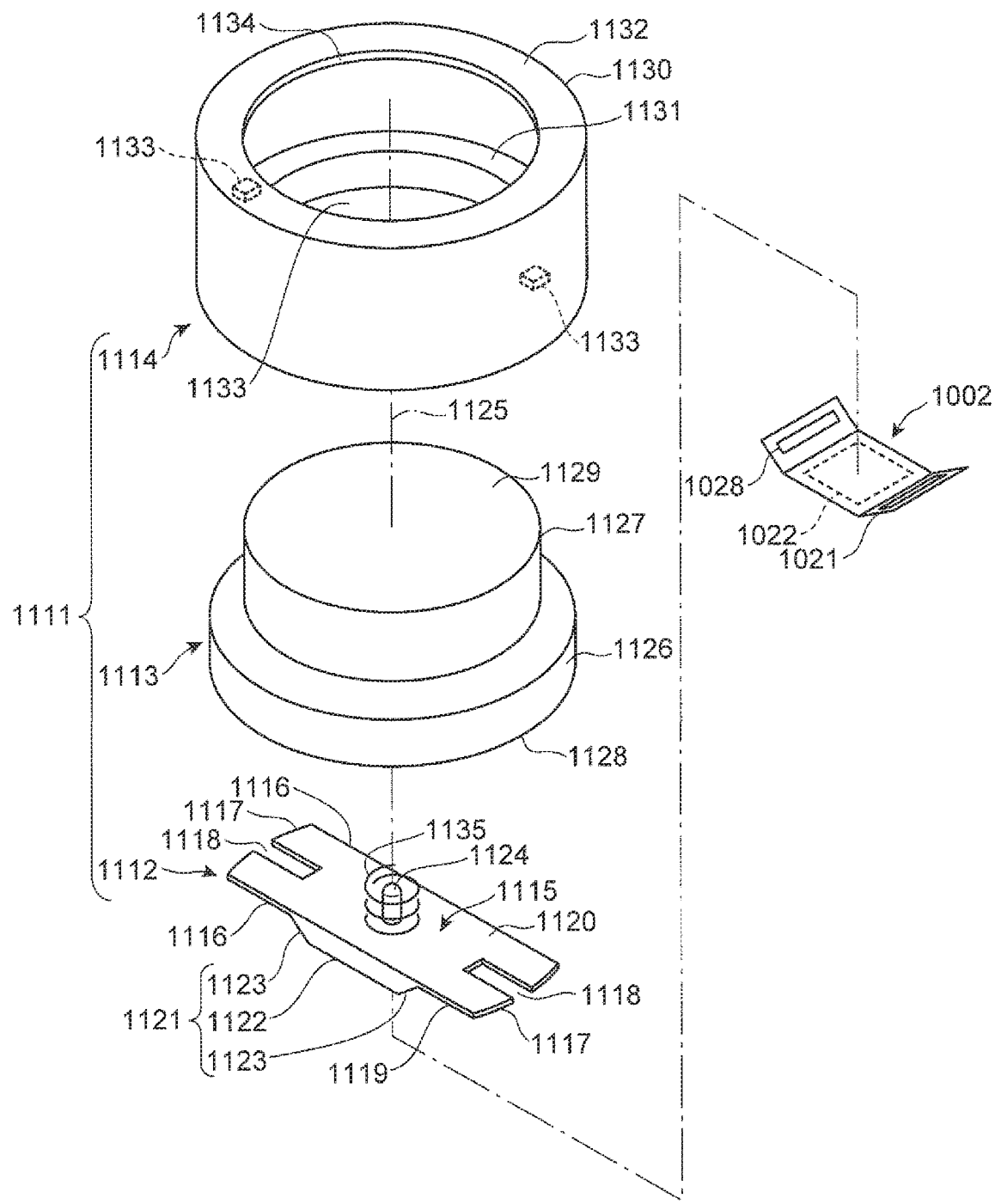
FIG. 25 is an exploded perspective view showing an applicator according to a third embodiment.

FIG. 25 shows a third embodiment of the microneedle patch applicator according to the invention. In the drawing, the applicator of the third embodiment is generally designated at reference numeral 1111 and includes a first element 1112, a second element 1113, and a third element 1114.

The first element 1112 has a plate member 1115. The plate member 1115 is outlined by a pair of longitudinal edges 1116 and a pair of short-side edges 1117. The pair of longitudinal edges 1116 are parallel to each other. The pair of short-side edges 1117 may be parallel to each other or may position on a circle around the center of plate member 1115. The transverse edges 1117 are formed with notches 1118 extending inward from the edges 1117.

The plate member 1115 has a bottom surface 1119 and a top surface 1120. These bottom surface 1119 and top surface 1120 form a first surface and a second surface, respectively, of the first element. As shown, in the third embodiment the bottom surface 1119 has at its center a trapezoidal portion 1121 formed integrally therewith. The trapezoidal portion 1121 has a rectangular planar central portion 1122 and inclined portions 1123 formed on opposite sides of the central portion 1122. The central portion 1122 and inclined portions 1123 form a pad support surface. The top surface 1120 of the plate member 1115 has a rod-shaped projection 1124 integrally formed therewith and extending upward along a central axis 1125 of the second element 1113 described below.

The second element 1113, which is made of a cylindrical member having the central axis 1125, includes a lower cylindrical portion 1126 with a predetermined outer diameter and an upper cylindrical portion 1127 with a smaller outer diameter than that of the lower cylindrical portion 1126. A bottom surface 1128 of the lower cylindrical portion 1126 and a top surface 1129 of the upper cylindrical portion 1127 are a first surface and a second surface, respectively, of the second element.

The third element 1114 includes a hollow cylindrical portion 1130 having the central axis 1125. The hollow cylindrical portion 1130 has at its lower and upper ends a lower flange 1131 and an upper flange 1132, respectively, which protrude inward to form a lower opening 1133 and an upper opening 1134 thereinside, respectively.

Figure 26:
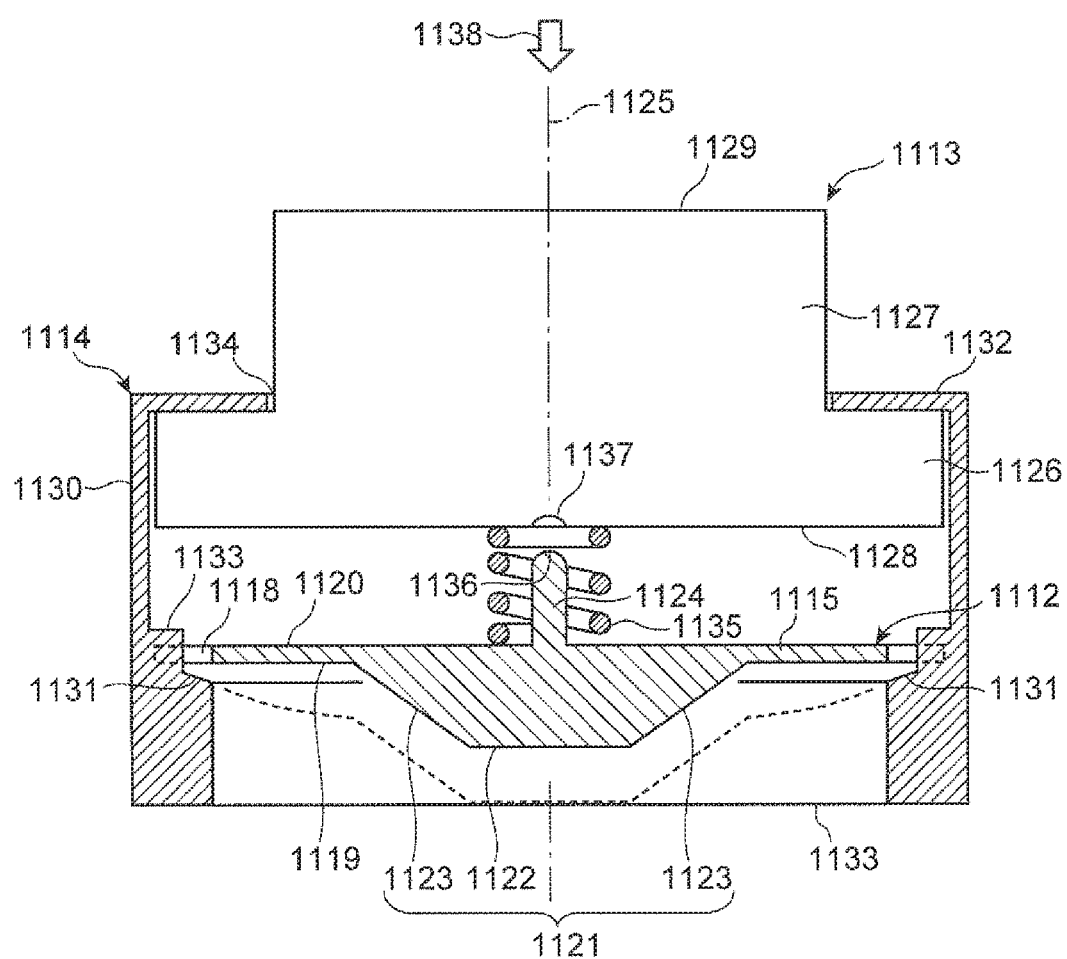
FIG. 26 is a sectional view of the applicator of the third embodiment shown in FIG. 25.

The first to third elements 1112, 1113, and 1114 so constructed are assembled with each other as shown in FIG. 26. Specifically, the first element 1112 and the second element 1113 are incorporated into the lower portion and the upper portion of the interior of the hollow cylindrical portion 1130 of the third element 1114. In the third embodiment, the longitudinal length of the plate member 1115 of the first element 1112 is slightly smaller than the inner diameter of the hollow cylindrical portion 1130 of the third element 1114 so that the longitudinal opposite ends of the plate member 1115 can rest on the lower flange 1131 of the hollow cylindrical portion 1130 in which, as shown in the drawing, the bottom surface 1119 of the plate member 1115 and the patch (not shown in FIG. 26) supported thereby lie inside the lower opening 1133 of the hollow cylindrical portion 1130.

Preferably, in order to prevent the plate member 1115 from rotating about the axis 1125, the plate member 1115 has a pair of diametrically opposed cutouts 1118 which engages with a pair of protrusions 1133 provided at diametrically opposed positions on the top surface of the lower flange 1131.

The second element 1113 is arranged so that the lower cylindrical portion 1126 positions inside the hollow cylindrical portion 1130 and also the upper cylindrical portion 1127 protrudes from the upper opening 1134 of the hollow cylindrical portion 1130. Therefore, in this embodiment, preferably the outer diameter of the lower cylindrical portion 1126 is slightly smaller than the inner diameter of the hollow cylindrical portion 1130 and also the outer diameter of the upper cylindrical portion 1127 is slightly smaller than the inner diameter of the upper opening 1134.

A spring 1135 is provided between the first and second elements 1112 and 1113 arranged in the hollow cylindrical portion 1130. In the third embodiment, the spring 1135 is provided to surround the central projection 1124. The spring 1135 urges the plate member 1115 of the first element 1112 against the lower flange 1131 and urges the lower cylindrical portion 1126 of the second element 1113 against the upper flange 1132 so that these first and second elements 1112 and 1113 are stably retained inside the hollow cylindrical portion 1130 while leaving a slight space between the upper end 1136 of the projection 1124 of the first element 1112 and a central portion (contact portion 1137) on the lower cylindrical portion bottom surface 1128 confronting the upper end 1136.

Although not shown, the hollow cylindrical portion 1130 of the third element 1114 is divided into a plurality of portions for the purpose of receiving the first element 1112 and the second element 1113 within the interior thereof. For example, the hollow cylindrical portion 1130 may be divided along a plane containing the central axis 1125 into two semicylindrical portions which may be combined together at the assembling thereof. Alternatively, the hollow cylindrical portion 1130 may be divided into the upper flange 1132 and a remaining cylindrical portion. In this embodiment, the remaining cylindrical portion is assembled with the upper flange 1132 after receiving the first and second elements and the spring in the cylindrical portion.

The patch 1002 so mounted in the applicator 1111 is attached to the trapezoidal portion 1121 of the bottom surface of the first element 1112. The microneedle array 1022 is provided at the central portion 1122 and the double-sided adhesive tape 1028 is attached on the inclined portion 1123.

The patch 1002 applied to the applicator 1111 in this manner is placed on the skin (not shown) so that the lower end of the hollow cylindrical portion 1130 of the third element 1114 opposes the skin. Then, a pressing force 1138 is applied to the upper cylindrical portion 1127 of the second element 1113. This allows the third member 1113 to descend against the biasing force of the spring 1135, until the tip 1136 of the projection 1124 abuts against the contact portion 1137. The pressing force 1138 applied is increased, which causes that the plate member 1115 of the first element 1112 bends downward as shown in FIG. 26 and the patch 1002 supported on the plate member 1115 is pressed onto the skin, allowing the needles to stick into the skin. Also, the pressure-sensitive adhesive layer of the patch 1002 adheres closely to the skin. Then, when the pressing force 1138 is removed, the first member 1112 and the second member 1113 return to the state indicated by a solid line in FIG. 26, due to the elastic recovering force of the plate member 115 and the spring 1124.

According to the applicator 1111 described above, even if the pressing force 1138 is applied at a portion away from the central axis 1125, it can securely be transmitted via the projection 1124 to the center of the plate member 1115. Consequently, the needles on the patch 1002 are ensured to be inserted vertically into the skin. This prevents the needles from being bent, damaged or broken at the insertion thereof.

Figure 27:
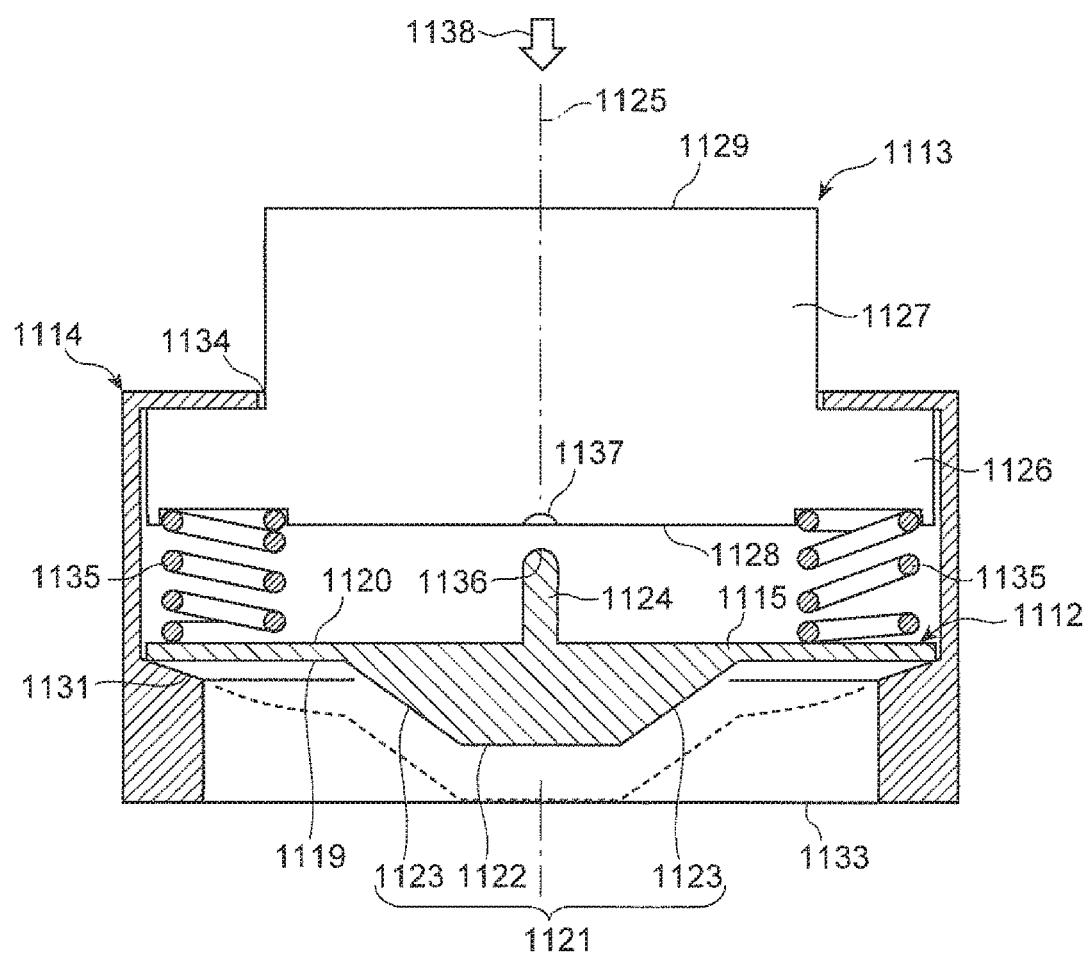
FIG. 27 is a sectional view showing a modification of the third embodiment.

Although in the third embodiment the central projection 1124 is provided on the top surface 1120 of the first element 1112 or the plate member 1115, it may be provided on the bottom surface 1128 of the second element 1113 as described in the first embodiment. Also, as described in the first embodiment, the rod-shaped projection may be replaced by the wall-shaped projection. The position and the number of the spring 1135 are not restrictive. Alternatively or additionally, the spring may be arranged on opposite sides of the plate member 1115 as shown in FIG. 27. Further, although in the third embodiment the bottom surface of the plate member 1115 bears the trapezoidal portion 1121 on which the patch is supported, the trapezoidal portion 1121 may not be necessarily needed.

As shown in FIG. 26, the contact portion 1137 of the second element 1113 where the tip 1136 of the projection 1124 contacts may be a recess. If the tip of the projection 1124 has a spherical shape, preferably the recess 1137 is a concave spherical surface portion having a shape corresponding thereto. The same applies to the wall-shaped projection, and the contact portion may be a curved concave corresponding to the tip curved surface of the projection. Those shapes of the projection and the associated contact portion may be employed in any of the embodiments and modifications described above and below.

Fourth Embodiment

Figure 28A:
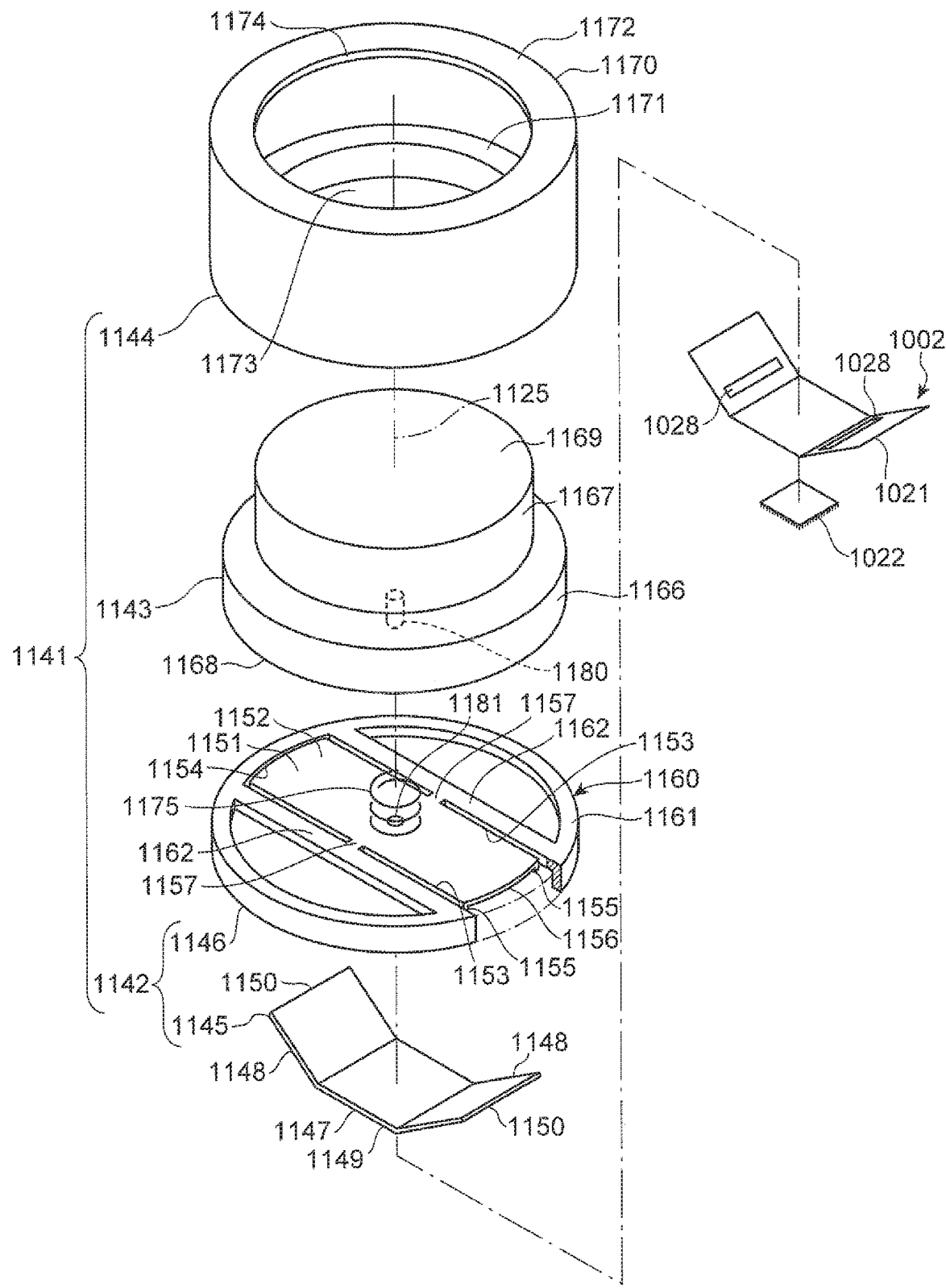
FIG. 28A is an exploded perspective view showing an applicator according to a fourth embodiment.
Figure 28B:
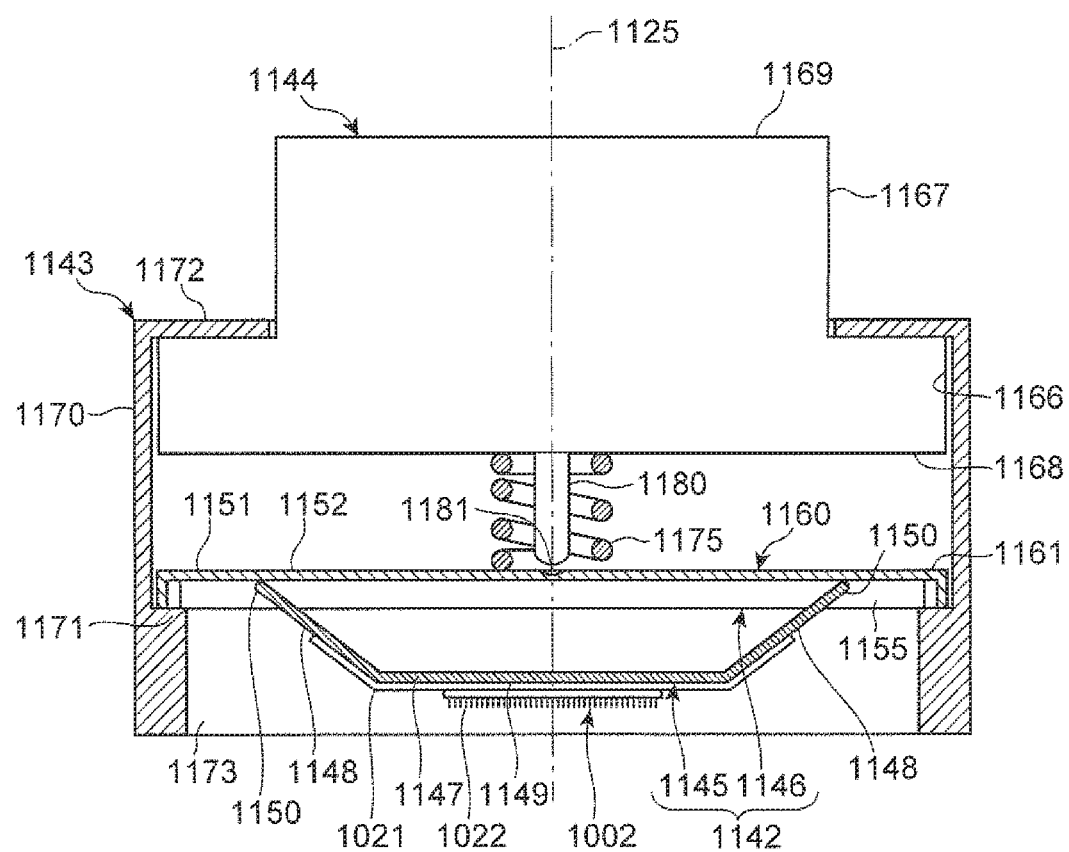
FIG. 28B is a sectional view showing the applicator according to the fourth embodiment.

FIGS. 28A and 28B show a fourth embodiment of the applicator according to the present invention. In the drawing, the applicator of the fourth embodiment, which is generally designated at reference numeral 1141, has a first element 1142, a second element 1143, and a third element 1114. The first element 1142 includes a first sub-element 1145 and a second sub-element 1146. The second element 1143 and the third element 1144 are substantially the same as the second element 1113 and the third element 1144 of the third embodiment described above, respectively.

The first sub-element 1145, which is of a trapezoidal shape similar to the first sub-element in the first embodiment, has a rectangular central plate portion 1147 and rectangular inclined plate portions 1148 connected integrally at a pair of opposed edges of the central plate portion 1147. In this embodiment, the bottom surface 1149 of the central plate portion 1147 and the inclined plate portions 1148 defines a first surface of the first sub-element. The structure, material, thickness, and so forth of the first sub-element 1145 are determined so that, when the outermost edges 1150 of the two inclined plate portions 1148 are pressed downward, a distance between the edges 1150 increases.

The second sub-element 1146 has a substantially rectangular plate portion 1151. A top surface 1152 of the plate portion 1151 is a second surface of the first element 1142. The plate portion 1151 is outlined by a pair of longitudinally extending edges 1153 and a pair of transversely extending edges 1154. In the fourth embodiment, the longitudinal edges 1153 are parallel to each other. The transverse edges 1154 may similarly be parallel to each other or may be positioned on a circle around a center of the plate portion 1151.

The longitudinal edges 1153 are each have a guide flange 1155 formed therewith to protrude downward therealong. A distance between the opposed surfaces of the guide flanges 1155 are equal to or slightly larger than the width of the inclined plate portions 1148 so that a bottom surface 1156 of the plate portion 1151 between the guide flanges 1155 functions as a guide surface for the inclined plate portions 1148.

The plate portion 1151 is supported at a central portion of the longitudinal edges 1153 thereof by support frames 1160 by way of connecting portions 1157. The support frame 1160 has an annular ring 1161 and two bridges 1162. The annular ring 1161 has an outer diameter slightly smaller than the inner diameter of the hollow cylindrical portion 1170 of the third element 1144. The bridges 1162 extend along and in parallel to the longitudinal side of the plate portion 1151 and are connected at the opposite ends integrally with the ring 1161. The bridges 1162 are connected at their central portions integrally with the plate portion 1151 by way of the connecting portion 1157.

The second element 1143 and the third element 1144 are substantially the same as the second element 1113 and the third element 1114 of the third embodiment described above, respectively. Accordingly, portions or elements of this embodiment are indicated by reference numerals which are obtained by adding "40" to the reference numerals given to the same or similar portions or elements of the above-described third embodiment and no duplicative description is made to those portions and elements. The difference is that in the fourth embodiment a projection 1180 is provided on a bottom surface 1181 of the second element 1143. The bottom surface 1181 is the first surface of the second element. Correspondingly, the contact portion 1181 is formed at the center on the plate portion 1151.

The first to third elements 1142, 1143, and 1144 so constructed are assembled so that the first element 1142 (only the second sub-element 1146) and the second element 1143 are incorporated in the lower portion and the upper portion within the interior of the hollow cylindrical portion 1170 of the third element 1144. The patch 1002 is adhered to the bottom surface 1149. Then, the first sub-element 1145 of the first element 1142 is mounted on the bottom surface 1156 of the second sub-element 1146. In this condition, the patch 1002 adhered to the first sub-element 1145 and the bottom surface 1149 may protrude downward from the lower opening 1173 of hollow cylindrical portion 1170.

In the second element 1143, the lower cylindrical portion 1166 is provided inside the hollow cylindrical portion 1170 so that the upper cylindrical portion 1167 protrudes from the upper opening 1174 of the hollow cylindrical portion 1170.

A spring 1175 is provided between the first and second elements 1142 and 1143 arranged within the hollow cylindrical portion 1170. Although in the fourth embodiment the spring 1175 is provided to surround the central projection 1180, the position or the number of the springs is not limited thereto. As a result, the plate portion 1151 of the first element 1142 is pressed against the lower flange 1171, and the lower cylindrical portion 1166 of the second element 1143 is pressed against the upper flange 1172, which results in that the first and second elements 1142 and 1143 are stably held inside the hollow cylindrical portion 1170, leaving a small gap between the projection 1180 and the contact portion 1181 opposing the projection 1180.

As described in the third embodiment, the hollow cylindrical portion 1170 of the third element 1144 is divided into a plurality of portions for the purpose of receiving the first element 1142 and the second element 1143 within the interior thereof. For example, the hollow cylindrical portion 1170 may be divided into two semi-cylindrical portions on a plane containing the central axis 1125. The divided portions are combined at the assembling the applicator. Alternatively, the hollow cylindrical portion may be divided into the upper flange 1172 and a remaining cylindrical portion. In this embodiment, the upper flange and the remaining portion may be assembled together after receiving the first and second elements and the spring in the cylindrical portion.

For the applicator 1111 so constructed, the patch 1002 is mounted to the bottom surface 1149 of the first element 1142. In this mounting, the microneedle array 1022 is provided on the central portion 1147, and the double-sided adhesive tapes 1028 are positioned on the inclined plate portions 1148.

According to this arrangement, the patch 2 adhered on the bottom surface of the first sub-element 1145 is placed on the skin, and then a pressing force is applied to the upper cylindrical portion 1167 of the second element 1143. This causes that the third member 1143 descends against the biasing force of the spring 1175 until the projection 1180 comes into contact with the associated contact portion 1181. Then, an increase of the pressing force cause the plate portion 1151 of the first element 1142 to bend downward and, thereby, the patch 1002 is pressed onto the skin (not shown), allowing the needles to insert into the skin. Also, the pressure-sensitive adhesive layer of the patch 1002 adheres closely to the skin. Afterward, when the pressing force is removed, the first element 1142 and the second element 1143 are restored to the original state, due to the elastic recovering force of the first element 1142 (the first sub-element 1145 and the second sub-element 1146) and the spring 1175.

According to the applicator 1141, even if the pressing force is not applied along the central axis, it is transmitted through the projection 1180 to the center of the plate member 1151. Consequently, the needles on the patch 1002 supported by the first element 1142 are ensured to insert vertically into the skin. This prevents the needles from being bent, damaged or broken at the insertion into the skin.

Figure 36:
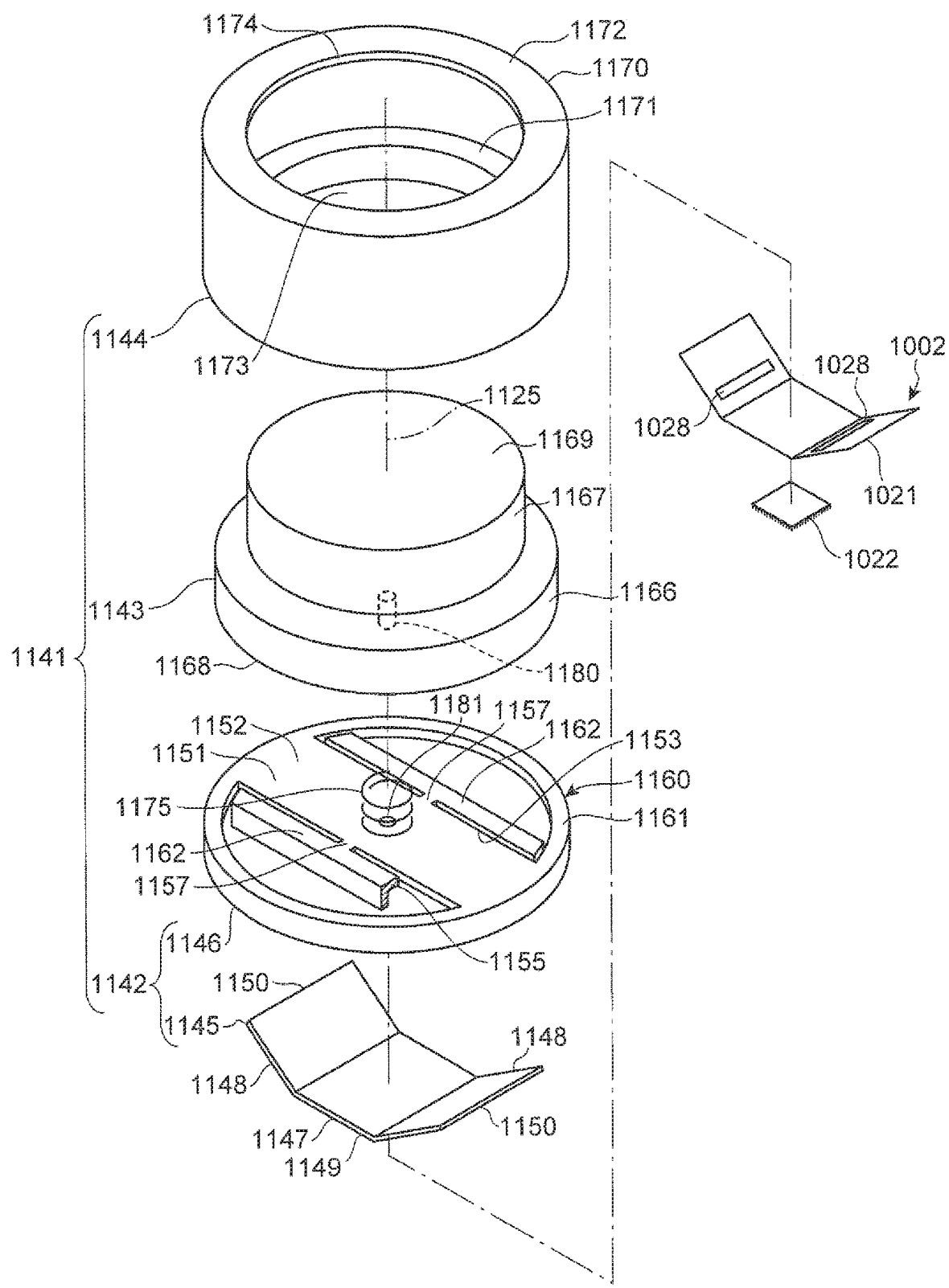
FIG. 36 is an exploded perspective view showing a modified example of the applicator according to the fourth embodiment.

Although in the fourth embodiment the opposite ends of the plate portion 1151 are separated from the annular rings 1161 and the opposite ends of the bridges 1162 are connected to the annular rings 1161, the opposite ends of the bridges 1162 may be separated from the annular rings 1161 and the opposite ends of the plate portion 1151 are connected to the annular rings 1161 as shown in FIG. 36, to form on the bottom surfaces of the bridges 1162 inverted-L-shaped guides 1155 along which the end corners of the inclined plate portions 1148 are guided.

Fifth Embodiment

FIGS. 29A-29D show a fifth embodiment of the applicator according to the present invention. In the drawing, the applicator of a fifth embodiment, which is generally designated at reference numeral 1201, includes a first element 1202 and a second element 1203. The second element 1203 includes a first sub-element 1204 and a second sub-element 1205.

The first element 1202 has a plate-like bridge 1207 including a pair of parallel edges 1206. The bottom surface 1208 and the top surface 1209 of the bridge 1207 define a first surface and a second surface, respectively, of the first element. The opposite ends of the bridge 1207 are connected integrally with upper ends of two arc-like walls 1210 extending partially along a circle around a center of the bridge 1207.

In the fifth embodiment, a thickness of the central region of the bridge 1207 has a larger plate thickness in its central region forming a patch support surface described later 1211 and a smaller plate thickness in side regions 1212 positioned on opposite sides of the central region 1211.

A projection 1213 is formed integrally at a center on the top surface 1209 of the bridge 1207. In the fifth embodiment, an upper end 1214 of the projection 1213 is shaped into a spherically.

The first sub-element 1204 of the second element 1203 has a hollow cylindrical body 1215. Preferably, the outer diameter of the hollow cylindrical body 1215 has a size which allows it to be held by human hand, e.g., 1 to 5 cm. The inner diameter of the hollow cylindrical body 1215 is larger than the diameter of a circle along the outer peripheral surface of the arc-like walls 1210 of the first element 1203 so that the first element 1203 can move inside the hollow cylindrical body 1215. The lower end of the hollow cylindrical body 1215 is open and the upper end of the hollow cylindrical body 1215 integrally supports a radially extending plate-like bridge 1217 provided orthogonal to the a central axis 1216 of the hollow cylindrical body 1215. In the fifth embodiment, a top surface 1218 of the bridge 1217 defines a second surface of the second element.

In the fifth embodiment, to facilitate the bending of the bridge 1217 when being pressed from above, the hollow cylindrical body 1215 is formed, at positions corresponding to both edges of the bridge 1217, with a pair of slits 1219 or notches extending downward from the upper end of the hollow cylindrical body 1215.

The second sub-element 1205 of the second element 1203 is received inside the hollow cylindrical body 1215 of the first sub-element 1204 so that it can move vertically. In the fifth embodiment, the second sub-element 1205 is made of a hollow or solid cylindrical body 1220.

Preferably, the outer diameter of the cylindrical body 1220 is substantially equal to the inner diameter of the hollow cylindrical body 1215. Although in the fifth embodiment the hollow cylindrical body 1215 and the cylindrical body 1220 are made of respective cylindrical bodies having circular cross sections, they may be cylindrical bodies having quadrangular or polygonal cross section. Preferably, the heights of the hollow cylindrical body 1215 and the cylindrical body 1220 are determined so that the first element 1202 is substantially received under the cylindrical body 1220 when the cylindrical body 1220 is received inside the hollow cylindrical body 1215.

A bottom surface 1221 of the cylindrical body 1220 defines a first surface of the second element that has a contact portion 1222 formed at its center. Preferably, the contact portion 1222 is of a shape corresponding to the shape of the projection upper end 1214. In the embodiment, the upper end of the contact portion is shaped in a spherical convex and, correspondingly, the contact portion is shaped into a spherical concave.

With the arrangement, the patch 1002 is held in the central region 1311 of the bottom surface of the bridge 1207 in the first element 1202. As shown, the first element 1202 holding the patch 1002 is received in the lower end of the hollow cylindrical body 1215 receiving the cylindrical body 1220. Thus, the patch 1002 is placed on the skin and then a pressing force is applied to the upper end bridge 1217 of the hollow cylindrical body 1215, which results in that the bridge 1217 curves downward to descent the inside cylindrical body 1220. The pressing force is then transmitted from the contact portion 1222 on the bottom surface 1221 of the cylindrical body through the projection 1213 to the bridge 1207 of the first element 1202. As a result, the bridge 1207 bends downward to force the patch 2 on the bottom surface thereof onto the skin, allowing the needles to insert into the skin.

In this operation, even if the hollow cylindrical body 1215 of the second element 203 is not directed vertically to the skin, the first element 1202 turns around the tip 1214 of the projection 1213 so that the bridge 1207 is directed parallel to the skin, allowing the needles supported on the bottom surface thereof to be inserted vertically into the skin. This prevents the needles from being bent, damaged, or broken at the insertion of the needles into the skin.

The above described applicator of the fifth embodiment may be modified in various ways.

Modification 5-1

Figure 30A:
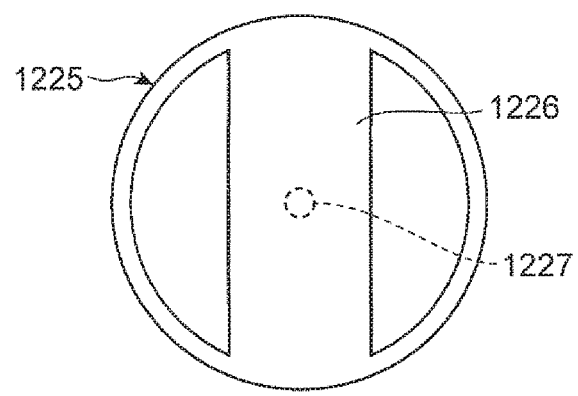
FIGS. 30A and 30B are views showing a modification 5-1 of the fifth embodiment.
Figure 30B:
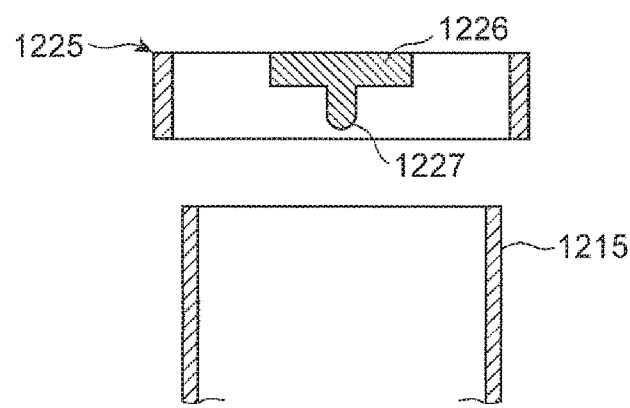

Although the bridge 1207 of the second element is formed integrally with the hollow cylindrical body 1215 in the previous embodiment, it may be a separate member separate, other than the hollow cylindrical body 1215. In this modification, for example, as shown in FIGS. 30A and 30B, the hollow cylindrical body 1215 is formed from a cylinder and does not have a bridge. An annular cap 1225 is mounted on the upper end of the hollow cylindrical body 1215. The cap has a bridge 1226 integrally formed therewith. According to this modification, the cap 1225 is mounted on the upper end of the hollow cylindrical body 1215 so that the bridge 1226 opposes the upper end surface of the cylindrical body 1220. A projection 1227 may be integrally formed at a center of the bridge 1226. Accordingly, the pressing force applied to the bridge 1226 is transmitted through the projection 1227 to the cylindrical body 1220.

Modification 5-2

Figure 31A:
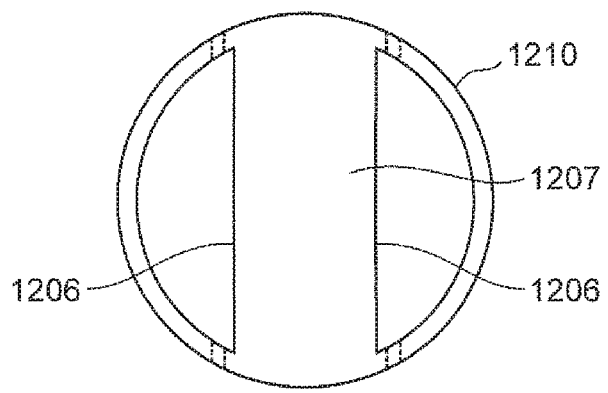
FIGS. 31A and 31B are views showing a modification 5-2 of the fifth embodiment.
Figure 31B:
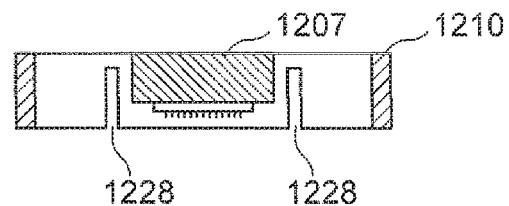

As shown in FIGS. 31A and 31B, the wall 1210 supporting the bridge 1207 in the first element may be annular. In this modification, the annular wall 1210 may be formed, outside of the longitudinal edges 1206 of the bridge 1207, respectively, cuts 1228 such as slots or slits extending from the lower end of the annular wall 1210 toward the upper end thereof or extending from the upper end of the annular wall 1210 toward the lower end thereof.

Modification 5-2

Figure 32:
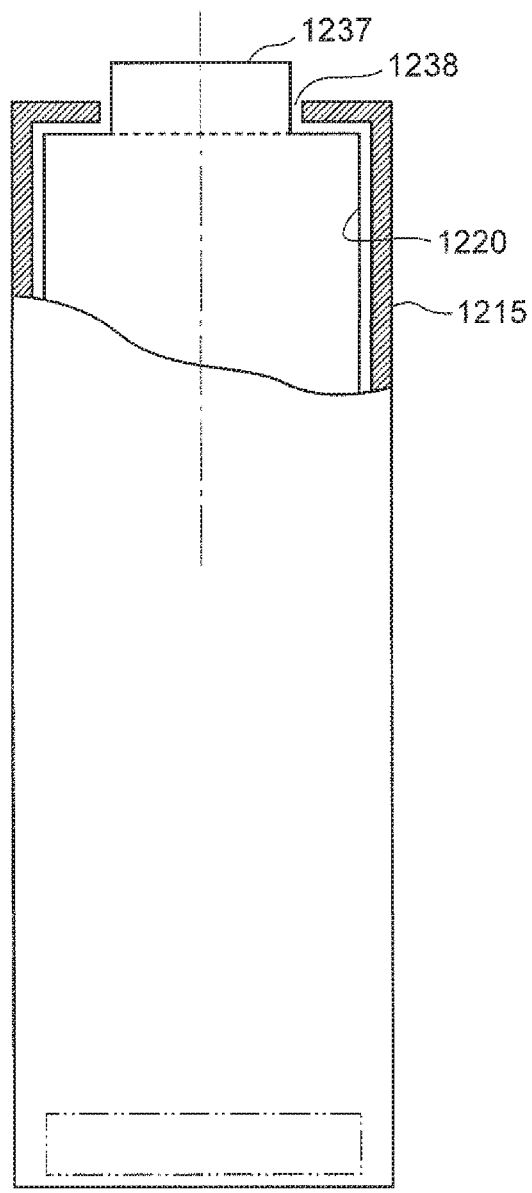
FIG. 32 is a view showing a modification 5-2 of the fifth embodiment.

Although in the fifth embodiment, the deformable bridge is provided on the upper end of the outer hollow cylindrical body and then is subjected to a pressing force, a small-diameter convex portion 1237 may be formed at a center on the upper end of the cylindrical body 1220 as shown in FIG. 32. An opening 1238 corresponding in shape to the convex portion 1237 may be formed on the upper end of the hollow cylindrical body 1215, allowing the convex portion 1237 to protrude from the opening 1238, to subject the convex portion 1237 to a pressing force.

Modification 5-3

Figure 33:
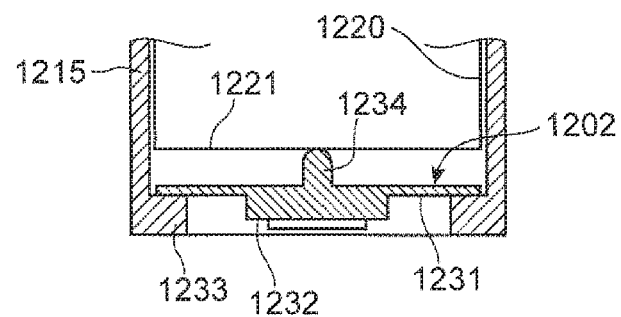
FIG. 33 is a view showing a modification 5-3 of the fifth embodiment.

The modifications described in connection with the second embodiment with reference to FIG. 26 may be combined with this embodiment. In this modification, as shown in FIG. 33, the first element 1202 includes a strip-like thin plate 1231. The plate 1231 has a bottom surface which forms a patch support platform 1232. The hollow cylindrical body 1215 has on its lower end inner surface an inward protruding flange 1233 on which the plate 1231 rests. According to this modification, when the cylindrical body 1220 descends, a projection 1234 provided at a center on the top surface of the plate 1231 abuts against a center of the bottom surface 1221 of the cylindrical body 1220 as shown, or, although not shown, a projection provided at a center on the bottom surface of the cylindrical body 1220 abuts against a center of the top surface of the plate 1231, allowing the plate 1231 to bend downward to press the patch 1002 against the skin.

Modification 5-4

Figure 34:
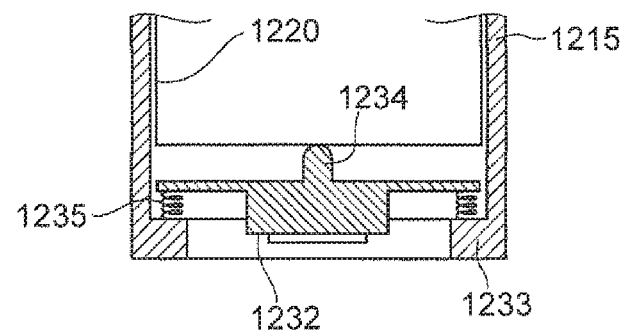
FIG. 34 is a view showing a modification 5-4 of the fifth embodiment.

As shown in FIG. 34, in this modification a spring 1235 is provided between the plate 1231 and the flange 1233, causing the projection to be in contact with the contact portion.

Sixth Embodiment

Figure 35:
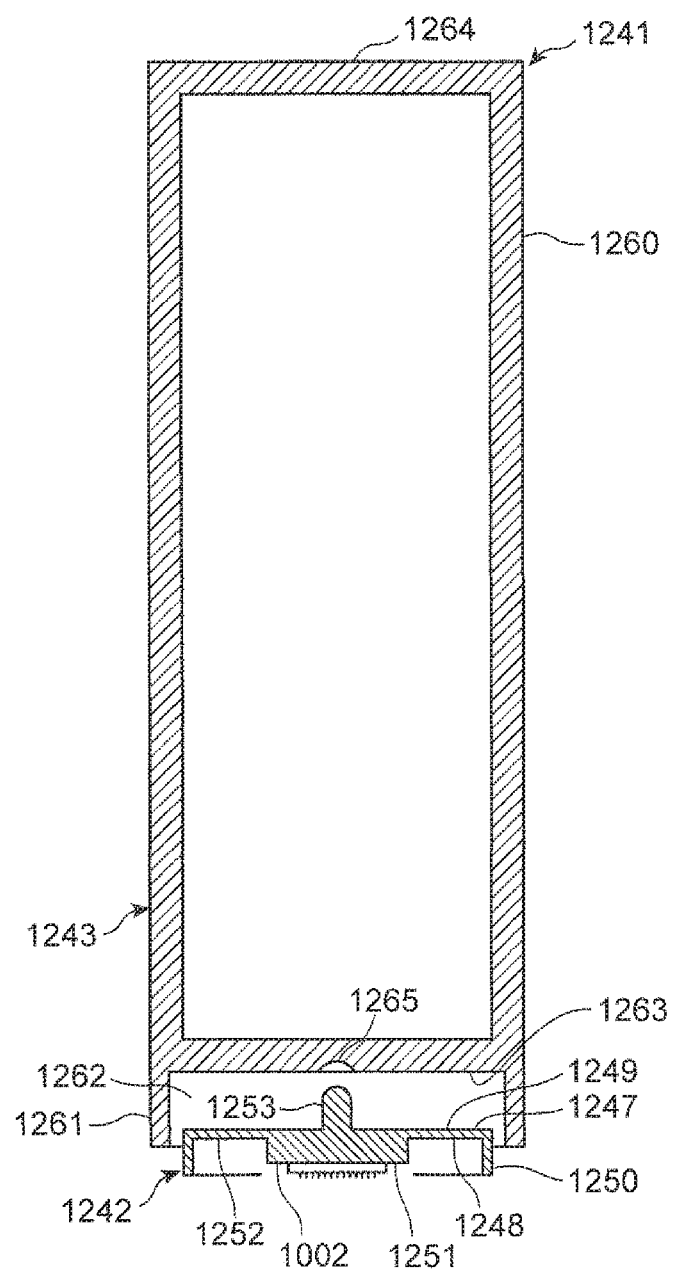
FIG. 35 is a view showing a modified example of an applicator according to a sixth embodiment.

FIG. 35 shows a sixth embodiment of the applicator according to the present invention. In the drawing, the applicator of the sixth embodiment, which is generally designated at reference numeral 1241, includes a first element 1242 and a second element 1243. The first element 1242, which is similar to the first element 1202 of the fifth embodiment in FIG. 29, is different in that the wall supported the opposite ends of the bridge is in the form of an annular continuous wall. Accordingly, portions of the first element 1242 of this embodiment are designated by reference numerals obtained by adding "40" to the reference numerals given to the same or similar portions or elements of the first element in FIG. 29 and no duplicative description is made to those portions and elements.

The second element 1243 includes a hollow or solid cylindrical body 1260. The cylindrical body 1260 is of a size capable of being grasped by human hand. An annular wall 1261 is formed continuously along the lower end periphery of the cylindrical body 1260, with a reception space 1262 for the first element being formed inside the annular wall 1261. The inner diameter of the annular wall 1261 is larger than the outer diameter of the annular wall 1250 of the first element 1242 so that the first element 1242 received in the reception space 1262 can sway.

In this embodiment, a bottom surface 1248 and a top surface 1249 of a bridge 1247 define a first surface and a second surface, respectively, of the first element, and a lower end surface 1263 and an upper end surface 1264 of the cylindrical body 1260 define a first surface and a second surface, respectively, of the second element. In the sixth embodiment, a projection 1253 is formed on the top surface 1249 of the bridge 1247, with a concave contact portion 1265 being formed on the lower end surface 1263 of the cylindrical body 1260.

In the applicator 1241 of the sixth embodiment so constructed, the first element 1242 supported the patch 2 is received in the reception space 1262 of the second element 1243. In this state, the second element 1243 is held by hand to press the first element 1242 against the skin. As a result, the needles on the patch 2 insert into the skin. At this time, even if the cylindrical body 1260 of the second element 1243 is not directed vertically toward the skin, the first element 1242 turns around the tip of the projection 1253 so that the bridge 1247 is directed parallel to the skin to allow the needles supported on the bottom surface thereof to vertically insert into the skin. This prevents the needles from being bent, damaged, or broken at the insertion of the needles.

Others

Although the embodiments and modifications of the applicator according to the present invention have been described hereinabove, portions of the applicator may be made of any material selected from a group consisting of metals, nonmetals and resins. As for the thicknesses and shapes of the portions such as the bridge and the inclined portions to be deformed in the applicator, they may be selected depending on the natures of the materials.

The shapes of the portions described in the above embodiments and modifications are merely examples and are not restrictive.

Seventh Embodiment

Figure 37:
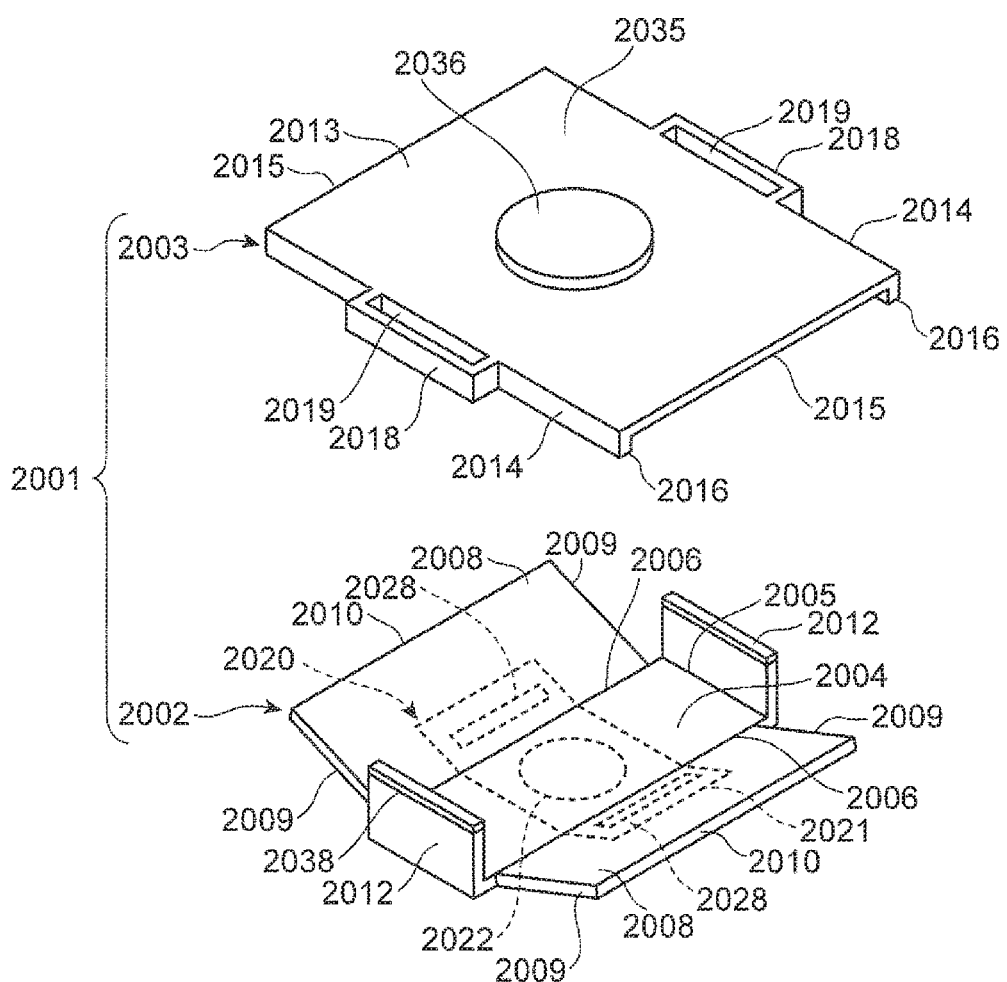
FIG. 37 is an exploded perspective view showing an applicator of a seventh embodiment according to the present invention.

FIG. 37 shows a seventh embodiment of the applicator according to the present invention. In the drawing, the applicator of the seventh embodiment is generally designated at reference numeral 2001 and includes a first element 2002 and a second element 2003. The first element 2002 and the second element 2003 may be made of a metal or a resin, or one may be made of a metal while the other may be made of a resin.

The first element 2002 has a central plate portion 2004 and inclined plate portions 2008 connected integrally to opposite sides of the central plate portion 2004. The central plate portion 2004 is a rectangular plate portion defined by edges 2005 and 2006 extending in the X-direction and Y-direction. The inclined plate portions 2008 are connected to the Y-direction edges 2006 of the central plate portion 2004. The inclined plate portions 2008 are rectangular plate portions each defined by a pair of parallel edges 2009 extending outward and upward from the vicinities of both ends of the Y-direction edges 2006 of the central plate portion 2004 so as to go apart from each other, and the edges 2006 and edges 2010 joining the ends of the edges 2009 and extending in parallel in the Y-direction.

The pair of X-direction edges 2005 of the central plate portion 2004 are formed integrally with rectangular vertical plate portions, i.e., sensor portions 2012 extending upward therefrom.

The second element 2003 has a plate portion 2013. The plate portion 2013 is a rectangular plate defined by edges 2014 and 1015 extending in the X-direction and Y-direction. The X-direction edges 2104 are formed integrally with lower flanges or horizontal guide portions 2016 extending along the edges 2014. In the embodiment, the Y-direction inner dimension between the opposed horizontal guide portions 2016 is substantially equal to the Y-direction length of the end edges 2010 of the inclined plate portions 2008 so that the end portions 2010 of the inclined plate portions 2008 can be received inside the opposed horizontal guide portions 2016. The distance between the opposed Y-direction edges 2015 is larger than the X-direction interval between the end edges 1010 of the pair of inclined plate portions 2008 so that the end edges 2010 of the pair of inclined plate portions 2008 are in contact with a bottom surface 2017 of the plate portion 2013 lying between the horizontal guide portions 2016 (see FIG. 41).

Therefore, in the embodiment, a bottom surface 2007 of the central plate portion 2004 forms a first bottom surface portion while bottom surfaces 2011 of the pair of inclined plate portions 2008 form a second bottom surface portion. The bottom surface 2017 (FIG. 41) of the plate portion 2013 forms a contact portion.

The X-direction edges 2014 of the plate portion 2013 are also formed integrally with outward protruding extended portions 2018. The extended portions 2018 are positioned at centers on the edges 2014 and have slots or apertures 2019 extending in the X-direction. The size, or cross sectional, of the aperture 2019 is slightly larger than the cross section of the vertical plate portions 2012 of the first element 2002 so that the vertical plate portions 2012 of the first element 2002 are inserted into the apertures 2019 from below.

In the embodiment, a finger rest 2036 of a predetermined shape is formed at a center on the top surface 2035 of the plate portion 2013. Although in the shown embodiment, the finger rest 2036 is a circular raised platform, its planar shape may be a raised portion or a recessed portion of another shape including a polygon such as a quadrangle, an oval, and a star, or may be a spherical raised or recessed portion, or may be a mere marking or pattern.

Figure 38:
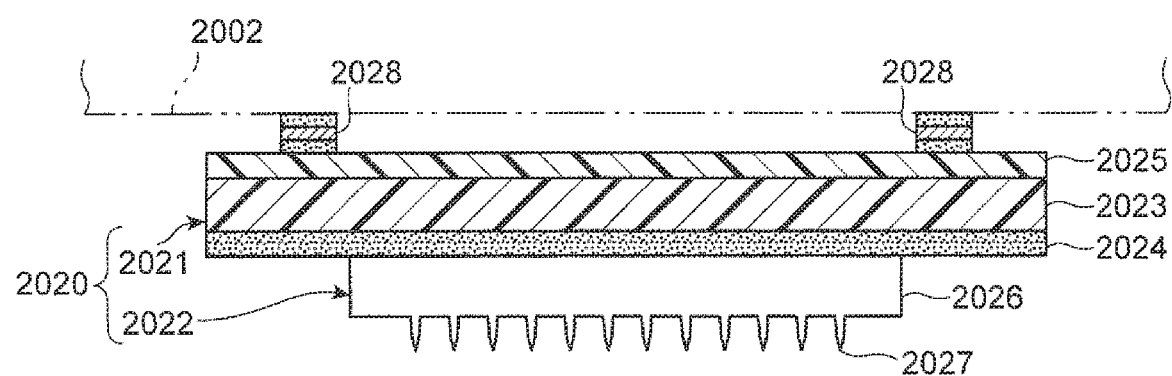
FIG. 38 is a sectional view showing a structure of the microneedle patch for use with the applicator of the seventh embodiment.
Figure 39:
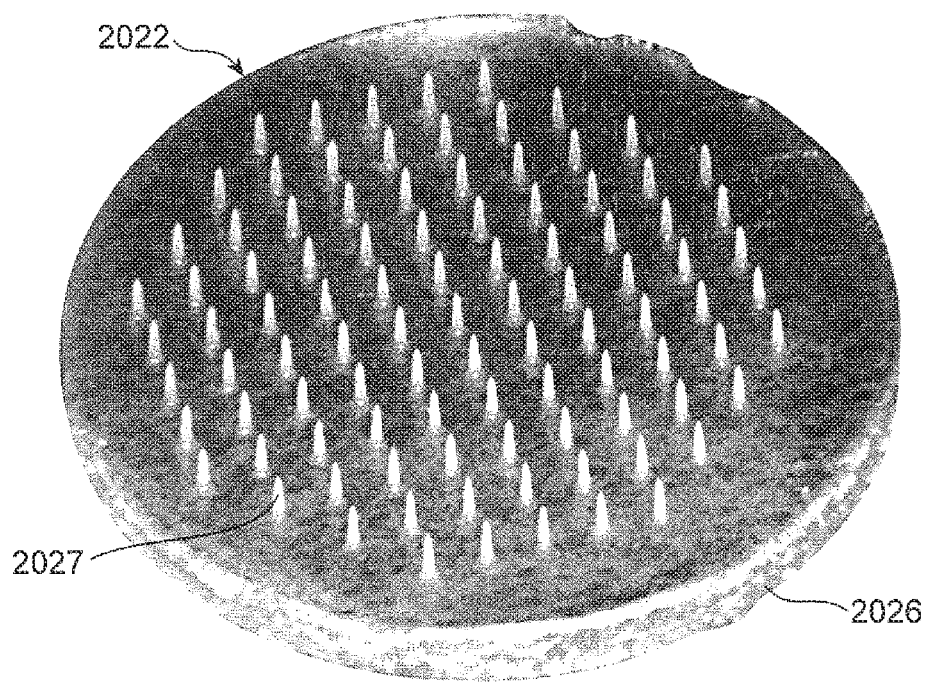
FIG. 39 is a photograph of an actual microneedle array shot from diagonally below.

As schematically shown in FIG. 38, a patch 2020 has a sheet substrate 2021 and a microneedle array 2022 supported thereon. The sheet substrate 2021 has a substrate film 2023, a pressure-sensitive adhesive layer 2024 provided on a bottom surface (a surface supporting the microneedle array 2022) of the substrate film 2023, and a release treatment layer (a releasing layer) 2025 provided on a top surface (a surface opposing the applicator 1) of the substrate film 2023. As shown in FIG. 39, the microneedle array 2022 has a circular or rectangular base 2026 and a multiplicity of elongated needles 2027 with a predetermined height (e.g., 300 to 1000 micrometers) arrayed at predetermined intervals (e.g., 300 to 1000 micrometers) in a lattice or honeycomb pattern on a bottom surface of the base 2026. The microneedle array 2022 is formed, for example, by filling a biodegradable synthetic polymer material (e.g., hyaluronic acid, collagen, polylactic acid, polyglycolic acid) into a correspondingly shaped mold. Although not shown, tip portions of the needles 2027 are coated with a target drug (molecules such as vaccine, protein, and peptide). Alternatively, or additionally, the target drug may be contained in the needles 2027 by being mixed with materials of the needles during molding of the microneedle array 2022.

The sheet substrate 2021 and the microneedle array 2022 are arranged so that the base 2026 of the microneedle array 2022 is applied on the pressure-sensitive adhesive layer 2024 of the sheet substrate 2021. As shown, the sheet substrate 2021 is larger than the microneedle array 2022 so that a sufficient area of the pressure-sensitive adhesive layer 2024 is exposed around the microneedle array 2022 when the microneedle array 2022 is applied on the sheet substrate 2021.

The thus formed patch 2020 is supported on the bottom surface 2007, 2011 of the first element 2003. Specifically, as shown in FIGS. 37 and 40, both-side substrate portions 2029 of the sheet substrate 2021 are adhered to the inclined plate portions 2008 by use of double-sided adhesive tapes 2028. At this time, as shown, the double-sided adhesive tapes 2028 are apart a predetermined distance from edges 2030 of the sheet substrate 2021. The double-sided adhesive tapes 2028 serve to retain the patch 2020 on the bottom surface 2007, 2011 of the first element 2002 before the patch 2020 is applied to the skin. Hence, the size, shape, position, and pressure-sensitive adhesive force of the double-sided adhesive tapes 2028 are preferably determined so that the patch 2020 can be retained on the first element 2002 and so that the patch 2020 applied to the skin by the pressure-sensitive adhesive layer 2024 cannot separate from the skin by an adhesive force between the skin double-sided adhesive tapes 2028 and the first element 2002 when the applicator 2001 is removed from the patch 2020 after attachment to the skin. Considering these conditions, in the seventh embodiment, the double-sided adhesive tapes 2028 are sized as small as possible and are applied to a position shifted a determined distance inward from both ends of the sheet substrate 2021.

When the patch 2020 is applied to the human or animal skin using the applicator 2001 holding the patch 2020 in this manner, the plate portion 2013 of the second element 2003 is pressed at its top surface center by a finger 2031 as shown in FIG. 41. A pressing force 2032 applied to the plate portion 2013 acts on the edges 2010 of the both inclined plate portions 2008 through the bottom surface (contact portion) 2017 of the plate portion 2013. As a result, the inclined plate portions 2008 resiliently deform allowing allow its ends to move downward with respect to the central plate portion 2004. This deformation allows that the edges 2010 of the inclined plate portions 2008 slide outwardly along the bottom surface (contact portion) 2017 of the plate portion 2013.

Figure 40A:
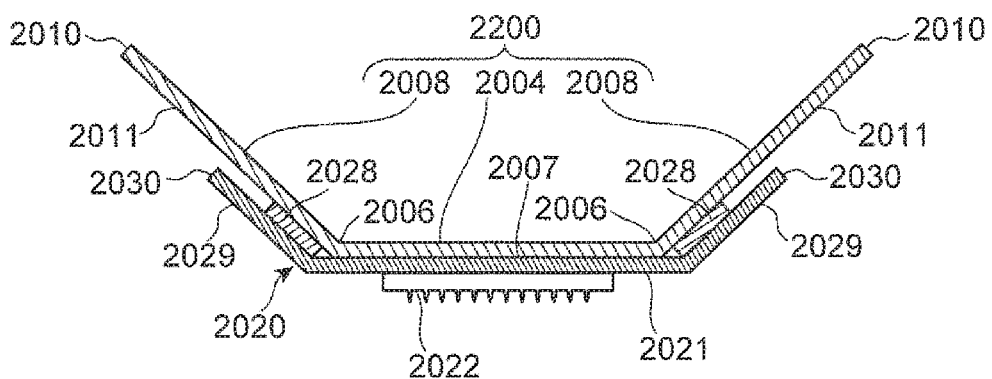
FIGS. 40A-40C are sectional views showing a function and and an action of a first element of the applicator shown in FIG. 37.
Figure 40B:
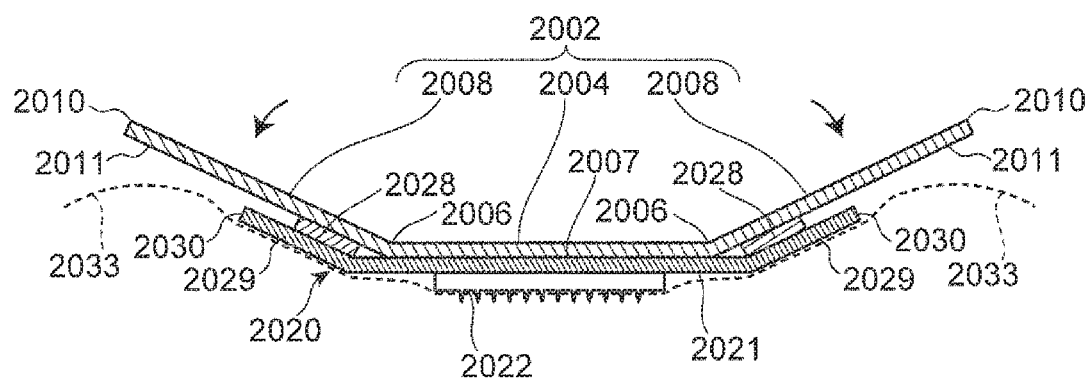

The pressing force 2032 is transmitted to the inclined plate portions 2008 and the central plate portion 2004 of the first element 2002. As a result, as shown in FIGS. 40A and 40B, the patch 2020 supported on the bottom surface 2007, 2011 of the central plate portion 2004 and the inclined plate portions 2008 is pressed against the skin 2033. At this time, not only the central plate portion 2004 but also the inclined plate portions 2008 are pressed against the skin 2033. Accordingly, the pressure-sensitive adhesive layers of the substrate portions 2029 supported on the inclined plate portions 2008 are pressed against the skin 2033 with a suitable force to adhere thereto.

Figure 40C:
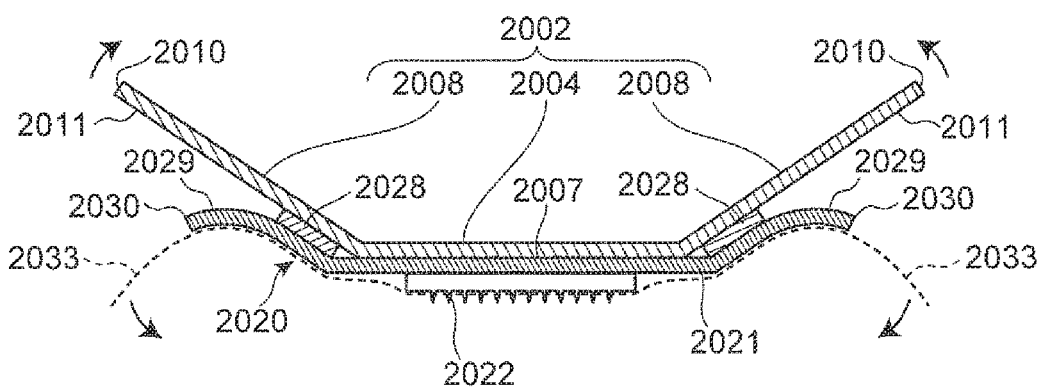

Thereafter, when the pressing force 2032 is removed, the inclined plate portions 2008 are restored to their pre-deformation states based on their resiliencies. At this time, as shown in FIGS. 40A-40C, the end edges 2030 of the sheet substrate 2021 adhered to the skin 2033 go apart from the inclined plate portions 2008, together with portions of the skin to which the end edges 2030 adhere. Consequently, in conjunction with the restoration to the pre-deformation states of the inclined plate portions 2008 apart from the skin 2033, the double-sided adhesive tapes 2028 are subjected at their outside edges to a concentrated peeling force. This allows the sheet substrate 2021 to peel off easily from the double-sided adhesive tapes 2028 while adhering to the skin 2033. Accordingly, the patch 2020 applied to the skin can be separated from the applicator 1 while being held securely on the skin.

In this manner, according to the applicator of this embodiment, the patch 2020 adhered to the skin 2033 comes apart from the applicator 1, starting from its distal end portions 2029. Thus, when separating the applicator 2001 from the skin 2033, the patch 2020 cannot peel off from the skin 2033 while adhering to the applicator 2001 so that the needles 2027 once stuck into the skin keeps its inserting state.

In the above embodiment, the boundaries or the edges 2006 of the central plate portion 2004 between the central plate portion 2004 and the side plate portions 2008 of the first element 2002 may have weakened portions extending therealong so that when the pressing force 2032 acts thereon, the side plate portions 2008 can easily resiliently deform. Specifically, as shown in FIG. 41, along top surface boundaries and bottom surface boundaries between the central plate portion 2004 and the inclined plate portions 2008, there may be formed a continuous notch 2034 (e.g., U-shaped or V-shaped notch) or an intermittent notch (e.g., slots or slits not shown).

In the above embodiment, as shown in FIG. 37, a finger rest 2036 with a predetermined shape may be formed at a center on the top surface 2035 of the plate portion 2013 of the second element 2003. Since in this modification, the plate portion 2013 can be pressed at its center, the pressing force 2032 acts uniformly on the right and left inclined plate portions 2008, resulting in an even improved vertical, penetration performance of the needles. Although in the shown example, the finger rest 36 is a circular raised platform, the planar shape thereof may be a raised portion or a recessed portion of another shape including a polygon such as a quadrangle, an oval, and a star, or may be a spherical raised or recessed portion, or may be a mere marking or pattern.

Figure 42:
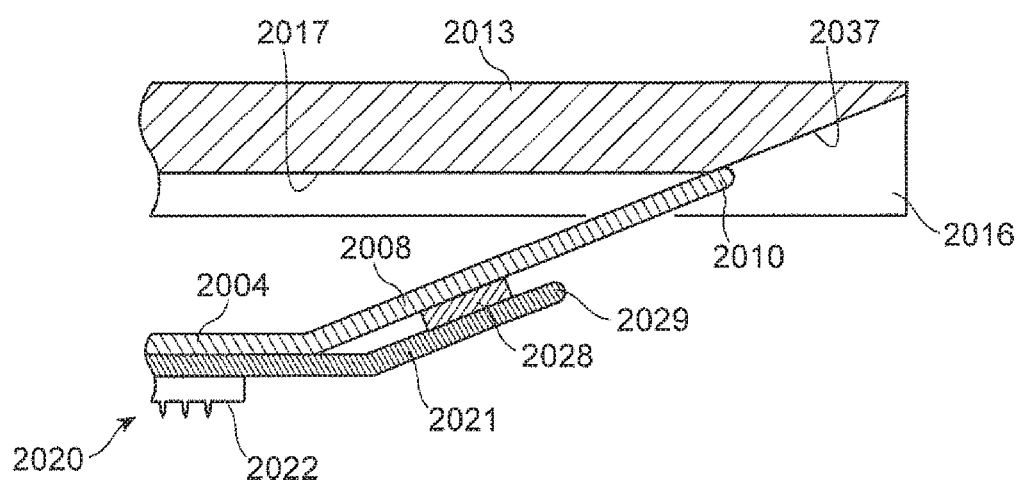
FIG. 42 is a sectional view showing a modification of the seventh embodiment.

As shown in FIG. 42, the bottom surface of the plate portion 2013 of the second element 2003 may have, in regions with which the edges 2010 on the distal ends of the inclined plate portions 2008 are in contact, an inclined surface 2037 or a convex or concave inclined curved surface that extend outward and diagonally upward. In this embodiment, when the pressing force 2032 is applied, the inclined plate portions 2008 resiliently deform more easily. This enables the inclined plate portions 2008 to deform with an even smaller pressing force. This modification is applicable to other embodiments that will be described later.

Although not shown, in the first element 2, the inclined plate portions 2008 may have a thickness smaller than that of the central plate portion 2004 so that the inclined plate portions 2008 can deform with a small pressing force.

Figure 41A:
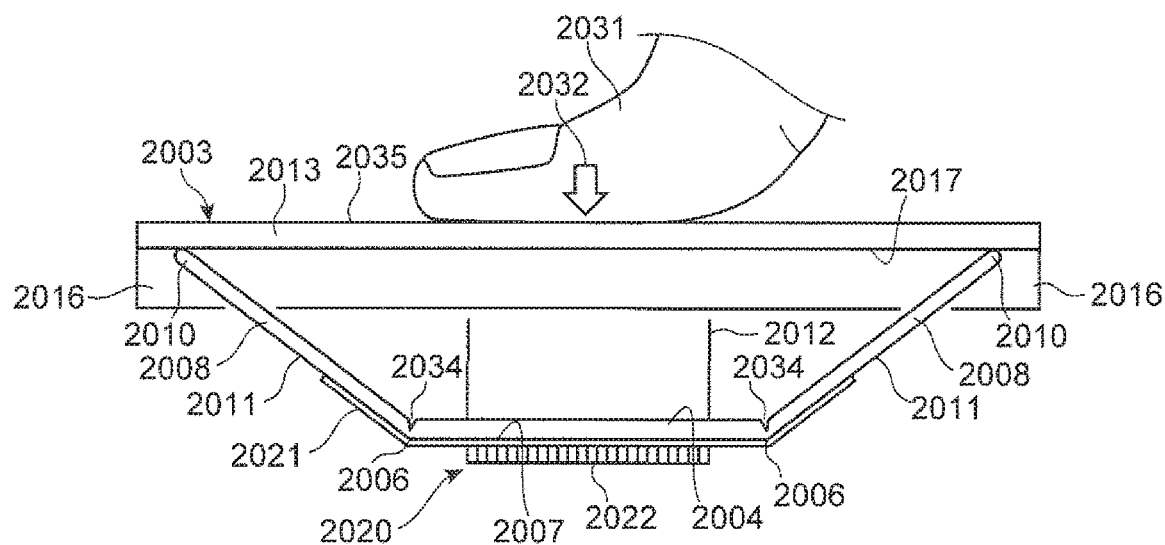
FIGS. 41A and 41B are sectional views showing a function and an action of the applicator shown in FIG. 37, in addition to FIG. 40.
Figure 41B:
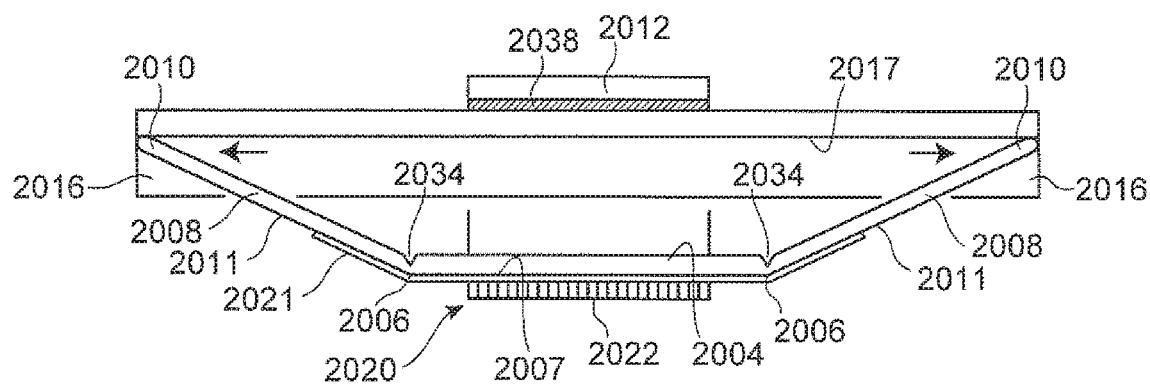

As shown in FIGS. 41A and 41B, the height of the vertical plate portions 2012 may be determined so that though the vertical plate portions 2012 cannot protrude from the top surface of the plate portion 2013 before the inclined plate portions 2008 deforms, the vertical plate portions 2012 protrude from the top surface of the plate portion 2013 when the predetermined pressing force 2032 is applied and the inclined plate portions 2008 deform a predetermined amount, or so that a marking 2038 (see FIG. 37) imparted to the vertical plate portions 2012 or another marking appears from the tip surface of the plate portion 2013 in that state. This allows the user to visually check the vertical plate portions 2012 appearing from the top surface of the plate portion 2013, to verify whether the desired pressing force 2032 is applied to the plate portion 2013. Since as shown, the central plate portion 2004 supporting the patch 2020 protrudes toward the skin so that almost of the pressing force 2032 acts as an inserting force of the needles 2027 on the patch 202 supported on the central plate portion 2004, appearing of the marking 2038 from the top surface 2035 of the plate portion 2013 substantially means that a predetermined inserting force acts on the needles 2027.

Figure 43:
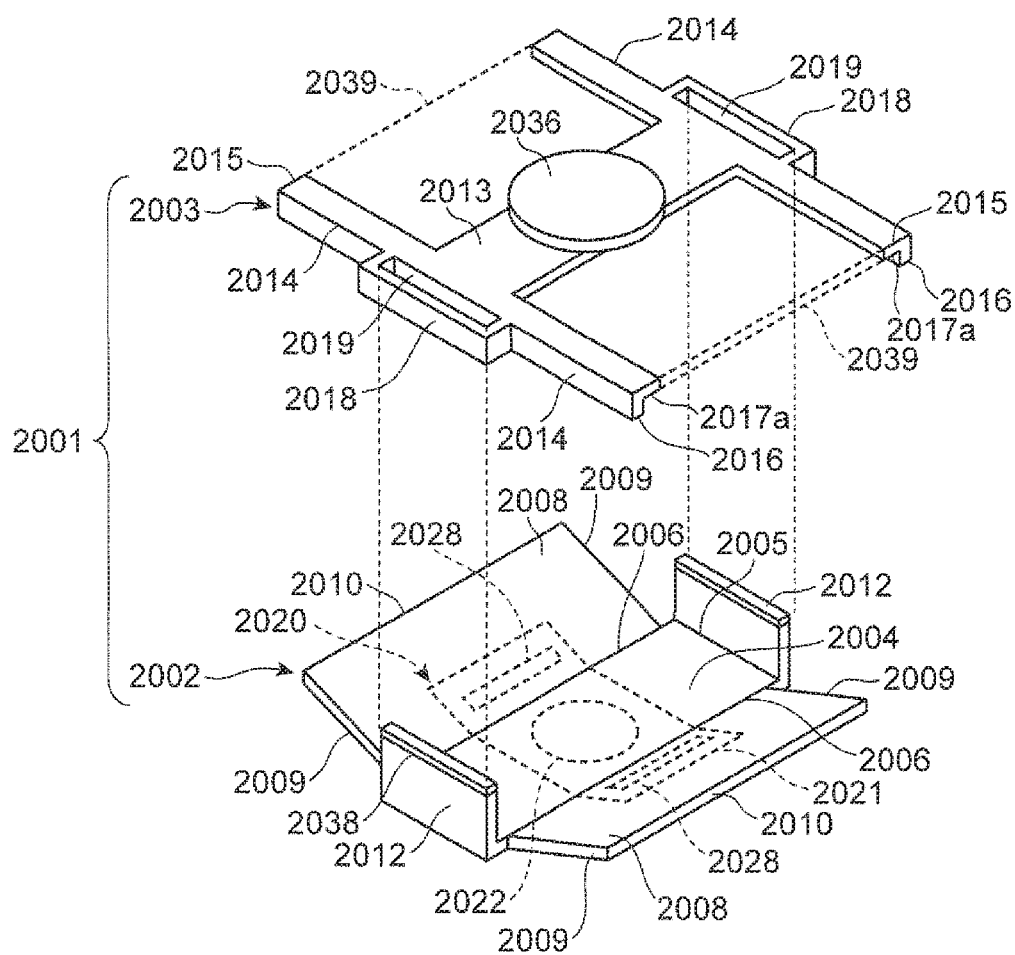
FIG. 43 is an exploded perspective view showing the modification of the seventh embodiment.

As shown in FIG. 43, the plate portion 2013 of the second element 2003 may be cut away at its center regions 2039 on the edges 2015 extending in Y-direction. In this case, bottom surface remainders 2017a in the vicinity of the X-direction edges 2014 and adjoining the lower flanges 2016 function as contact portions or guide portions guiding the inclined plate portions 2008.

Eighth Embodiment

Figure 44:
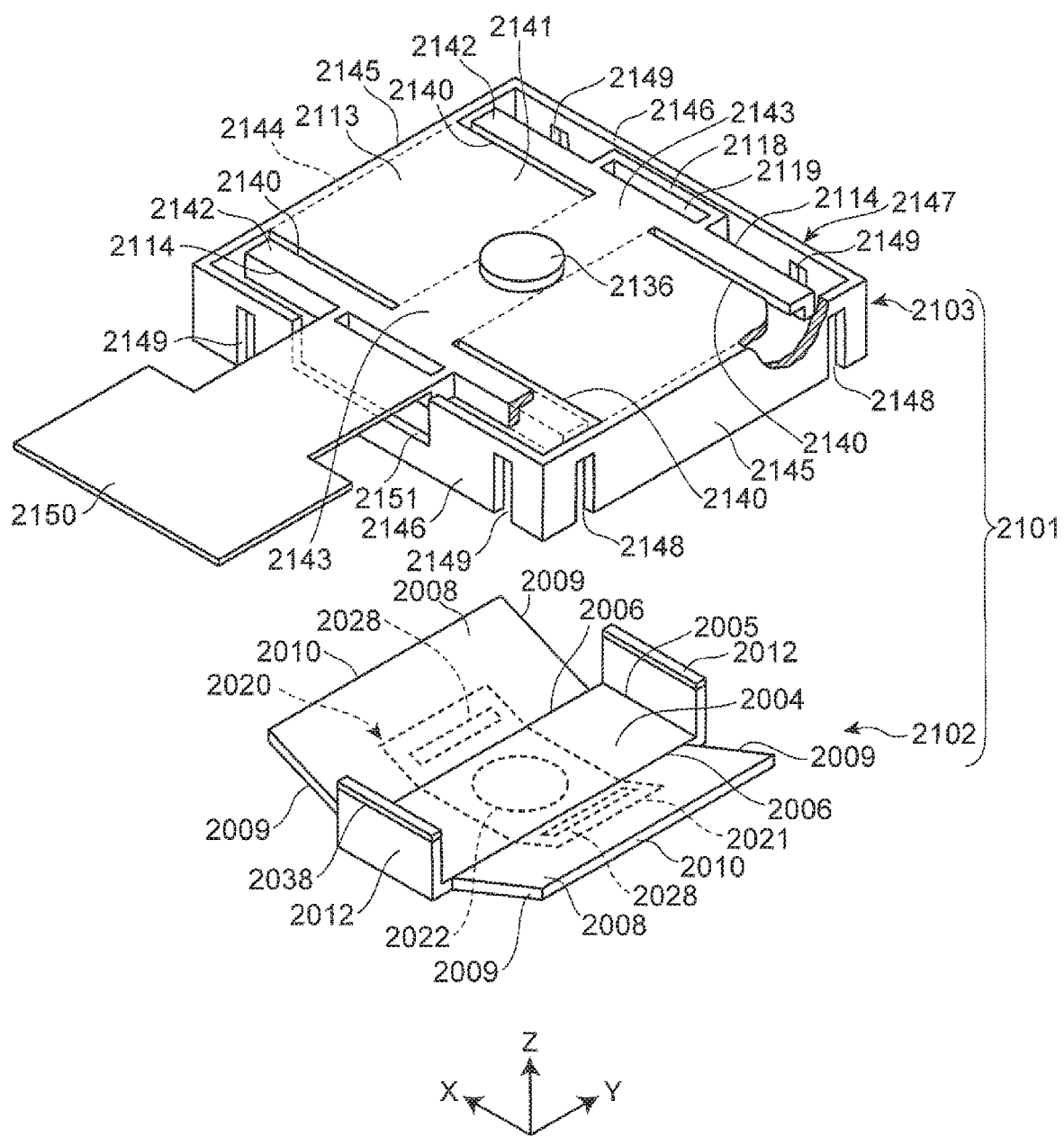
FIG. 44 is an exploded perspective view showing an applicator of an eighth embodiment.

FIG. 44 shows an eighth embodiment of the applicator according to the present invention.

As shown, the applicator of the eighth embodiment is generally designated at reference numeral 2101 and includes a first element 2102 and a second element 2103. The first element 2102 and the second element 2103 may be made of a metal or a resin or one may be made of a metal and the other may be made of a resin.

The first element 2102 is the same as the first element 2002 of the seventh embodiment described above. Accordingly, in the following description of the eighth embodiment, portions in connection with the first element among features contained in the eighth embodiment are designated by reference numerals imparted to the first element in the seventh embodiment and will not again be described.

In the second element 2103, the plate portion 2113 has, at positions apart a predetermined distance inwardly (in the Y-direction) from X-direction edges 2114, slits or notches 2140 extending inwardly from Y-direction edges, by which the plate portion 2113 is divided into deformation portions 2141 lying between the pair of notches 2140 and a pair of inverted-L-shaped guide portions 2142 lying on the outsides of the deformation portions 2141. The deformation portions 2141 and the guide portions 2142 are connected together by a central connecting portion 2143 remaining between the notches 2140 aligned in the X-direction.

Edges 2145 extending in the Y-direction of the deformation portions 2141 are integrally connected to walls 2146 extending in the Y-direction. Both ends of the walls 2145 are integrally connected to walls 2146 extending in the X-direction, with these walls 2144 and 2146 forming a rectangular frame 2147.

Figure 45A:
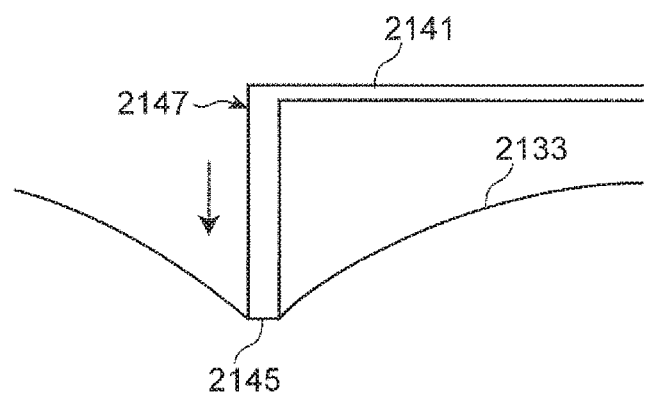
FIGS. 45A and 45B are views showing an action of the applicator of the embodiment shown in FIG. 44.

Preferably, in this embodiment the Y-direction walls 2145 have at their respective both end portions a notch 2148 in the form of a slot or a slit extending upward from the lower ends of the walls 2145. In this instance, as shown in FIGS. 45A and 453, when the deformation portions 2141 are subjected to the pressing force 2132 and deform or bend downward, the walls 2145 integrally connected to the deformation portions 2141 deform so that the lower ends thereof are displaced outward. As a result, a skin 2133 lying between the walls 2145 is pulled outward by the contact with the walls 2145, improving the vertical penetration performance of the needles. Although in the state where the skin is not subjected to any tension (e.g., state where the skin is loose), the needles cannot insert into the skin until the needles are thrust into the skin with a substantial force, the needles can insert into the skin with a less pressing force or with a less push amount in the state where the skin is tensioned as above.

In addition to the walls 2145, the X-direction walls 2146 may also have a similar notch 2149 at their respective both ends. Since in this case, the skin 2133 in the region surrounded by the frame 2147 is pulled on all sides, the penetration performance of the needles into the skin 2133 is further improved. Moreover, as described above, the needles can insert into the skin with a less pressing force or with a less push amount.

While the deformation portions 2141 deform due to the pressing force 2132 acting thereon, the inclined plate portions 2008 of the first element 2102 are guided by respective end corners by the guide portions 2142. Because the amount of deformation of the end portions of the deformation portions 2141 at this moment is small, the motions of the inclined plate portions 8 are not restricted by the deformation.

Figure 45B:
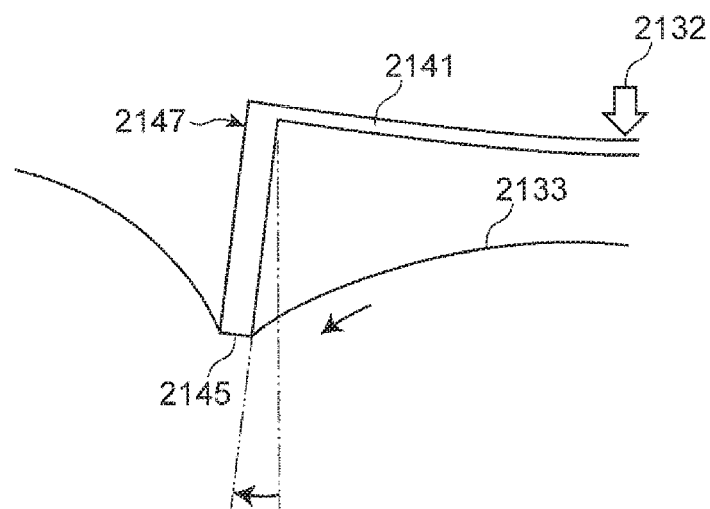

As shown in FIG. 44, an extended portion 2118 on one hand of the second element 2103 may be extended outward in Y-direction to form a grip 2150. Preferably, the adjoining X-direction wall 2146 is partially cut away at its upper portion to form an opening 2151 so that the grip 2150 cannot interfere with the wall 2146. According to this modification, in use, the user can depress the plate portion 2136 with the thumb to impart the pressing force 2132 (FIG. 45) thereto while holding the grip 2150 in hand, advantageously enabling a single-hand operation for good operability.

Ninth Embodiment

Figure 46:
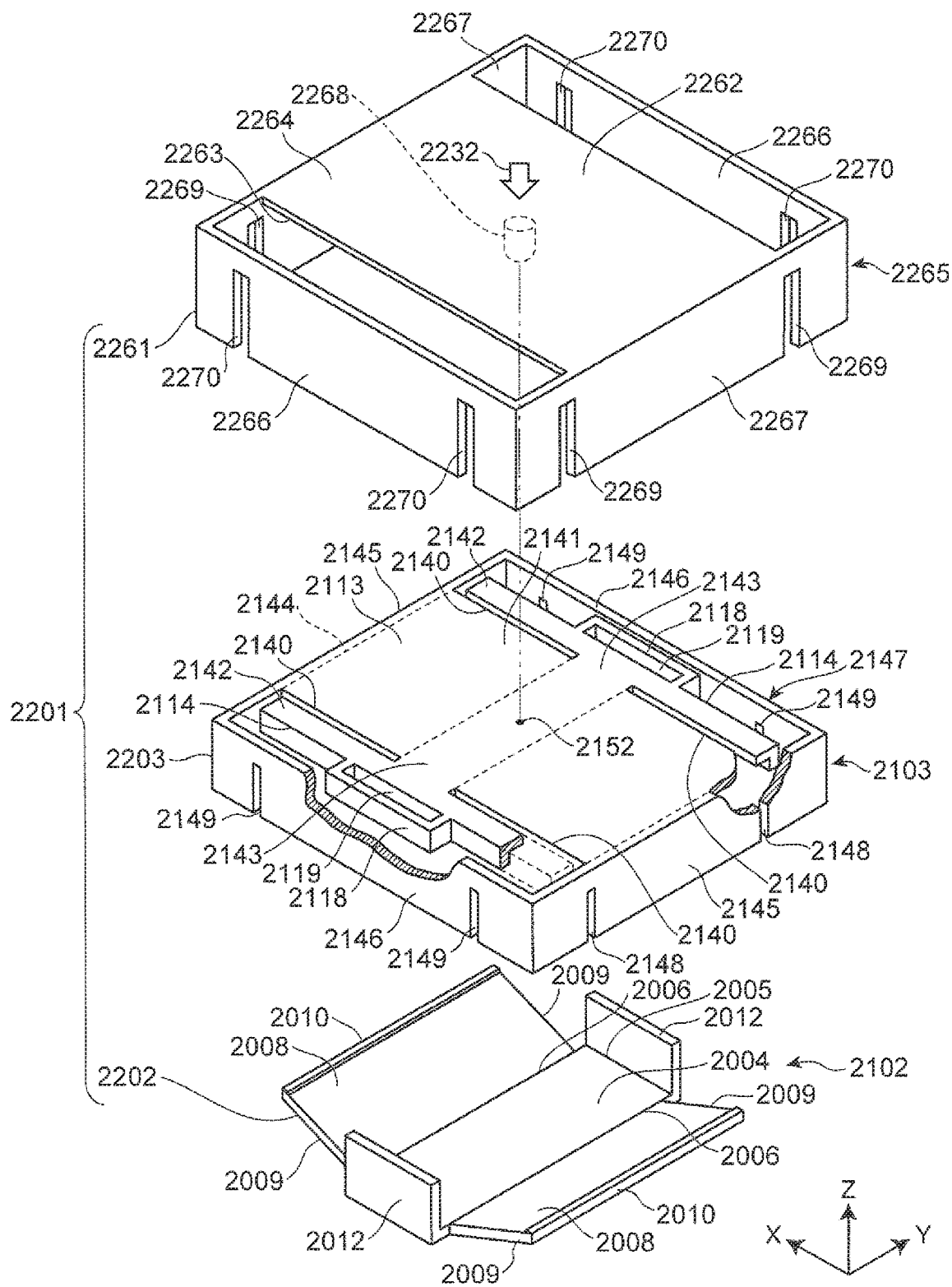
FIG. 46 is an exploded perspective view showing an applicator of a ninth embodiment.

FIG. 46 shows a ninth embodiment of the applicator according to the present invention.

In the drawing, the applicator of the ninth embodiment, which is generally designated at reference numeral 2201, includes a first element 2202, a second element 2203, and a third element 2261. The first element 2202, the second element 2203, and the third element 2261 may be made of any metal or resin, or one or two thereof may be made of a metal and the remainder may be made of a resin.

The first element 2202 is the same as the first element of the eighth embodiment described above. Accordingly, in the following description of the ninth embodiment, portions in connection with the first element among features contained in the ninth embodiment are designated by reference numerals imparted to the first element in the eighth embodiment and will not again be described.

The second element 2203 is the same as the second element of the above eighth embodiment except that the grip and the opening are deleted. Accordingly, in the following description of the ninth embodiment, portions in connection with the second element among features contained in the ninth embodiment are designated by reference numerals provided for the second element in the eighth embodiment and will not again be described.

The third element 2261 has a plate-like bridge 2262 extending in the X-direction. As shown, the bridge 2262 has a bottom surface 2263 and a top surface 2264. The bridge 2262 is connected at its both ends to a frame 2265. The frame 2265 is configured by connecting a pair of walls 2266 extending in the X-direction and a pair of walls 2267 extending in parallel in the Y-direction, with ends of the bridge 2262 being integrally connected to central upper ends of the Y-direction walls 2267.

The inner peripheral shape of the frame 2265 formed by inner surfaces of the walls 2266 and 2267 is slightly larger than the outer peripheral shape of the frame 2147 of the second element 2203. Specifically, X- and Y-direction inner dimensions of the frame 2265 of the third element 2261 are slightly larger than X and Y direction outer dimensions of the frame 2147 of the second element 2203, whereby the second element 2203 can be received inside the frame 2265 of the third element 2261 so that the second element 2203 received inside the frame 2265 of the third element 2261 may move relative to the third element 2261.

The bridge 2262 has a projection 2268 formed integrally on the bottom surface 2263 thereof. The projection 2268 is positioned so as to oppose a top surface center (a contact portion 2152) of the plate portion 2113 when the second element 2203 is received in the frame 2265 of the third element 2261. In the eighth embodiment, the projection 2268 is in the shape of an elongated rod extending in the vertical direction. The projection 2268 may be provided at a center on the plate portion 2113 of the second element 2203, instead of on the bridge 2262 of the third element 2261.

In use of the applicator 2201 of the ninth embodiment configured in this manner, the first element 2202 is assembled to the second element 2203 as above. The second element 2203 having the first element 2202 assembled thereto is received inside the third element 2261.

The patch 2020 is adhered to the bottom surface of the first element 2202 as described above.

In order to attach the patch 202 to the human or animal skin from this state, the pressing force 2232 is applied to a center on the bridge 2262 of the third element 2261. The pressing force 2232 is transmitted through the central projection 2268 to the plate portion 2113 of the second element 2202. The pressing force 2232 is further transmitted from the plate portion 2113 through the connecting portion 2143 and the horizontal guide portions 2142 to the inclined plate portions 2008 of the first element 2202. As a result, the patch 2020 supported on the bottom surface of the first element 2202 is pressed against the skin. The inclined plate portions 2008 spread outward while the end corners 2010 are guided by the inverted-L-shaped guide portions 2142. At this time, the vertical plate portions 2012 of the first element 2202 are guided into the apertures 2119 of the second element 2203. As a result, the pressure-sensitive adhesive layer of the sheet substrate 2021 supported on the inclined plate portions 2008 is pressed against the skin with a suitable force to adhere thereto.

Afterward, when the pressing force 2232 is removed, the inclined plate portions 2208 of the first element 2202 return to their pre-deformation states. At this time, the side substrate portions 2029 of the sheet substrate 2021 adhering to the skin are separated from the inclined plate portions 2008 together with the skin portions to which the portions 2029 adhere. As a result, in conjunction with the restoration to the pre-deformation states of the inclined plate port ions 2008 apart from the skin, the double-sided adhesive tapes are subjected at their outer edges to a concentrated peeling force. This allows the sheet substrate 2021 to peel off easily from the double-sided adhesive tapes 2028 while adhering to the skin. Accordingly, the patch 2020 adhered to the skin can be separated from the applicator while being securely retained on the skin.

The pressing force 2232 applied to the bridge 2262 of the third element 2261 is transmitted through the projection 2268 to the central contact portion 2152 of the first element 2202. Hence, even if the point of action of the pressing force 2232 is off-center on the bridge 2262, the pressing force 2232 applied to the bridge 2262 acts on the center of the second element 2202. Therefore, the needles 2027 penetrate vertically into the skin. This prevents the needles 2027 from being bent, damaged, or broken at the insertion of the needles.

Preferably, the walls 2267 supporting the bridge 2262 in the third element 2261 have slits 2269 extending from the lower end of the walls 2267 toward the upper end. In this instance, when the pressing force 2232 is applied to the top surface of the bridge 2262 to bend the bridge 2262 downward, the portions of the walls between the slits 2269 easily move away from each other. Similarly, remaining portions of the walls 2266 of the frame 2265 of the third element 2261 may also have similar slits 2270. Thus, although in the state where the skin is not subjected to any tension (e.g., the state where the skin is loose), the needles cannot insert into the skin until the needles are thrust into the skin with a substantial force, the needles can insert into the skin with a less pressing force or with a less push amount when the skin is tensioned as above. The slits may extend in the opposite direction from the upper end toward the lower end.

Figure 47:
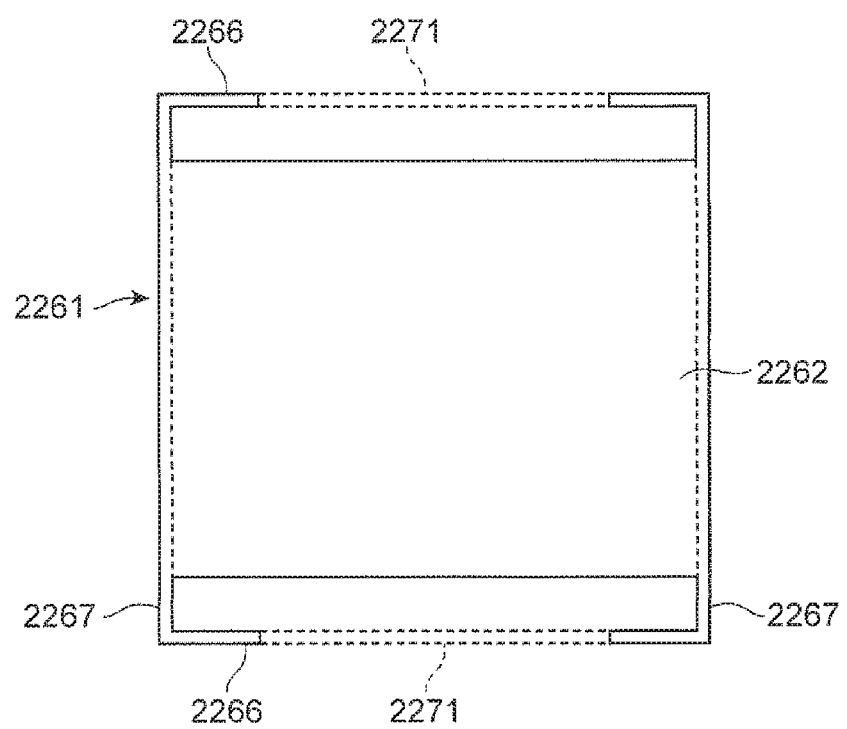
FIG. 47 is a plan view showing a modification of the ninth embodiment.

As shown in FIG. 47, the walls 2266 of the third element 2261 may be cut away at a part 2271. In this instance, the bridge 2262 can undergo a large deformation with a small pressing force 2232.

Figure 48:
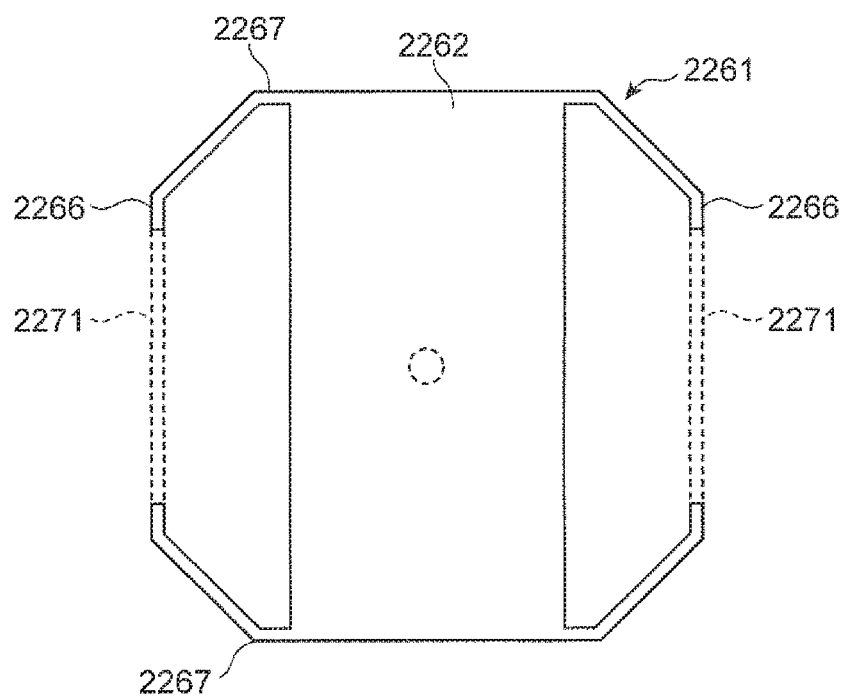
FIG. 48 is a plan view showing a modification of the ninth embodiment.

The frames of the second element 2203 and the third element 2261 may be of a shape other than the quadrangle, e.g., a circle, a hexagon, or an octagon (see FIG. 48).

Tenth Embodiment

Figure 49:
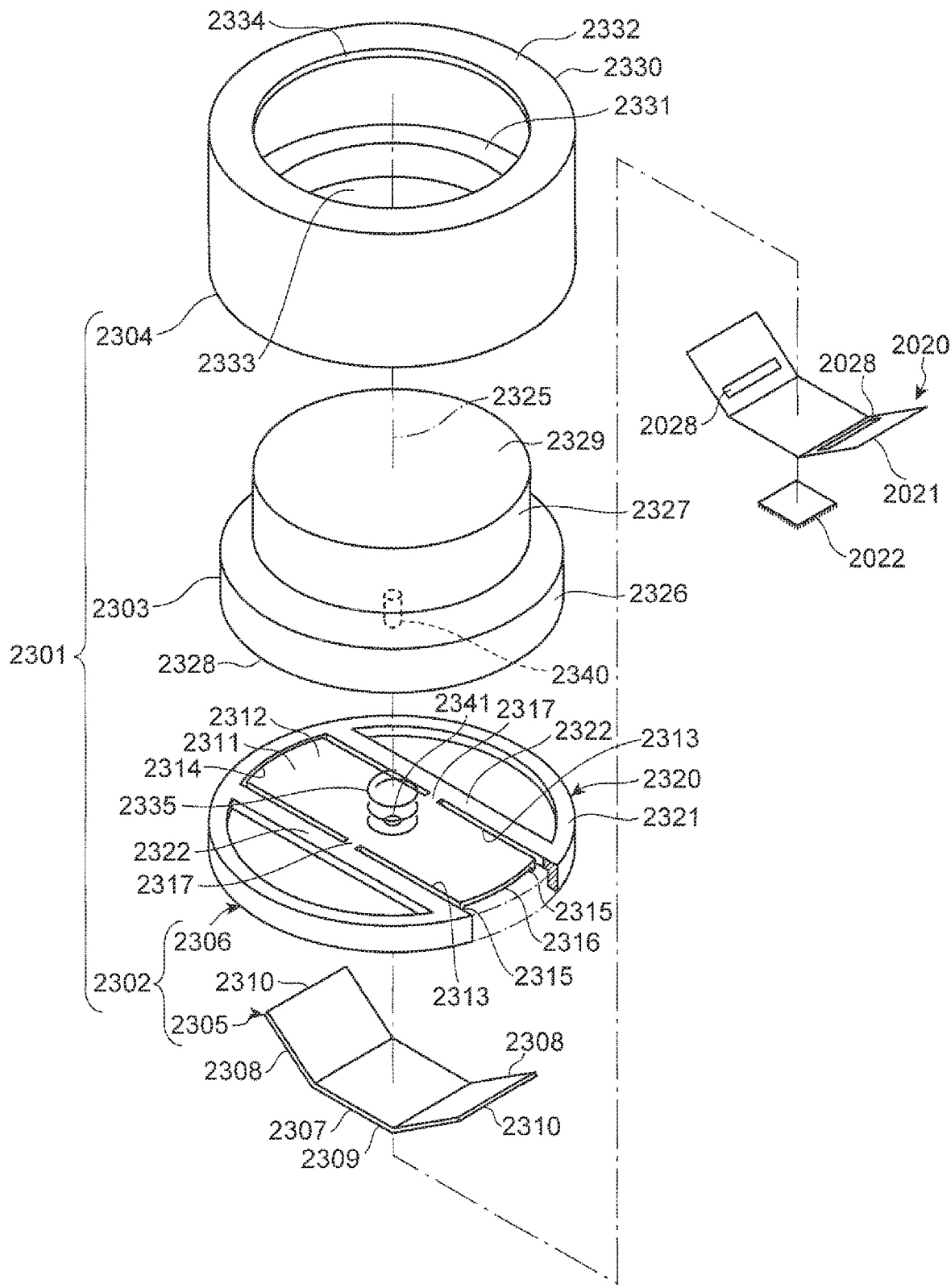
FIG. 49 is an exploded perspective view showing an applicator of a tenth embodiment.
Figure 50:
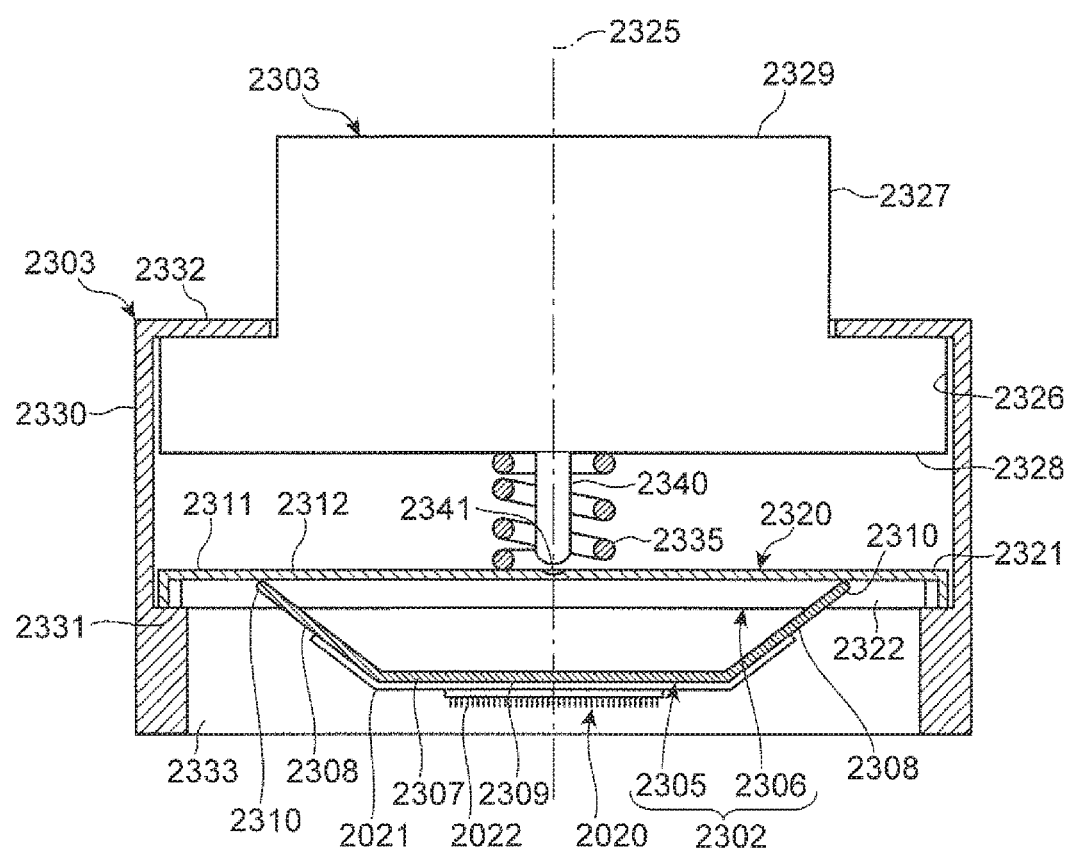
FIG. 50 is a longitudinal sectional view of the applicator of the tenth embodiment.
Figure 51:
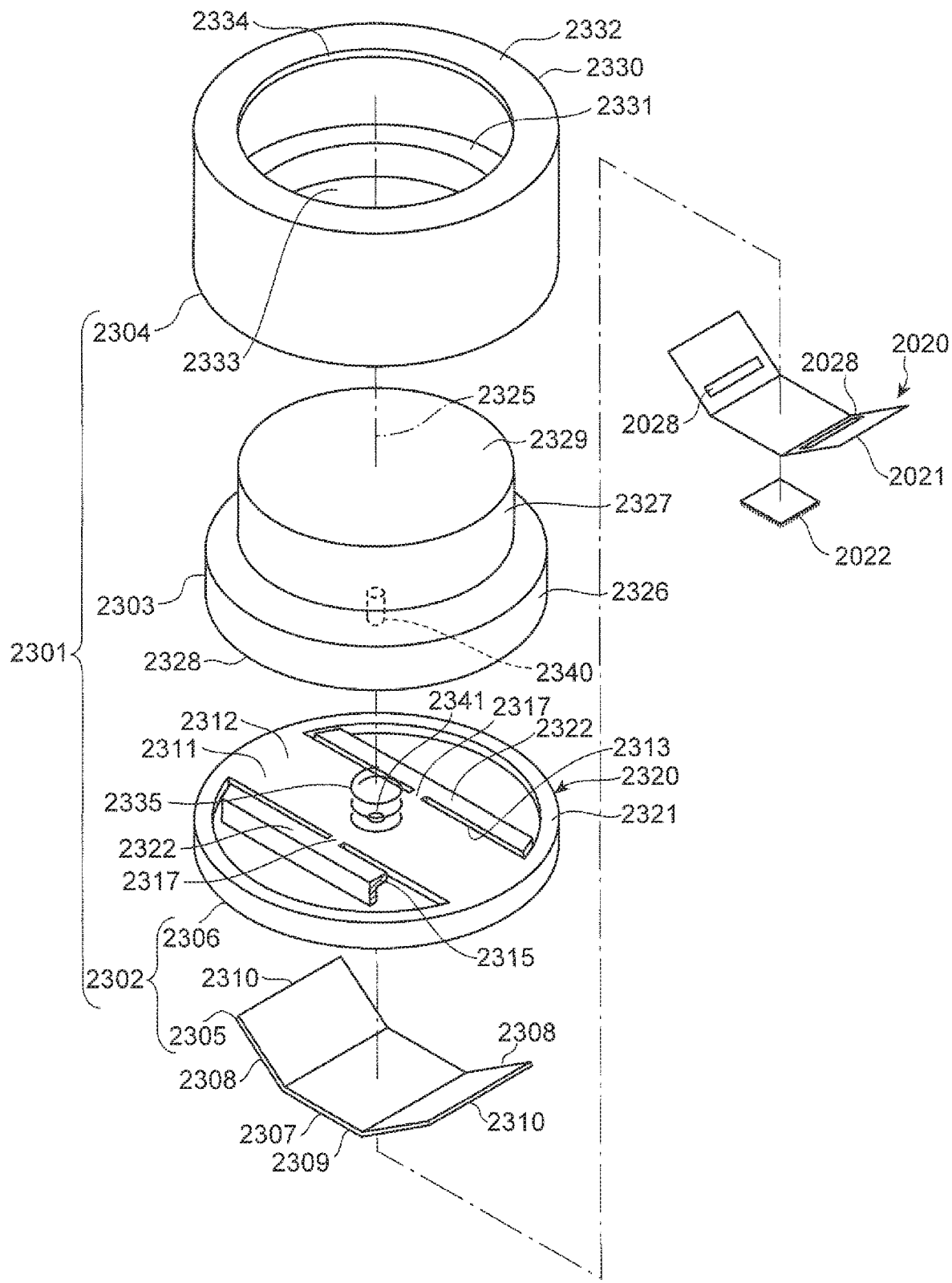
FIG. 51 is an exploded perspective view showing a modified example of the applicator of the tenth embodiment.

FIGS. 49 and 50 in which the microneedles are not shown show a tenth embodiment of the applicator according to the present invention.

In the drawing, the applicator of the tenth embodiment is generally designated at reference numeral 2301 and includes a first element 2302, a second element 2303, and a third element 2304, the first element 2302 including a first sub-element 2305 and a second sub-element 2306.

The first sub-element 2305 has a rectangular central plate portion 2307 and rectangular inclined plate portions 2308 connected integrally to a pair of opposed edges of the central plate portion 2307, with bottom surfaces 2309 of the central plate portion 2307 and of the inclined plate portions 2308 forming a first bottom surface portion and a second bottom surface portion, respectively. The structures, materials, thicknesses, etc., of the first sub-element 2305 are selected so that deformation is made so that when end edges 2310 of the both inclined plate portions 2308 are depressed downward, the distance between the end edges of the both inclined plate portions 2308 increases.

The second sub-element 2306 has a substantially rectangular plate portion 2311. The plate portion 2311 is bordered by a pair of longitudinally extending edges 2313 and a pair of widthwise extending edges 2314. In the tenth embodiment, the pair of longitudinally extending edges 2313 are parallel to each other. The pair of widthwise extending edges 2314 may similarly be parallel to each other, or they may lie on a circumference around a center of the plate portion 2311.

The longitudinal edges 2313 each have a guide flange 2315 protruding downward therealong. The distance between the opposed surfaces of the guide flanges 2315 is equal to or slightly larger than the width of the inclined plate portions 2308 so that a bottom surface 2316 of the plate portion 2311 lying between the guide flanges 2315 acts as a guide surface for the inclined plate portions 2308.

The plate portion 2311 is supported at central portions of the longitudinal edges 2313 by support frames 2320 by way of connecting portions 2317. The support frame 2320 has an annular ring 2321 and two bridges 2322. The annular ring 2321 has an outer diameter slightly smaller than the inner diameter of a hollow cylindrical portion 2330 of the third element 2304. The bridge 2322 extends in parallel along the longitudinal sides of the plate portion 2311 and, at its both ends, is integrally connected to the ring 2321. The bridge 2322 is integrally connected, at its center, to the plate portion 2311 by way of the connecting portion 2317.

The second element 2303 is a cylindrical member having a central axis 2325 and includes a lower cylindrical portion 2326 with a predetermined outer diameter and an upper cylindrical portion 2327 with an outer diameter smaller than that of the lower cylindrical portion 2326.

The third element 2304 includes a hollow cylindrical portion 2330 having the central axis 2325. The hollow cylindrical portion 2330 has at its lower end and upper end a lower flange and an upper flange, respectively, that extend inward, with a lower opening 2333 and an upper opening 2334 being formed inside the lower flange 2331 and the upper flange 2332, respectively.

The first to third elements 2302, 2303, 2304 configured as above are arranged so that the first element 2302 (only the second sub-element 2306) and the second element 2303 are incorporated into the lower portion and the upper portion within the hollow cylindrical portion 2330 of the third element 2304. The first sub-element 2305 of the first element 2302 is applied to the bottom surface 2316 of the second sub-element 2306 while supporting the patch 2020 adhered onto the bottom surface 2309.

The second element 2303 is arranged so that the lower cylindrical portion 2326 is provided inside the hollow cylindrical portion 2330, with the upper cylindrical portion 2327 protruding from the upper opening 2334 of the hollow cylindrical portion 2330.

A spring 2335 is provided between the first and second elements 2302 and 2303 located within the hollow cylindrical portion 2330. Although in the tenth embodiment, the spring 2335 is provided so as to surround a central projection 2340, the position to dispose the spring 2340 and the number thereof are not restrictive. Thus, the rings 2321 of the first element 2302 are pressed against the lower flange 2331 while the lower cylindrical portion 2326 of the second element 2303 is pressed against the upper flange 2332, whereby these first and second elements 2302 and 2303 are stably retained inside the hollow cylindrical portion 2330 with a slight gap left between the projection 2340 and a projection contact portion 2181 opposed thereto.

As described in the ninth embodiment, the hollow cylindrical portion 2330 of the third element 2304 is divided and formed into a plurality of portions for the purpose of receiving the first element 2302 and the second element 2303 inside thereof. For example, along a plane containing the central axis 2325, the hollow cylindrical portion 2330 may be divided into two semi-cylindrical portions, which may be combined together when assembling. Alternatively, the hollow cylindrical portion 2330 may be divided into the upper flange 2332 and a remaining cylindrical portion so that after receiving the first and second elements and the spring within the cylindrical portion, the upper flange 2332 may be assembled to the cylindrical portion.

In the applicator 2301 configured as above, the patch 2020 is applied to the bottom surface of the first element 2302. At this time, the microneedle array is provided on the central portion 2307 while the double-sided adhesive tapes 2028 are provided on the inclined plate portions 2308.

According to such a shape, by applying a pressing force to the upper cylindrical portion 2327 of the second element 2303 while abutting the patch 2020 applied to the bottom surface of the first sub-element 2305 against the skin, the third member 2303 descends against the biasing force of the spring 2335, allowing the projection 2340 to abut against the projection contact portion 2341 on the plate portion top surface 2312. When applying the pressing force, the plate portion 2311 of the first element 2302 curves downward to press the patch 2020 against a skin (not shown) and insert the needles into the skin. The pressure-sensitive adhesive layer of the patch 2020 adheres closely to the skin. Afterward, when the pressing force is removed, the first element 2302 and the second element 2303 are restored to the pre-application states of the pressing force by the actions of spring 2335 and of the resilient restoration force of the first element 2302.

In this manner, according to the applicator 2301, similar to the embodiments described above, the patch 2020 adhered to the skin can be detached from the applicator while securely holding the patch 2020 on the skin. Even though the point of action of the pressing force is offset from the central axis 2325, the pressing force can securely be transmitted through the projection 2080 to the center of the plate portion 2311. Hence, the needles of the patch 2020 supported on the first element 2302 insert vertically into the skin. This prevents the needles from being bent, damaged, or broken at the insertion of the needles.

Although in the tenth embodiment, the plate portion 2311 is separated at its both ends from the annular rings 2321 with the both ends of the bridges 2322 on both sides being connected to the annular rings 2321, the plate portion 2311 may be connected at its both ends to the annular rings while the bridges 2322 are separated at their both ends from the annular rings 2321, with the bottom surfaces of the bridges 2322 having the inverted-L-shaped guides 2315, respectively, along which the end corners of the inclined plate portions 2308 are guided.

Although the embodiments and Modifications of the applicator according to the present invention have been described hereinabove, portions of the applicator may be made of any material selected from a group consisting of metals, nonmetals and resins. As for the thicknesses and shapes of the portions (e.g., the bridge and the inclined portions) to be deformed in the applicator, the thicknesses and shapes achieving desired functions may be selected depending on the natures of the materials.

The shapes of the portions described in the above embodiments and Modifications are merely examples and are not restrictive.

Eleventh Embodiment

Figure 52:
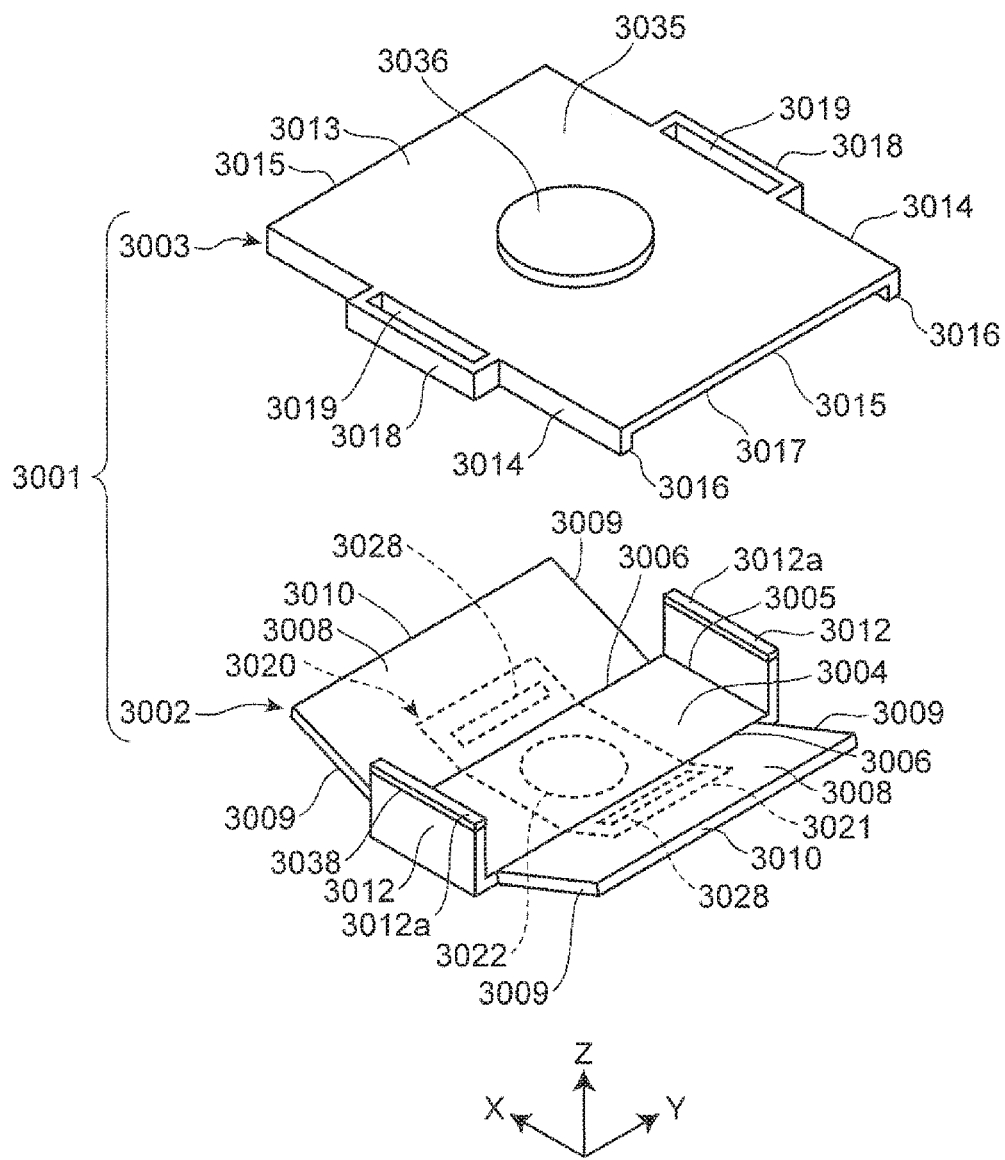
FIG. 52 is an exploded perspective view showing an applicator of an eleventh embodiment according to the present invention.

FIG. 52 shows an eleventh embodiment of the applicator according to the present invention. In the drawing, the applicator of the eleventh embodiment is generally designated at reference numeral 3001 and includes a first element 3002 and a second element 3003. The first element 3002 and the second element 3003 may both be made of a metal or a resin, or one may be made of a metal but the other may be made of a resin.

The first element 3002 has a central plate portion 3004 and inclined plate portions 3008 connected integrally to both sides of the central plate portion 3004. The central plate portion 3004 is a rectangular plate portion surrounded by edges 3005 and 3006 extending in X-direction and Y-direction, respectively. The inclined plate portions (stretchable members) 3008 are connected to the Y-direction edges 3006 of the central plate portion 3004. The inclined plate portion 3008 is a rectangular plate portion surrounded by a pair of parallel edges 3009 extending from the vicinities of both ends of the Y-direction edge 3006 of the central plate portion 3004 outward and upward so as to go apart from each other, and the edge 3006 and an edge 3010 extending in parallel in the Y-direction to connect ends of the edges 3009 together.

The pair of X-direction edges 3005 of the central plate portion 4 are each formed integrally with a rectangular vertical plate portion 3012 extending upward therefrom. The vertical plate portion 3012 has a marking (indication) 38 at a position downward apart a predetermined distance from the upper end thereof. In the embodiment, the marking 3038 is a horizontally extending line bearing a color different from the color forming the first element 3002. For example, if the surface of the first element 2 is white, the marking 3038 is represented by a visually noticeable color, e.g., red.

The second element 3003 has a plate portion 3013. The plate portion 3013 is a rectangular plate surrounded by edges 3014 and 3015 extending in the X-direction and Y-direction. The X-direction edges 3014 are formed integrally with lower flanges or horizontal guide portions 3016 extending along the edges 3014.

In the embodiment, the Y-direction inner dimension between the opposed horizontal guide portions 3016 is substantially equal to the Y-direction length of the end edges 3010 of the inclined plate portions 3008 so that the end edges 3010 of the inclined plate portions 3008 can be received inside the opposed horizontal guide portions 3016. The distance between the opposed Y-direction edges 3015 is larger than the X-direction interval between the end edges 3010 of the pair of inclined plate portions 3008 so that the end edges 3010 of the pair of inclined plate portions 8 come into contact with a bottom surface 3017 of the plate portion 3013 lying between the horizontal guide portions 3016 (see FIGS. 56A and 56B).

The X-direction edges 3014 of the plate portion 3013 are also formed integrally with outward protruding extended portions 3018. The extended portions 3018 are positioned at centers on the edges 3014 and have slots or through-holes 3019 extending in the X-direction. The size (cross section) of the through-hole 3019 is slightly larger than the cross section of the vertical plate portions 3012 of the first element 3002 so that the vertical plate portions 3012 of the first element 3002 are inserted into the through-holes 3019 from below.

Figure 56A:
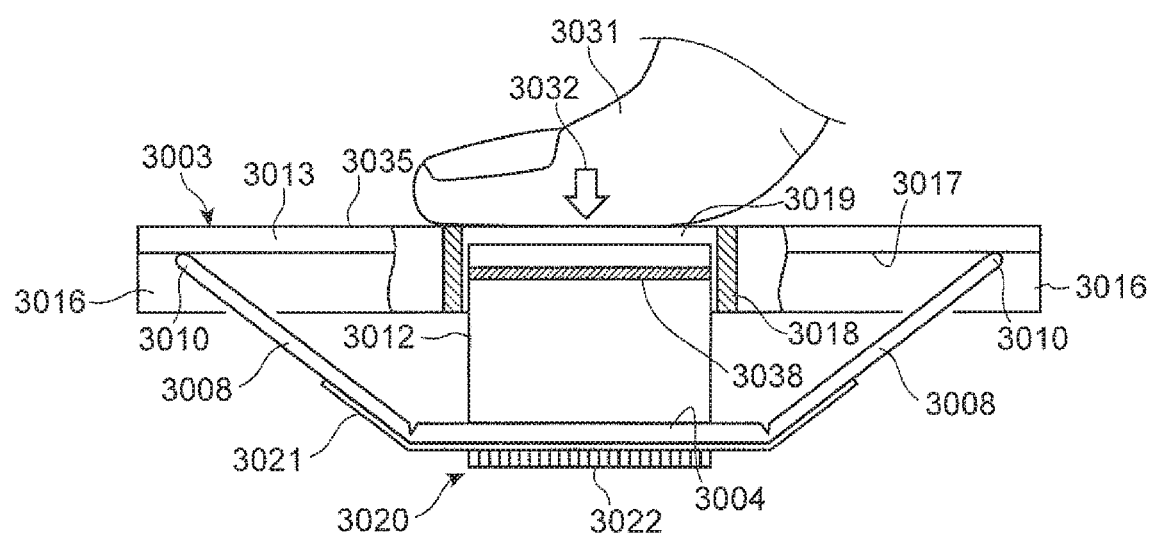
FIGS. 56A and 56B are sectional views showing a function and an action of the applicator according to the eleventh embodiment.
Figure 56B:
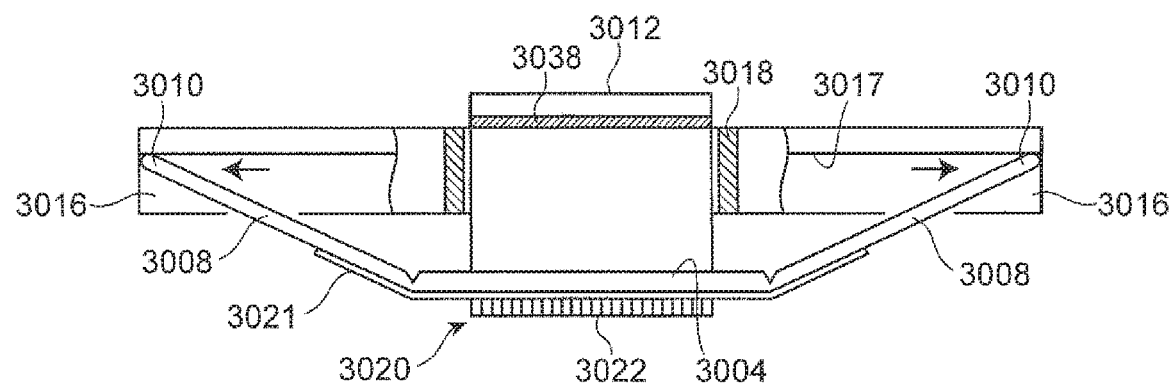

The thickness of the plate portion 3013, the material of the first element 3002, the heights of the inclined plate portions 3008 and the vertical plate portions 3012, and the position (height) of the marking 3038 are determined so that as shown in FIGS. 56A and 56B, when the inclined plate portions 3008 are in their pre-deformation states, the upper ends of the vertical plate portions 3012 inserted into the through-hole 3019 stay inside the through-holes 3019 and do not appear on the surface of the plate portion 3013 and so that when the plate portion 3013 is subjected to a predetermined pressing force, the inclined plate portions 3008 are displaced at their end edges 3010 by a predetermined amount so that the markings 3038 on the vertical plate portions 3012 emerge from the top surface 3035 of the plate portion 3013. As used herein, the "predetermined pressing force" refers to a force required to insert the needles 3027 of the patch 20 described later into the skin to a predetermined depth. Since as shown, the central plate portion 3004 supporting the patch 3020 protrudes toward the skin so that almost of the pressing force acts as an inserting force of the needles 27 on the patch 3020 supported on the central plate portion 3004, appearance of the markings 3038 on the top surface 3035 of the plate portion 3013 substantially means that a predetermined inserting force acts on the needles 3027.

In the embodiment, a finger rest 3036 of a predetermined shape is formed at a center on the top surface 3035 of the plate portion 32013. Although in the shown embodiment, the finger rest 3036 is a circular raised platform, its planar shape may be a raised portion or a recessed portion of another shape including a polygon such as a quadrangle, an oval, and a star, or may be a spherical raised or recessed portion, or may be a mere marking or pattern.

Figure 53:
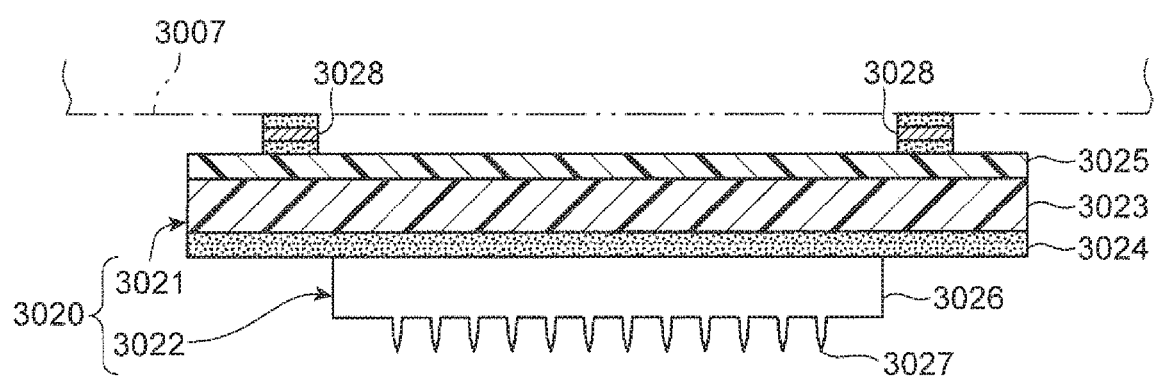
FIG. 53 is a sectional view showing a structure of the microneedle patch for use with the applicator of the eleventh embodiment.
Figure 54:
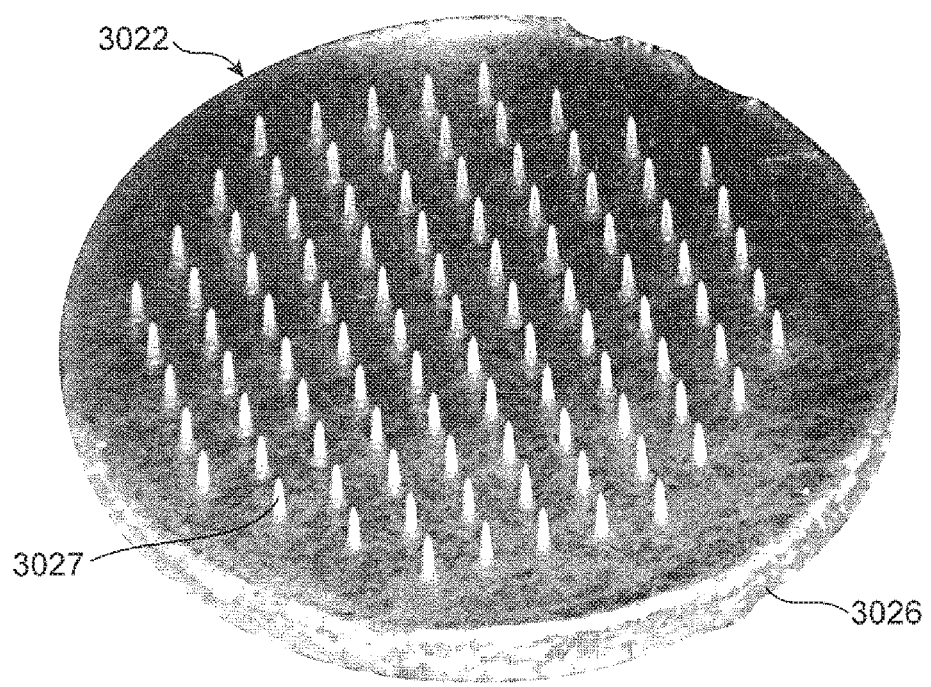
FIG. 54 is a photograph of an actual microneedle array shot from diagonally below.

As schematically shown in FIG. 53, the patch 3020 has a sheet substrate 3021 and a microneedle array 3022 supported thereon. The sheet substrate 3021 has a substrate film 3023, a pressure-sensitive adhesive layer 3024 provided on a bottom surface (a surface supporting the microneedle array 3022) of the substrate film 3023, and a release treatment layer (a releasing layer) 3025 provided on a top surface (a surface opposing the applicator 3001) of the substrate film 3023. As shown in FIG. 54, the microneedle array 3022 has a circular or rectangular base 3026 and a multiplicity of elongated needles 3027 with a predetermined height (e.g., 300 to 1000 micrometers) arrayed at predetermined intervals (e.g., 300 to 1000 micrometers) in a lattice or honeycomb fashion on a bottom surface of the base 3026. The microneedle array 3022 is formed, for example, by filling a biodegradable synthetic polymer material (e.g., hyaluronic acid, collagen, polylactic acid, polyglycolic acid) into a correspondingly shaped mold. Although not shown, tip sides of the needles 3027 are coated with a target drug (molecules such as vaccine, protein, and peptide). Alternatively, or additionally, the target drug may be contained in the needles 3027 by being mixed with materials of the needles during molding of the microneedle array 3022.

The sheet substrate 3021 and the microneedle array 3022 are arranged so that the base 3026 of the microneedle array 3022 is applied on the pressure-sensitive adhesive layer 3024 of the sheet substrate 3023. As shown, the sheet substrate 3021 is larger than the microneedle array 3022 so that a sufficient area of the pressure-sensitive adhesive layer 3024 is exposed around the microneedle array 3022 when the microneedle array 3022 is applied on the sheet substrate 3021.

The thus formed patch 3020 is supported on the bottom surface of the first element 3003. Specifically, as shown in FIGS. 52 and 53, both-side substrate portions 3029 of the sheet substrate 3021 are adhered to the inclined plate portions 3008 by use of double-sided adhesive tapes 3028. At this time, as shown, the double-sided adhesive tapes 3028 are apart a predetermined distance from edges 3030 of the sheet substrate 3021. The double-sided adhesive tapes 3028 serve to retain the patch 3020 on the bottom surface 3007, 3011 of the first element 3002 before the patch 3020 is applied to the skin. Hence, the size, shape, position, and pressure-sensitive adhesive force of the double-sided adhesive tapes 3028 are preferably determined so that the patch 3020 can be retained on the first element 3003 and so that the patch 3020 applied to the skin by the pressure-sensitive adhesive layer 3024 cannot peel off from the skin by an adhesive force between the skin double-sided adhesive tapes 3028 and the first element 3002 when the applicator 3001 is removed from the patch 3020 after attachment to the skin. Considering these conditions, in the eleventh embodiment, the double-sided adhesive tapes 3028 are sized as small as possible and are applied to a position shifted a determined distance inward from both ends of the sheet substrate 3021.

When the patch 3020 is applied to the human or animal skin using the applicator 3001 holding the patch 3020 in this manner, the plate portion 3013 of the second element 3003 is pressed at its top surface center by a finger 3031 as shown in FIGS. 56A and 56B. A pressing force 3032 applied to the plate portion 3013 acts on the edges 3010 of the both inclined plate portions 3008 through the bottom surface (contact portion) 3017 of the plate portion 3013. As a result, the both inclined plate portions 3008 resiliently deform allowing allow its ends to move downward with respect to the central plate portion 3004, following which deformation the both edges 3010 of the inclined plate portions 3008 slide along the bottom surface (contact portion) 3017 of the plate portion 3013 to spread outward.

Figure 55A:
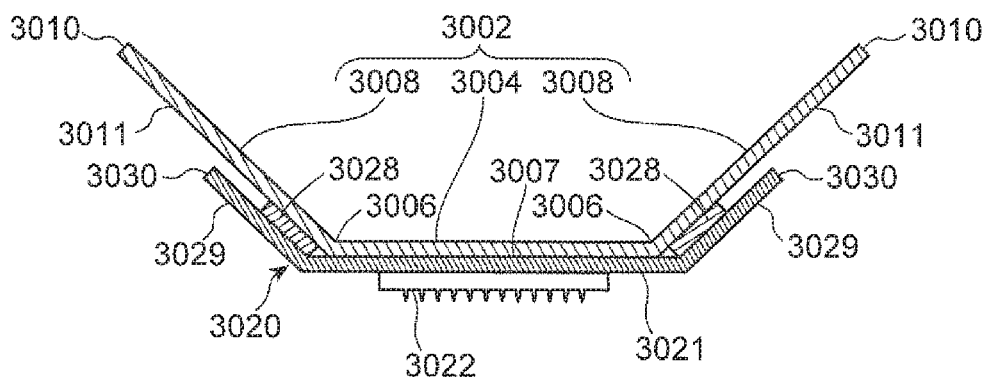
FIGS. 55A-55C are sectional views showing a function and an action of a first element of the applicator according to the eleventh embodiment.
Figure 55B:
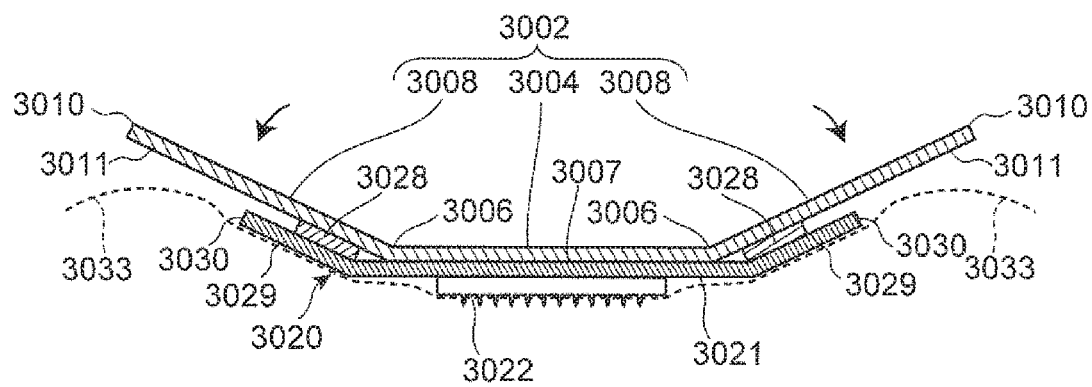

The pressing force 3032 is transmitted to the inclined plate portions 3008 and the central plate portion 3004 of the first element 3002. As a result, as shown in FIGS. 55A and 55B, the patch 3020 supported on the bottom surface 3007, 3011 of the central plate portion 3004 and the inclined plate portions 3008 is pressed against the skin 3033. At this time, not only the central plate portion 3004 but also the inclined plate portions 3008 are pressed against the skin 3033. Accordingly, the pressure-sensitive adhesive layers of the both-side substrate portions 3029 supported on the inclined plate portions 3008 are pressed against the skin 3033 with a suitable force to adhere thereto.

Figure 55C:
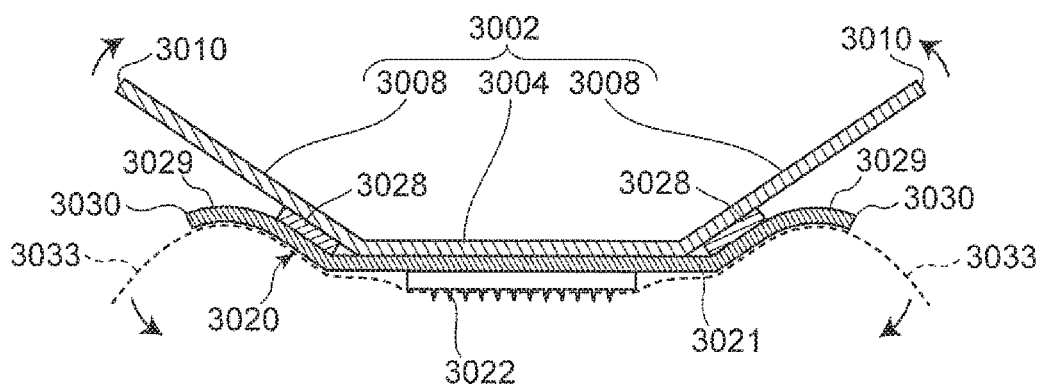

Thereafter, when the pressing force 3032 is removed, the inclined plate portions 3008 are restored to their pre-deformation states based on their resiliencies. At this time, as shown in FIG. 55C, the end edges 3030 of the sheet substrate 3021 adhered to the skin 3033 go apart from the inclined plate portions 3008, together with portions of the skin to which the end edges 3030 adhere. Consequently, in conjunction with the restoration to the pre-deformation states of the inclined plate portions 3008 apart from the skin 3033, the double-sided adhesive tapes 3028 are subjected at their outside edges to a concentrated peeling force. This allows the sheet substrate 3021 to peel off easily from the double-sided adhesive tapes 3028 while adhering to the skin 3033. Accordingly, the patch 3020 applied to the skin can be separated from the applicator 3001 while being held securely on the skin.

In this manner, according to the applicator of this embodiment, the patch 3020 adhered to the skin 3033 comes apart from the applicator 3001, starting from its both-side substrate portions 3029. Thus, when separating the applicator 3001 from the skin 3033, the patch 3020 cannot peel off from the skin 3033 while adhering to the applicator 3001 so that the needles 3027 once stuck into the skin keeps its inserting state.

As described above, when a predetermined pressing force is applied to the plate portion 3013, as shown in FIG. 56B the inclined plate portions 3008 deform by a predetermined amount, allowing the markings 3030 imparted to the vertical plate portions 3012 to appear on the surface of the plate portion 3013. Thus, by visually recognizing the markings 3038 appearing on the top surface of the plate portion 3013, it is possible for the user to verify, by a visual change, whether a desired pressing force 3032 is applied to the plate portion 3013.

Although in this embodiment, the markings 3038 imparted to the side surfaces of the vertical plate portions 3012 are configured to serve as indicators, upper end surfaces 3012a of the vertical plate portions 3012 may be used as the indicators so that when a predetermined pressing force is applied to the plate portion 3013, the upper end surfaces 3012a of the vertical plate portions 3012 are exposed on the top surface of the plate portion 3013. In this instance, by coloring the upper end surfaces of the vertical plate portions 3012 with a color different from the surface color of the first element 3002 or the third element 3003, it can easily be verified whether the upper end surfaces 3012a of the vertical plate portions 3012 reach the top surface of the plate portion 3013, i.e., whether a predetermined pressing force is applied to the plate portion 3013.

The method of verifying whether a predetermined pressing force is applied is not limited to one utilizing the visual sense, but may be ones utilizing the auditory sense or the tactile sense, as described hereinafter.

Twelfth Embodiment

Figure 57:
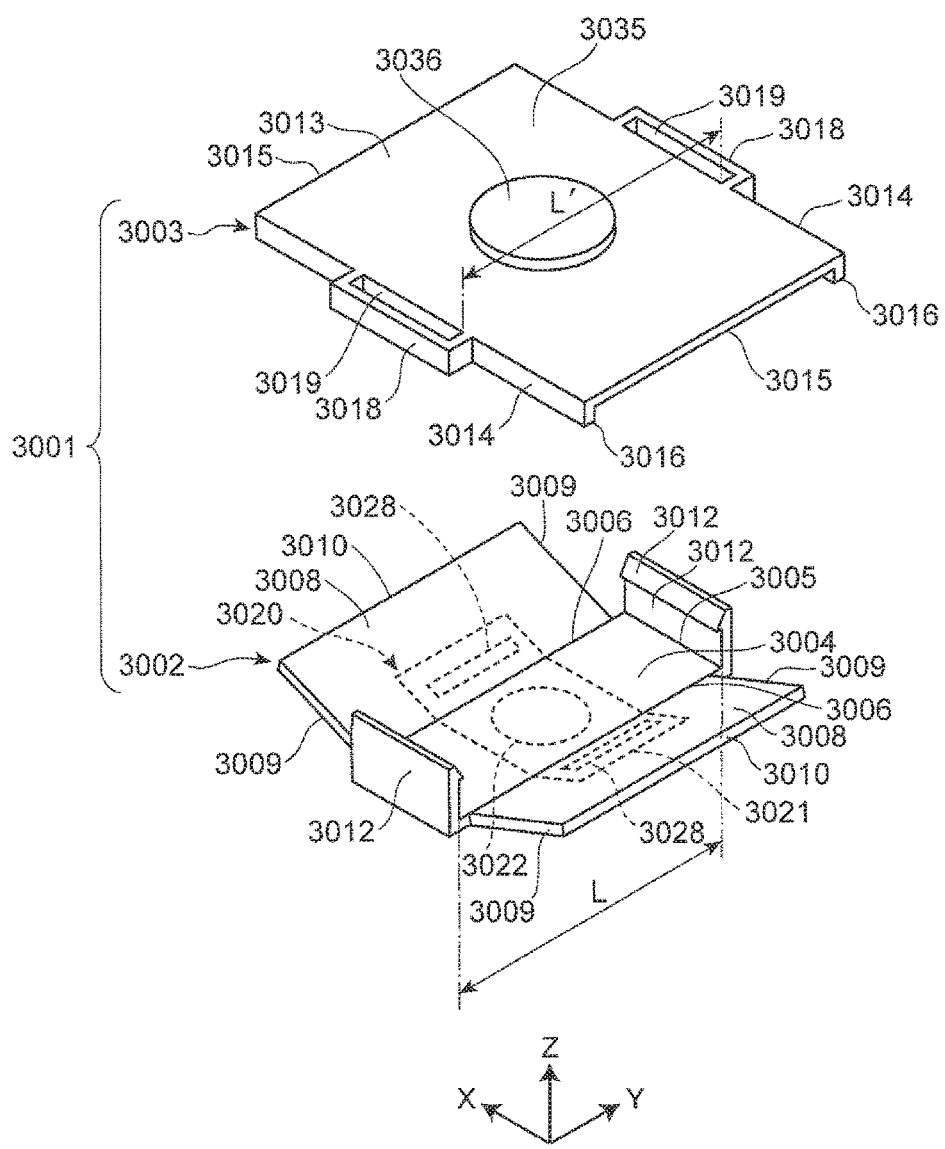
FIG. 57 is a sectional view of an applicator according to a twelfth embodiment.
Figure 58A:
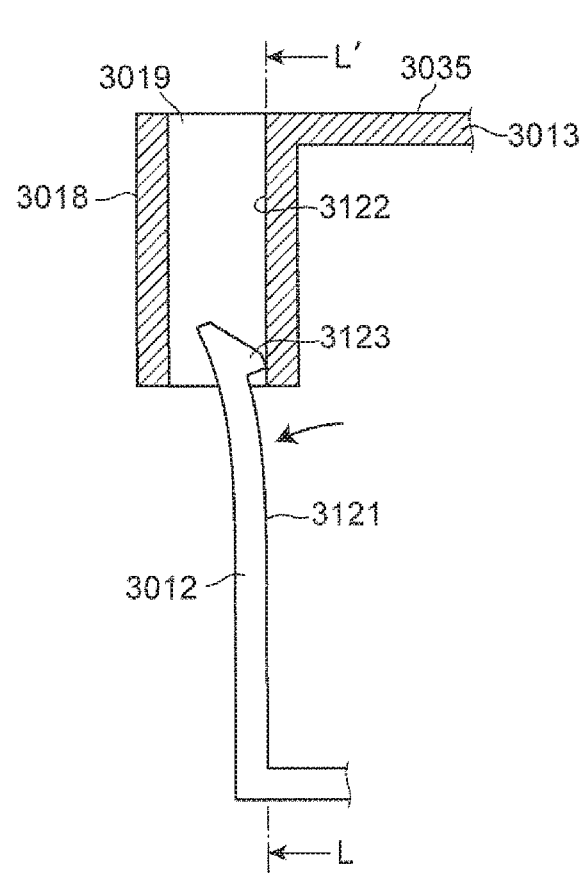
FIGS. 58A and 58B are views showing an action of the applicator according to the twelfth embodiment.
Figure 58B:
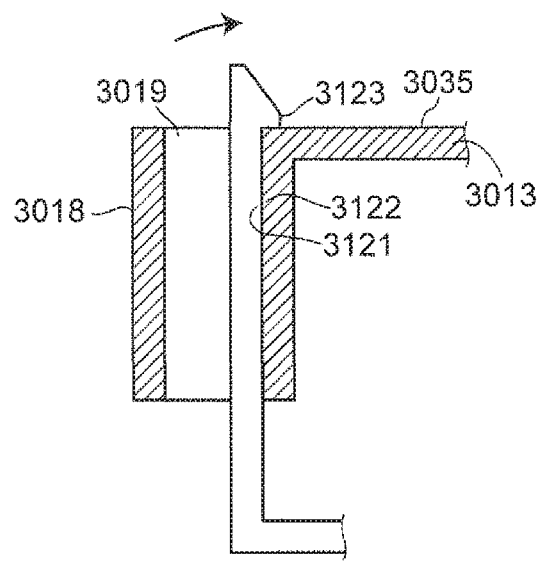

FIGS. 57 and 58 show a twelfth embodiment of the applicator having an indicator utilizing the auditory sense. In this embodiment, a distance L between inner surfaces 3121 opposed in Y-direction of the pair of vertical plate portions 3012 is substantially equal to a distance L' between opposed inward wall surfaces 3122 of the pair of the through-holes 3019. The vertical plate portion 3012 has at its upper end an inward-directed protrusion 3123. The sizes and shapes of the vertical plate portion 3012 and of the protrusion 3123 are determined so that, as shown in FIG. 58A, when the inclined plate portions 8 are in their non-deformation states, the upper portion of the vertical plate portion 3012 lies within the corresponding through-hole 3019, with the upper portion of the vertical plate portion 3012 being deformed outward by the abutment of the protrusion 3123 against an inward wall surface 3123 of the through-hole 3019 and so that, as shown in FIG. 58B, when the inclined plate portions 3008 are deformed as a result of action of a predetermined pressing force on the plate portion 3013, the protrusion 3123 passes through the through-hole 3019 to appear on the top surface 3035 of the plate portion 3013, whereupon the vertical plate portions 3012 are resiliently restored to their non-deformation states, allowing the inner surface 3121 of the vertical plate portion 3012 to resiliently collide with the inward wall 3122 of the through-hole 3019 to issue a sound.

Thus, according to this embodiment, the user is notified by a collision sound (an auditory change) that the inclined plate portions 8 have deformed by a predetermined amount as a result of application of a predetermined pressing force to the plate portion 3013, i.e., that a predetermined force has been applied to the needles.

According to this embodiment, as shown in FIG. 58B, when a collision sound occurs as a result of application of a predetermined pressing force, the protrusion 3123 engages with the top surface 3035 of the plate portion 3013 so that the first element 3002 is fastened to the third element 3003, to prevent reuse of the applicator 1.

Thirteenth Embodiment

Figure 59:
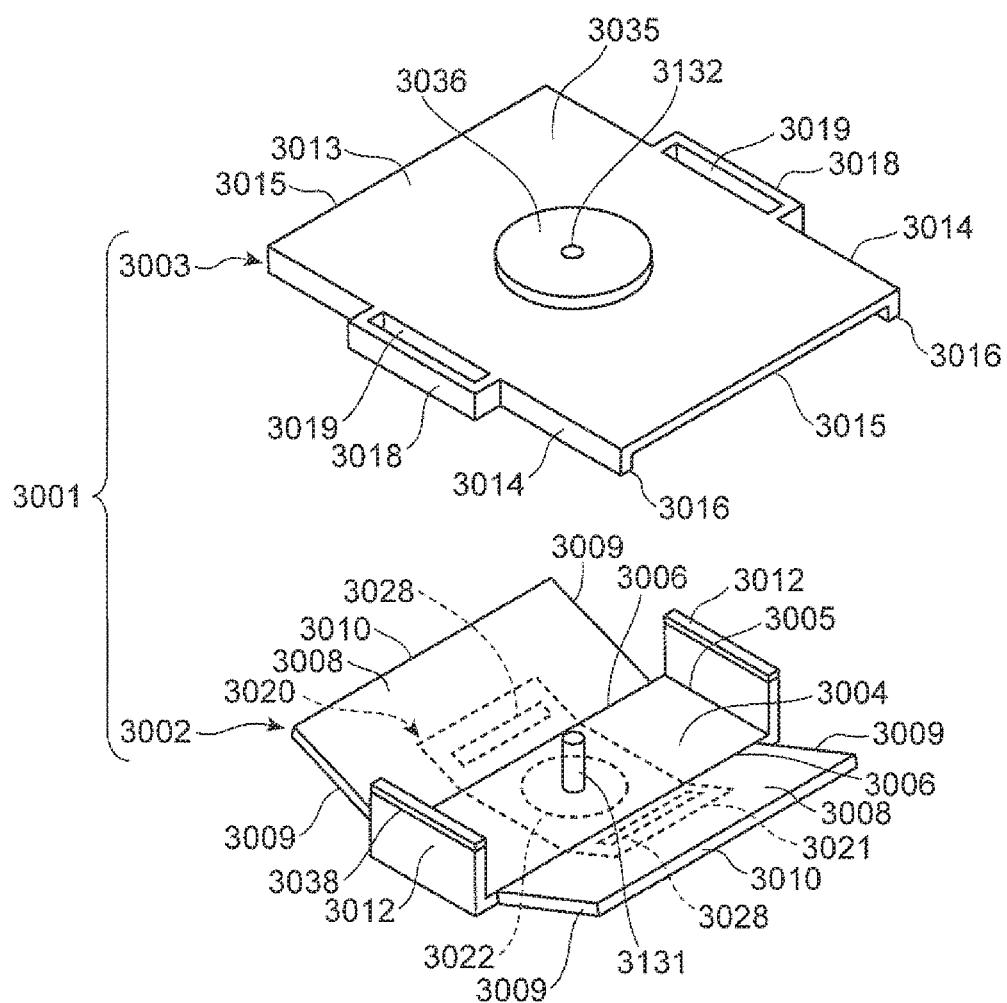
FIG. 59 is a sectional view of an applicator according to a thirteenth embodiment.
Figure 60A:
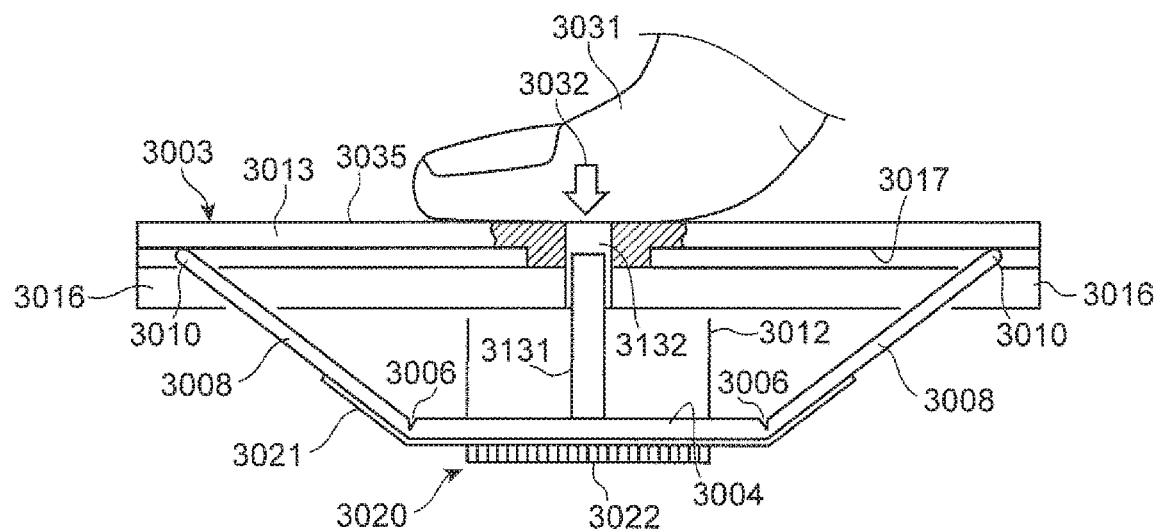
FIGS. 60A and 60B are views showing an action of the applicator according to the thirteenth embodiment.
Figure 60B:
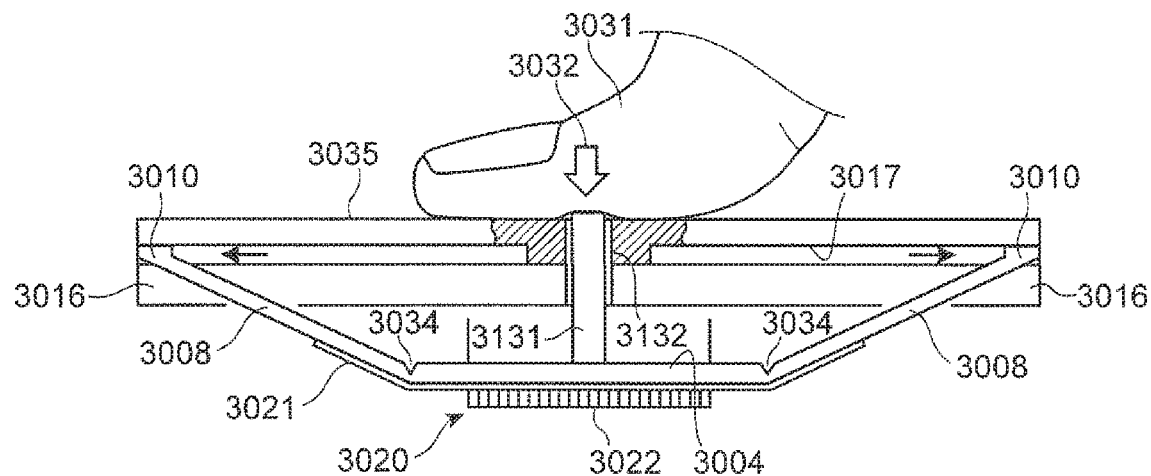

FIGS. 59 and 60 show a third embodiment of the applicator having an indicator utilizing the tactile sense. In this embodiment, a cylindrical projection 3131 is formed at a center on the top surface of the central plate portion 3004 of the first element 3002. The plate portion 3013 has at its center a through-hole 3132 passing through the top surface and the bottom surface. The sizes and shapes of the projection 3131 and of the through-hole 3132 are determined so that, as shown in FIG. 9A, when the inclined plate portions 3008 are in their non-deformation states, the upper portion of the projection 3131 lies within the corresponding through-hole 3132 and so that, as shown in FIG. 9B, when the inclined plate portions 3008 are deformed as a result of action of a predetermined pressing force on the plate portion 3013, the projection 3131 passes through the through-hole 3132 to appear on the top surface 3035 of the plate portion 3013, coming into contact with the finger 3031 resting on the top surface of the plate portion 3013.

Thus, according to this embodiment, the user is informed, by a feel (a tactile change; of the projection 3131 transmitted to the finger 3031, that the inclined plate portions 3008 have deformed by a predetermined amount as a result of application of a predetermined pressing force to the plate portion 3013, i.e., that a predetermined force has been applied to the needles.

Fourteenth Embodiment

Figure 61:
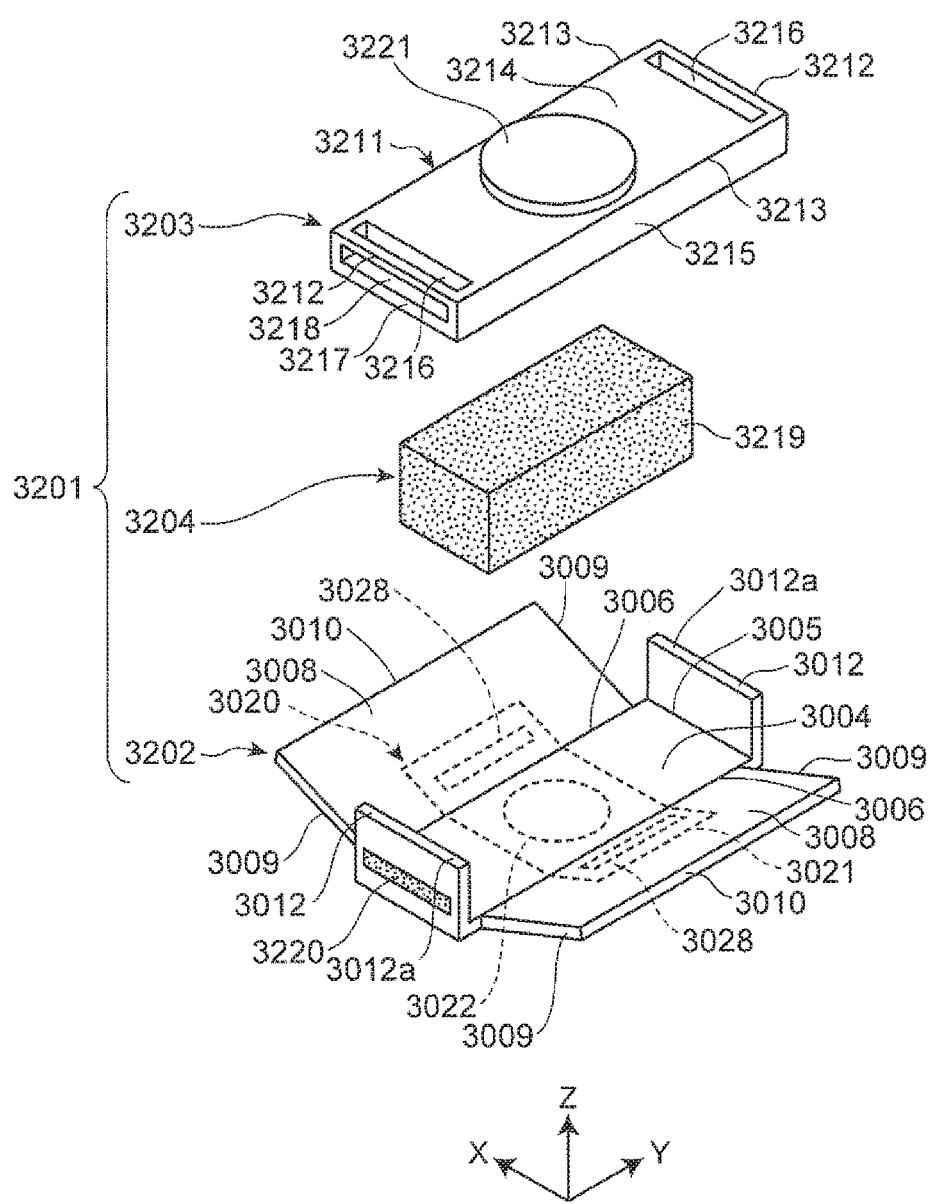
FIG. 61 is an exploded perspective view of an applicator according to a fourteenth embodiment.
Figure 62:
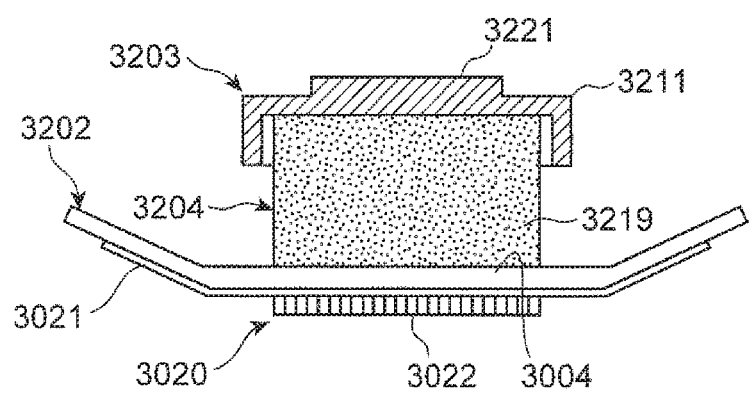
FIG. 62 is a sectional view of the applicator according to the fourteenth embodiment.

FIGS. 61 and 62 show a fourteenth embodiment of the applicator having an indicator utilizing the visual sense. The applicator 3201 of this embodiment has a first element 3202, a second element 3203, and a third element 3204. The first element 3202 is the same as the first element 3002 of the above embodiment except that a laterally elongated rectangular marking 3220 or pattern is imparted onto the outer surface of the vertical plate portion 3012 on one hand. The second element 3203 has a lid-shaped pressing member 3211 that is substantially rectangular when viewed from above. Specifically, the pressing member 3211 has a top plate 3214 surrounded by a pair of edges 3212 extending in the X-direction and a pair of edges 3213 extending in the Y-direction, and a wall 3215 extending downward from the perimeter of the top plate 3214. The pressing member 3211 has, in the vicinity of the X-direction edges 3212, through-holes 3216 passing through the top plate 3214 to enable the vertical plate portions 3012 of the first element 3202 to be inserted thereinto. A window 3218 leading to the through-hole 3216 is formed in a wall portion 3217 adjoining the X-direction edge 3212 on one hand. The window 3218 is of a laterally rectangular shape corresponding to the shape of the marking 3220 on the first element 3202.

The third element 3204 is in the form of an elastic member 3219. In the embodiment, the elastic member 3219 is a box-shaped member made of a material (e.g., elastomer such as polyurethane sponge, silicone, and rubber) having elasticity.

In the applicator 3201 having such a shape, the elastic member 3219 of the third element 3204 is provided on the central plate portion 3004 of the first element 3202. The second element 3203 is then provided on the elastic member 3219. At this time, the vertical plate portions 3012 of the first element 3202 are inserted into the through-holes 3216 of the second element 3203. If needed, the elastic member 3219 may be fastened to the top surface of the central plate portion 3004 or the bottom surface of the top plate 3214 by use of an adhesive, etc.

Thus, at the time of application of the patch 302C, when a pressing force is applied to the top plate 3214 of the pressing member 3211, the elastic member 3219 is deformed by the pressing force. When applying a predetermined pressing force required to insert the needles into the skin, the elastic member 3219 deforms by a predetermined amount, allowing the entirety of the marking 3220 to appear inside the window 3218. Accordingly, by visually checking the size of the marking 3220 appearing in the window 3218, it can be verified whether a predetermined pressing force has been applied to the pressing member 3211.

It may merely be judged whether the distance between the central plate portion 3004 and the plate portion 3013 has reduced. The central plate portion 3004 may be of a curved surface, instead of the planar surface.

In this embodiment, the portion to dispose the microneedle array is positionally shifted to act as an indicator. If the positionally shifted portion is e.g., the upper portion of the central plate portion 3004, instead of the portion to dispose the microneedle array, a stress exerted on the frame 1089 of FIG. 21 for example is also picked up in addition to a stress applied to the microneedle array, whereupon it is difficult to detect only the stress applied to the microneedle array, resulting in a lowered stress detection accuracy.

In order to detect the stress applied to the microneedle array at a high accuracy, the displacement of the positionally shifted microneedle array disposition portion may visually be read or the displacement may preferably be used as an indicator for auditory and tactile conversion and detection.

It is preferred to dispose a member such as a coil spring, a leaf spring, or a sponge-like resin that elastically deforms due to stress, between the portion externally stressed to insert the microneedle array into the skin and the portion to dispose the microneedle array. More preferably, it may be coaxially provided.

In order to detect only the stress applied to the microneedles, it is preferable to size the microneedle disposition surface as small as possible, and it is most preferable that it have the same size as that of the microneedles. The area of the microneedle disposition portion exceeding the size of the microneedles may have a structure hard to transmit the stress to the indicator. For example, a method may be conceivable in which instantly when subjected to a stress, the area bends so as not to transmit the stress to the indicator.

The indicator as the indicator is configured by a single indication, i.e., visual, auditory, or tactile indication or is configured by a combination of plural indications.

Although the embodiments and modifications of the applicator according to the present invention have been described hereinabove, the portions of the applicator may be made of any material among metals, nonmetals, and resins. If reused several times like the cartridge type, a metal is preferred from the viewpoint of durability. Preferably, the metal is a stainless steel. The thicknesses and shapes of portions to be deformed in the applicator may be selected depending on the natures of the materials so that desired functions are acquired.

In the above embodiment, the elastic member intervening between the first element and the second element may be inclined plates, a coil spring, or a leaf spring, or may be made of a material (e.g., elastomer such as polyurethane sponge, silicone, and rubber) having elasticity other than the spring.

Also in this embodiment, a finger rest 3221 may be provided at a center on the top plate 3214 of the pressing member 3211. The finger rest may be a raised portion or a recess in the shape of a circle, polygon, oval, star, etc., or may be a mere marking or pattern.

Fifteenth Embodiment

Figure 63:
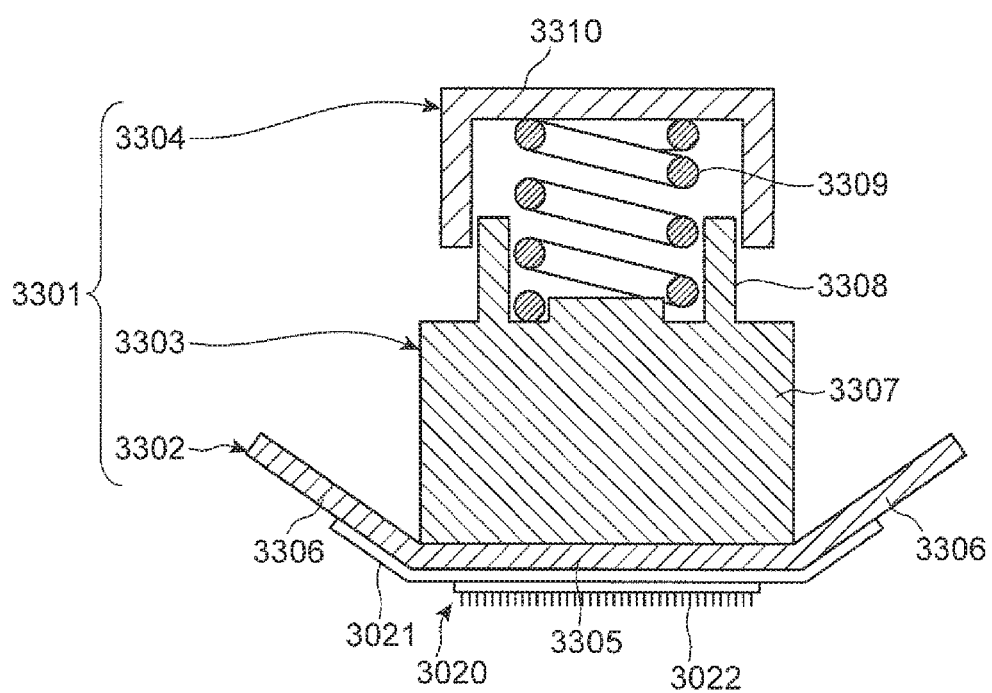
FIG. 63 is a sectional view of an applicator according to a fifteenth embodiment.

FIG. 63 shows a fifteenth embodiment of the applicator having an indicator utilizing the visual sense. The applicator 3301 of this embodiment has a first element 3302, a second element 3303, and third element 3304. The first element 3302 is similar to the first element of the above embodiment and has a central plate portion 3305 and inclined plate portions 3306 formed integrally on both sides thereof. The second element 3303 has a support block 3307 with a rectangular section formed on the central plate portion 3305 of the first element 3302, a spring support 3308 formed integrally on the top surface of the support block 3307, and a spring 3309 supported on the spring support 3308, with the support block 3307 being fastened to the top surface of the central plate portion 3305 by an adhesive, etc. Accordingly, the support block 3307 may be formed integrally with the first element 3302. The third element 3304 has a cap 3310 surrounding the upper portion of the spring 3309. In the applicator 3301 of the embodiment configured in this manner, a patch (not shown) is applied to the bottom surface of the central plate portion 3305 and of the inclined plate portions 3306. At the time of application of the patch, the cap 3310 is depressed at its upper end surface to press the patch against the skin. At this time, when a predetermined pressing force is applied to the cap 3310, the lower end of the cap 3310 comes into abutment against the upper surface of the support block 3307. Thus, the user can verify that the needles have been subjected to a predetermined inserting force, by visually or tactilely sensing the abutment of the cap 3310 against the support block 3307. Hence, the resiliency of the spring 3309 and the distance (cap movement distance) between the cap 3310 and the support block 3307 are determined so that when the cap 3310 is subjected to a predetermined pressing force, the cap 3310 is brought into abutment against the support block 3307.

The shapes of the portions described in the above embodiments and modifications are mere examples and are not restrictive.

Figure 64A:
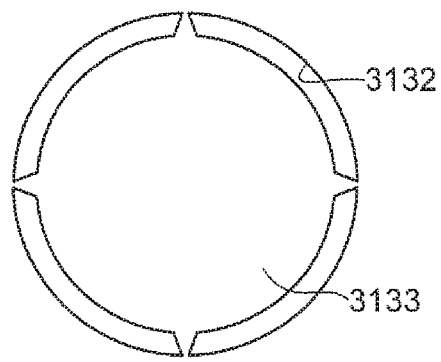
FIGS. 64A and 64B are views showing an embodiment of another indicator.
Figure 64B:
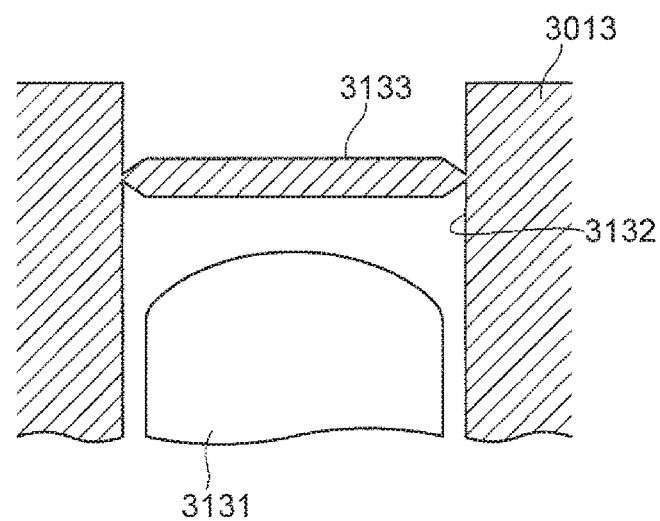
Figure 65:
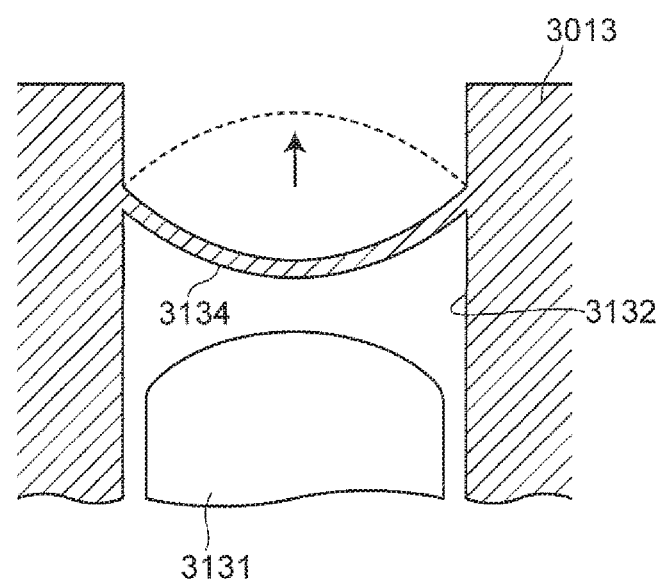
FIG. 65 is a view showing an embodiment of another indicator.

Specifically, in the embodiments utilizing the auditory sense or the tactile sense, as shown in FIG. 64, a break portion 3133 breakable by the projection 3131 may be provided inside the through-hole 3132 formed in the plate portion 3013 of the second element so that when a predetermined pressing force is applied to the needles, the break portion 3133 is broken to issue a break sound. As shown in FIG. 65, a downward curving deformation portion 3134 is formed inside the through-hole 3132 so that when a predetermined pressing force is applied to the needles, the deformation portion 3134 deforms into an upward curving state to issue a sound at that time. The indication mechanism utilizing the auditory sense may be one having a convex member and a concave member, such as a snap button, to issue a sound when the convex member is fitted in the concave member. For example, the convex member may be provided on the central plate portion 3004, with the concave member being provided in the plate portion 3013, or, the convex member may be provided on the plate portion 3013, with the concave member being provided in the central plate portion 3004. The place to dispose these members to issue a sound may be a place ensuring a suitable action, other than the portion of space between the central plate portion 3004 and the plate portion 3013.

Basic Modification

A basic modification of the microneedle patch according to the present invention and an embodiment embodying the basic modification will be described hereinbelow.

Figure 66:
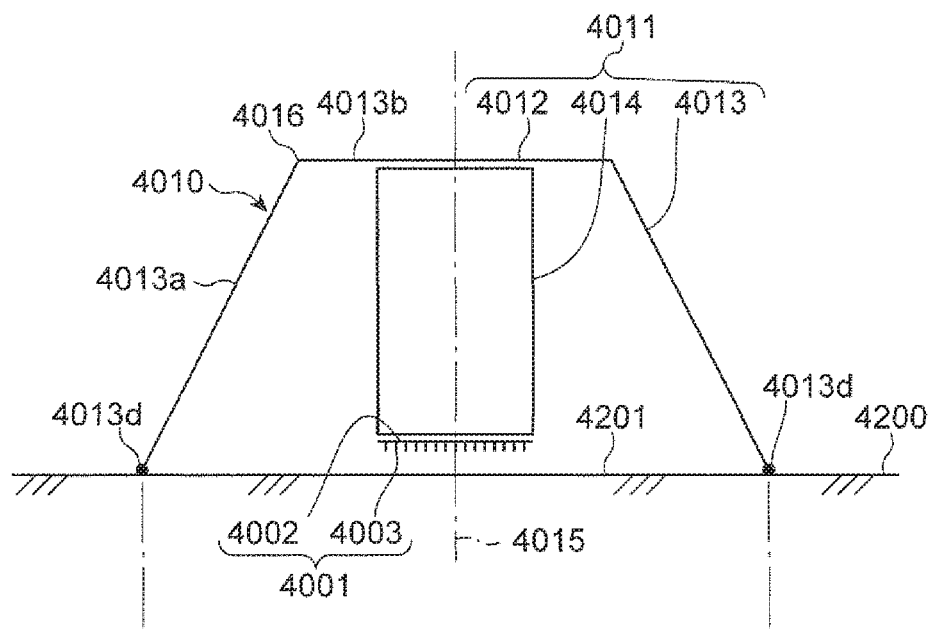
FIG. 66 is a side view showing schematically a principle of a device applying a microneedle patch to a skin of a human being or an animal, according to sixteenth to eighteenth embodiments.
Figure 67:
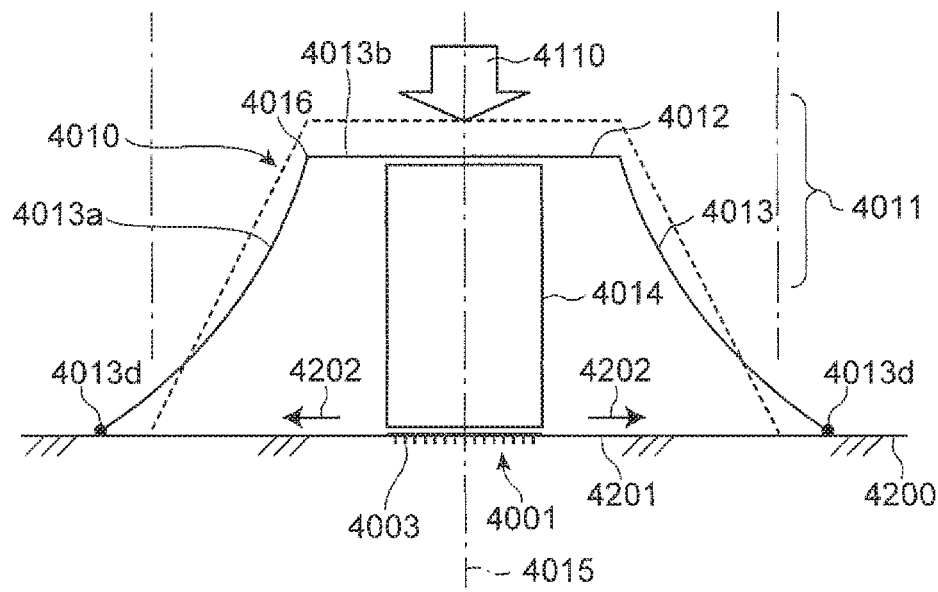
FIG. 67 is a side view showing schematically a principle of the device, in addition to FIG. 66.

The basic modification of the device applying the microneedle patch onto the skin, according to the present invention, will be described. FIG. 66 shows the device in its "ready condition" prior to the application of the microneedle patch to a skin of a human being or of an animal other than the human being, while FIG. 67 shows the device in its "inserting condition" in which the needles on the microneedle patch are stuck into the skin. The ready condition of the device refers to the state where the device is not subjected to any force (force for pushing the needles into the skin), while resting on the skin. The inserting condition of the device refers to the state where the needles on the microneedle patch are inserted into the skin as a result of application of the force to the device in its ready condition.

The following description assumes the state where the microneedle patch is applied from above onto a substantially horizontally directed skin. Hence, the following description uses terms meaning the directions such as "top", "bottom" "outside", and "inside". However, use of those terms is for the purpose of facilitating the understanding of the structures and actions of the device. It is therefore natural that the technical scope of the invention should not be limited by the use of those terms.

As shown in FIG. 66, a device 4010 has a housing 4011. The housing 4011 has a pressure-receiving portion 4012 receiving a user's pressing force 4110 (see FIG. 67) when the device 4010 transitions from the ready condition to the inserting condition, and a plurality of leg portions supporting the pressure-receiving portion 4012. In the shown embodiment, the pressure-receiving portion 4012 is represented as a horizontally extending straight member and the plurality of leg portions 4013 are represented as members extending from the outer edges of the pressure-receiving portion 4012 toward a skin 4200, with the pressure-receiving portion 4012 and the leg portions 4013 being connected together by connecting portions 4016.

The pressure-receiving portion 4012 may be of any shape, when viewed from above, among a polygon (triangle (not shown), quadrangle (see FIG. 68), pentagon (not shown), hexagon (see FIG. 70), other polygons), a circle (see FIG. 69) and a shape (see FIG. 71) having alternate arc and straight edges. The plurality of leg portions 4013 are separate from and independent of the adjacent leg portions. In the embodiment, the plurality of leg portions 4013 are arranged symmetrically with respect to a central axis 4015 extending vertically through a center of the pressure-receiving portion 4012. However, this is not essential for the present invention.

A support portion 4014 for supporting the microneedle patch 4001 is supported under the pressure-receiving portion 4012. The size and shape of the support portion 4014 are determined so that in the ready condition, the microneedle patch 4001 supported on the support portion 4014 opposes the skin 4200 with a predetermined gap therebetween. As shown, the patch 4001 is detachably supported on the bottom surface of the support portion 4014 by way of an application member (e.g., application sheet, double-sided adhesive, adhesive) not shown. The microneedle patch 4001 has a substrate 4002 supported on the support portion 4014 and minute needles 4003 formed on the bottom surface of the substrate 4002. The needles 4003 are thin protuberances of e.g., several hundred microns in length for carrying thereon or therein a target drug (molecules such as vaccine, protein, and peptide).

Figure 68:
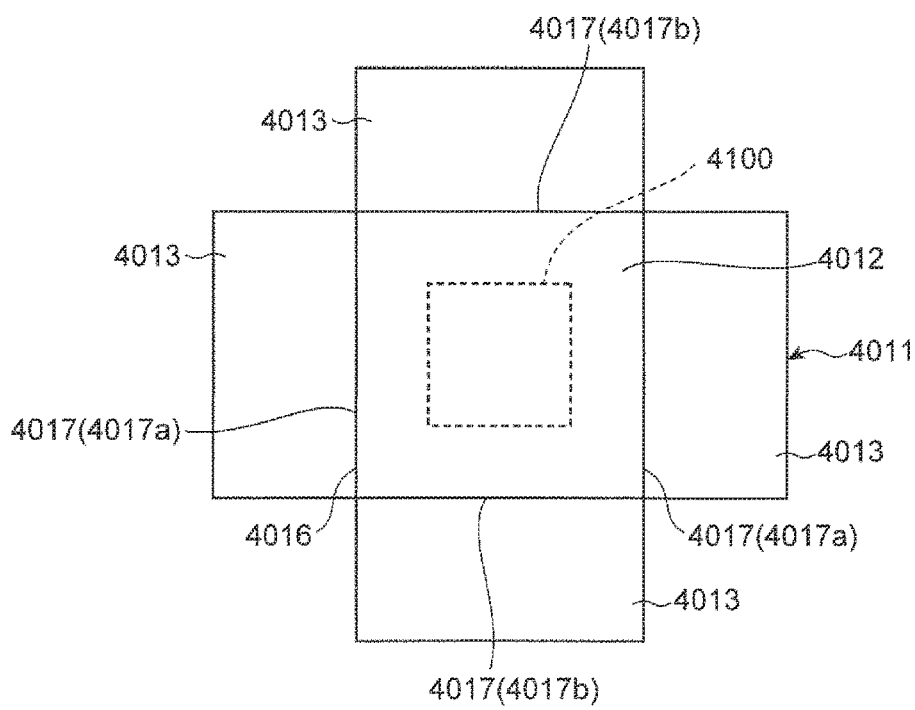
FIG. 68 is a plan view of a schematic device having a rectangular pressure-receiving portion and four leg portions.
Figure 69:
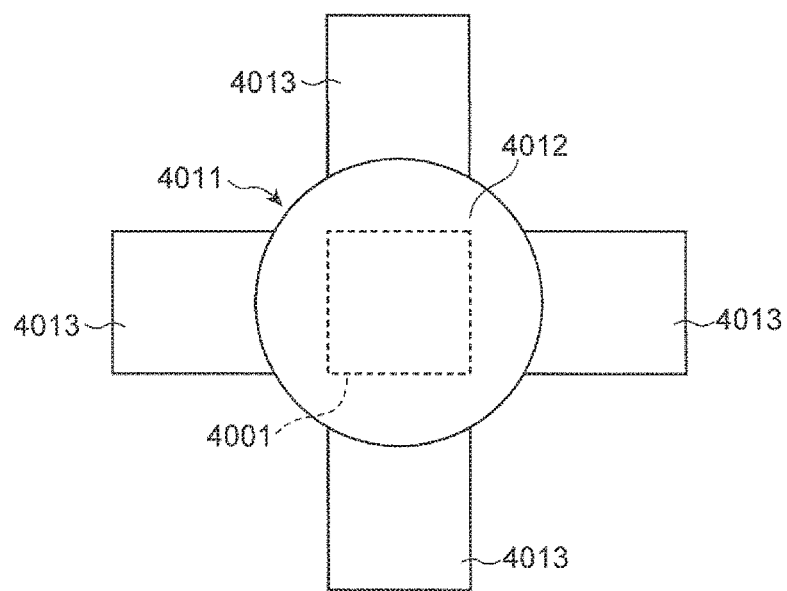
FIG. 69 is a plan view of a schematic device having a circular pressure-receiving portion and four leg portions.
Figure 70:
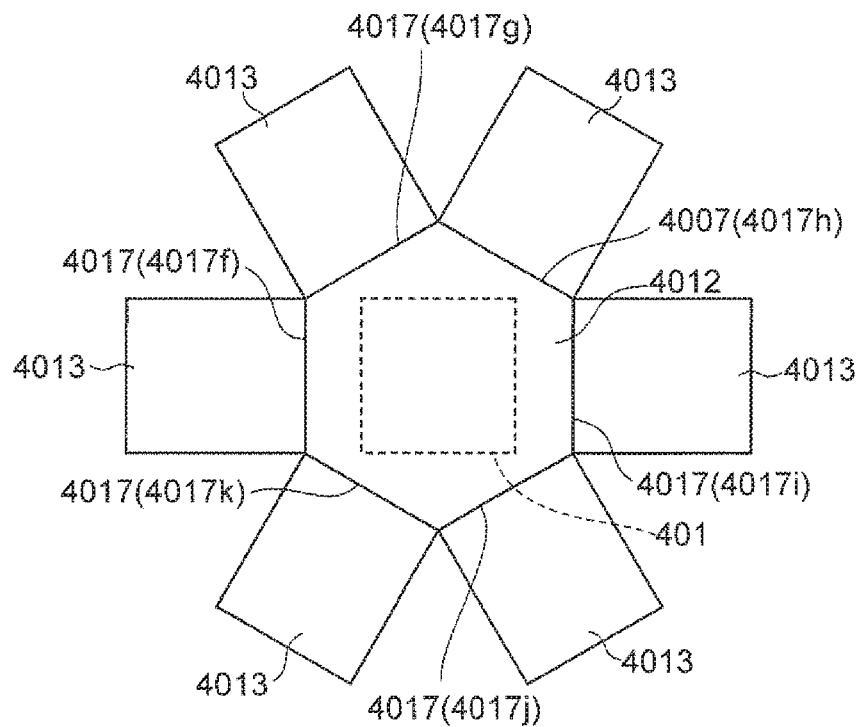
FIG. 70 is a plan view of a schematic device having a hexagonal pressure-receiving portion and six leg portions.
Figure 71:
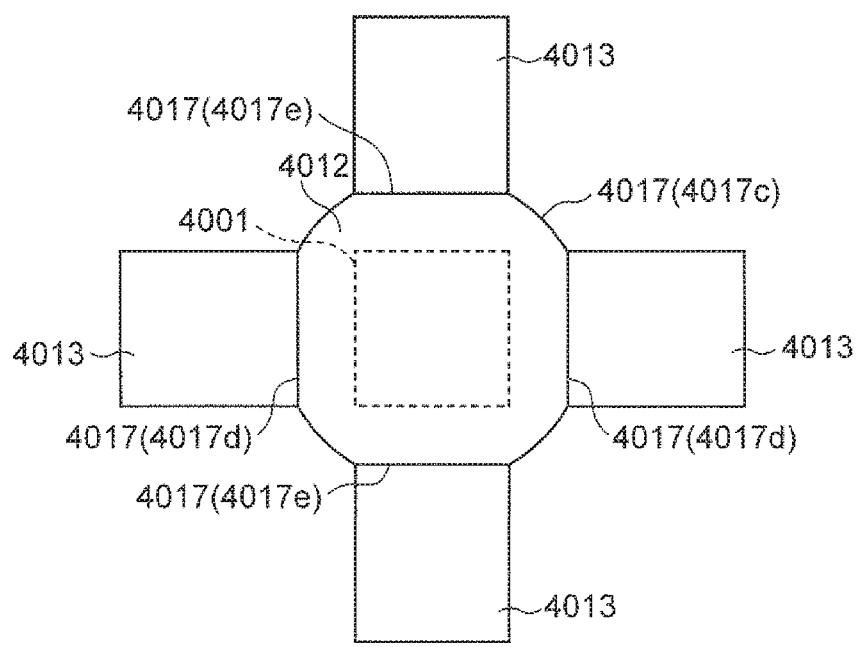
FIG. 71 is a plan view of a schematic device having a pseudo-rectangular pressure-receiving portion and four leg portions.

The number of the leg portions can optionally be determined depending on e.g., the shape of the pressure-receiving portion 4012. For example, it the pressure-receiving portion 4012 is rectangular, the leg portion 4013 may be connected to only a pair of opposed edges 4017*a* of the pressure-receiving portion 4012 or may be connected to two pairs of opposed edges 4017 (4017*a* and 4017*b*) thereof as shown in FIG. 68. If the pressure-receiving portion 12 is circular as shown in FIG. 69, two, three, four, or more number of leg portions 4013 may be provided circumferentially at equiangular intervals. When using a pseudo-rectangular pressure-receiving portion 4012 having alternately arc edges 4017 (4017*c*) and straight edges 4017 (4017*d*, 4017*e*) as shown in FIG. 71, the leg portion 4013 may be connected to only a pair of opposed edges 4017 (4017*d*) or may be connected to two pairs of opposed edges 4017 (4017*d*, 4017*e*). For a hexagonal pressure-receiving portion 4012 shown in FIG. 70, the leg portion 4013 may be provided on all edges (4017*f* to 4017*k*) or may be provided on only odd-numbered edges (4017*f*, 4017*h*, 4017*j*) or on only even-numbered edges (4017*g*, 4017*i*, 4017*k*).

Preferably, as shown in FIG. 66, the leg portion 4013 extends outward and diagonally downward from the edges of the pressure-receiving portion 4012. However, this is not essential as will be described later.

At least one of the plurality of leg portions 4013 or at least one of the plurality of connecting portions 4016 is configured so that when the force 4110 is applied to the pressure-receiving portion 4012 in its ready condition, a tip portion 4013*d* of the corresponding leg portion 4013 moves toward a direction away from central axis 4015 while being in contact with the skin 4200, to consequently pull a portion 4201 of the skin facing the support portion 4014 toward the same direction due to a friction with the skin 4200 so as to impart a tension to the portion 4201 of the skin.

Specifically, in the device 4010 of FIG. 66, at least one of the plurality of leg portions 4013 is made of a material deformable. This allows the leg portion 4013 to deform (bend) concavely when the force 4110 is applied to the pressure-receiving portion 4102, to shift from the dotted line state (ready condition) to the solid line state (inserting condition) as shown in FIG. 67. As a result, the leg-portion tip portion 4013*d* in contact with the skin 4200 moves toward a direction away from the central axis 4015 so as to impart a desired tension 4202 to the portion 4201 of the skin facing the support portion 4014 due to the friction with the skin 4200. Thus, the needles 4003 on the microneedle patch insert easily into the portion 4201 of the skin to which the tension 4202 is imparted. Accordingly, without any damage or breakage of the needles, substantially all the needles insert securely into the skin so that the drug carried on the needles can certainly be administered.

Figure 72:
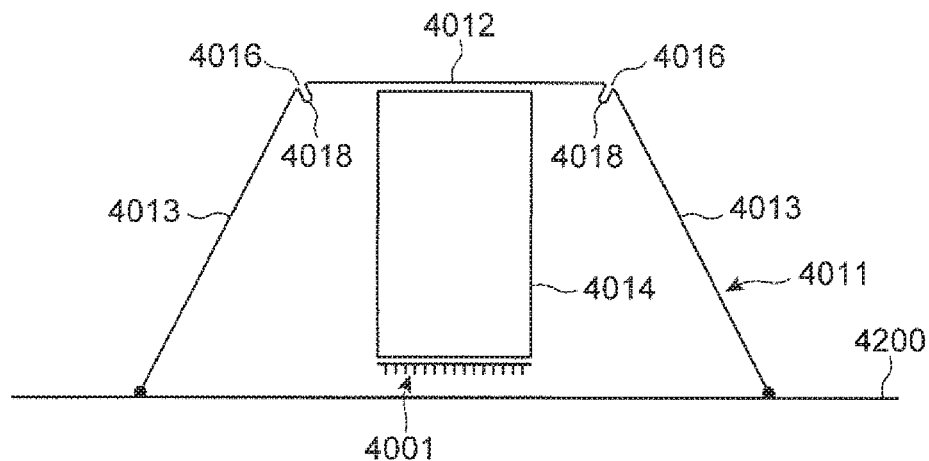
FIG. 72 is a sectional view of a schematic device having an deformable portion at a connecting portion between the pressure-receiving portion and the leg portion.

Although in the above description, the leg portions 4013 are configured to deform when a force is applied to the pressure-receiving portion 4012, the connecting portion 4016 may have a U-shaped or groove-like or thin-walled deformable portion 4018 that deforms easily when the force 4110 acts on the pressure-receiving portion 4012 as shown in FIG. 72 so that a desired amount of deformation can be obtained by a small pressurizing force due to the deformation of the deformable portion 4018 in combination with the resilient deformation of the leg portions 4013.

Figure 73:
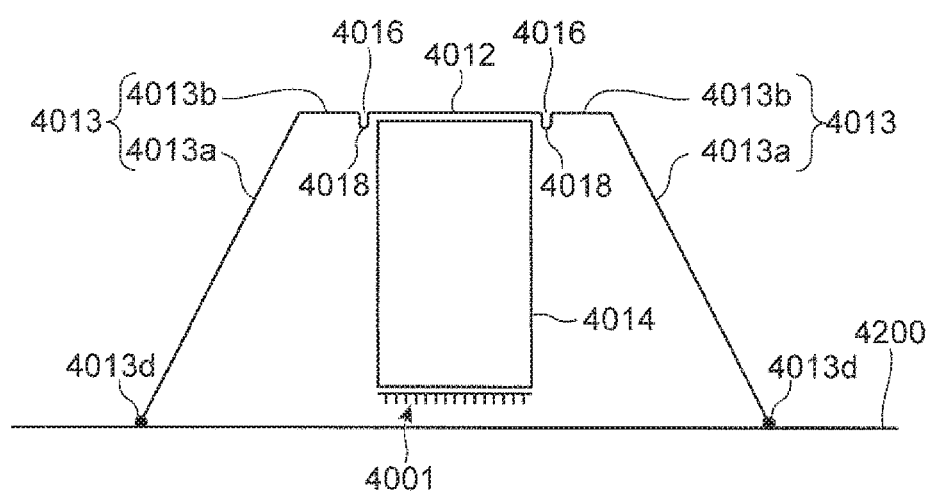
FIG. 73 is a sectional view of a schematic device having an deformable portion at a connecting portion between the pressure-receiving portion and the leg portion.

Although the leg portion 4013 is represented as a diagonally extending member in the modification of FIG. 66, the leg portion 4013 may be formed, as shown in FIG. 73, as a member including a diagonally extending portion 4013*a* and a portion 4013*b* that extends horizontally from the upper end of the diagonally extending portion 4013*a* toward the central axis 4015. In this modification, the horizontally extending portion 4013*b* is connected through the connecting portion 4016 to the pressure-receiving portion 4012. The deformable portion 4018 is formed in the connecting portion 4016. Hence, when a force is applied to the pressure-receiving portion 4012, the connecting portion 4016 deforms and the tip portion 4013*d* of the leg portion 4013 moves toward a direction away from the central axis 4015 while being in frictional contact with the skin 4200, imparting a tension 4202 to the portion 4201 of the skin facing the support portion 4014.

Figure 74:
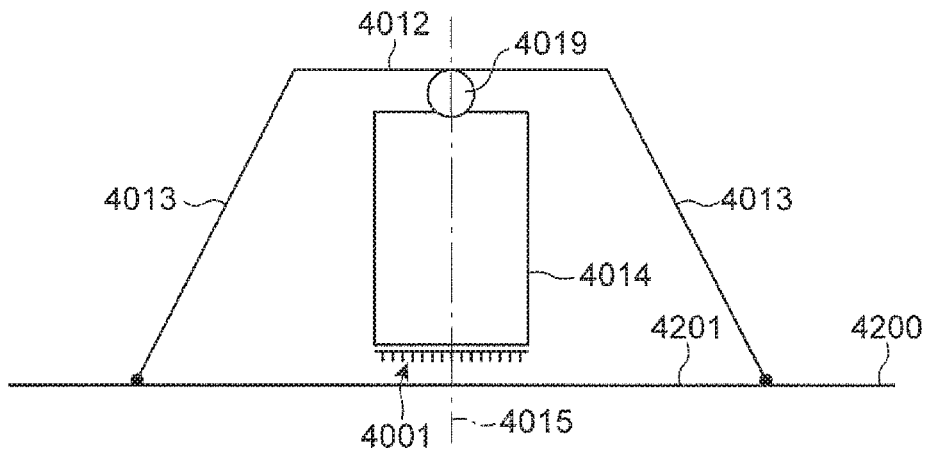
FIG. 74 is a sectional view of a schematic device having a ball-joint.

In order that the entire surface of the microneedle patch 4001 is pressed against the skin with a uniform force when a force is applied to an off-centered point of the pressure-receiving portion 4012, or when an uneven force is applied to the top surface of the pressure-receiving portion 4012, a ball-joint 4019 preferably lying on the central axis 4015 may be provided between the support portion 4014 and the pressure-receiving portion 4012 to couple the two together, as shown in FIG. 74.

The deformation abilities of the leg portion 4013 and the deformable portion 4018 can be adjusted by selecting the materials and the sizes (thicknesses) thereof.

The pressure-receiving portion 4012 and the leg portion 4013 are each made up of a single or a plurality of parts made of a synthetic resin or a metal. The portions 4012 and 4013 may be made as a single member or formed integrally. One of the pressure-receiving portion 4012 and the leg portion 4013 may be made of a synthetic resin, with the other being made of a metal, and the two may be integrally coupled together by suitable coupling means, e.g., by welding a resin to a metal. Examples of a preferred resin include polypropylene, polyethylene, nylon, ABS resin, PET, acrylic resin, polystyrene, vinylidene chloride, polycarbonate, fluorine (Teflon), vinyl chloride, polyamide, rubber, and silicone. Examples of a preferred metal include titanium, stainless, aluminum, and magnesium alloys.

Figure 75:
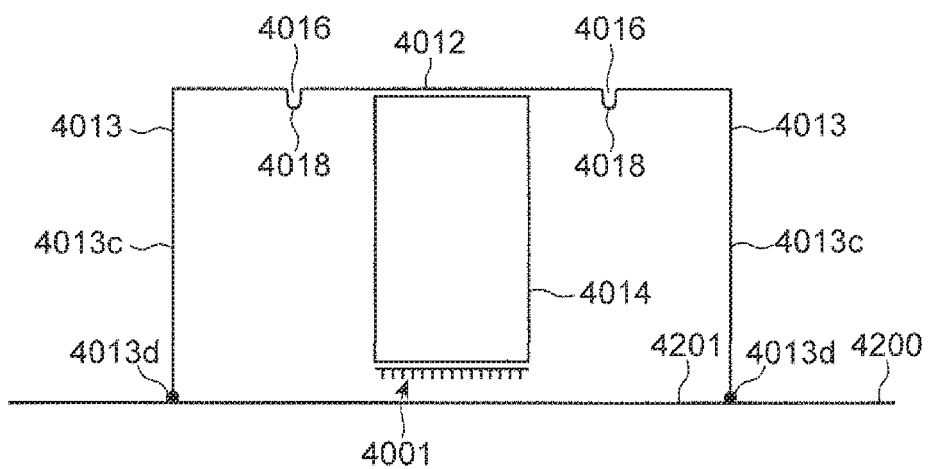
FIG. 75 is a sectional view of a schematic device having a leg portion with a horizontal portion and a vertical portion.
Figure 76:
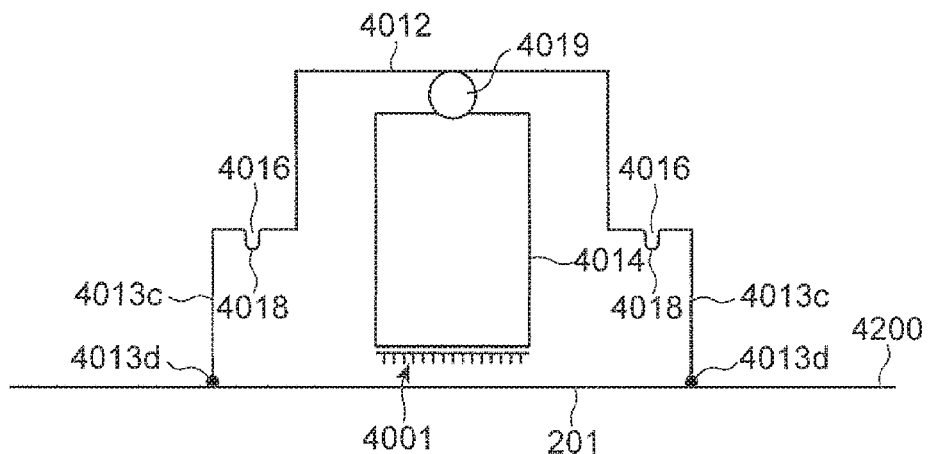
FIG. 76 is a sectional view of a schematic device having a leg portion with a horizontal portion and a vertical portion.
Figure 77:
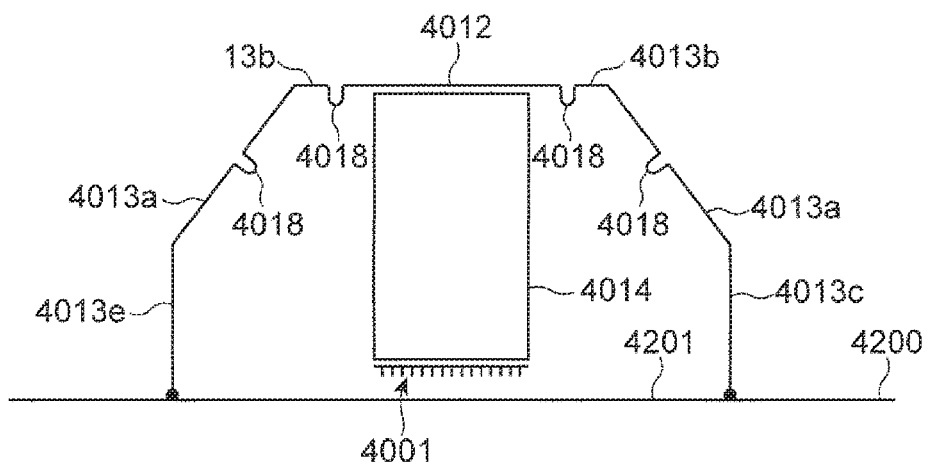
FIG. 77 is a sectional view of a schematic device having a leg portion with a horizontal portion, a vertical portion, and a diagonal portion.

As described above, the tip portion 4013d of the leg portion 4013 moves away from the central axis 4015 when a force is applied to the pressure-receiving portion 4012. To this end, the weak or deformable portion is desirably provided closer to the central axis than the skin contact portion. As long as such a function is obtained, the shape of the leg portion 4013 is not restrictive. For example, as shown in FIGS. 75 and 76, a tip-side portion (portion designated by reference numeral 4013c) of the leg portion 4013 may extend vertically toward the skin 4200. For example, as shown in FIG. 77, the deformable portion 4018 may be formed, in addition to in the connecting portion 4016 connecting the horizontally extending portion 4013b of the leg portion 4013 and the pressure-receiving portion 4012, or instead thereof, in the diagonally extending portion 4013a connecting the horizontally extending portion 4013b and the vertically extending portion 4013c. In these modifications, pressing the pressure-receiving portion 4012 causes the deformable portion 4018 to deform, allowing the vertically extending portion 4013c (in particular, tip portion 4013d) of the leg portion 4013 to move away from the central axis 4015.

Figure 78:
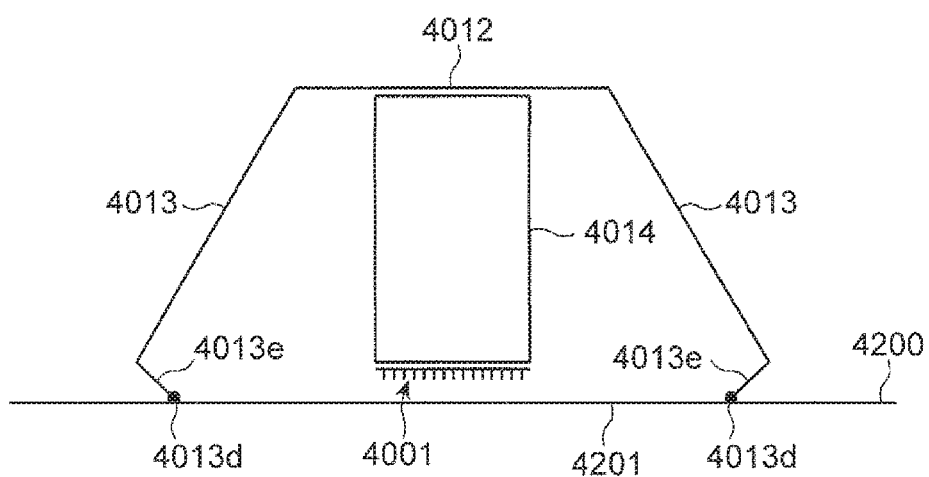
FIG. 78 is a sectional view of a schematic device having the leg portion whose tip is directed inward.

As long as the above functions are obtained, a tip portion 4013e of the leg portion 4013 may extend diagonally from outside toward inside as shown in FIG. 78.

Figure 79:
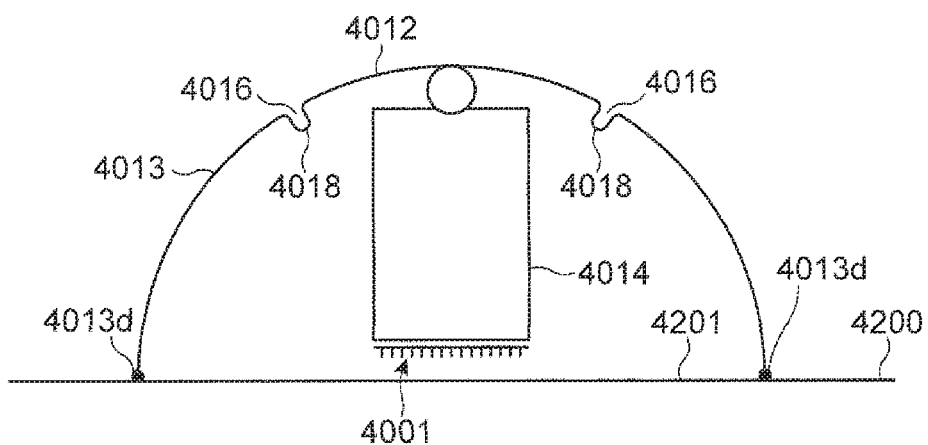
FIG. 79 is a sectional view of a schematic device having the pressure-receiving portion and the leg portion connected together in an arc.

Although in the above modifications, the housing 4011, in particular, the structure joining the pressure-receiving portion 4012 and the leg portions 4013, has a substantially rectangular section or a substantially trapezoidal section, the scope of the present invention encompasses a modification in which the pressure-receiving portion 4012 and the leg portions 4013 are joined in an arc as shown in FIG. 79. In this case, as shown, the deformable portion 4018 is preferably provided in the boundaries between the pressure-receiving portion 4012 and the leg portions 4013 or in the leg portions 4013.

Figure 80:
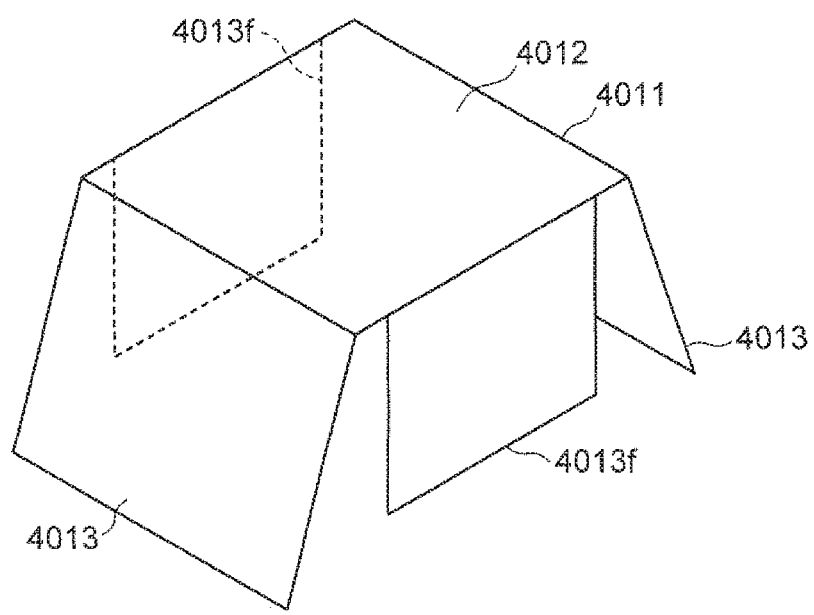
FIG. 80 is a perspective view of a schematic device having a leg portion regulating the amount of deformation.

The vertical leg portion and the diagonal leg portion may be combined together. For example, although not shown, one of a pair of leg portions may be a vertical leg portion, with the other being a diagonal leg portion. In the device having two pair of opposed leg portions (four leg portions), a pair of opposed leg portions may be vertical leg portions, with the remaining pair of opposed leg portions being diagonal leg portions. In the latter, as shown in FIG. 80 for example, the length in the vertical direction of the diagonal leg portions 4013 is formed to be greater than the length in the vertical direction of the vertical leg portions 13f, thereby enabling the tension applied to the skin by the diagonal leg portions 4013 to be retained by the vertical legs 4013f.

According to this modification of the device according to the present invention configured in this manner, by pressing the pressure-receiving portion by a finger with the device mounted on the skin, a portion in contact with the skin of at least one leg portion pulls the skin outward from the center of the device, imparting a tension to a portion of the skin facing the microneedle patch. Thus, the needles on the microneedle patch insert easily into the portion of the skin to which the tension is imparted. Accordingly, without any damage or breakage of the needles, substantially all the needles insert securely into the skin so that the drug carried on the needles can certainly be administered.

In order to facilitate the outward spreading from the device center, of a portion in contact with the skin of the leg portion, it is desirable that the deformable portion 4018 lie at a position closer to the device center than the portion in contact with the skin of the leg portion. By taking this positional relationship, an intended object of the device of the present invention can be attained of spreading out the skin, instead of fixing the housing, by the leg portions pushing the skin.

A plurality of embodiments embodying the above basic modification will be described.

Sixteenth Embodiment

Figure 81:
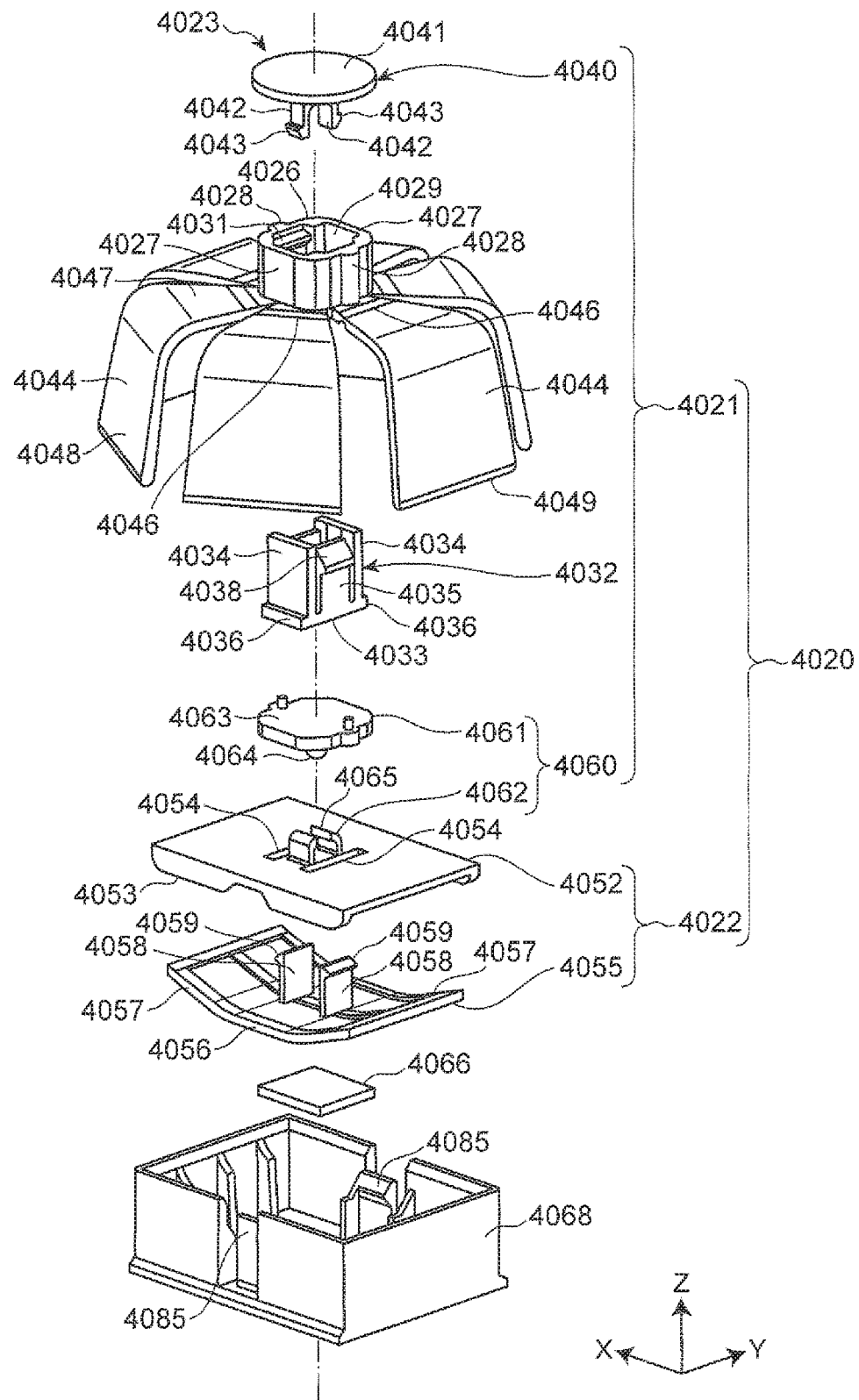
FIG. 81 is an exploded perspective view of a device according to the sixteenth embodiment.

FIG. 81 shows a sixteenth embodiment of the device applying a microneedle patch onto a skin according to the present invention. The device of the shown embodiment is generally designated at reference numeral 4020 and schematically includes a housing 4021 and a support portion 4022 for a microneedle patch.

The housing 4021 has a pressure-receiving portion 4023 and a plurality of leg portions 4044.

Figure 83:
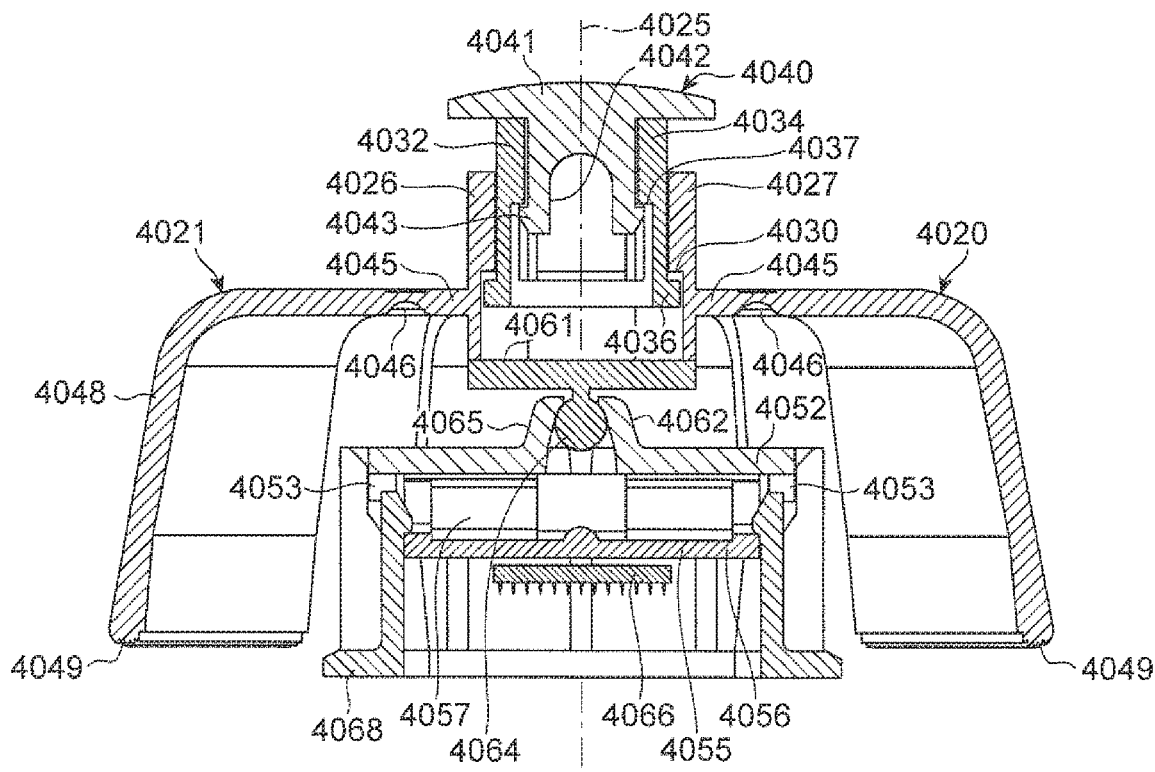
FIG. 83 is a sectional view of the device according to the sixteenth embodiment.
Figure 84:
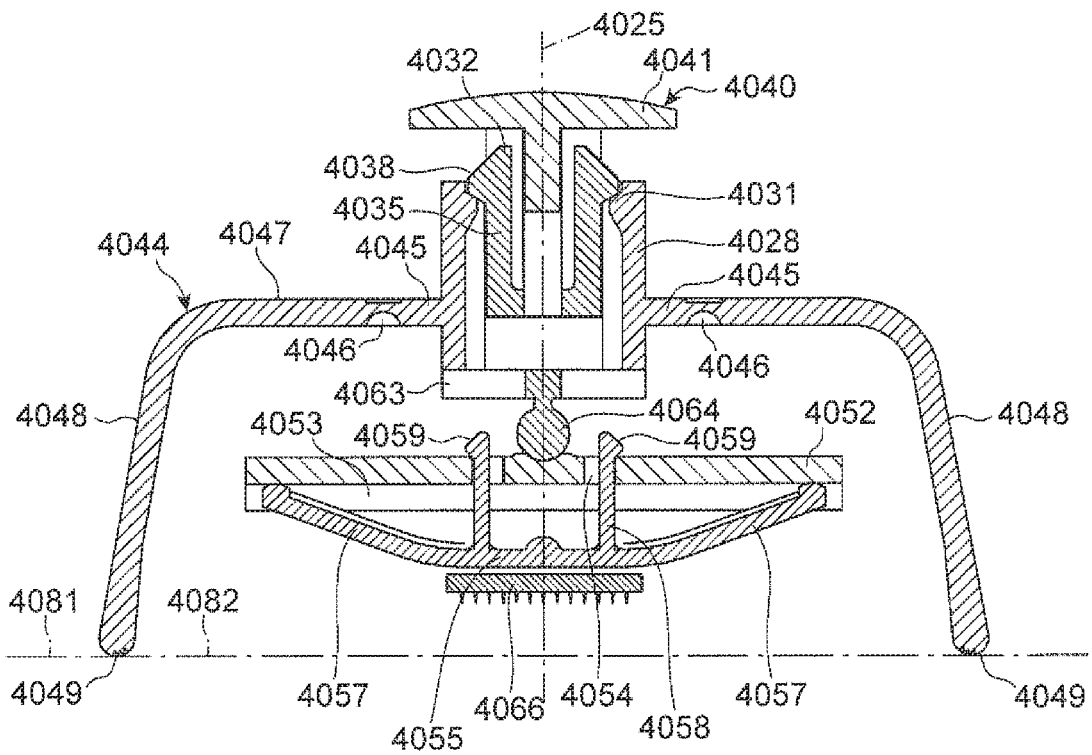
FIG. 84 is a sectional view of the device according to the sixteenth embodiment.

The pressure-receiving portion 4023 has a cylindrical portion 4026 extending vertically along a central axis 4025 of the device 4020. The cylindrical portion 4026 has a pair of walls 4027 extending in parallel in the X-direction and a pair of walls 4028 extending in parallel in the Y-direction orthogonal to x-axis, with these four walls 4027 and 4028 defining a substantially rectangular cylindrical space 4029 thereinside. As shown in FIG. 83, the pair of x-direction walls 4027 have stepped portions 4030 formed between an inner-surface upper portion and an inner-surface lower portion so that the opposing distance at the inner-surface upper portion is smaller than the opposing distance at the inner-surface lower portion. As shown in FIG. 84, the pair of y-direction walls 4026 have, near an opening at the inner-surface upper portion, inward protrusions 4031 protruding toward the inside.

The cylindrical portion 4026 receives an indicator 4032 within the interior space 4029. As shown in FIG. 81, the indicator 4032 has a rectangular bottom frame 4033. The top surface of the bottom frame 4033 is formed integrally with a pair of vertical walls 4034 extending upward from portions of the frame extending in the X-direction and a pair of vertical walls 4035 extending upward from portions of the frame extending in the Y-direction. As shown in FIGS. 81 and 83, the vertical walls 34 extending in the X-direction are positioned inward a predetermined distance from outer edges of the corresponding portions of the frame, to define a pair of engagement portions 4036 protruding outward from the vertical walls 4034. The vertical walls 4034 have stepped portions 4037 (shown in only FIG. 83) formed between an inner-surface upper portion and an inner-surface lower portion so that the opposing distance at the inner-surface upper portion is smaller than the opposing distance at the inner-surface lower portion. As shown in FIGS. 81 and 84, the vertical walls 4035 extending in the Y-direction have, at their upper portions, outward protrusions 4038 extending toward the outside.

The sizes and the shapes of the portions of the cylindrical portion 4026 and of the indicator 4032 are determined so that when inserting the indicator 4032 into the interior space 4029 of the cylindrical portion 4026 as shown in FIGS. 83 and 84, the engagement portions of the indicator 4032 are engaged with the stepped portions 4030 of the cylindrical portion 4026 as shown in FIG. 83, the lower portions of the outward protrusions 4038 of the indicator 4032 being engaged with the upper portions of the inward protrusions 4031 of the cylindrical portion 4026 as shown in FIG. 84, the indicator 4032 being retained at a shown ascent position relative to the cylindrical portion 4026.

Figure 82:
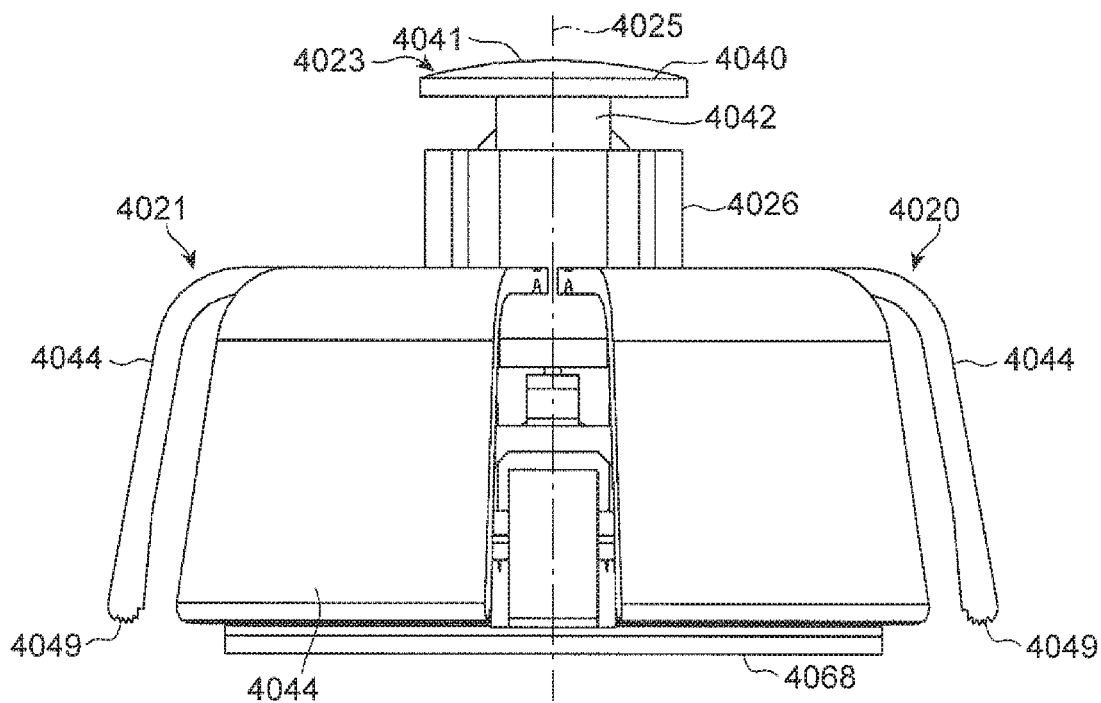
FIG. 82 is a side view of the device according to the sixteenth embodiment.

As shown in FIGS. 81 to 83, the indicator 4032 supports a pressure-receiving button 4040. The pressure-receiving button 4040 has a finger rest 4041 to which the user applies a force and a pair of vertical walls 4042 extending downward from a bottom surface of the finger rest 4041 and extending in parallel in the X-direction. The vertical wall 4042 has on its outer surface an outward protrusion 4043 protruding toward the outside. The sizes and shapes of the portions of the indicator 4032 and of the pressure-receiving button 4040 are determined so that when inserting the vertical walls 4042 into the upper opening of the indicator 4032 as shown in FIG. 83, the outward protrusions 4043 of the vertical walls 4042 are engaged with the inner-surface stepped portions 4037 of the indicator 4032.

The plurality of leg portions 4044 are connected to the outer surface of the cylindrical portion 4026. In the embodiment, six flanges 4045 are formed integrally on the outer surface of the cylindrical portion 4026 at circumferentially 60-degree intervals around the central axis 4025. The leg portion 4044 is connected integrally with a connecting portion 4046 lying at the tip of each of the six flanges 4045. As shown, each of the plurality of leg portions 4044 is not connected to the adjoining different leg portions and is independent of the others. As shown, the leg portion 4044 has a portion (horizontal portion) 4047 extending horizontally from the connecting portion 4046 outward and a portion (diagonal portion) 4048 extending diagonally downward from the outside end of the horizontal portion 4047 outward. In the embodiment, to increase the friction with the skin, fine grooves or unevennesses (not shown) are formed at a tip portion 4049 of the diagonal portion 4048, i.e., a portion in contact with the skin in use.

As shown in FIG. 81, the connecting portions 4046 extend straightforward along the sides of the regular hexagon around the central axis 4025. In the embodiment, the connecting portion 4046 is thinned and weakened than the flange 4045 and the leg portion 4044, to form an deformable portion. Hence, when a force is applied to the pressure-receiving portion 4023, the housing 4021 bends at the connecting portion 4046 (the deformable portion).

The support portion 4022 supporting the microneedle chip is provided under the pressure-receiving portion 4023 and inside the plurality of leg portions 4044. The support portion 4022 has a horizontally provided plate-like holder 4052. The holder 4052 has a pair of guide flanges 4053 formed on its bottom surface. The guide flanges 4053 extend symmetrically with respect to the central axis 4025 and in parallel in the X-direction in FIG. 16. The holder 4052 also has, on both sides of the central axis 4025, apertures 4054 passing vertically through the holder 4052.

A trapezoidal spring 4055 is provided between the guide flanges 4053 on the bottom surface of the holder 4052. The trapezoidal spring 4055 has integrally a rectangular central plate portion 4056 supporting the microneedle patch, inclined plate portions 4057 extending diagonally upward from a pair of opposed edges of the central plate portion 4056, and a pair of vertical walls 4058 lying in the vicinity of the connecting portion between the central plate portion 4056 and the inclined plate portions 4057 and extending upward from the top surface of the central plate portion 4056. The vertical wall 4058 has at its upper end an outward protrusion 4059 protruding toward the outside.

The thus configured trapezoidal spring 4055 is assembled to the holder 4052, with free ends of the inclined plate portions 4057 being located between the guide flanges 4053, with the upper-end outward protrusions 4059 of the vertical walls 4058 being engaged with the top surface of the holder 4052 while inserting the vertical walls 4058 into the apertures 4054 of the central plate portion 4056.

The holder 4052 having the trapezoidal spring 4055 assembled thereto is connected to the underside of the pressure-receiving portion 4040 by way of, preferably, a ball joint 4060. In the embodiment, the ball joint 4060 has an upper structure 4061 provided under the pressure-receiving portion 4040 and a lower structure 4062 provided on top of the support portion 4022. The upper structure 4061 has a plate portion 4063 connected to the lower end of the cylindrical portion 4026 and a spherical ball 4064 fixed at the center on the bottom surface of the plate portion 4063. The lower structure 4062 has a ball retaining portion 4065 formed at the center on the top surface of the holder 4052. The ball 4064 of the upper structure 4061 is retained in the ball retaining portion 4065 of the lower structure 4062 so that the support portion 4022 can turn around the ball 4064.

The sizes and shapes of the portions of the above device 4020 are determined so that in the ready condition where the device 4020 supporting the microneedle patch 4066 on the support portion 4022 is placed on the skin 4081, the microneedle patch 4066 cannot come into contact with the skin with a predetermined gap formed between the microneedle patch 4066 and the skin, as shown in FIGS. 83 and 84. In order to prevent the user's finger, etc., from coming into contact with the microneedle patch supported on the support portion 4022, it is preferred to detachably provide the support portion 4022 with a protection cover 4068 surrounding the bottom surface of the microneedle patch, as shown in FIGS. 81 and 83.

Figure 87:
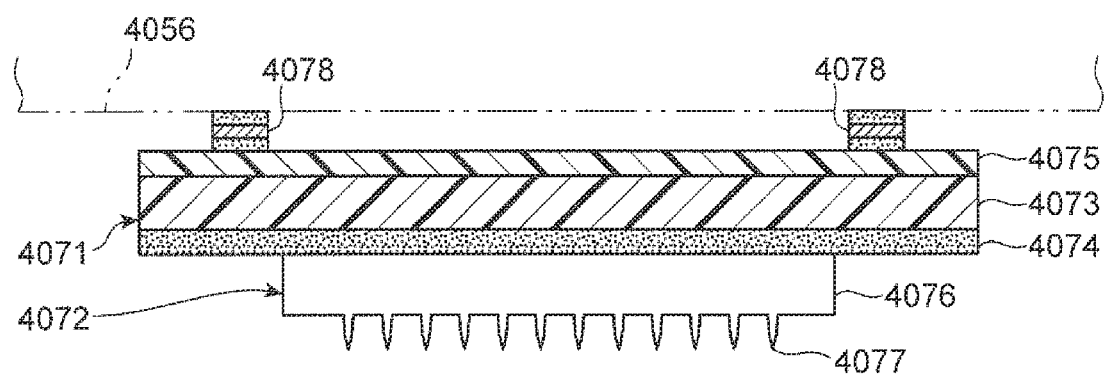
FIG. 87 is a view showing schematically a section of the microneedle patch.
Figure 88:
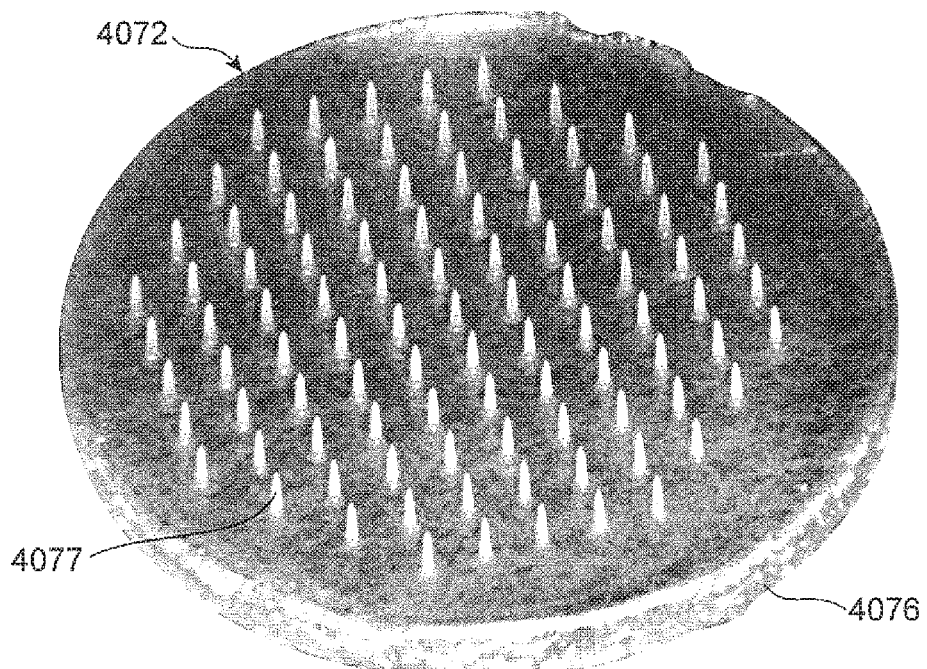
FIG. 88 is a view showing a photograph of the microneedle patch.

In the device 4020 having the above shape, the microneedle patch 4066 is retained on the bottom surface of the central plate portion of the trapezoidal spring 4055. As shown in FIGS. 87 and 88, the microneedle patch 4066 has a sheet substrate 4071 and a microneedle array 4072 supported thereon. The sheet substrate 4071 has a substrate film 4073, a pressure-sensitive adhesive layer 4074 provided on a bottom surface (a surface supporting the microneedle array 4072) of the substrate film 4073, and a release treatment layer (a releasing layer) 4075 provided on a top surface (a surface opposing the applicator 4001) of the substrate film 4073. The microneedle array 4072 has a circular or rectangular base 76 and a multiplicity of elongated needles 4077 with a predetermined height (e.g., 300 to 1000 micrometers) arrayed at predetermined intervals (e.g., 300 to 1000 micrometers) in a lattice or honeycomb pattern on a bottom surface of the base 4076. The microneedle array 4072 is formed, for example, by filling a biodegradable synthetic polymer material (e.g., hyaluronic acid, collagen, polylactic acid, polyglycolic acid) into a correspondingly shaped mold. Although not shown, tip sides of the needles 77 are coated with a target drug (molecules such as vaccine, protein, and peptide). Alternatively, or additionally, the target drug may be contained in the needles 77 by being mixed with materials of the needles during molding of the microneedle array 4072.

The sheet substrate 4071 and the microneedle array 4072 are arranged so that the base 4076 of the microneedle array 4072 is applied on the pressure-sensitive adhesive layer 4074 of the sheet substrate 4071. As shown, the sheet substrate 4071 is larger than the microneedle array 4072 so that a sufficient area of the pressure-sensitive adhesive layer 4074 is exposed around the microneedle array 4072 when the microneedle array 4072 is applied on the sheet substrate 4071.

The sheet substrate 4071 of the thus formed microneedle patch 4066 is applied onto the central plate portion 4056 of the trapezoidal spring 4055 by use of double-sided adhesive tapes 4071 having pressure-sensitive adhesive layers provided on both surfaces of a sheet substrate. The double-sided adhesive tapes 4078 serve to retain the microneedle patch 4066 on the central plate portion 4056 before applying the microneedle patch 4066 onto the skin. Thus, the conditions (size, shape, attachment position, adhesive force) of the double-sided adhesive tapes 4078 are preferably determined so that the microneedle patch 4066 can be retained on the first element 4003 and so that when separating the applicator 4001 from the microneedle patch 4066 after attachment onto the skin, the microneedle patch 4066 is prevented from peeling off from the skin due to the adhesive force between the skin double-sided adhesive tapes 4078 and the central plate portion 4056. Considering these conditions, the double-sided adhesive tapes 4078 are sized as small as possible and are applied to positions apart a determined distance inward from both ends of the sheet substrate 4071.

Figure 85:
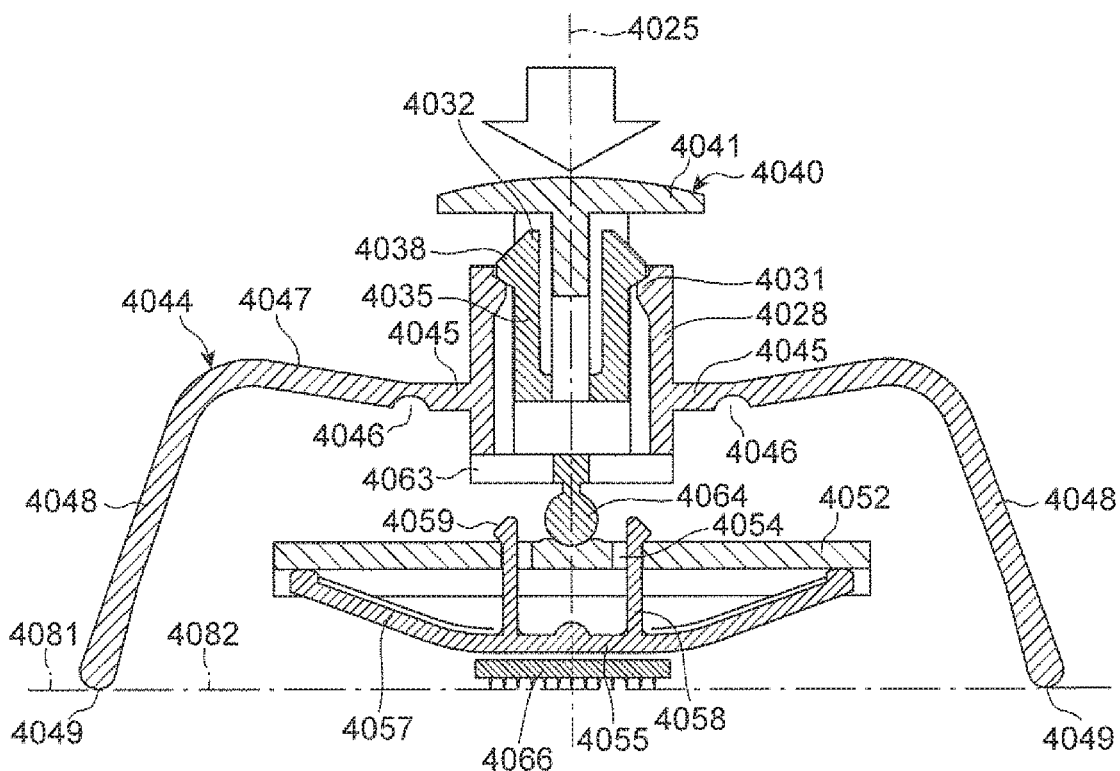
FIG. 85 is a sectional view for showing an action of the device according to the sixteenth embodiment.
Figure 86:
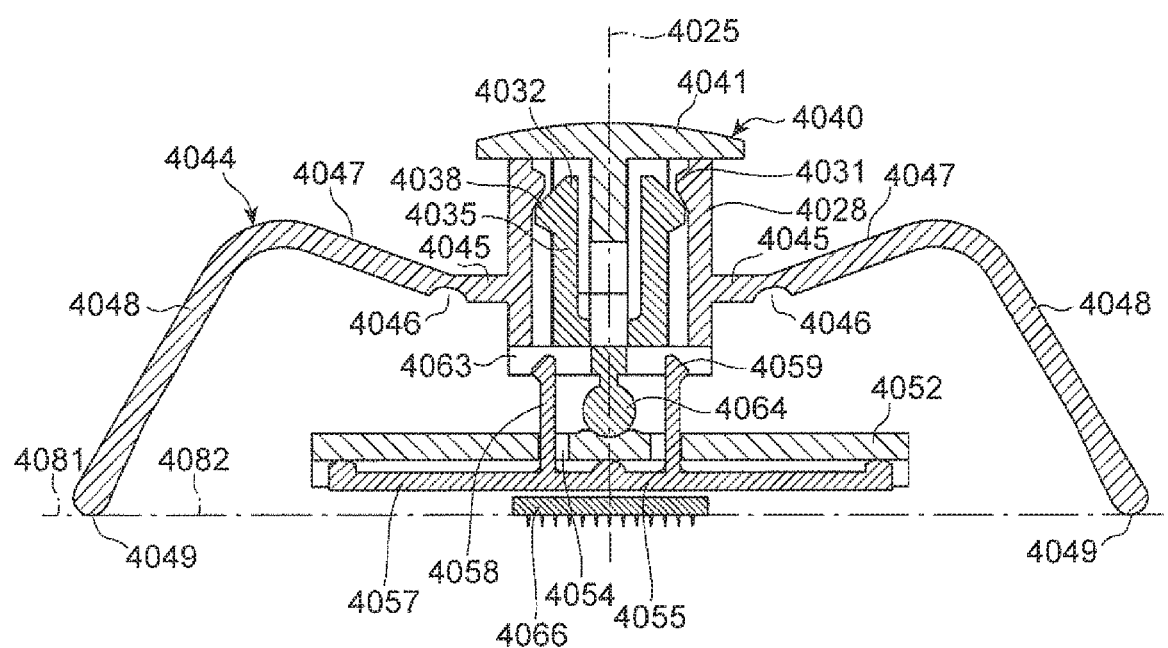
FIG. 86 is a sectional view for showing an action of the device according to the sixteenth embodiment.

When applying the microneedle patch 4066 onto a skin 4081 of a human being or an animal using the device 4020 configured as above, the device 4020 without the protection cover 4068 is placed on the skin 4081, as shown in FIGS. 84 to 86. In this ready condition, the microneedle patch 4066 is held apart from the skin 4081 above the skin 4081. The finger rest 4041 of the pressure-receiving button 4040 is then depressed by, e.g., a thumb. As a result, the housing 4021 is bent at the connecting portions 4046 (deformable portions) connecting the pressure-receiving portion 4023 and the leg portions 4044, allowing the microneedle patch 4066 to move toward the skin together with the pressure-receiving portion 4023. At this time, the leg portions 4044 pivot on the connecting portions 4046, with the result that the tip portions 4049 of the leg portions 4044 move in the direction away from the central axis 4025 correspondingly to the amount of movement of the connecting portions 4046. Hence, a portion 4082 of the skin surrounded by the tip portions 4049 of the six leg portions 4044 are pulled toward the direction away from the central axis 4025 due to the friction between the tip portions 4049 and the skin 4081, to be "tensioned". Accordingly, when the needles 4077 on the microneedle patch 4066 come into contact with the portion 4082 of the skin, the needles 4077 insert easily into the "tensioned" portion 4082 of the skin, without any retreat of the portion 4080 of the skin caused by the advancement of the needles 4077. Therefore, without any damage or breakage of the needles, substantially all the needles insert securely into the skin so that the drug carried on the needles can certainly be administered.

When the needles 4077 insert into the portion 4082 of the skin as a result of application of a desired force onto the pressure-receiving button 4040, the outward protrusions 4038 provided on the vertical walls 4035 of the indicator 4032 receive reaction forces from the inward protrusions 4031 engaged therewith of the cylindrical portion 4026 so that the vertical walls 4035 curve inward, with the result that the pressure-receiving button 4040 and the indicator 4032 move to a descent position shown in FIG. 86 with respect to the cylindrical portion 4026. When the outward protrusions 4038 of the vertical walls 4035 get over the inward protrusions 4031 of the cylindrical portion 4026, the vertical walls 4035 restore resiliently to their original straight states (unbent states), as shown in FIG. 86. At this time, the outward protrusions 4038 of the vertical walls 4035 collide with the walls 4028 of the cylindrical portion 4026, to issue a sound. At the same time, the pressure-receiving button 4040 comes into abutment against the upper end of the cylindrical portion 4026, to prohibit a further descent. Thus, the user can recognize that the needles 4077 have stuck into the skin, from the collision sound and a shock transmitted from the pressure-receiving button 40. As a result, the user does not apply an additional force to the device 4020.

The device according to the sixteenth embodiment is partially reused as a cartridge. For example, when the protection cover 4068 is again set after insertion, the support portion 4022 (e.g., holder 4052) is engaged, at its opposed edges, with engagement protrusions 4085 of the protection cover 4068 so that it is held in the protection cover 4068. Thus, by pulling down the protection cover 4068 by hand from this state, the support portion 4022 without the microneedle patch can be removed from the housing 4021 together with the protection cover 4068. At this time, the ball-joint lower mechanism 4062 formed integrally with the holder 4052 is detached from the ball-joint upper mechanism 4061 fastened to the housing 4021. The indicator 4032 returns to its origin shown in FIG. 18 by pulling up the pressure-receiving button, to provide for reuse. Thus, the size and shape of the vertical walls 4035 and the size and shape of the outward protrusions 4038 are determined so that the indicator 4032 returns to its origin by pulling up the indicator 4032. The housing 4021, from which the holder 4052, etc., are removed in this manner, is set to its reuse-enabled state by mounting the housing 4021 with the protection cover 4068 accommodating another support portion 4022 having the microneedle patch 4066. On the other hand, the microneedle patch is again applied to the holder 4052, etc., removed from the housing 4021, to provide for reuse.

Although in the above description, the lower structure 4062 of the ball-joint 4060 is separated from the upper structure 4061 thereof for reuse, instead of this, only the trapezoidal spring 4055 may be separated, or the support portion 4022 and the ball-joint 4060 (including the upper structure 4061 and the lower structure 4062) may be separated from the housing 4021, or only the microneedle patch 4066 may be changed.

Seventeenth Embodiment

FIG. 18 shows a seventeenth embodiment of the device applying a microneedle patch onto a skin, according to the present invention. The device of the shown embodiment is generally designated at reference numeral 4120 and schematically includes a housing 4121 and a support portion 4122 for a microneedle patch.

The housing 4121 has a pressurized portion 4123 and a plurality of leg portions 4144.

Figure 92:
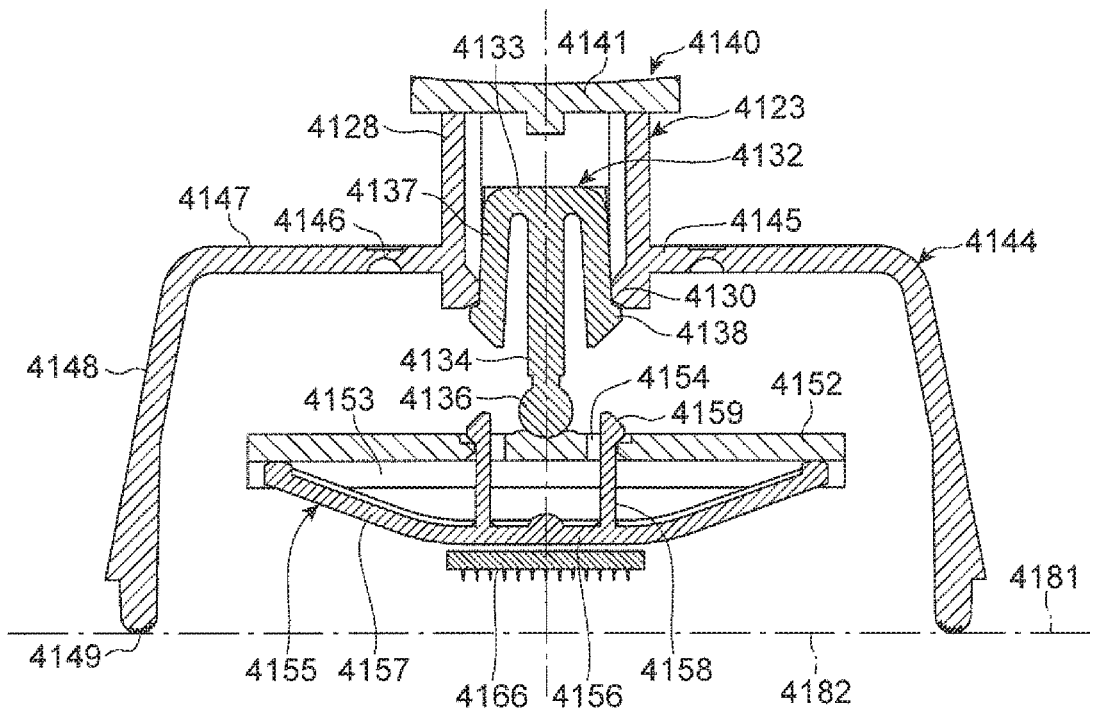
FIG. 92 is a sectional view of the device according to the seventeenth embodiment.
Figure 93:
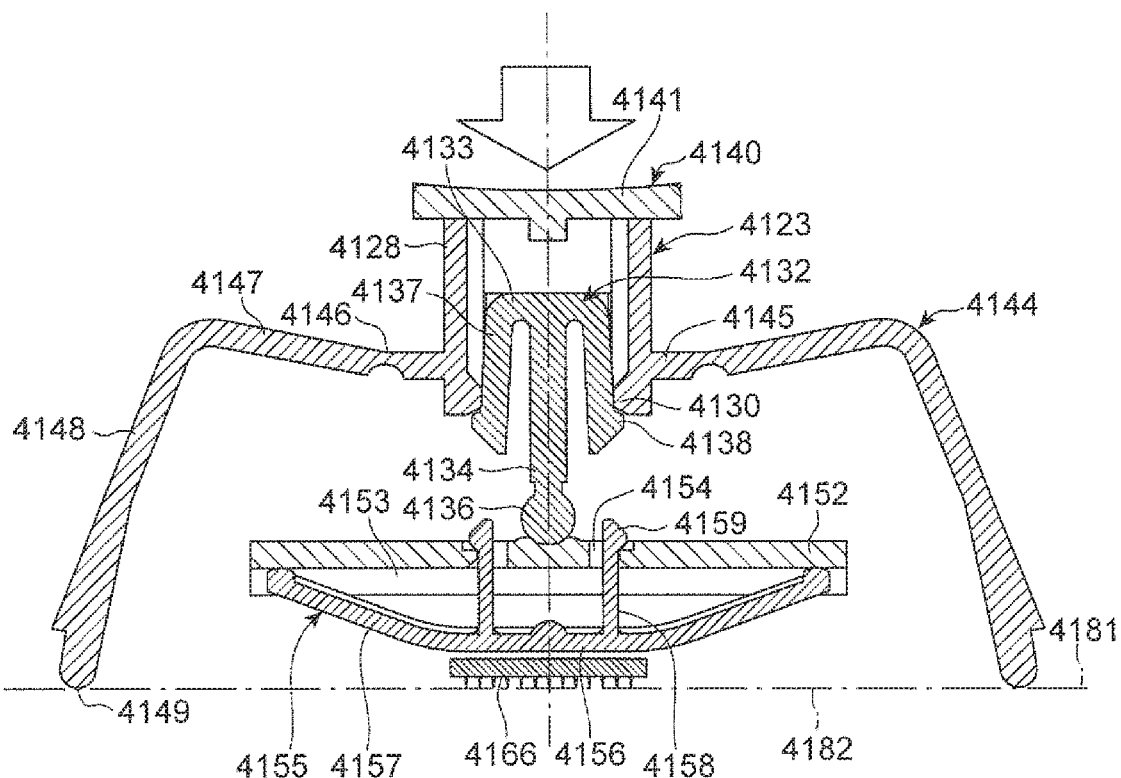
FIG. 93 is a sectional view for showing an action of the device according to the seventeenth embodiment.

The pressurized portion 4023 has a cylindrical portion 4126 extending vertically along a central axis 4125 of the device 4120. The cylindrical portion 4126 has a pair of walls 4127 in parallel in the X-direction and a pair of walls 4128 in parallel in the Y-direction, with the four walls 4127 and 4128 defining a substantially rectangular cylindrical space 4129 thereinside. As shown in FIG. 92, the pair of x-direction walls 4127 have, at their inner-surface lower portions, an inward protrusion 4130 protruding inward. As shown in FIG. 93, the pair of y-direction walls 4128 have, near an opening at their inner-surface lower portions, an inward protrusion 4131 extending toward the inside.

Figure 89:
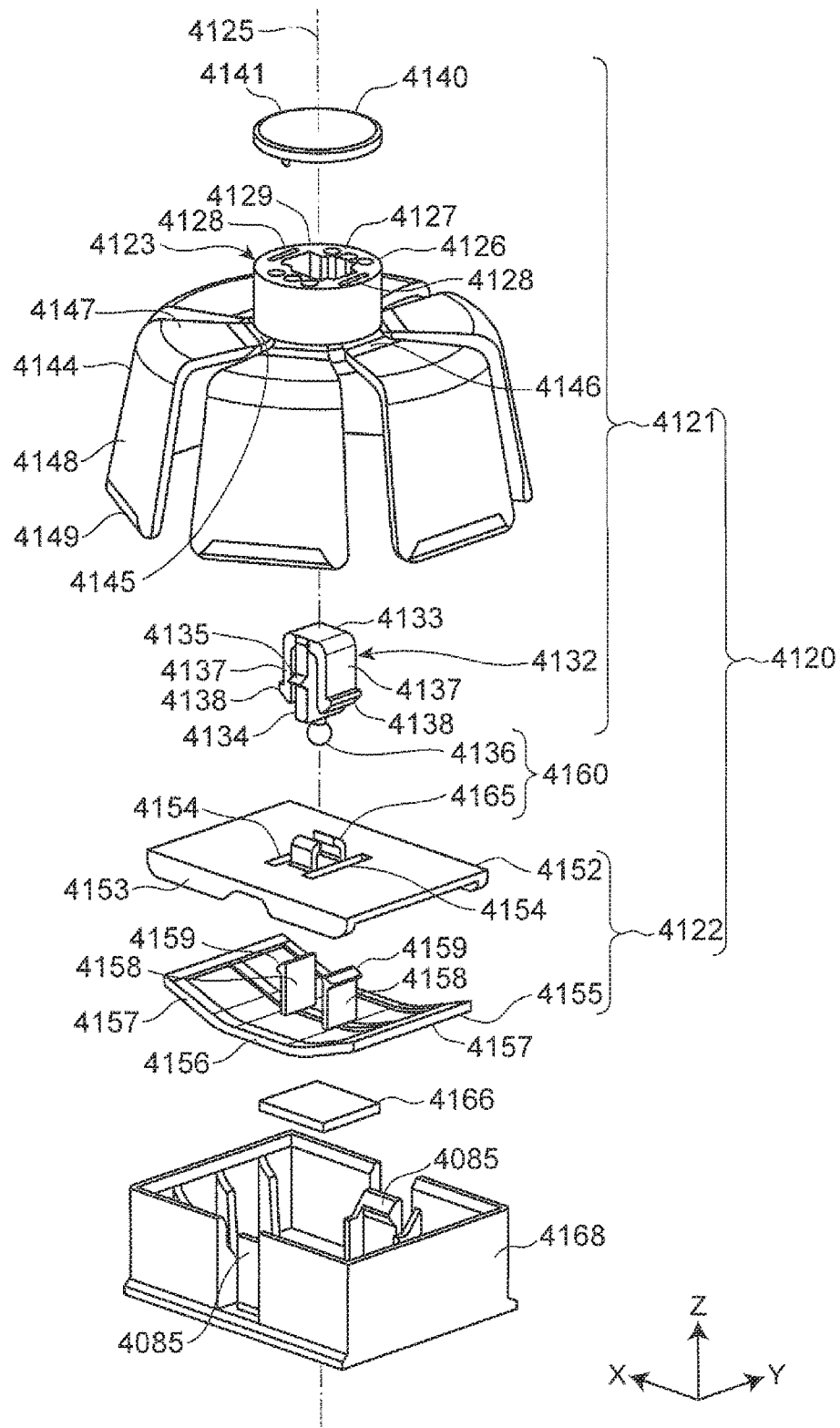
FIG. 89 is an exploded perspective view of a device according to the seventeenth embodiment.

The cylindrical portion 4126 receives an indicator 4132 within the interior space 4129. As shown in FIG. 89, the indicator 4132 has a rectangular top wall 4133. The top wall 4133 has, at a center on its bottom surface, a central vertical wall 4134 extending in the Y-direction formed integrally therewith. Side surfaces (surfaces opposing in y-direction) of the central vertical wall 4134 have at an intermediate position an outward protrusion 4135 protruding outward formed integrally therewith. The central vertical wall 4134 has at a center on its lower end a ball 4136 for a ball-joint formed integrally therewith. The top wall 4133 has on its bottom surface outside vertical walls (leaf spring portions) 4137 on both sides of the vertical wall 4134, formed integrally therewith. The outside vertical walls 4137 have at their lower ends an outward protrusion 4138 protruding toward the outside, formed integrally therewith.

Figure 91:
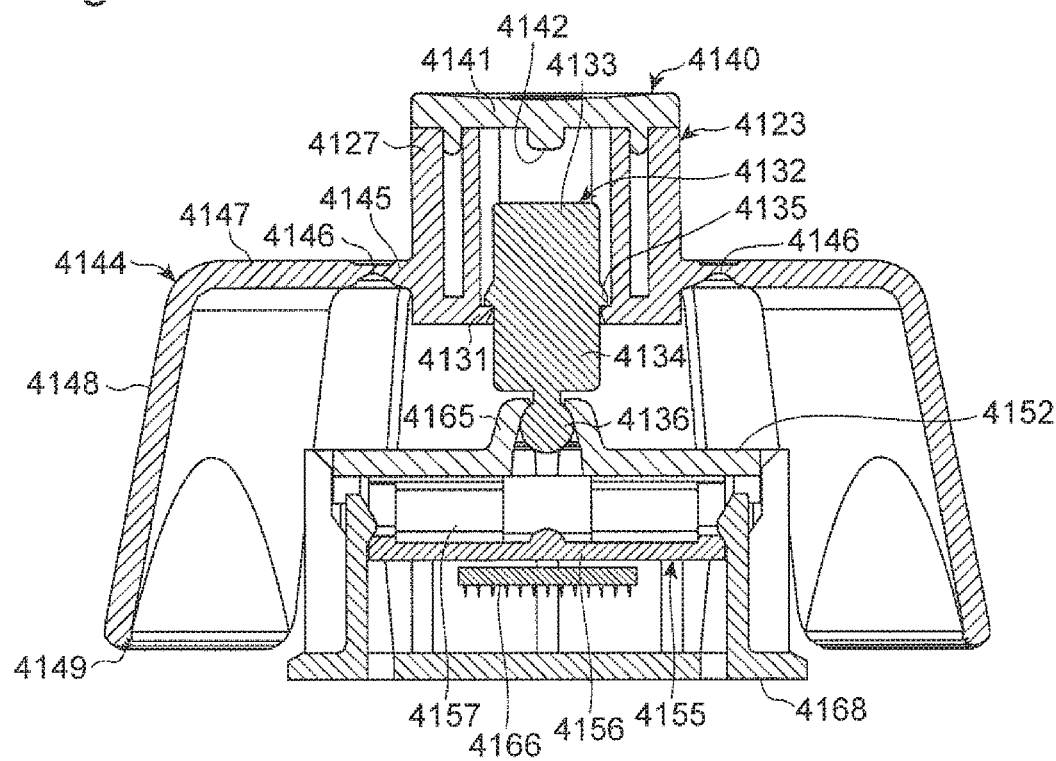
FIG. 91 is a sectional view of the device according to the seventeenth embodiment.

The sizes and the shapes of the portions of the cylindrical portion 4126 and of the indicator 4132 are determined so that when inserting the indicator 4132 into the interior space 4129 of the cylindrical portion 4126 as shown in FIGS. 91 and 92, the intermediate outward protrusions 4135 of the indicator 4132 are engaged with the lower-end inward protrusions 4131 of the cylindrical portion 4126 as shown in FIG. 91, the lower-end outward protrusions 4138 of the indicator 4132 being engaged with the inner-surface inward protrusions 4130 of the cylindrical portion 4126 as shown in FIG. 92, the indicator 4132 being retained at a shown descent position relative to the cylindrical portion 4126.

As shown in FIGS. 89 to 92, the cylindrical portion 4128 supports a pressurized button 4140. The pressurized button 4140 has a finger rest 4141 to which the user applies a force and has at a center on its bottom surface a boss portion 4142 formed integrally therewith.

The plurality of leg portions 4144 are connected to the outer surface of the cylindrical portion 4126. In the embodiment, the cylindrical portion 4126 has on its outer surface six flanges spaced apart 60 degrees circumferentially around the central axis 4125, formed integrally therewith. The leg portions 4144 are connected integrally with the connecting portions 4146 provided on the tips of the six flanges 4145. As shown, each of the plurality of leg portions 4144 is not connected to the adjoining different leg portions and is independent of the others. As shown, the leg portion 4144 has a portion (horizontal portion) 4147 extending horizontally from the connecting portion 4136 outward and a portion (diagonal portion) 4148 extending diagonally downward from the outside end of the horizontal portion 4147 outward. In the embodiment, to increase the friction with the skin, fine grooves or unevennesses (not shown) are formed at a tip portion 4149 of the diagonal portion 4148, i.e., a portion in contact with the skin in use.

As shown in FIG. 89, the connecting portions 4146 extend straightforward along the sides of the regular hexagon around the central axis 4125. In the embodiment, the connecting portion 4146 is thinned and weakened than the flange 4145 and the leg portion 4144, to form an deformable portion. Hence, when a force is applied to the pressurized portion 4123, the housing 4121 bends at the connecting portion 4146 (the deformable portion).

The support portion 4122 supporting the microneedle chip is provided under the pressurized portion 4123 and inside the plurality of leg portions 4144. The support portion 4122 has a horizontally provided plate-like holder 4152. The holder 4152 has a pair of guide flanges 4153 formed on its bottom surface. The guide flanges 4153 extend symmetrically with respect to the central axis 4125 and in parallel in the X-direction in FIG. 89. The holder 4152 also has, on both sides of the central axis 4125, apertures 4054 passing vertically through the holder 4152.

A trapezoidal spring 4155 is provided between the guide flanges 4153 on the bottom surface of the holder 4152. The trapezoidal spring 4155 has integrally a rectangular central plate portion 4156 supporting the microneedle patch, inclined plate portions 4157 extending diagonally upward from a pair of opposed edges of the central plate portion 4156, and a pair of vertical walls 4158 lying in the vicinity of the connecting portion between the central plate portion 4156 and the inclined plate portions 4157 and extending upward from the top surface of the central plate portion 4156. The vertical wall 4158 has at its upper end an outward protrusion 4159 protruding toward the outside.

The thus configured trapezoidal spring 4155 is assembled to the holder 4152, with free ends of the inclined plate portions 4157 being located between the guide flanges 4153, with the upper-end outward protrusions 4159 of the vertical walls 4158 being engaged with the top surface of the holder 4152 while inserting the vertical walls 4158 into the apertures 4154 of the central plate portion 4156.

The holder 4152 having the trapezoidal spring 4155 assembled thereto is connected to the underside of the pressurized portion 4140 by way of, preferably, a ball joint 4160. In the embodiment, the ball joint 4160 includes a ball 4136 provided on the indicator 4132 and a ball retaining portion 4165 formed at a center on the top surface of the holder 4152, with the ball 4136 being retained on the ball retaining portion 4165 so that the support portion 4122 can turn around the ball 4136.

Figure 90:
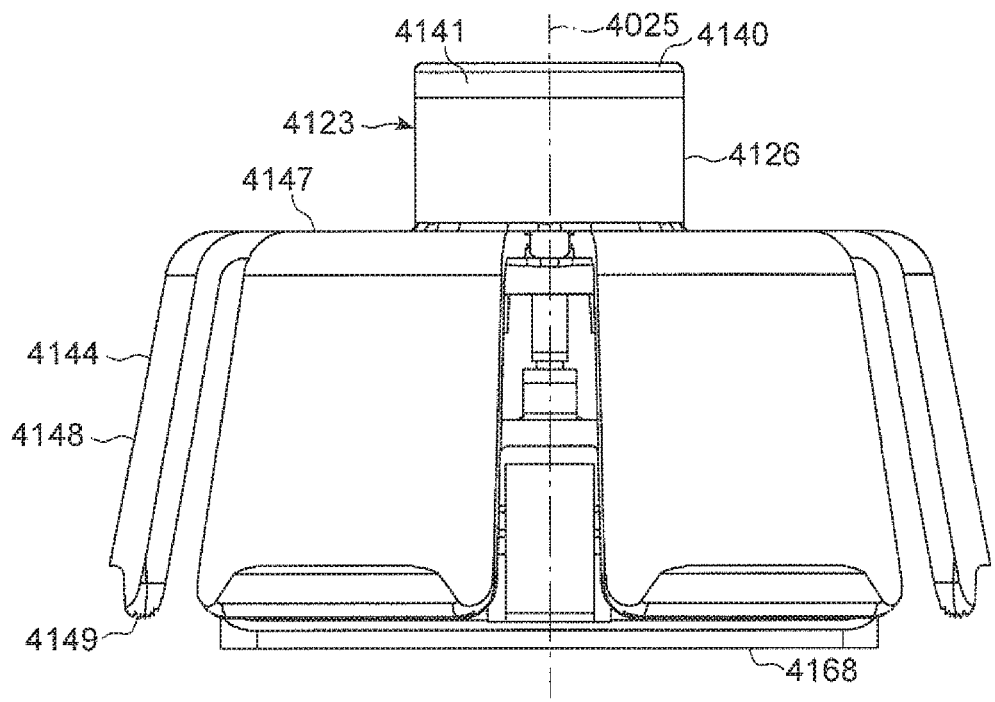
FIG. 90 is a side view of the device according to the seventeenth embodiment.

The sizes and shapes of the portions of the above device 4120 are determined so that in the ready condition where the device 4120 supporting the microneedle patch 4166 on the support portion 4122 is placed on the skin 4181, the microneedle patch 4166 cannot come into contact with the skin with a predetermined gap formed between the microneedle patch 4166 and the skin, as shown in FIG. 92. In order to prevent the user's finger, etc., from coming into contact with the microneedle patch supported on the support portion 4122, it is preferred to detachably provide the support portion 4122 with a protection cover 4168 surrounding the bottom surface of the microneedle patch, as shown in FIGS. 90 and 91.

In the device 4120 having the above shape, the microneedle patch 4166 is retained on the bottom surface of the central plate portion of the trapezoidal spring 4155. The microneedle patch 4166 is the same as the microneedle patch shown in FIGS. 87 and 88.

Figure 94:
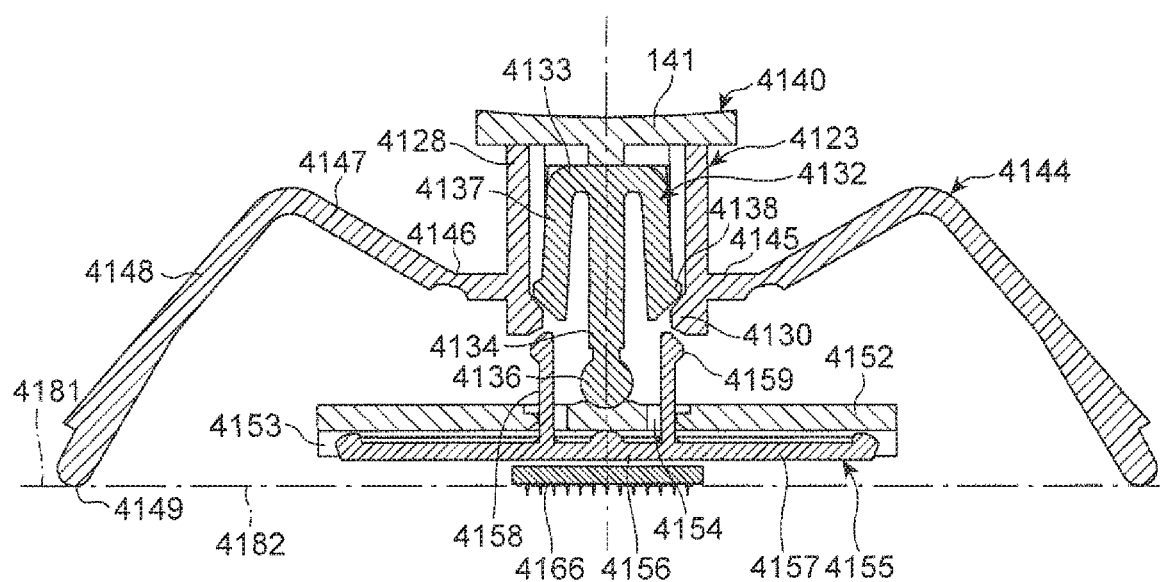
FIG. 94 is a sectional view for showing an action of the device according to the seventeenth embodiment.

When applying the microneedle patch 4166 onto a skin 4181 of a human being or an animal using the device 4120 configured as above, the device 4120 without the protection cover 4168 is placed on the skin 4181, as shown in FIGS. 92 to 94. In this ready condition, the microneedle patch 4166 is held apart from the skin 4181 above the skin 4181. The finger rest 4141 of the pressurized button 4140 is then depressed by, e.g., a thumb. As a result, the housing 4121 is bent at the connecting portions 4146 (deformable portions) connecting the pressurized portion 4123 and the leg portions 4144, allowing the microneedle patch 4166 to move toward the skin together with the pressurized portion 4123. At this time, the leg portions 4144 pivot on the connecting portions 4146, with the result that the tip portions 4149 of the leg portions 4144 move in the direction away from the central axis 4125 correspondingly to the amount of movement of the connecting portions 4146. Hence, a portion 4182 of the skin surrounded by the tip portions 4149 of the six leg portions 4144 are pulled toward the direction away from the central axis 4125 due to the friction between the tip portions 4149 and the skin 4181, to be "tensioned". Accordingly, when the needles on the microneedle patch 4166 come into contact with the portion 4182 of the skin, the needles insert easily into the "tensioned" portion 4182 of the skin, without any retreat of the portion 4180 of the skin caused by the advancement of the needles. Therefore, without any damage or breakage of the needles, substantially all the needles insert securely into the skin so that the drug carried on the needles can certainly be administered.

When the needles insert into the portion 4182 of the skin as a result of application of a desired force onto the pressurized button 4140, the outward protrusions 4138 provided on the vertical walls (leaf spring portions) 4137 of the indicator 4132 receive reaction forces from the inward protrusions 4130 engaged therewith of the cylindrical portion 4126 so that the vertical walls 4137 curve inward, with the result that the cylindrical portion 4126 moves downward with respect to the indicator 4132. When the outward protrusions 4138 of the vertical walls 4137 get over the inward protrusions 4130 of the cylindrical portion 4126, the vertical walls 4137 restore resiliently to their original straight states (unbent states), as shown in FIG. 94. At this time, the outward protrusions 4138 of the vertical walls 4137 collide with the walls 4127 of the cylindrical portion 4126, to issue a sound. At the same time, the boss portion 4142 of the pressurized button 4140 comes into abutment against the upper end of the indicator 4132, to prohibit a further descent. Thus, the user can recognize that the needles have stuck into the skin, from the collision sound and a shock transmitted from the pressurized button 4140. As a result, the user does not apply an additional force to the device 120.

The device according to the seventeenth embodiment is partially reused as a cartridge. For example, when the protection cover 4168 is again set after insertion, the support portion 4122 (e.g., holder 4152) is engaged, at its opposed edges, with engagement protrusions 4185 of the protection cover 4168 so that it is held in the protection cover 4168. Thus, by pulling down the protection cover 4168 by hand from this state, the support portion 4122 without the microneedle patch can be removed from the housing 4121 together with the protection cover 4168. At this time, the ball retaining portion 4165 of the ball-joint 4160 formed integrally with the holder 4152 is detached from the ball 4136 of the ball-joint 4160 connected to the housing 4121. The indicator 4132 is returned to its origin shown in FIG. 91 by being pulled down from the housing 4121 by hand, to provide for reuse. The housing 4121, from which the holder 4152, etc., are removed in this manner, is set to its reuse-enabled state by mounting the housing 4121 with the protection cover 4168 accommodating another support portion 4122 having the microneedle patch 4166. On the other hand, the microneedle patch 4166 is again applied to the holder 4152, etc., removed from the housing 4121, to provide for reuse.

Although in the above description, the lower structure (ball-retaining portion 4165) of the ball-joint 4160 is separated from the upper structure (ball 4136) thereof for reuse, instead of this, only the trapezoidal spring 4155 may be separated, or the support portion 4122 including the holder 4152 and the trapezoidal spring 4155 may be separated from the housing 4121, or only the microneedle patch 4166 may be changed. It is to be noted that between the above seventeenth embodiment and an eighteenth embodiment described later that portions detached from the housing in the embodiment on one hand can be mounted and used on the housing of the embodiment on the other.

Interval Between Leg Portions

As described above, the device of the present invention securely inserts the needles into a skin by utilizing a force applied to the pressure-receiving portion to impart a tension to the skin. In order to attain such a unique function, the interval between adjacent leg portions and the positional relationship between the deformable portion and the skin contact portion of the leg portion are significant elements. Experiments and results thereof arriving at this knowledge will be described below.

Experiment 1

Figure 110:
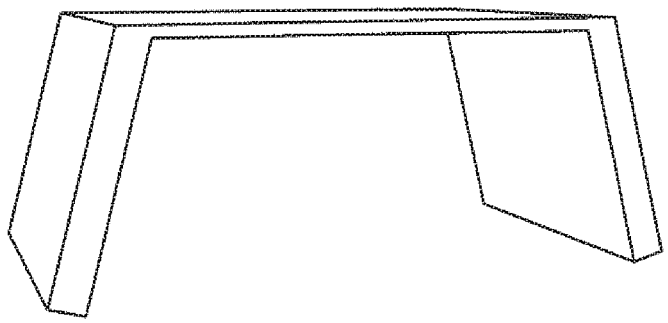
FIG. 110 is a perspective view showing a housing modification having two leg portions.

Three different housing modifications were prepared for the experiment. A first housing modification has a rectangular pressure-receiving portion and a pair of leg portions extending downward from a pair of opposed edges (connecting portions) of the pressure-receiving portion as shown in FIG. 110. For the first housing modification, four different samples A to D with angles (interior angles) of 90 degrees, 95 degrees, 100 degrees, and 105 degrees, respectively, between the pressure-receiving portion and the leg portion were prepared. The samples A to D were molded from a UV curable resin. In the samples A to D, the pressure-receiving portion is equal in size to the leg portions. From the angular differences, in the samples A to D, distances between tips (portions in contact with a skin) of opposed leg portions were 30 mm, 33 mm, 35 mm, and 37 mm, respectively.

Figure 111:
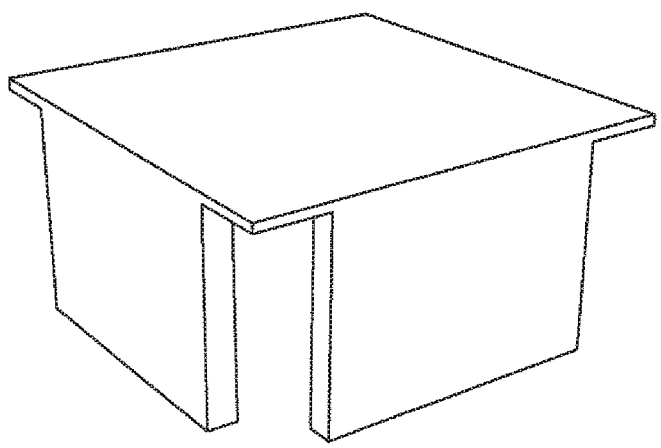
FIG. 111 is a perspective view showing a housing modification having four leg portions.

A second housing modification has a rectangular pressure-receiving portion and four leg portions extending downward from edges (connecting portions) of the pressure-receiving portion as shown in FIG. 111. For the second housing modification, two different samples E and F with angles (interior angles) of 90 degrees and 105 degrees, respectively, between the pressure-receiving portion and the leg portions were prepared. The samples E and F were molded from a UV curable resin. In the samples E and F, the pressure-receiving portion is equal in size to the leg portions. From the angular differences, in the samples E and F, distances between tips (portions in contact with a skin) of opposed leg portions were 30 mm and 37 mm, respectively.

Figure 112:
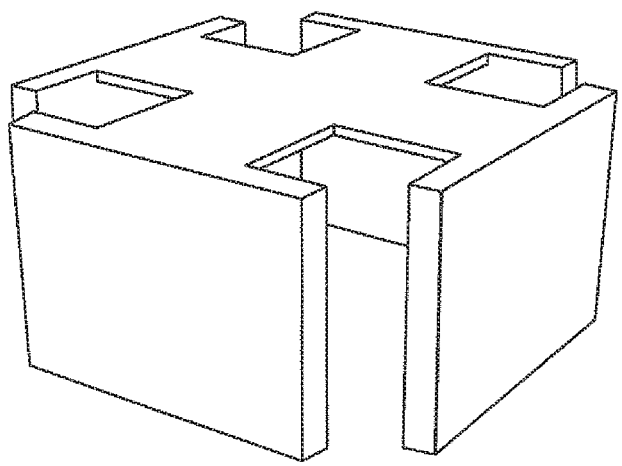
FIG. 112 is a perspective view showing a housing modification having four leg portions.

A third housing modification has a cruciate pressure-receiving portion and four leg portions extending downward from edges (connecting portions) of the pressure-receiving portion as shown in FIG. 112. For the third housing modification, two different samples G and H with angles (interior angles) of 90 degrees and 105 degrees, respectively, between the pressure-receiving portion and the leg portions were prepared. The samples G and H were molded from a UV curable resin. In the samples G and H, the pressure-receiving portion is equal in size to the leg portions. From the angular differences, in the samples G and H, distances between tips (portions in contact with a skin) of opposed leg portions were 30 mm and 42 mm, respectively.

The samples were placed on a skin and a force of 10 N was applied to the pressure-receiving portion to measure a spread (i.e., distance between the leg portions) of the skin. The measurement results are shown in Table 1.

TABLE 1

| SAMPLES | INTERIOR ANGLE (DEGREES) | LEG TIP DISTANCE (mm) (PRE-DEFORMATION → POST-DEFORMATION) | LEG SPREAD (mm) |
| --- | --- | --- | --- |
| A | 90 | 30 → 32 | 2 |
| B | 95 | 33 → 35 | 2 |
| C | 100 | 35 → 39 | 4 |
| D | 105 | 37 → 43 | 6 |
| E | 90 | 30 → 30 | 0 |
| F | 105 | 42 → 42 | 0 |
| G | 90 | 30 → 30 | 0 |
| H | 105 | 42 → 42 | 5 |

As shown in Table 1, in the samples A to D having two leg portions, the spread of the skin became large according as the interior angle increased. On the other hand, in the samples E and F having four leg portions, no spread of the skin was found out. In the sample H having four diagonal leg portions, a spread of the skin was found out, whereas in the sample G having four vertical (non-diagonal) leg portions, no spread was found out.

According to the inventors' consideration, the cause that the spread of the skin was found out in the samples A to D and H, with no spread of the skin in the samples E to G, in this manner lies in that, due to the leg portions having a higher rigidity with respect to the applied stress, the leg portions were prevented from spreading because the housing could not deform in shape. It was further found for the purpose of facilitating the outward spreading of the skin contact portions of the leg portions from the device center toward the outside that, for easier spreading out of the skin, the deformable portions should be located at positions closer to the device center than the skin contact portions of the leg portions.

In G, the cause was considered to lie in the distance between adjacent leg portions. Based on this consideration, the interval between adjacent leg portions required to obtain a maximum spreading rate of 10% was studied with the maximum spreading rate being 30% when pulling the skin, with a target skin spreading rate (target value) of 10%.

Deforming of the housing shape to spread the legs is achieved by the disposition of the deformable portions. The deformable portions may be e.g., combinations of shapes such as notches and unevennesses, thicknesses, hinges, or materials having different rigidities.

The maximum spreading rate is obtained from experiments and is preferably 20%, more preferably 30%, and even more preferably 40%. In the experiments, the forearm, upper arm, and abdomen of 40s of Japanese men were pulled along the skin. As a result, the maximum spreading rate of the forearm was 34.5%, the maximum spreading rate of the upper arm was 36.7%, and the maximum spreading rate of the abdomen was 26.6%. Hence, the maximum skin spreading rate was determined to be 30% as a representative.

Figure 113:
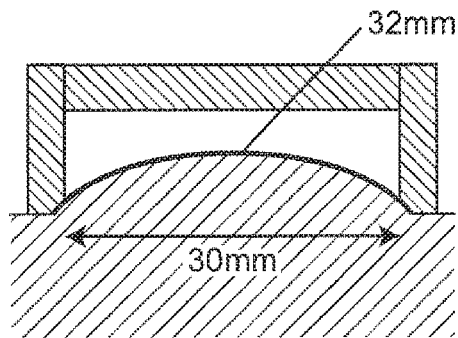
FIG. 113 is a view showing a rise of a skin.

The following is the reason that the target value was determined as preferably 6%, more preferably 10% or 15%. For example, when two leg portions are abutted against the skin as shown in FIG. 113, a skin lying therebetween rises.

If the distance between leg portions is 30 mm with a skin abutment force of 10 N, the rise causes an approx. 2 mm (=6.7%) expansion of the skin between the leg portions. Thus, the target value to impart a further tension to the skin by the increase of the distance between the leg portions was set to minimum 6% and 10% as a representative. This value coincides with the experimental results of the inventors that 10% skin expansion enabled the needles to insert relatively easily into the skin.

Figure 114:
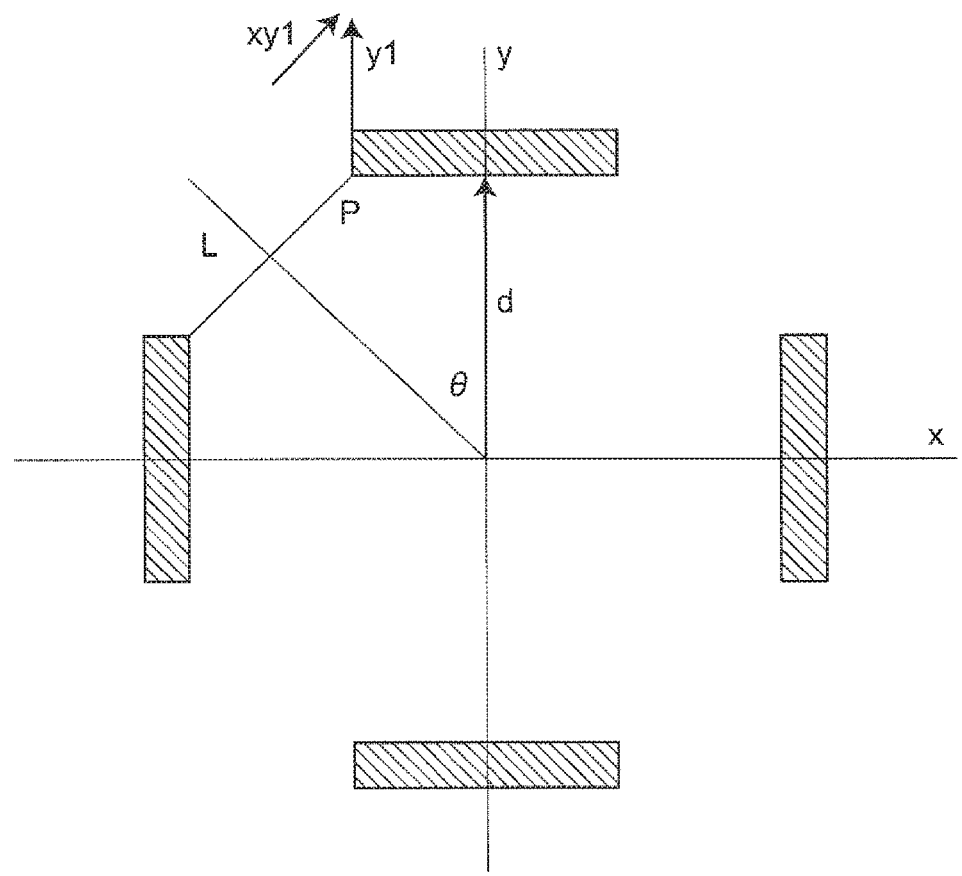
FIG. 114 is a view showing a modification for calculating a required distance between leg portions.
Figure 115:
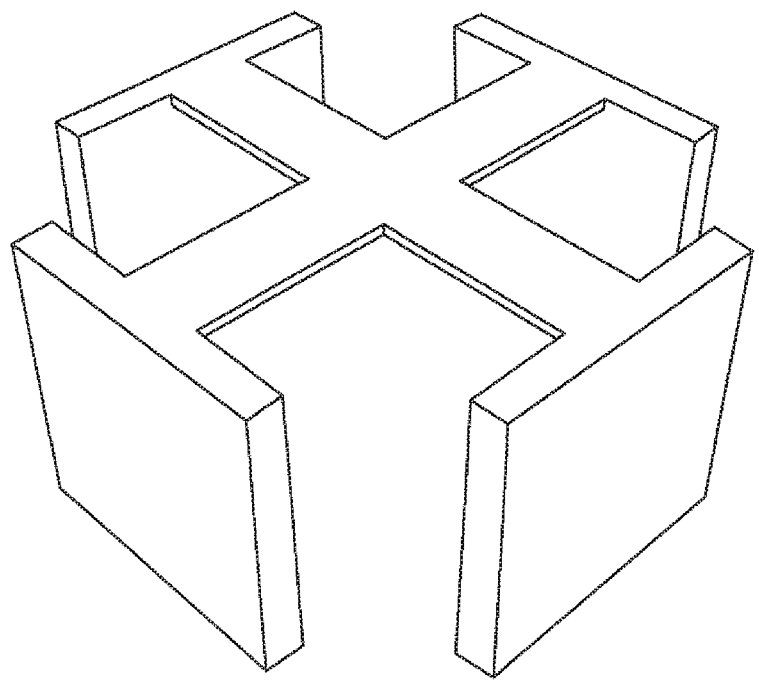
FIG. 115 is a perspective view showing a housing modification having four leg portions.

Such a situation was considered that as shown in FIG. 114, by four leg portions spaced a predetermined interval (2d) in x-direction and y-direction orthogonal thereto, a portion of the skin surrounded by the four leg portions is spread in x-direction and y-direction. In this case, adjacent end points of two adjacent leg portions are each pulled in y-direction and x-direction. At this time, as for an end point P, in order to move the end point P by y1 in y-direction, the end point P needs to move simultaneously by xy1 in the diagonal direction. When applying this condition to the maximum skin spreading rate 30% and the target value 10%, it is necessary in order to move the point P by 0.1d (distance from the central axis to the leg portion) that $0.1 \sin \theta$ ($\theta$: center angle between adjacent leg portions/2) be less than 30% of L/2 (L: distance between adjacent leg extremity portions). This relationship is expressed by the following equations.

$$0.1d \sin \theta \leq (0.3/2)L$$

$$L \geq (2d/3)\sin \theta$$

For the modification with four leg portions (the lengths of the leg portions are the same) as shown in FIG. 116, when calculating the distance L between adjacent leg portions based on the above equations, L is 6.5 mm with the maximum skin spreading rate being 30% and with the skin spreading rate (target value) of 10%.

Three housing modifications having conditions shown in FIG. 116 were prepared and subjected at their respective pressure-receiving portions to a force of 10 N to measure a skin expansion between opposed leg portions. In consequence, the skin expansion rate between opposed leg portions was 13.3% when the distance between adjacent leg portions was 7 mm. However, the skin expansion rate between opposed leg portions was 6.7% (<10%) when the distance between adjacent leg portions was 5 mm (<6.5 mm). It was found out from these results that the skin expansion rate between opposed leg portions can be 10% or more if the distance between adjacent leg portions satisfies the relationship of equation 2.

Figure 117:
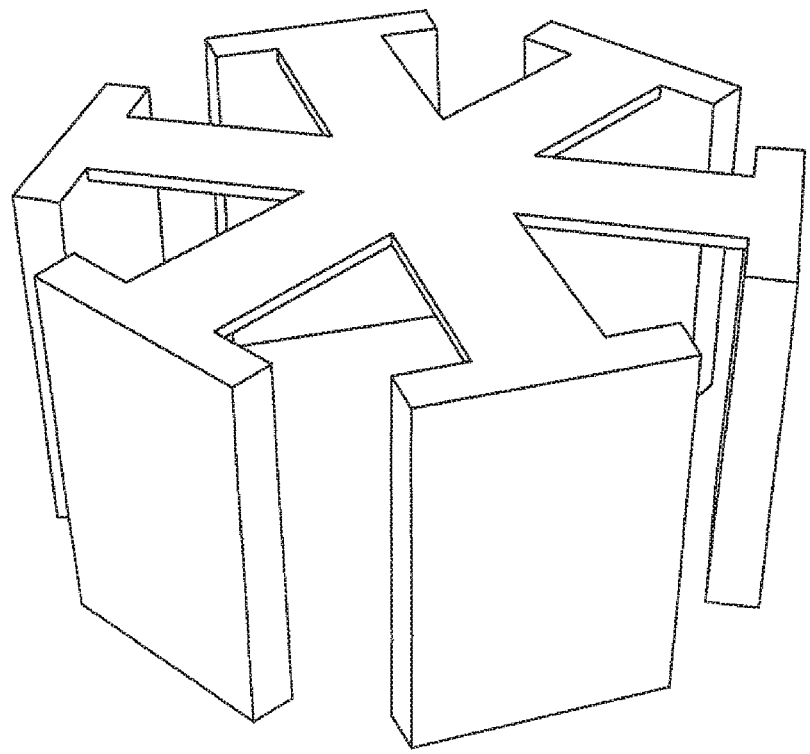
FIG. 117 is a perspective view showing a housing modification having four leg portions.

For six leg portions (the lengths of the leg portions are the same) shown in FIG. 117, L is 4.5 mm when calculating the distance (L) between adjacent leg portions with the maximum skin spreading rate being 30% and with the skin spreading rate (target value) of 10%.

Three modifications having conditions shown in FIG. 118 were prepared and subjected at their respective pressure-receiving portions to a force of 10 N to measure a skin expansion between opposed leg portions. In consequence, the skin expansion rate between opposed leg portions was 13.3% when the distance between adjacent leg portions was 4.5 mm. However, the skin expansion rate between opposed leg portions was 6.7% (<10%) when the distance between adjacent leg portions was 2 mm (<6.5 mm). It was found out from these results that the skin expansion rate between opposed leg portions can be 10% or more if the distance between adjacent leg portions satisfies the relationship of equation 2.

Although in the embodiments described hereinbefore, the leg portions are exemplified as extending radially from a central axis and as being arranged at regular intervals along the circumferential direction of a circle around the central axis, the leg portions need not be arranged at regular intervals along the circumferential direction of the circle around the central axis, but instead, may be arranged along concentric circles, or may be arranged horizontally or vertically asymmetrically. The "d" shown in the above equations represents a minimum distance among the distances from a center of gravity on skin contact surfaces of all the leg portions to the leg portions.

Figure 119:
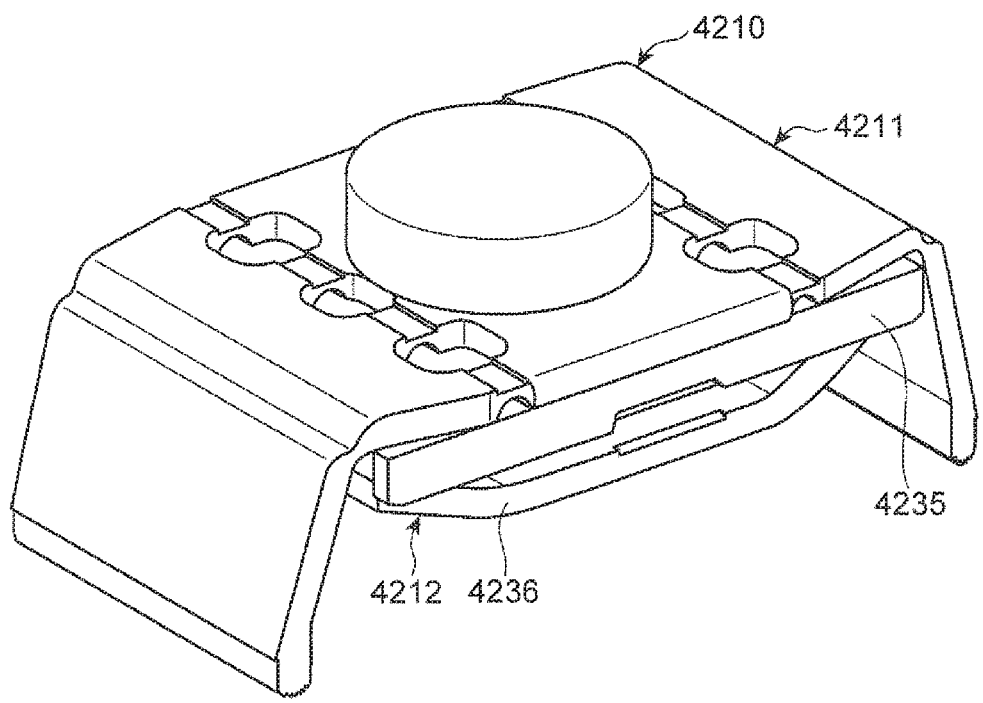

Although in this manner, it was found out in order to impart an effective mechanism for spreading the skin onto the skin that the extension of adjacent legs must be designed to 30% or less, a modification achieving the maximum interval between adjacent legs may be a two-leg modification shown in FIG. 119. A stabilizer may further be mounted for the skin surface and insertion stabilities.

Eighteenth Embodiment

Figure 95:
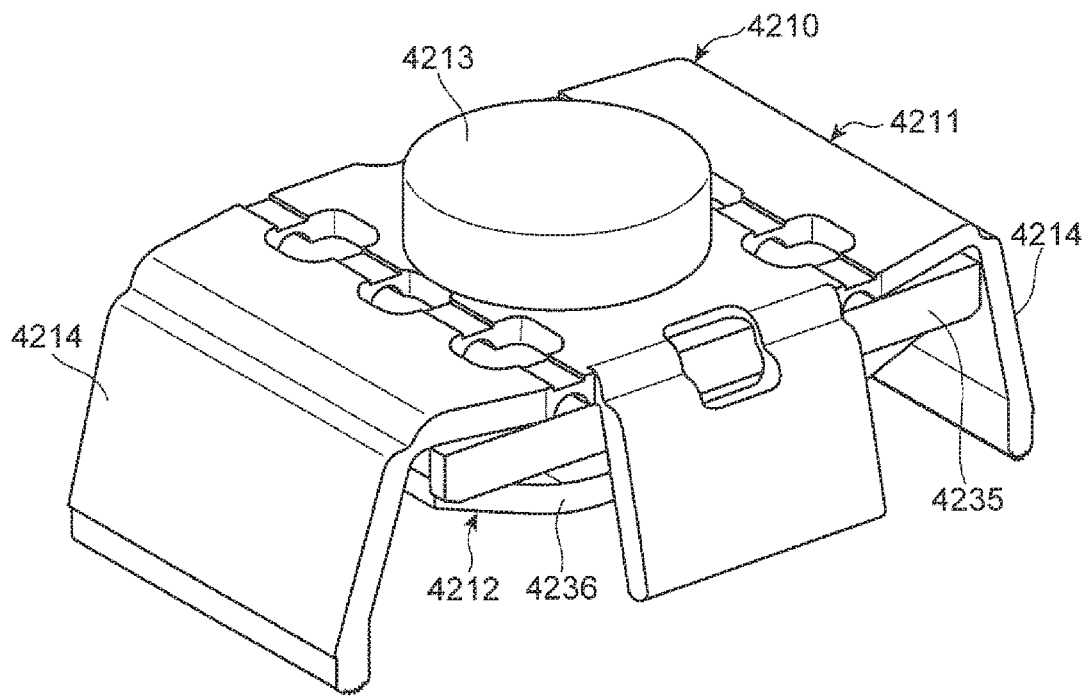
FIG. 95 is a perspective view of a device according to the eighteenth embodiment, viewed from diagonally above.
Figure 96:
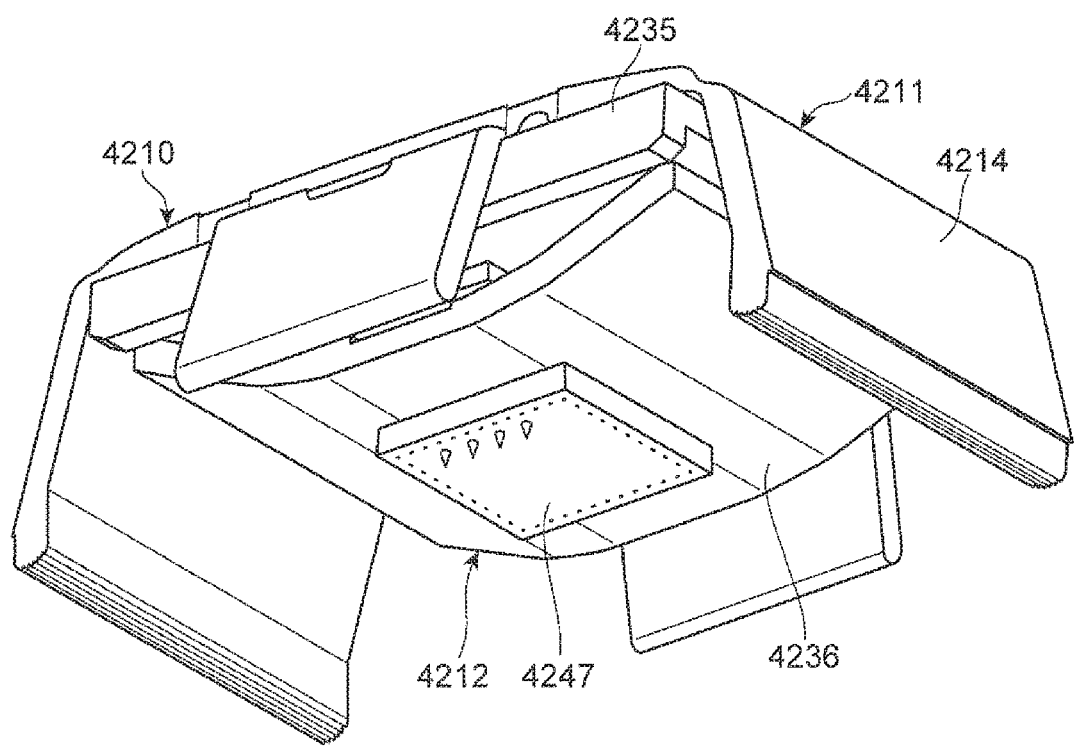
FIG. 96 is a perspective view of the device according to the eighteenth embodiment, viewed from diagonally below.
Figure 97:
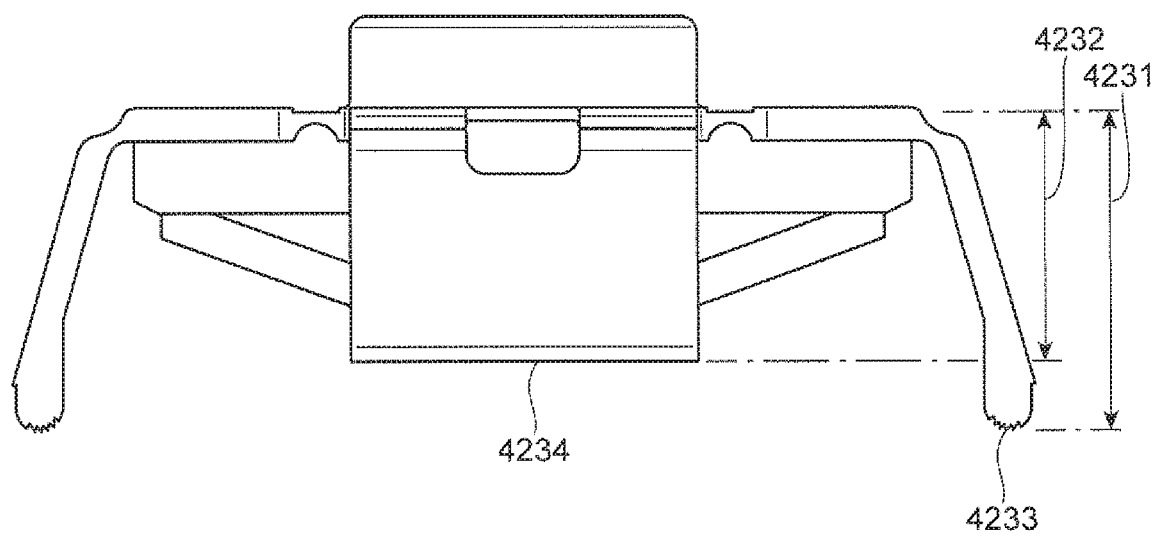
FIG. 97 is a sectional view of the device according to the eighteenth embodiment.

FIGS. 95 to 97 show an eighteenth embodiment of the device applying a microneedle patch onto a skin, according to the present invention. The device of the shown embodiment is generally designated at reference numeral 4210 and includes schematically a housing 4211 and a support portion 4212 for the microneedle patch.

Figure 98:
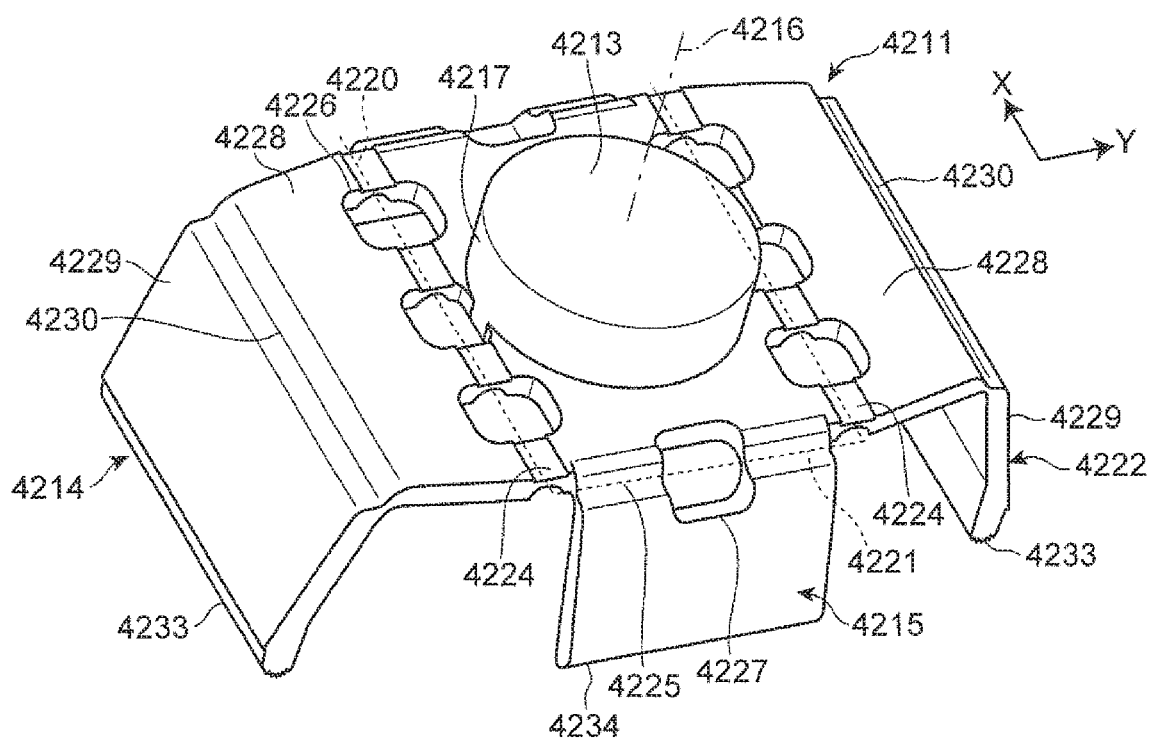
FIG. 98 is a perspective view of a housing of the device according to the eighteenth embodiment, viewed from diagonally above.
Figure 99:
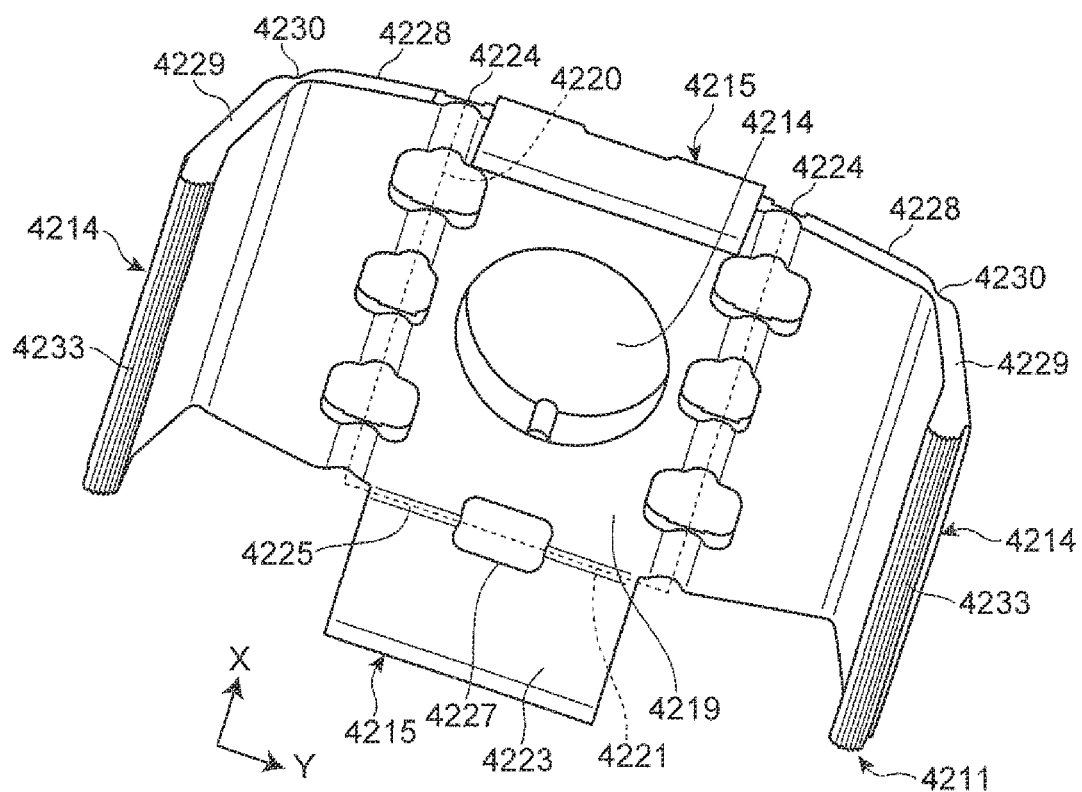
FIG. 99 is a perspective view of the housing of the device according to the eighteenth embodiment, viewed from diagonally below.

As shown in FIGS. 98 and 99, the housing 4211 has a pressure-receiving portion 4213, a plurality of first leg portions 4214, and a plurality of stabilizers 4215 (hereinafter, referred to as "stabilizer"). Although the device 4210 has the stabilizers 4215, it is to be understood that a stabilizer-free modification (see FIG. 119) also be encompassed in one embodiment of the present invention.

For the action of causing the microneedles to proceed into the skin and for the action of spreading the skin, it is preferred that both the functions be executed by a single operation. This single operation is applying a stress to the pressure-receiving portion by hand, the stress being an only one force imparted for the action of causing the microneedles to proceed into the skin and for the action of spreading the skin. Application of the imparted force to the leg portions in contact with the skin generates a more friction between the leg portions and the skin, facilitating the spread of the skin. The stress applied to the leg portions is 0.1 N or more, preferably 0.2 N or more, more preferably 0.5 N or 2 N or more. If no friction is exerted due to a weak stress applied to the leg portions, the leg portions slide on the skin so that the skin cannot be spread.

The pressure-receiving portion 4213 has a substantially cylindrical portion 4217 extending vertically along an central axis 4216 of the device 4210, a pressure-receiving wall (pressure-receiving surface 4218) as a ceiling wall closing the upper end of the cylindrical portion 4217, and a flange 4219 extending horizontally outward from the lower end of the cylindrical portion 4217. In the embodiment, the geometry of the flange 4219 is a substantially rectangular when viewed from above and has, on a plane orthogonal to the central axis 4216, a pair of first edges 4220 extending in the Y-direction symmetrically with respect to the central axis 4216 and a pair of second edges 4221 extending in the X-direction orthogonal thereto. The first edges 4220 support a pair of the first leg portion 4214 extending in y-direction outward relative to the central axis 4216, while the second edges 4221 support a pair of the stabilizers 4215 extending downward along the central axis.

As described above, the first edge 4220 forms a first connecting portion between the pressure-receiving portion 4213 and the first leg portion 4214. The second edge 4221 forms a second connecting portion between the pressure-receiving portion 4213 the stabilizer 4215. In the following description, the first connecting portion is designated at reference numeral 4220 and the second connecting portion is designated at reference numeral 4221.

The first connecting portion 4220 has a plate thickness smaller than the plate thicknesses of the flange 4219 and of the first leg portion 4214, to form an deformable portion 4224. Similarly, the second connecting portion 4221 has a plate thickness smaller than the plate thicknesses of the flange 4219 and of the stabilizer 4215, to form an deformable portion 4225. The deformable portion 4224 may deform more easily by forming a single or a plurality of apertures 4226 in the first connecting portion 4220. Similarly, the deformable portion 4225 may deform more easily by forming a single or a plurality of apertures 4226 in the second connecting portion 4221.

The first leg portion 4214 has a first leg portion 4228 adjoining the first connecting portion 4220 and extending substantially horizontally, and a second leg portion 4229 extending diagonally downward and outward from the extremity of the first leg portion 4228. At the boundary between the first leg portion 4228 and the second leg portion 4229, an deformable portion 4230 is formed that extends continuously or intermittently in the X-direction, by thinning the boundary than the first leg portion 4228 and the second leg portion 4229. Although not shown, a single or a plurality of apertures may be formed for easier deformation at the boundary between the first leg portion 4228 and the second leg portion 4229. The thicknesses of the thinned portions and the size and the number of the apertures in the deformable portion 4224 and the deformable portion 4230 are determined so that the deformable portion 4224 can deform easier than the deformable portion 4230 when a force is applied to the pressure-receiving portion 4213 with the housing 4211 being placed on the skin. Furthermore, by making a difference between the amount of deformation of the deformable portion 4224 and the amount of deformation of the deformable portion 4230, it is possible to spread the skin with a constant force, in other words, to control the spreading of the skin by a force applied. When a force is applied to the pressure-receiving portion 4213, first the force is majorly born by the deformable portion 4224, which in turn deforms to spread out the skin, and then, after a deformation of the deformable portion 4224 to a certain extent, the force applied to the pressure-receiving portion 4213 is born by the deformable portion 4230 on the other, which in turn deforms majorly, causing the microneedles to proceed toward the skin.

The stabilizer 4215 may extend vertically downward substantially in parallel to the central axis 4316 from the second connecting portion 4221, or may extend diagonally outward relative to the central axis 4216.

As shown in FIG. 97, it is preferred that a vertical length 4231 (distance from the top surface of the first leg portion 4214 to an extremity portion 4233) of the first leg portion 4214 be larger than a vertical length 4232 (distance from the top surface of the stabilizer 4215 to an extremity portion 4234) of the stabilizer 4215.

Figure 100:
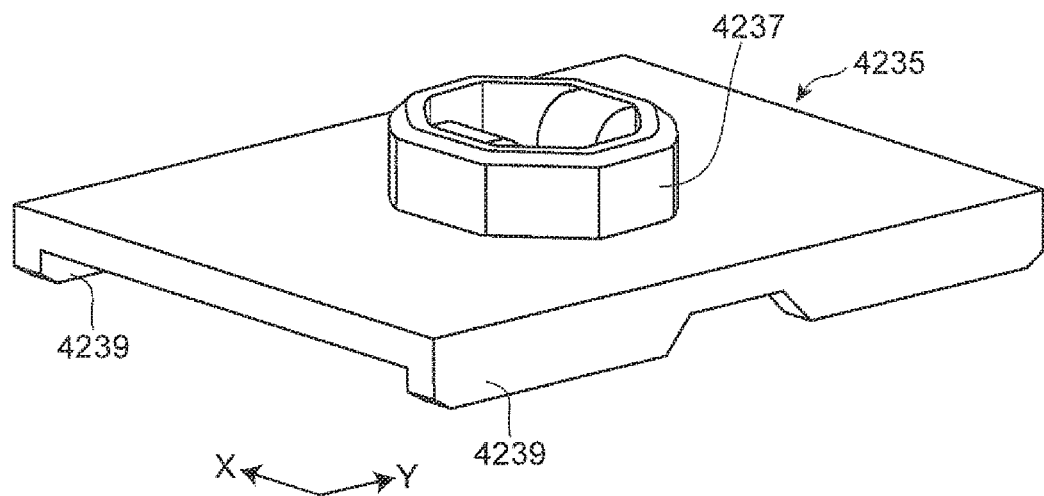
FIG. 100 is a perspective view of a holder of the device according to the eighteenth embodiment, viewed from diagonally above.
Figure 105:
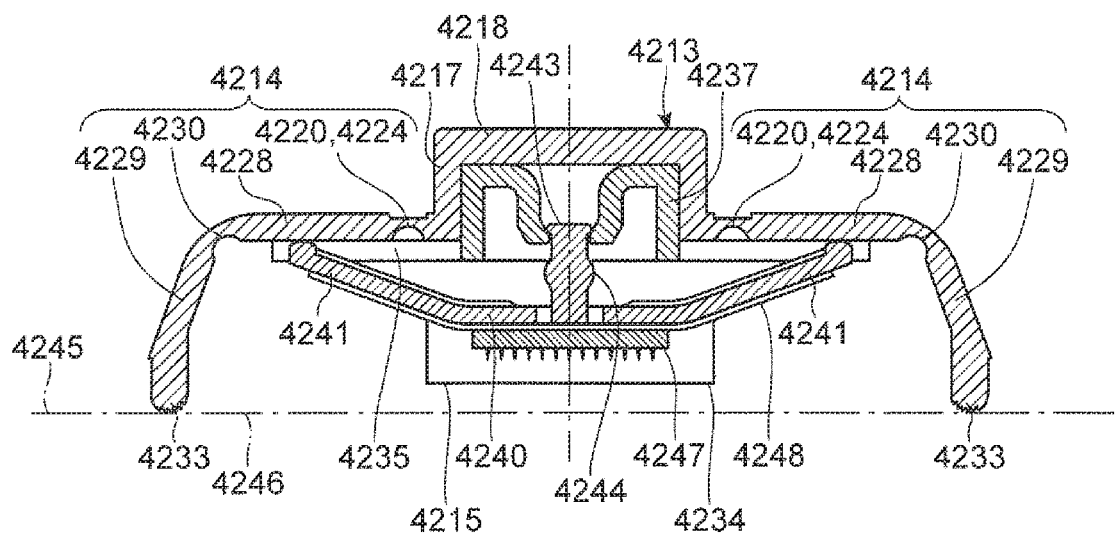
FIG. 105 is a sectional view for showing an action according to the eighteenth embodiment.

The support portion 4212 has a holder 4235 (see FIGS. 100 and 101) fitted to the bottom surface of the housing 4211 and a trapezoidal spring portion 4236 (FIGS. 102 and 103) fitted to the bottom surface of the holder 4235. The holder 4235 is in the shape of a substantially rectangular plate, when viewed from above, which has at its center an upward extending annular cylindrical portion 4237 formed integrally therewith. The exterior shape of the cylindrical portion 4237 corresponds to the interior shape of the pressure-receiving-portion cylindrical portion 4217 so that the holder cylindrical portion 4237 can fit snugly from below into the inside of the pressure-receiving-portion cylindrical portion 4217. The holder cylindrical portion 4237 has on its inner surface a pair of opposed engaging claws 4238 extending inward from the inner-surface upper portion and thereafter extending downward, formed symmetrically with respect to the central axis (this central axis coincides with the central axis 4216 of the device when the holder 4235 is assembled to the pressure-receiving portion 4213) of the holder cylindrical portion 4237. As shown in FIG. 105, it is preferred that the lower ends of the engaging claws 4238 be above the bottom surface of the holder 4235.

Figure 101:
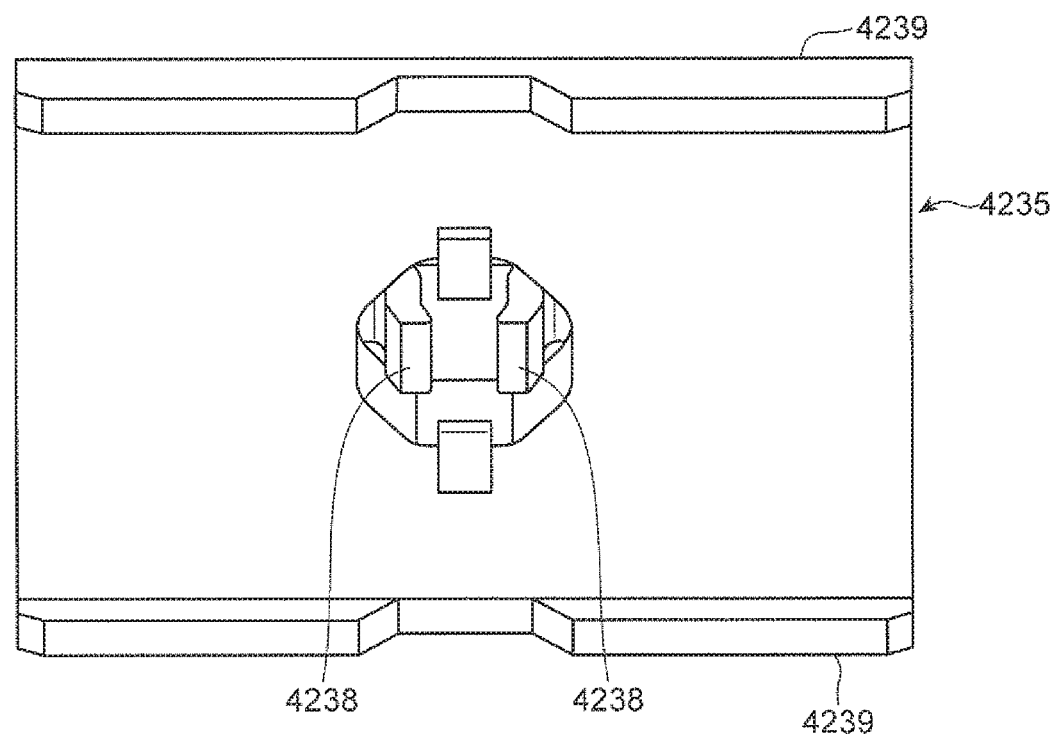
FIG. 101 is a perspective view of the holder according to the eighteenth embodiment, viewed from diagonally below.

As shown in FIG. 101, the holder 4235 has on its bottom surface a pair of guide flanges 4239 extending along a pair of opposed edges (In the drawing, edges extending in the Y-direction).

Figure 102:
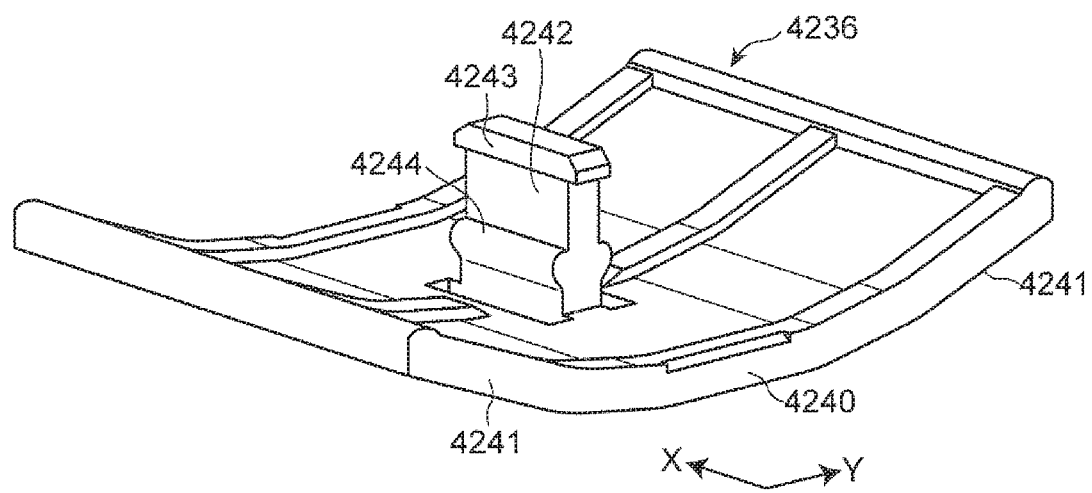
FIG. 102 is a perspective view of a trapezoidal spring portion according to the eighteenth embodiment, viewed from diagonally above.
Figure 103:
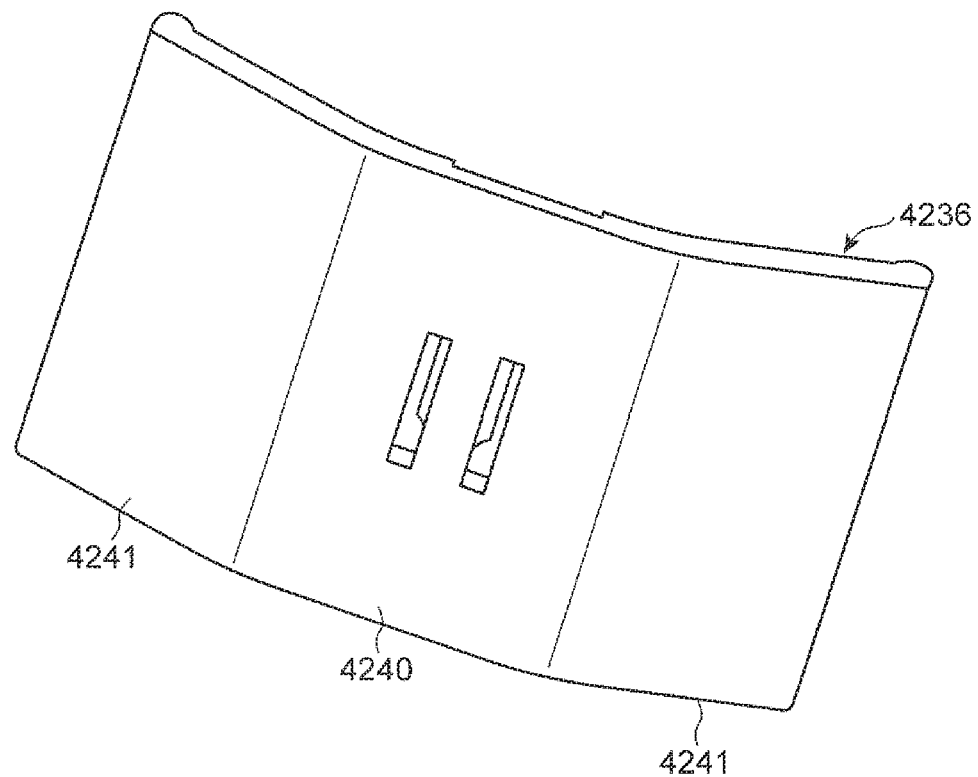
FIG. 103 is a perspective view of the trapezoidal spring portion according to the eighteenth embodiment, viewed from diagonally above.

As shown in FIG. 102, the trapezoidal spring portion 4236 has integrally a rectangular central plate portion 4240 supporting the microneedle patch, inclined plate portions 4241 extending diagonally upward and outward from a pair of opposed edges of the central plate portion 4240, and a vertical wall 4242 laying at a central portion on the central plate portion 4240 and extending upward from the top surface of the central plate portion 4240. The vertical wall 4242 has an upper protrusion 4243 and a lower protrusion 4244 formed integrally therewith and protruding outward from side surfaces thereof. The width of the central plate portion 4240 and the inclined plate portions 4241, esp., the width between free ends of the inclined plate portions 4241 is slightly smaller than the interval between the guide flanges 4239.

The thus configured trapezoidal spring portion 4236 is assembled to the holder 4235, with the free ends of the inclined plate portions 4241 being positioned between the guide flanges and with the upper protrusion 4243 of the vertical wall 4242 being engaged between the opposed engaging claws 4238 of the holder 4235 as shown in FIG. 105.

As shown, the trapezoidal spring 4236 and the holder 4235 are flexibly engaged with each other and are designed so that, even if the microneedles are not directed vertically to the skin when the microneedles come into contact with the skin, the verticality between the microneedles and the skin is corrected due to the flexible engagement portions so that the microneedles penetrate vertically into the skin.

The sizes and shapes of the portions of the above device 4210 are determined so that in the ready condition where the device 4210 having the housing 4211 mounted with the holder 4235 and the trapezoidal spring portion 4236 supporting the microneedle patch is placed on a skin 4245, the microneedle patch cannot come into contact with the skin 4245 with a predetermined gap formed between the microneedle patch and the skin 4245.

A microneedle patch 4247 has a sheet substrate and a microneedle array supported thereon, as described above. The microneedle array has a circular or rectangular base and a multiplicity of elongated needles with a predetermined height (e.g., 300 to 1000 micrometers) arrayed at predetermined intervals (e.g., 300 to 1000 micrometers) in a lattice or honeycomb pattern on the bottom surface of the base. The microneedle array is formed, for example, by filling a biodegradable synthetic polymer material (e.g., hyaluronic acid, collagen, polylactic acid, polyglycolic acid) into a correspondingly shaped mold. Although not shown, tip sides of the needles are coated with a target drug (molecules such as vaccine, protein, and peptide). Alternatively, or additionally, the target drug may be contained in the needles by being mixed with materials of the needles during molding of the microneedle array.

In use, as shown in FIG. 105, the microneedle patch 4247 is applied through an attachment sheet 4248 onto the bottom surface of the trapezoidal spring portion 4236. The attachment sheet 4248 has a sheet substrate and a pressure-sensitive adhesive layer provided on the bottom surface of the sheet substrate, the microneedle patch 4247 being applied to and supported on the pressure-sensitive adhesive layer. The attachment sheet 4248 is applied at its both side portions to the inclined plate portions 4241 by double-sided adhesive tapes (not shown) in the state where the microneedle patch 4247 is positioned on the bottom surface of the central plate portion 4240. It is preferred that the adhesive force (area×adhesive force per unit area) of the double-sided adhesive tape be determined so that, with the pressure-sensitive adhesive layer on both side portions of the attachment sheet 4248 being adhered to the skin, the pressure-sensitive adhesive force between the pressure-sensitive adhesive layer and the skin far exceeds the adhesive force between the double-sided adhesive tapes and the sheet substrate so that the attachment sheet 4248 can easily be detached from the trapezoidal spring portion 4236.

Figure 106:
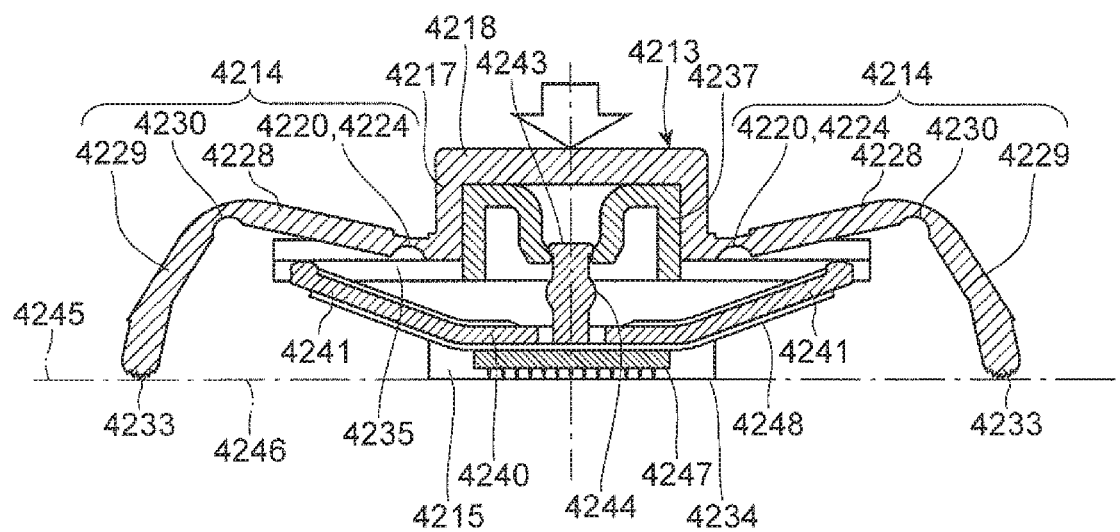
FIG. 106 is a sectional view for showing an action according to the eighteenth embodiment.

When applying the microneedle patch 4247 onto the skin 4245 of a human being or an animal using the device 4210 configured as above, the device 4210 is placed on the skin by way of the bottom surface of the trapezoidal spring portion 4236, as shown in FIGS. 105 and 106. In this ready condition, the microneedle patch 4247 is held above the skin 4245 and apart from the skin 4245. The pressure-receiving surface 4218 is then depressed by a thumb for example. As a result, the deformable portion 4224 of the first leg portion 4214 bends and then the deformable portion 4230 bends, allowing the microneedle patch 4247 to move toward the skin 4245. Since the deformable portion 4224 deforms more easily than the deformable portion 4230 as described above, the bending angle of the deformable portion 4224 is larger than the bending angle of the deformable portion 4230. When pulling of the skin arrives at the vicinity of a preset stress limit, the deformable portion 230 starts to deform, causing the microneedle patch 4247 to advance toward the skin surface. This enables the microneedles to advance toward and insert into the skin even in the state where the skin is hardly stretched.

Figure 107:
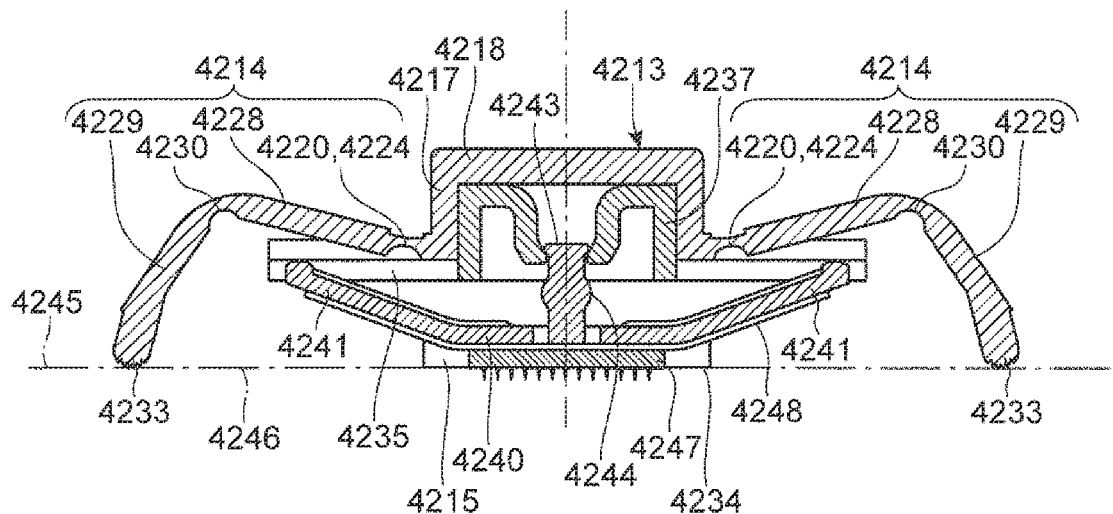
FIG. 107 is a sectional view for showing an action according to the eighteenth embodiment.

As described above, bending of the deformable portion 4224 results in a movement of the leg extremity portions 4233 in contact with the skin 4245 toward the direction away (outward) from the central axis 4216. Consequently, a portion 4246 of the skin sandwiched between the two leg extremity portions 4233 is pulled toward the both sides due to the friction between the leg extremity portions 4233 and the skin 4245, to be "tensioned". Accordingly, when the needles on the microneedle patch 4247 come into contact with the portion 4246 of the skin, the needles insert easily into the "tensioned" portion 4246 of the skin, without any retreat of this portion 4246 of the skin as a result of being pushed by the needles (see FIG. 107). Thus, without any damage or breakage of the needles, substantially all the needles insert securely into the skin so that the drug carried on the needles can certainly be administered.

Immediately before the needles on the microneedle patch insert into the skin, or when the needles start inserting into the skin, the extremity portions 4234 of the stabilizers 4215 come into contact with the skin 4245. This keeps the tension that occurs in the portion 4246 of the skin lying between the extremity portions 4233 of the first leg portions 4214. Giving a specific description, for example, when a rectangular elastic plate is pulled outward while holding a pair of opposed edges thereof by hand, edges orthogonal thereto are drawn toward the inside due to Poisson effect. In the same manner, the portion 4246 of the skin pulled in predetermined directions by the first leg portions 4214 tries to contract collaterally in the directions orthogonal thereto. However, such Poisson effect is suppressed by the stabilizers 4215 so that the tension imparted to the skin portion in the region surrounded by the leg portions 4233 is maintained. Furthermore, when the needles insert into the skin, the stabilizers 215 come into contact with the skin to keep the tension in a suitable state, improving the needle insertion performance into the skin.

Figure 108:
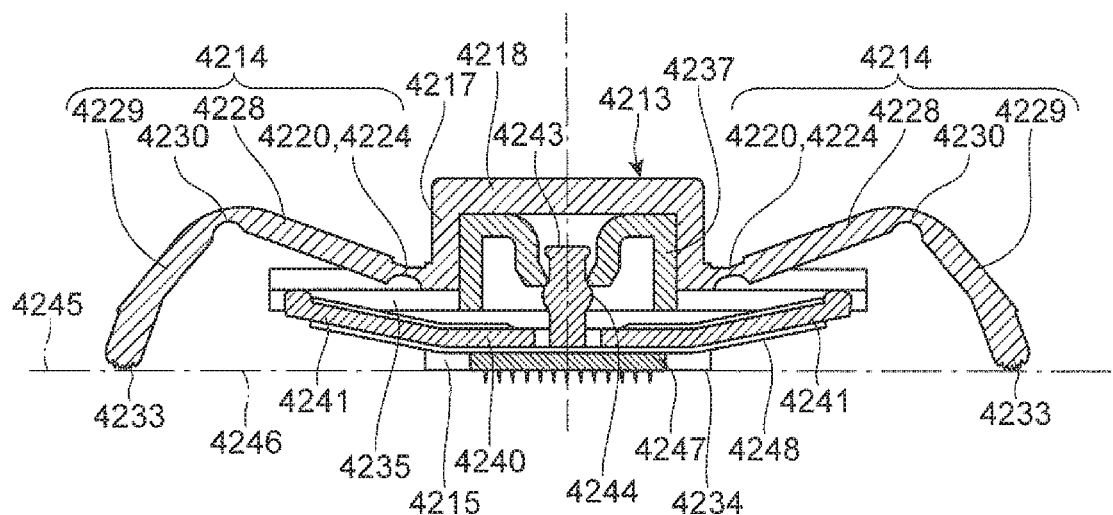
FIG. 108 is a sectional view for showing an action according to the eighteenth embodiment.
Figure 109:
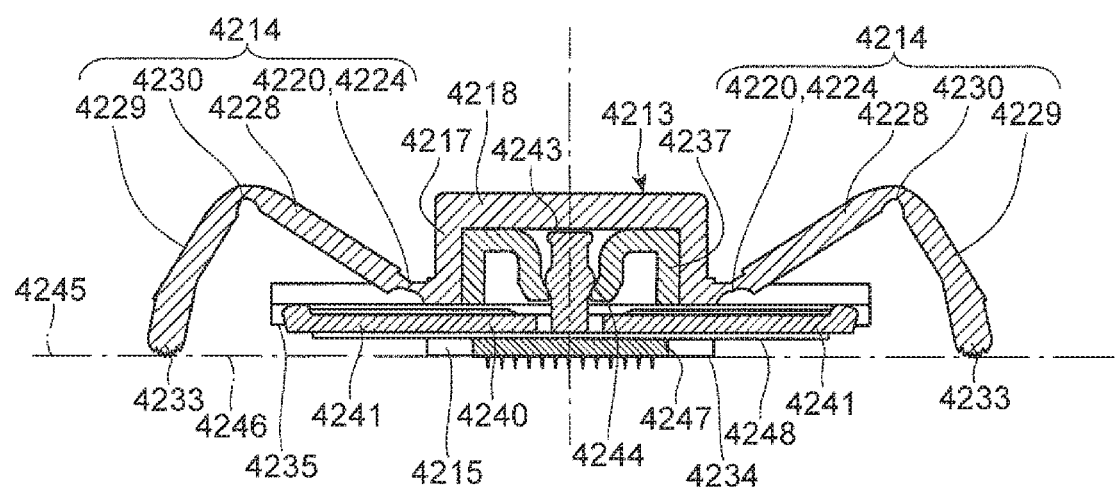
FIG. 109 is a sectional view for showing an action according to the eighteenth embodiment.

When the pressure-receiving surface 4218 continues to be depressed in the state where the needles insert into the skin portion 4246, the inclined plate portions 4241 of the trapezoidal spring portion 4236 deform due to the pressing force received from the pressure-receiving surface 4218 and a repellent force received from the skin 4245. Simultaneously with the deformation, the extremity portions of the trapezoidal spring portion 4236 move outward along the bottom surface of the holder 4235 while being guided by the guide flanges 4239. When subjected to a force necessary to securely insert all the needles into the skin 4245, the trapezoidal spring portion 4236 is deformed into a desired shape, as shown in FIG. 108, with the result that the lower protrusion 4244 on the central vertical wall 4242 passes between the engaging claws 4238. The deformation state of the trapezoidal spring portion 4236 is kept by the engagement of the engaging claws 4238 with the lower protrusion 4244. When the lower protrusion 4244 comes into contact with the engaging claws 4238 and when the lower protrusion 4244 passes between the engaging claws 4238, a sound occurs and a shock is transmitted to the finger. This enables the user to recognize that a force necessary to attach the microneedle patch 4247 has been applied to the pressure-receiving surface 4218.

In the state where a necessary force is applied to the pressure-receiving surface 4218, the skin portion 4246 retained between the leg extremity portions 4233 rises relative to the leg extremity portions 4233. Thus, the pressure-sensitive adhesive layer of the attachment sheet 4248 retained on the inclined plate portions 4241 of the trapezoidal spring portion 4236 is pressed against and adhered to the skin 4245.

When removing, from this state, the force applied to the pressure-receiving surface 4218 and raising the device 4210 from the skin 4245, the attachment sheet 4248 is peeled off from the both-sided tapes adhered to the inclined plate portions 4241 of the trapezoidal spring portion 4236, while the microneedle patch 4247 remains kept on the skin 4245 by the attachment sheet 4248 with the needles inserting into the skin 4245.

Figure 104:
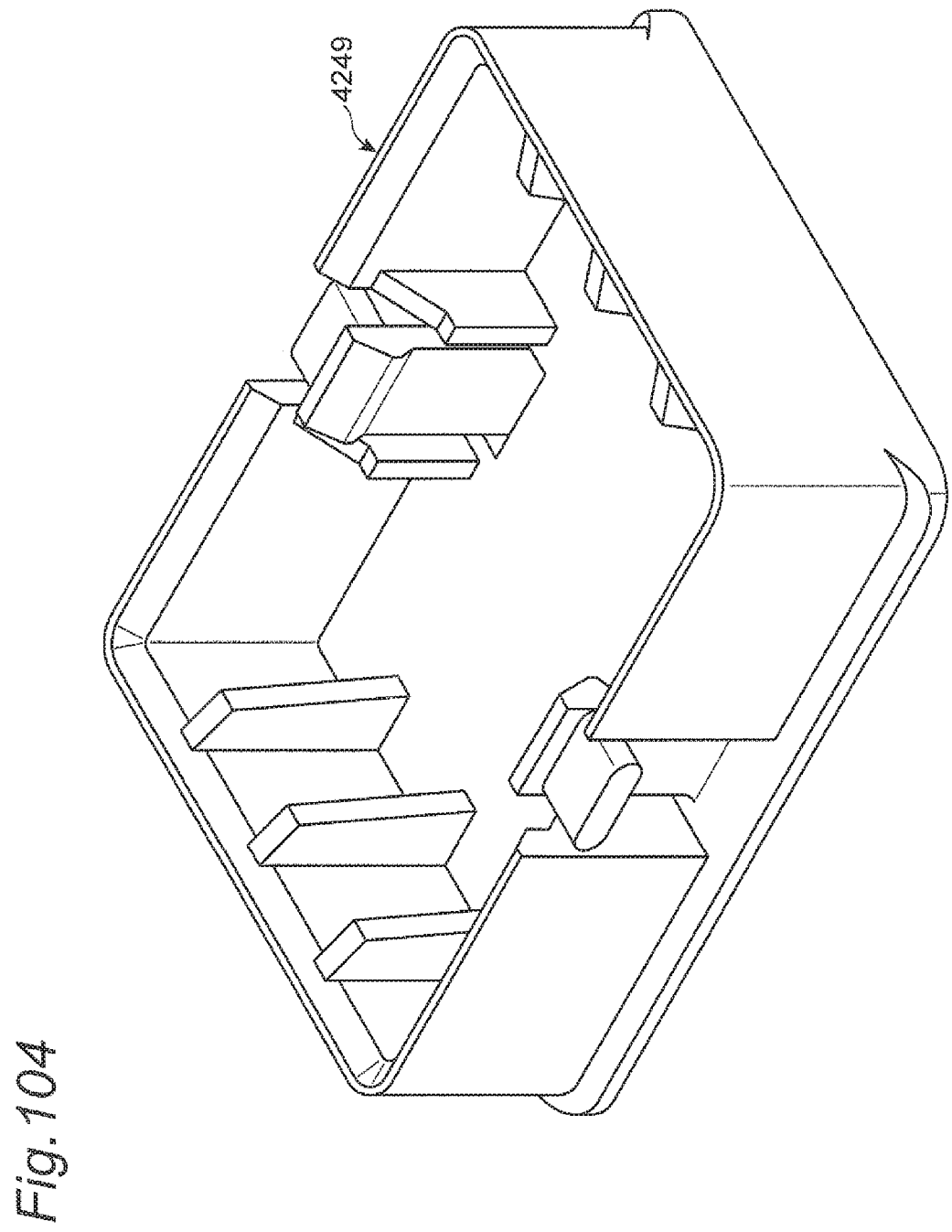
FIG. 104 is a perspective view of a protection cover according to the eighteenth embodiment, viewed from diagonally above.

Similar to the other embodiments, it is preferred also in the device of the eighteenth embodiment that the support portion 4212 be removably provided with a protection cover 4249 surrounding the bottom surface of the microneedle patch, as shown in FIG. 104, so as to prevent the microneedle patch supported on the support portion 4212 from coming into contact with a finger, etc., of the user.

The device according to the eighteenth embodiment may partially be reused as a cartridge. For example, when inserting the protection cover 4249 into the housing 4211 after insertion, the support portion 4212 without the microneedle patch is coupled to the interior of the protection cover, while when removing the protection cover 4249 from the housing 4211, the support portion 4212 including the trapezoidal spring 4236 and the holder 4235 is also removed together with the protection cover 4249.

At the time of reuse, the protection cover accommodating the holder 4235 and the trapezoidal spring 4236 fitted with the microneedle patch is thrust into the housing, whereby the support portion 4212 fitted with the microneedle patch is joined to the housing 4211, resulting in the start-of-use enabled state. The indicator may again be provided by replacing the trapezoidal spring, as in the shown embodiment, or by utilizing a force of the trapezoidal spring returning to its original trapezoidal shape after deformation of the trapezoidal spring under pressure at the insertion of the needles, the lower protrusion 4244 may pass between the engaging claws 4238 in the opposite direction to that upon the thrusting so that the indicator returns to its origin.

Repetition of this operation enables a hygienic reuse. The portions replaceable as the cartridge can be combinations of the holder 4235, the trapezoidal spring 4236, and the microneedle patch, or of the trapezoidal spring 4236 and the microneedle patch, or of the microneedle patches, which can be joined together in use. The indicator returns to its origin, to provide for reuse. For return to the origin, the indicator is designed, depending on e.g., the shape of the claws, so as to obtain a load stress toward the direction of movement to act as the indicator and a stress necessary to return to its origin.

It is preferred as a distribution form that irrespective of the embodiments, the cartridge members including the holder, the trapezoidal spring, and the microneedle patch be individually or in plural combinations housed in a housing or mounted with a protection cover in such a manner that the microneedles are protected so as not to subject the microneedles to a shock. To that end, a protection housing is selected that has a structure of preventing a contact with the microneedles using a rigid material or a structure of weakening the shock by a cushion material.

The protection housing comprised of an individual member or a combination of plural members may have a form in which required members are joined simply to the housing for use available state, by setting the protection housing in the housing.

Use as the cartridge enabled a good distributability, a simple operation and puncturing, and even patient's own treatment.

As described above, the spreading rate of skin of human beings has limitations. It is therefore preferred that after application of a pulling force to the skin to a certain degree, the leg portions in contact with the skin slide on the skin so as not to apply a further pulling force to the skin. More preferably, after application of a predetermined pulling force to the skin, the action to spread the skin is stopped. This is achievable in the embodiment in which each leg portion has a plurality of deformable portions, by imparting different deformation performances to the deformable portions, respectively. In that instance, first, one deformable portion deforms to spread the skin and, after application of a certain or more pulling force (this pulling force is preferably determined within a range of 0.1 N to 100 N for example) to the skin, the one deformable portion stops its action to spread the skin, but instead, another deformable portion deforms to allow the microneedles to advance into the skin.

The housing having the pressure-receiving portion and a plurality of leg portions may be shaped as shown in FIGS.

120, 121, 122, and 123. In these modifications, the deformable portions of the leg portions or of the pressure-receiving portion or of both thereof are comprised of curvilinear or straight resilient deformation portions or of combinations thereof. A small deformable portion with a small curvature may be subjected locally to a great force, reducing the durability and reproducibility. It is therefore preferred for keeping the durability and reproducibility that the curvilinear deformable portion have a large curvature. However, since an increased curvature results in a poor moldability, more preferably, the deformable portion is comprised of a curvilinear or straight resilient plate portion or of a combination thereof. The combination of the curvilinear or straight plate portions facilitates the regulation of a pulling force applied to the skin.

Figure 120:
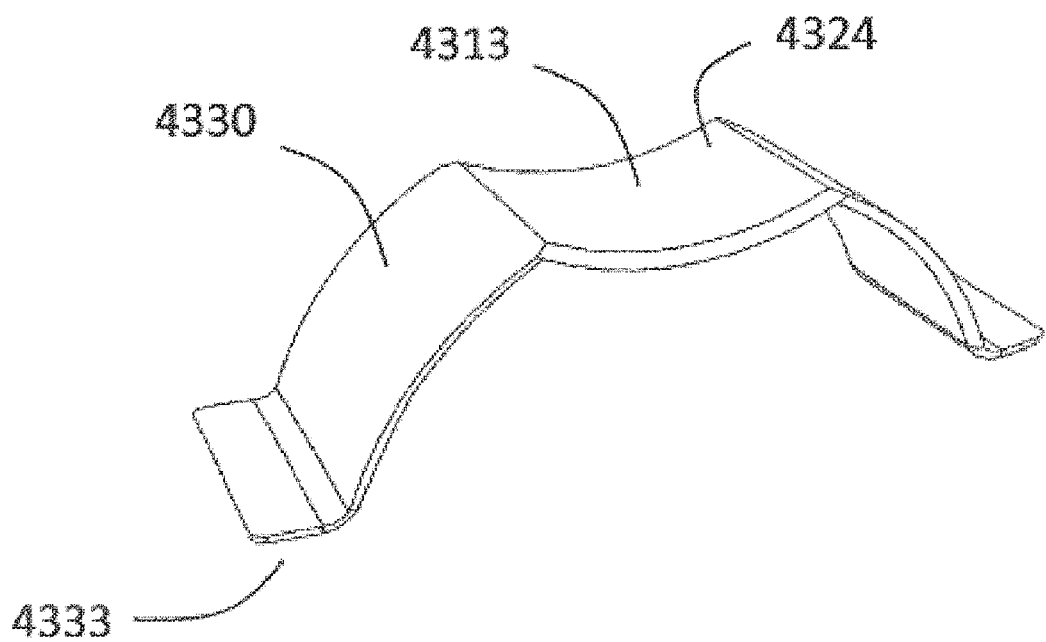
Figure 121:
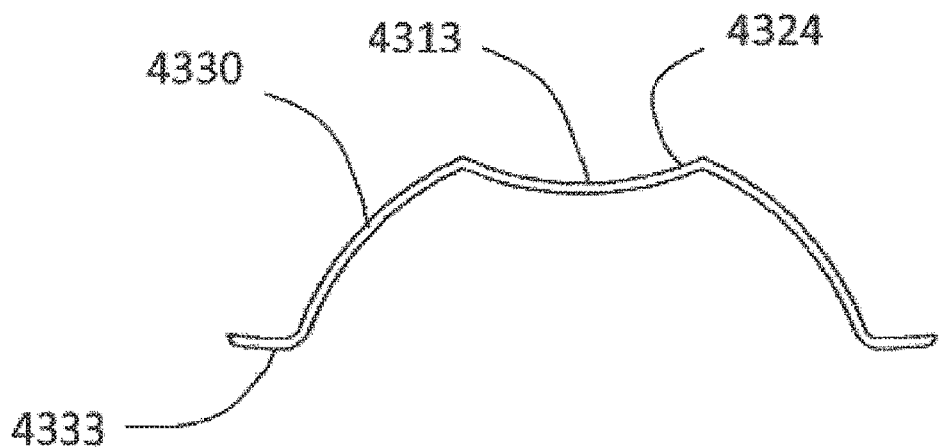

For example, the housing of the modifications shown in FIGS. 120 and 121 includes a combination of an deformable portion 4330 having a curvilinear plate portion and an deformable portion 4324 having a curvilinear plate portion. In these modifications, a region of the deformable portion 4324, esp., its central region is used as a pressure-receiving portion 4313. The pressure-receiving portion may be provided in a different place or member. Although not shown, under the deformable portion 4324 there may be arranged a microneedle patch support member, a spring member for stress detection, a resilient member, or an indicator, or any combination thereof.

According to this modification, when the pressure-receiving portion 4313 is pressed, the deformable portion 4324 deforms to spread the distance between the leg portions. Until the skin pulling force arrives at its limit, substantially the deformable portion 4324 deforms allowing the microneedles to advance toward the skin. When the skin pulling force arrives at its limit, subsequently the deformable portion 4330 deforms allowing the microneedles to advance toward the skin.

Figure 122:
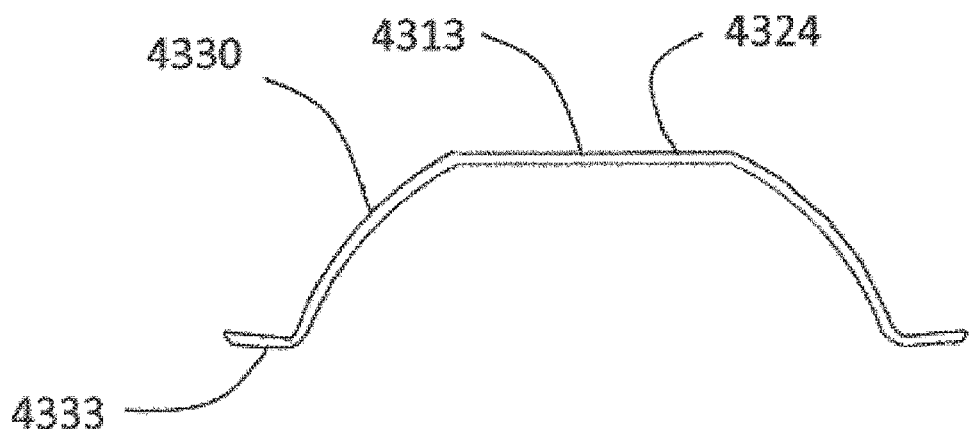
Figure 123:
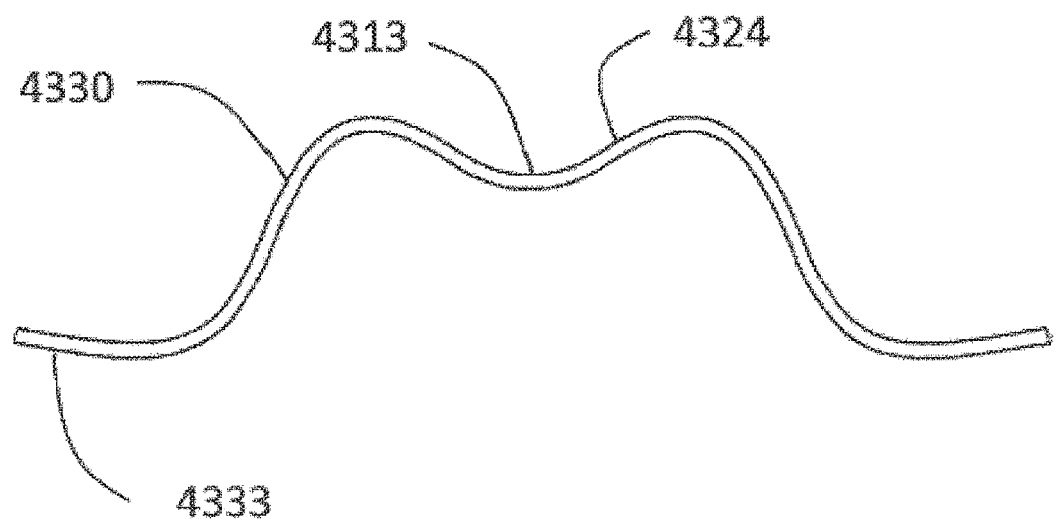

In the modification shown in FIG. 122, the pressure-receiving portion is formed as a straight resilient deformation portion. In the modification shown in FIG. 123, both the pressure-receiving portion and the leg portions are formed as curvilinear resilient deformation portions.

Naturally, not only the deformations of the deformable portion 4324 and of the deformable portion 4330, but also the deformations of connecting portions between the deformable portion and the deformable portion or of portions between the deformable portion and the leg extremities can be utilized. By increasing the area of disposition of the leg extremity portions onto the skin, a more force is applied to the leg extremity portions to increase the friction with the skin so that the skin can spread easily.

Nineteenth Embodiment

Figure 124:
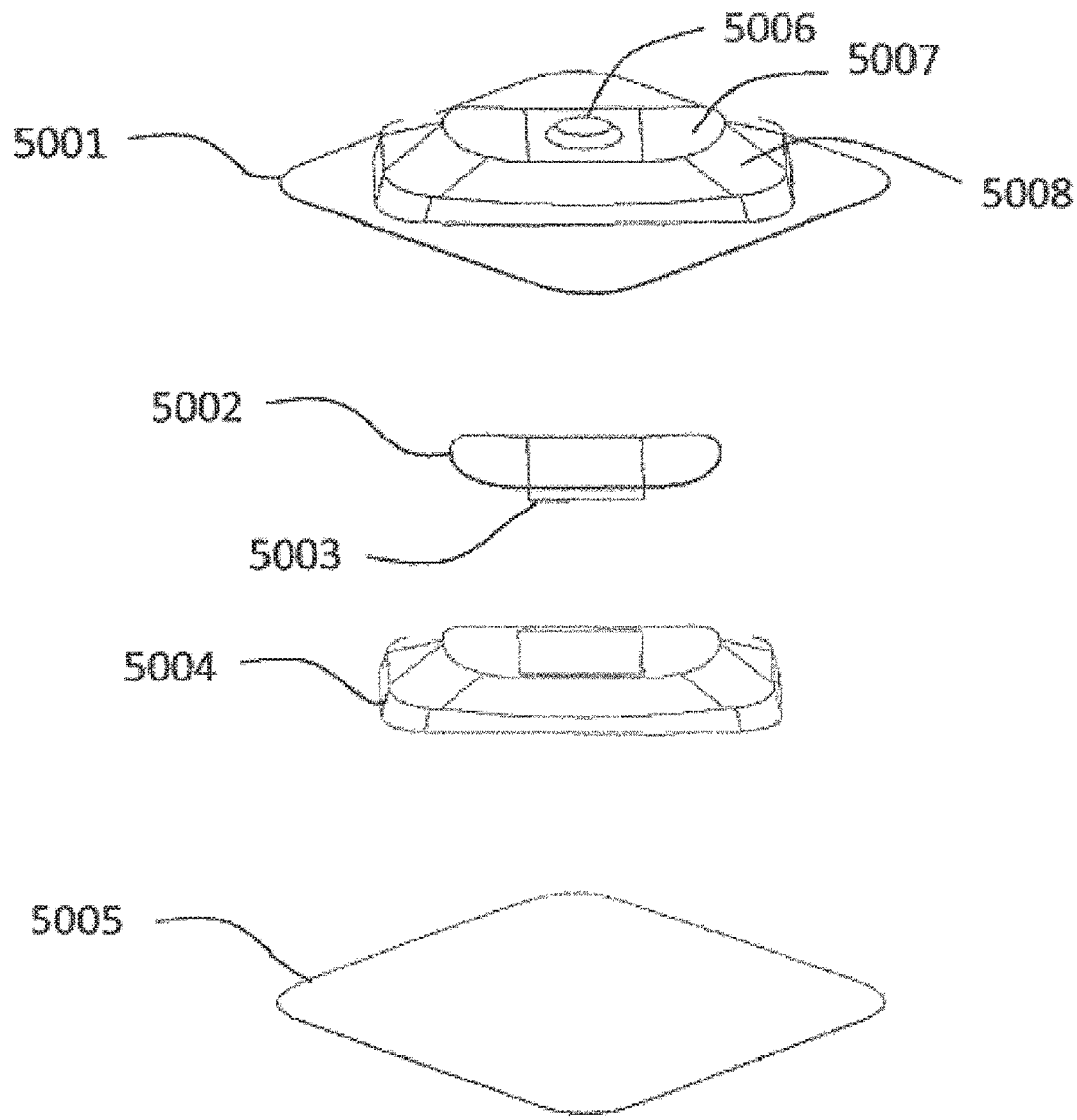
Figure 125:
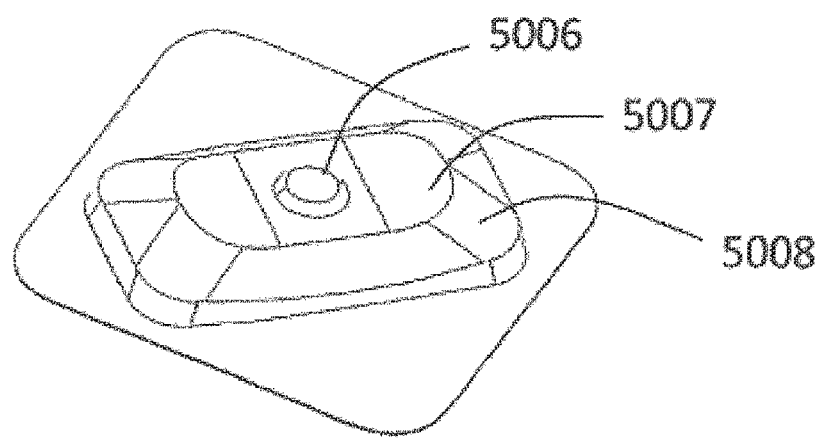
Figure 126:
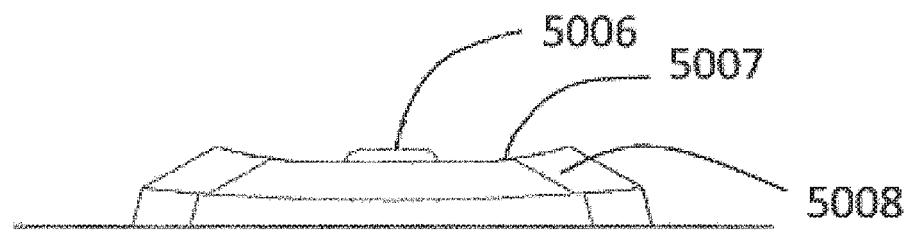

In a nineteenth embodiment, the device for inserting microneedles into a skin is configured from a protection housing for accommodating a microneedle patch or from a distribution housing. For example, as shown in FIGS. 124 to 126, the device has a microneedle patch 5002 including microneedles 5003, a container 5001 containing the microneedle patch 5002, and a seal member 5005 sealing an opening of the container 5001.

Figure 127:
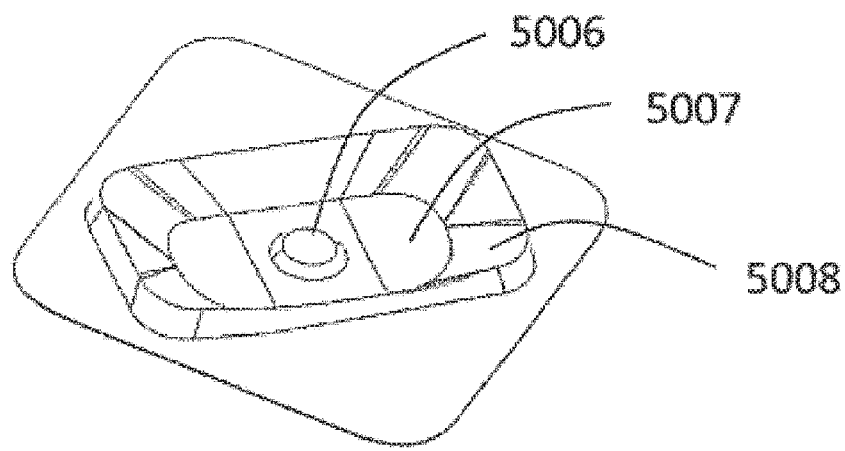

In use, the seal member 5005 is removed and the container 5001 containing the microneedle patch 5002 is placed on a skin. Next, when a load is applied to a pressure-receiving portion 5006 by hand, finger, etc., an deformable portion 5008 deforms to press the microneedle patch 5002 located under the container ceiling portion 5006 against a skin (FIG. 127). The microneedles arrive at the skin. Next, when the pressure-receiving portion 5006 is further pushed by hand, the microneedles insert deeply into the skin. It is preferred for stable vertical advancement of the microneedles into the skin to dispose the deformable portion 5008. Preferably, the housing is configured to return resiliently to its original shape when the puncturing of the microneedles is completed. This helps the microneedle patch transfer easily from the housing to the skin. Additionally, the deformation of the ceiling portion may be reduced to improve the vertical penetration performance of the microneedles.

Although the material of the housing is not particularly limited, a resin or a metal is used in general. Examples of a preferred resin include resins such as polypropylene, polyethylene, nylon, ABS resin, PET, acrylic resin, polystyrene, vinylidene chloride, polycarbonate, fluorine (Teflon), vinyl chloride, polyamide, rubber, and silicone, and foam resins such as foamed styrene, foamed urethane, and foamed melamine. Examples of a preferred metal include titanium, stainless, aluminium, and magnesium alloys.

The deformable portions may be provided as edges, folds, and thinned portions in portions (i.e., ceiling portion, side wall portions, and skirt portions) of the housing so that the housing can deform evenly.

In order to protect the microneedles 5003 from a shock, a spacer 5004 may be provided between the microneedle patch 5002 and the seal member 5005. In this instance, the shock to the microneedles is cushioned, preventing the microneedles from being damaged during the distribution and storage. Although the material of the spacer is not particularly limited, examples of a preferred resin include resins such as polypropylene, polyethylene, nylon, ABS resin, PET, acrylic resin, polystyrene, vinylidene chloride, polycarbonate, fluorine (Teflon), vinyl chloride, polyamide, rubber, and silicone, and foam resins such as foamed styrene, foamed urethane, and foamed melamine. Examples of a preferred metal include titanium, stainless, aluminium, and magnesium alloys.

Figure 128:
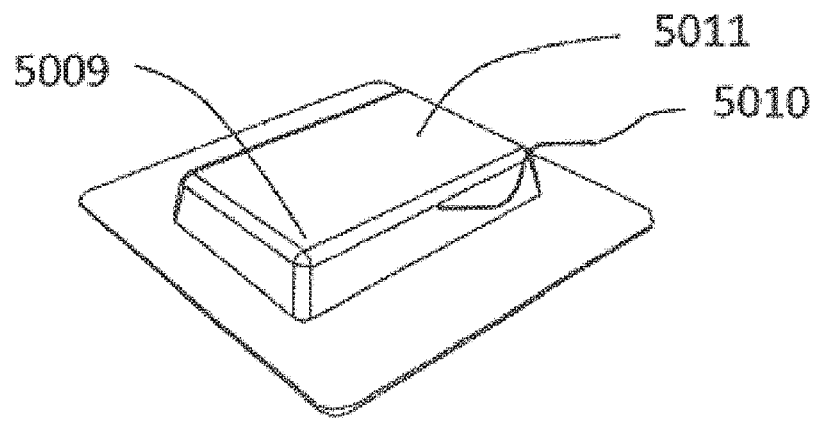

FIG. 128 shows a modification. In this modification, the container 5001 has a plurality of edges 5009 to improve the vertical penetration performance of the microneedles into the skin. Accordingly, in use, the seal is removed and the housing 5010 fitted with the microneedle patch is placed on the skin. Next, when the ceiling portion acting as the pressure-receiving portion is pressed by a finger, the ceiling portion 5011 deforms so that the ceiling portion 5011 and the microneedle patch positioned on the skin-side of the ceiling portion advance toward the skin, allowing the microneedle patch to come into contact with the skin. Subsequently, when the pressure-receiving portion is further pressed, the microneedles insert deeply into the skin. Preferably, the housing is configured to return resiliently to its original shape when the puncturing of the microneedles is completed. This helps the microneedle patch transfer easily from the housing to the skin.

Figure 129:
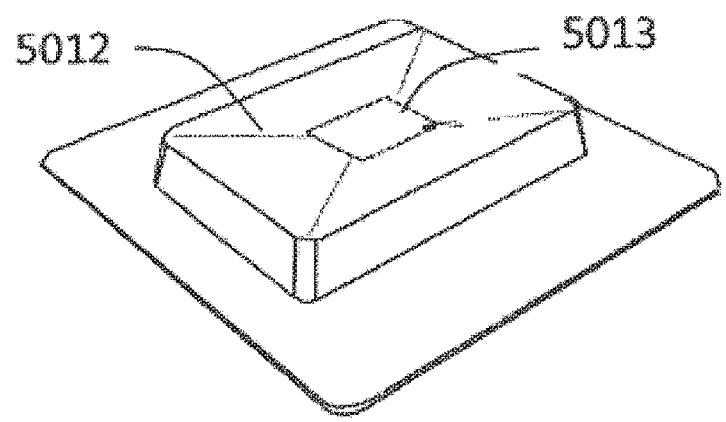
Figure 130:
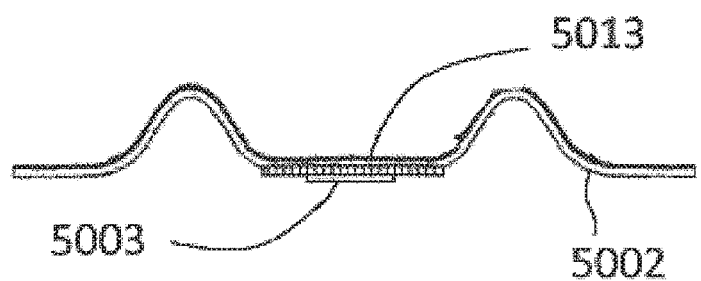

As shown in FIG. 129, deformable portions 5012 may further be provided in the form of folds or thinned portions in the ceiling portion so that the ceiling portion deforms evenly. Preferably, a thickened rigid portion 5013 is provided at a center on the ceiling portion, thereby advancing the microneedles toward the skin while keeping the microneedles substantially in parallel to the skin as shown in FIG. 130 so that forces the microneedles receives from the skin can be dispersed symmetrically.

Preferably, the ceiling portion has a flat, convex, or concave shape. More preferably, the convex or concave ceiling portion is unable to be inverted, i.e., concaved or convexed, which stabilizes the deformation of the ceiling portion. Also, the concaved shape is more likely to induce the deformation of the ceiling portion, which ensures a stable movement of the microneedles toward the skin.

Preferably, the housing may be configured to return resiliently to its original shape when the puncturing of the microneedles is completed. This helps the microneedle patch transfer easily from the housing to the skin.

An indicator may be provided to indicate a sufficient insertion of the microneedles into the skin. The indicator may be provided inside the housing or may be provided outside of the housing. In order to ensure asepsis of the microneedles, it is preferred that the indicator be provided outside of the housing. This simplifies the device aseptic processing.

In order to improve the stability of a drug carried on the microneedles, it is preferred that a desiccant be received in the housing to remove the moisture. Together with the desiccant or in lieu of the desiccant, dry nitrogen may be added to the interior of the housing. Instead of adding the desiccant, or in addition to adding the desiccant, the housing or the seal member may be made of a moisture absorption resin.

In order to improve the stability of a drug carried on the microneedles, oxygen scavenger may be enclosed in the housing or dry nitrogen may be enclosed therein. In addition to oxygen scavenger or dry nitrogen, or in place thereof, the housing or the seal may be made of an oxygen absorption resin.

As described above, according to the nineteenth embodiment using the housing as the device for inserting microneedles into the skin, there can be provided a low-cost, compact, and well-operable device capable of reducing wastes.

In order to protect the pressure-sensitive adhesive surface of the microneedle patch during the distribution and storage, release paper may be provided on a portion of pressure-sensitive adhesion to the skin, of the microneedle patch. It is preferred that the release paper can easily be released in use by silicone coating, embossing, etc. It is preferred when releasing the release paper to adjust a release starting point of the release paper so as to prevent also the microneedle patch from being detached together from the device. For example, when the microneedle patch and the device are partially adhered to each other, the release stating point is preferably designed to lie at the same position as that of the adhered portion. This can prevent also the microneedle patch from being detached together when removing the release paper. In order to prevent also the microneedle patch from being detached together, it is preferred that the release be feasible with a small force and that the shape of the release paper be taken into consideration. Furthermore, when there are any parts (e.g., protection housing, seal, spacer, etc.) to be removed before use among parts annexed to the device, a more preferable structure is so that the release paper is also removed at the same time when removing those parts. To that end, it is preferred that the release paper and the removal parts be partially or entirely adhered together. The removal parts may have silicone coating or embossing so as to act as an alternative of the release paper.

EXPLANATIONS OF LETTERS OR NUMERALS 1001, 2001: microneedle patch applicator
1002: microneedle patch
1003: first element
1004: second element
1022: microneedle array
1027: needles
4010: microneedle patch applicator
4011: housing
4012: pressure-receiving portion
4013: leg portion
4018: deformable portion
4066: microneedle patch

The invention claimed is:

1. A device for applying a microneedle patch onto a skin, comprising
   a housing for supporting the microneedle patch, the housing comprising:
      a support portion supporting the microneedle patch in a state where needles on the microneedle patch are directed toward the skin;
      a pressure-receiving portion to which a user applies a force to press the microneedle patch against the skin in a ready condition where the housing is placed on the skin;
      a plurality of legs each having at its one end a connecting portion connected to the pressure-receiving portion and having at its other end an extremity portion coming into contact with the skin in the ready condition, the plurality of legs keeping the support portion apart from the skin in the ready condition;
      each of the plurality of legs having a pair of first and second deformable portions, each pair of the first and second deformable portions being formed between the pressure-receiving portion and the extremity portion of each of the plurality of legs, the first deformable portion being positioned closer to the pressure-receiving portion than the second deformable portion;
      each of the plurality of legs further having a first leg portion extending between the first deformable portion and the second deformable portion and a second leg portion extending between the second deformable portion and the extremity portion;
      wherein the first and second deformable portions are designed such that, when the force is applied to the pressure-receiving portion,
         the first deformable portion deforms easier than the second deformable portion, and
         the first deformable portion bends to move closer toward the skin, and an angle between the first leg portion and the second leg portion and facing the skin becomes smaller.

2. The device of claim 1, further comprising:
   the pressure-receiving portion for receiving the force applied along a direction of a central axis extending substantially vertically with respect to the skin in an applying condition where the microneedle patch is being applied onto the skin; and
   the plurality of legs extend radially from the central axis and are arranged at regular intervals along a circle around the central axis, wherein the plurality of legs each have the extremity portion pressed against the skin, and wherein d, θ, and L satisfy the following equation:

$$L \geq (2d/3)\sin \theta$$

where
"d" is a distance from the central axis to the extremity portion;
"2θ" is a center angle between adjacent legs; and
"L" is a distance between adjacent leg extremity portions.

3. The device of claim 2, wherein, when the force is applied to the pressure-receiving portion of the housing, the distance L from the central axis to the extremity portion is extendable by 10% or more, and the distance L between the adjacent legs is extendable by 30% or less.

4. The device of claim 1, wherein the first deformable portion and the second deformable portion are not in direct contact with each other.

5. The device of claim 1, wherein the first leg portion is designed to extend substantially parallel to the skin in the ready condition before the force is applied to the pressure-receiving portion.

6. The device of claim 1, wherein when the force is applied to the pressure-receiving portion, the first and second leg portions do not bend.

7. A device for applying a microneedle patch onto a skin, comprising
  a housing for supporting the microneedle patch, the housing comprising:
    a support portion supporting the microneedle patch in a state where needles on the microneedle patch are directed toward the skin;
    a pressure-receiving portion to which a user applies a force to press the microneedle patch against the skin in a ready condition where the housing is placed on the skin;
    a pair of legs each having at its one end a connecting portion connected to the pressure-receiving portion and having at its other end an extremity portion coming into contact with the skin in the ready condition, the pair of legs keeping the support portion apart from the skin in the ready condition;
    each of the pair of legs having first and second deformable portions, each pair of the first and second deformable portions being formed between the pressure-receiving portion and the extremity portion of each of the legs, the first deformable portion being positioned closer to the pressure-receiving portion than the second deformable portion;
    each of the pair of legs further having a first leg portion extending between the first deformable portion and the second deformable portion and a second leg portion extending between the second deformable portion and the extremity portion;
  wherein the first and second deformable portions are designed such that, when the force is applied to the pressure-receiving portion,
    the first deformable portion deforms easier than the second deformable portion, and
    the first deformable portion bends to move closer toward the skin, and an angle between the first leg portion and the second leg portion and facing the skin becomes smaller.

8. The device of claim 7, further comprising:
  the pressure-receiving portion for receiving the force applied along a direction of a central axis extending substantially vertically with respect to the skin in an applying condition where the microneedle patch is being applied onto the skin; and
  the pair of legs extend radially from the central axis and are arranged at regular intervals along a circle around the central axis, wherein
  the pair of legs each have the extremity portion pressed against the skin, and wherein
  d, θ, and L satisfy the following equation:

$$L \geq (2d/3)\sin \theta$$

where
"d" is a distance from the central axis to the extremity portion;
"2θ" is a center angle between adjacent legs; and
"L" is a distance between adjacent leg extremity portions.

9. The device of claim 7, wherein, when the force is applied to the pressure-receiving portion of the housing, the distance L from the central axis to the extremity portion is extendable by 10% or more, and the distance L between the adjacent legs is extendable by 30% or less.

* * * * *